(12) United States Patent
Cook et al.

(10) Patent No.: US 7,618,958 B2
(45) Date of Patent: Nov. 17, 2009

(54) STEREOSPECIFIC ANXIOLYTIC AND ANTICONVULSANT AGENTS WITH REDUCED MUSCLE-RELAXANT, SEDATIVE-HYPNOTIC AND ATAXIC EFFECTS

(75) Inventors: James M. Cook, Whitefish Bay, WI (US); Hao Zhou, Milwaukee, WI (US); Shengming Huang, Milwaukee, WI (US); P.V.V. Srirama Sarma, Germantown, WI (US); Chunchun Zhang, Nanuet, NY (US)

(73) Assignee: WISYS Technology Foundation, Inc., Madison, WI (US)

( * ) Notice: Subject to any disclaimer, the term of this patent is extended or adjusted under 35 U.S.C. 154(b) by 456 days.

(21) Appl. No.: 11/173,981

(22) Filed: Jun. 30, 2005

(65) Prior Publication Data

US 2006/0003995 A1   Jan. 5, 2006

Related U.S. Application Data

(60) Provisional application No. 60/584,143, filed on Jun. 30, 2004.

(51) Int. Cl.
| | |
|---|---|
| *A61P 25/22* | (2006.01) |
| *A61K 31/5513* | (2006.01) |
| *C07D 243/14* | (2006.01) |
| *C07D 243/18* | (2006.01) |
| *C07D 487/04* | (2006.01) |
| *C07D 495/04* | (2006.01) |
| *C07D 495/14* | (2006.01) |

(52) U.S. Cl. .................... 514/220; 540/560; 540/562

(58) Field of Classification Search ............... 514/220; 540/560, 562
See application file for complete search history.

(56) References Cited

U.S. PATENT DOCUMENTS 4,621,083 A * 11/1986 Casals-Stenzel et al. .... 514/220

FOREIGN PATENT DOCUMENTS

| EP | 0 320 992 A2 | 6/1989 |
|---|---|---|
| WO | WO 03/082832 A2 | 10/2003 |

OTHER PUBLICATIONS

He X et al: "Pharmacophoren/Receptor Models for GABAA/BZR ALPHA3BETA3GAMMA2 and ALPHA4BETA3GAMMA2 Recombinant Subtypes. Included Volume Analysis and Comparison to ALPHA1BETA3GAMMA2, ALPHA5BETA3GAMMA2 and ALPHA6BETA3GAMMA2 Subtypes" Drug Design and Discovery, Hardwood Academic Publishers GMBH, vol. 17, No. 2, 2000.

Zhang, P., et al., "Synthesis of Novel Imidazobenzodiazepines as Probes of the Pharmacophore for 'Diazepam-Insensitive' GABAA Receptors," J. Med Chem. 38:1679-1688 (1995).

* cited by examiner

*Primary Examiner*—Brenda L Coleman
(74) *Attorney, Agent, or Firm*—Quarles & Brady LLP

(57) ABSTRACT

The present invention provides compositions and methods of using stereospecific benzodiazepine derivatives, their salts and prodrugs for the treatment of anxiolytic or convulsant disorders having the side effects of reduced alcohol craving in human alcoholics and a concomitant reduced sedative, hypnotic, muscle relaxant and ataxic side-effects. The invention further provides pharmaceutical compositions for treatment of anxiolytic and convulsant disorders in subjects in need thereof, comprising a compound, prodrug or a salt having a chemical structure represented by any one of Formula I-XXI and a pharmaceutically-acceptable carrier.

9 Claims, 2 Drawing Sheets

STEREOSPECIFIC ANXIOLYTIC AND ANTICONVULSANT AGENTS WITH REDUCED MUSCLE-RELAXANT, SEDATIVE-HYPNOTIC AND ATAXIC EFFECTS

RELATED APPLICATIONS

This application claims benefit of U.S. Provisional Patent Application 60/584,143 filed Jun. 30, 2004, the entire contents of which are incorporated by reference for all purposes.

GOVERNMENT RIGHTS

This invention was made with Government support under NIMH grant number MH46851. The Government has certain rights in this invention.

BACKGROUND OF THE INVENTION

The present invention generally relates to anxiolytic and anticonvulsant agents, specifically the invention relates to a class of stereospecific benzodiazepine derivatives which possess anxiolytic, anticonvulsant activity with decreased muscle-relaxant, sedative-hypnotic and ataxic side effects.

The most frequently prescribed medication for treatment of anxiety or convulsant disorders (such as phobias, obsessive compulsive disorders) and seizure disorders are benzodiazepines such as diazepam (Valium), triazolam (Halcion), midazolam (Versed), lorazepam (Ativan), chlordiazepoxide (Librium), alprazolam (Xanax), and other benzodiazepine-based medications. However, these benzodiazepine-based medications have side effects such as drowsiness, sedation, motor incoordination, memory impairment, potentiation of effects of alcohol, tolerance and dependence, and abuse potential. Buspirone, tandospirone, and other serotonergic agents have been developed as anxiolytics with a potentially reduced profile of side effects. However, while these medications do show a reduced profile of side effects, they have other characteristics which make them less than ideal for treatment of anxiety disorders. In some cases, these agents cause anxiety before a therapeutic dose can be obtained or require dosing of the drug for several days before a therapeutic effect is seen. Development of anxiolytics with even fewer side effects is desired.

Receptors for the major inhibitory neurotransmitter, gamma-aminobutyric acid (GABA), are divided into three main classes: (1) $GABA_A$ receptors, which are members of the ligand-gated ion channel superfamily; (2) $GABA_B$ receptors, which may be members of the G-protein linked receptor superfamily; and (3) $GABA_C$ receptors, also members of the ligand-gated ion channel superfamily, but their distribution is confined to the retina. Benzodiazepine receptor ligands do not bind to $GABA_B$ and $GABA_C$ receptors. Since the first cDNAs encoding individual $GABA_A$ receptor subunits were cloned, the number of known members of the mammalian family has grown to 21 including $\alpha$, $\beta$, and $\gamma$ subunits ($6\alpha$, $4\beta$, $4\gamma$, $1\delta$, $1\epsilon$, $1\pi$, $1\theta$, and $3\rho$).

Subtype assemblies containing an $\alpha 1$ subunit ($\alpha 1\beta 2\gamma 2$) are present in most areas of the brain and are thought to account for 40-50% of $GABA_A$ receptors in the rat brain. Subtype assemblies containing $\alpha 2$ and $\alpha 3$ subunits respectively are thought to account for about 25% and 17% $GABA_A$ receptors in the rat brain. Subtype assemblies containing an $\alpha 5$ subunit ($\alpha 5\beta 3\gamma 2$) are expressed predominately in the hippocampus and cortex and are thought to represent about 4% of $GABA_A$ receptors in the rat brain.

A characteristic property of all known $GABA_A$ receptors is the presence of a number of modulatory sites, one of which is the benzodiazepine binding site. The benzodiazepine binding site is the most explored of the $GABA_A$ receptor modulatory sites, and is the site through which benzodiazepine-based anxiolytic drugs exert their effect. Before the cloning of the $GABA_A$ receptor gene family, the benzodiazepine binding site was historically subdivided into two subtypes, BENZODIAZEPINE1 and BENZODIAZEPINE2, on the basis of radioligand binding studies on synaptosomal rat membranes. The BENZODIAZEPINE1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain, as stated.

Two other major populations are the $\alpha 2\beta 2/3\gamma 2$ and $\alpha 3\beta 2/3\gamma 2/3$ subtypes. Together these constitute approximately a further 35% of the total $GABA_A$ receptor population. Pharmacologically this combination appears to be equivalent to the BENZODIAZEPINE2 subtype as defined previously by radioligand binding, although the BENZODIAZEPINE2 subtype may also include certain $\alpha 5$-containing subtype assemblies. The physiological role of these subtypes has hitherto been unclear because no sufficiently selective agonists or antagonists were known.

It is now believed that agents acting as benzodiazepine agonists at $GABA_A/\alpha 2$, $GABA_A/\alpha 3$, and/or $GABA_A/\alpha 5$ receptors, will possess desirable anxiolytic properties. Compounds which are modulators of the benzodiazepine binding site of the $GABA_A$ receptor by acting as benzodiazepine agonists are referred to hereinafter as "$GABA_A$ receptor agonists." The $GABA_A/\alpha 1$-selective ($\alpha 1\beta 2\gamma 2$) agonists alpidem and zolpidem are clinically prescribed as hypnotic agents, suggesting that at least some of the sedation associated with known anxiolytic drugs which act at the BENZODIAZEPINE1 binding site is mediated through $GABA_A$ receptors containing the $\alpha 1$ subunit. Accordingly, it is considered that $GABA_A/\alpha 2$, $GABA_A/\alpha 3$, and/or $GABA_A/\alpha 5$ receptor agonists rather than $GABA_A/\alpha 1$ receptors will be effective in the treatment of anxiety or convulsant disorders with a reduced propensity to cause sedation. For example, QH-ii-066 binds with high affinity to $GABA_A/\alpha 5$ receptors (Ki<10 nM), intermediate affinity to $GABA_A/\alpha 2$ and $GABA_A/\alpha 3$ (Ki<50 nM), and lower affinity to $GABA_A/\alpha 1$ receptors (Ki>70 nM), unlike diazepam which binds with high affinity to all four diazepam-sensitive $GABA_A$ receptors (Ki<25 nM), as disclosed in Huang, et al., *J. Med. Chem.* 2000, 43, 71-95. Also, agents which are antagonists or inverse agonists at $\alpha 1$ receptors might be employed to reverse sedation or hypnosis caused by $\alpha 1$ agonists.

There are yet further advantages to targeting specific GABA receptors, namely in the treatment of alcohol addiction. Alcohol addiction and dependence remain a significant public health concern, impacting physical and mental well-being, family structure and occupational stability. While advances have been made in the development of novel therapies to treat alcoholism (O'Malley S S, et al., (1992) Arch Gen Psychiatry 49: 881-887; Volpicelli J R, et al., (1992) *Arch Gen Psychiatry* 49: 876-880; Kranzler H R (2000) *Alcohol* 35:537-547; Spanagel R, Zieglgansberger (1997) Trends Pharmacol Sci 18:54-59), alcohol-dependent individuals represent a heterogeneous group (Cloninger (1987) Science 236: 410-416; Li T-K, et al. (1991): Molecular and genetic approaches to understanding alcohol-seeking behavior. In Meyer R E, Koob G F, Lewis M J, Paul S P (eds), Neuropharmacology of ethanol. Boston: Birkhauser, pp 107-124; Li T-K (2000): Pharmacogenetics of responses to alcohol and genes that influence alcohol drinking. J Stud Alcohol 61: 5-12), and it is unlikely that a single pharmacological treatment will be effective for all alcoholics. Hence, a better understanding of the neuromechanisms which regulate alcohol seeking behaviors and the design of clinically safe and effective drugs that reduce alcohol addiction and dependence remain a high priority (Johnson B A, Ait-Daoud N (2000): Neuropharmacological treatments for alcoholism: scientific basis and clinical findings. Psychopharmacology (Berlin) 149:327-344). While the precise neuromechanisms regulating alcohol-seeking behaviors remain unknown, there is now compelling evidence that the $GABA_A$ receptors within the striatopallidal and extended amygdala system are involved in the "acute" reinforcing actions of alcohol (Koob G F et al., (1998) Alcoholism: Clin Exper Res 22:3-9; June et al., 1998c; McBride W J, Li T (1998): Animal models of alcoholism: Neurobiology of high alcohol-drinking behavior in rodents. Critical Reviews in Neurobiology 12(4):339-369). The striatopallidal and extended amygdala system include the subventicular extended amygdala [substantia innominata-ventral pallidum (VP)], shell of the nucleus accumbens, and central nucleus of the amygdala (Heimer et al., 1991; Heimer and Alheid, 1991). Among the potential $GABA_A$ receptor isoforms within the VP regulating alcohol-seeking behaviors, $GABA_A$ receptors containing the α1 receptor subtype ($GABA_{A1}$) appear preeminent. Thus, Criswell et al., (1993, 1995) observed that acute alcohol administration selectively enhanced the effects of ionotophoretically applied GABA in the VP (Criswell H E, et al., (1993): Molecular basis for regionally specific action of ethanol on γ-aminobutyric acidA receptors: Generalization to other ligand-gated ion channels. J Pharmacol Exper Ther 267:522-527; Criswell H E, et al (1995): Effect of zolpidem on γ-aminobutyric acid (GABA)-induced inhibition predicts the interaction of ethanol with GABA on individual neurons in several rat brain regions. J Pharmacol Exper Ther 273:525-536). However, no effects were seen in the septum, VTA, and CA1 hippocampus. Further, a positive correlation was observed between alcohol-induced GABA enhancement and [$^3$H] zolpidem binding (an α1 subtype selective agonist). Other investigators have identified a dense reciprocal projection from the VP to the NACC (Nauta H J, et al., (1978a) Neuroscience, 3:189-202; Nauta W J, et al., (1978b) Neuroscience 3: 385-401; Zahm D S and Heimer L (1988) J Comp Neurol 272: 516-535; Groenewegen H J, et al., (1993) Neuroscience 57:113-142), and many of these have been found to be GABA ergic neurons (Mogenson G J, Nielson M A (1983) Brain Res Bulletin 11: 309-314; Kuo H and Chang H T (1992): Ventral-pallidostriatal pathway in the rat brain: A light electron microscopic study. J Comp Neurol 321:626-636; Churchill L, Kalivas P W (1994): A topographical organized GABA projection from the ventral pallidum to the nucleus accumbens in the rat. J Comp Neurol 345:579-595). The NACC is well established as a substrate that regulates the reinforcing properties of abused drugs. Finally, immunohistochemical (Turner J D, Bodewitz G, Thompson C L, Stephenson F A (1993): Immunohistochemical mapping of gamma-aminobutyric acid type-A receptor alpha subunits in rat central nervous system. In: Anxiolytic β-carbolines: from Molecular Biology to the Clinic (D. N. Stephens, ed), pp 29-49 New York: Springer-Verlag; Fritschy J M, Mohler H (1995): $GABA_A$-receptor heterogenetity in the adult rat brain. Differential regional and cellular distribution of seven major subunits. J Comp Neurol 359:154-194) and in situ hybridization studies (Churchill et al., 1991; Wisden et al., 1992; Duncan et al., 1995) have demonstrated that the VP contains one of the highest concentrations of mRNA encoding the α1 subunit in the CNS. These findings, together with pharmacological studies suggesting the VP plays a role in reward-mediated behaviors of psychostimulants and opiates (Hubner C B, Koob G F (1990) Brain Res 508:20-29; Napier and Chrobak, 1992; Gong et al., 1996; 1997), suggest a possible role of the VP-α1 receptors in the euphoric properties of alcohol.

Since the compounds of the present invention exhibit increased agonist efficacy at only a few $GABA_A$ types of receptors and/or selective efficacy at one or more ion channels and have been shown to be effective in animal models of anxiety and seizures, with reduced severity and/or incidence of side effects, they are useful in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, general anxiety disorder, attention deficit disorders, stress disorders including post-traumatic and acute stress disorder, and generalized or substance-induced anxiety disorder, neuroses, convulsions; migraine; depressive or bipolar disorders, for example single episode or recurrent major depressive disorder, dysthymic disorder, bipolar I and bipolar II manic disorders, and cyclothymic disorder, psychotic disorders including schizophrenia, alcoholism and emesis, with reduced side effects.

SUMMARY OF THE INVENTION

The present invention provides compounds that are stereospecific benzodiazepine derivatives, their salts and prodrugs, compositions and methods of using such stereospecific benzodiazepine derivatives for the treatment of anxiolytic or convulsant disorders. Such stereospecific benzodiazepine derivatives also can reduce alcohol craving and self administration. The stereospecific benzodiazepine derivatives of the present invention have reduced sedative, hypnotic, muscle relaxant and ataxic side-effects compared to compounds currently available. The invention further provides pharmaceutical compositions for treatment of anxiolytic and convulsant disorders in subjects in need thereof. The compounds of the present invention can be synthesized as substantially pure enantiomers as described herein or resolved from racemic mixtures produced by methods disclosed herein or known in the art. Generally such methods produce the separation of diastereomers obtained from the enantiomers and an optically active resolving agent.

The present invention provides compositions which are described as compounds, salt or prodrug for the following chemical structures described by Formulas I through XVIII, as shown below:

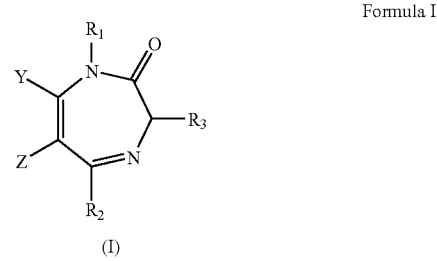

Formula I (I)

where Y and Z are taken together with the two intervening carbon atoms to form a ring selected from phenyl and thienyl, which ring is substituted at the C(7) position with at least the substituent —C≡C—R, where R is H, Si (CH$_3$)$_3$, t-butyl, isopropyl, methyl, or cyclopropyl; R$_1$ is one of H, CH$_3$, C$_2$H$_4$N(C$_2$H$_5$)$_2$, CH$_2$CF$_3$, CH$_2$CCH or an alkyl cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); R$_3$ (R and/or S) is CH$_3$, OH, OAc, OCON(CH$_3$)$_2$, COOCH$_3$ or COOC$_2$H$_5$.

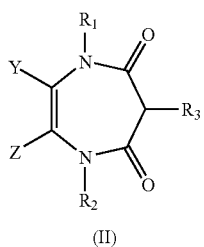

Formula II (II)

where Y and Z are taken together with the two intervening carbon atoms to form a ring selected from phenyl and thienyl, which ring is substituted at the C(7) position with at least the substituent —C≡C—R, where R is H, Si (CH$_3$)$_3$, t-butyl, isopropyl, methyl, or cyclopropyl; R$_1$ is one of H, CH$_3$, C$_2$H$_4$N(C$_2$H$_5$)$_2$, CH$_2$CF$_3$, CH$_2$CCH or an alkyl cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ (R and/or S) is one of CH$_3$, OH, OAc, OCON(CH$_3$)$_2$, COOCH$_3$ or COOC$_2$H$_5$.

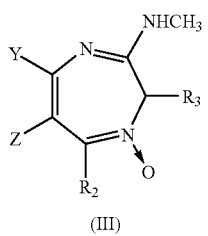

Formula III (III)

where Y and Z are taken together with the two intervening carbon atoms to form a ring selected from phenyl and thienyl, which ring is substituted at the C(7) position with at least the substituent —C≡C—R, where R is H, Si (CH$_3$)$_3$, t-butyl, isopropyl, methyl, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ (R and/or S) is one of CH$_3$, OH, OAc, OCON(CH$_3$)$_2$, COOCH$_3$ or COOC$_2$H$_5$.

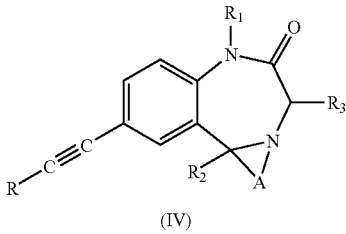

Formula IV (IV)

where R is H, Si (CH$_3$)$_3$, t-butyl, isopropyl, methyl, or cyclopropyl; R$_1$ is one of H, CH$_3$, C$_2$H$_4$N(C$_2$H$_5$)$_2$, CH$_2$CF$_3$, CH$_2$CCH, or an alkyl cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ (R and/or S) is one of CH$_3$, OH, OAc, OCON(CH$_3$)$_2$, COOCH$_3$ or COOC$_2$H$_5$, A is an ethoxide or a propoxide.

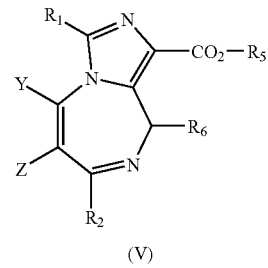

Formula V (V)

where Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; R$_1$ is one of H, CH$_3$, CF$_3$, CH$_2$CF$_3$, CH$_2$CH$_3$, CH$_2$C≡CH, an alkyl, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); R$_5$ is a branched or straight chain C$_1$ to C$_4$ halogenated or unhalogenated alkyl or a methyl cyclopropyl and R$_6$(R and/or S) is one of CH$_3$, OH, OAc, OCON(CH$_3$)$_2$, COOCH$_3$ or COOC$_2$H$_5$.

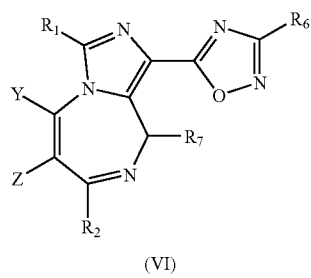

Formula VI (VI)

where Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; R$_1$ is one of H, CH$_3$, CF$_3$, CH$_2$CH$_3$, CH$_2$CF$_3$, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); R$_6$ is a branched or straight chain C$_1$ to C$_4$ alkyl or a methyl cyclopropyl; R$_7$ (R and/or S) is one of CH$_3$, OH, OAc, OCON(CH$_3$)$_2$, COOCH$_3$ or COOC$_2$H$_5$.

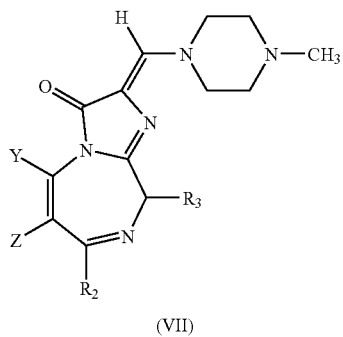

Formula VII (VII)

where said compound includes E or Z isomers; and where Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); R$_3$ (R and/or S) is one of CH$_3$, OH, OAc, OCON(CH$_3$)$_2$, COOCH$_3$ or COOC$_2$H$_5$.

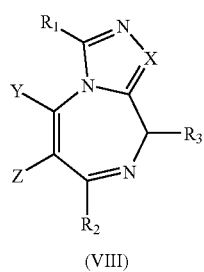

Formula VIII (VIII)

where X is N or CH; Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; R$_1$ is H, CH$_3$, CF$_3$, CH$_2$CH$_3$, CH$_2$CF$_3$, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ (R and/or S) is one of CH$_3$, OH, OAc, OCON(CH$_3$)$_2$, COOCH$_3$ or COOC$_2$H$_5$.

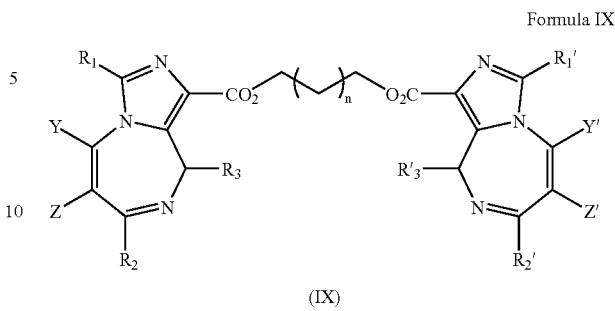

Formula IX (IX)

where n is 0 to 4; Y and Z are taken together with the two intervening carbon atoms to form a ring selected from phenyl and thienyl, which ring is substituted at the C(8) position with at least the substituent ≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, Si (CH$_3$)$_3$, t-butyl, isopropyl, methyl, or cyclopropyl; R$_1$ and R$_1$' are independently one of H, CH$_3$, CF$_3$, CH$_2$CF$_3$, CH$_2$CH$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ or R'$_3$ (R and/or S) is one of CH$_3$, OH, OAc, OCON (CH$_3$)$_2$, COOCH$_3$ or COOC$_2$H$_5$.

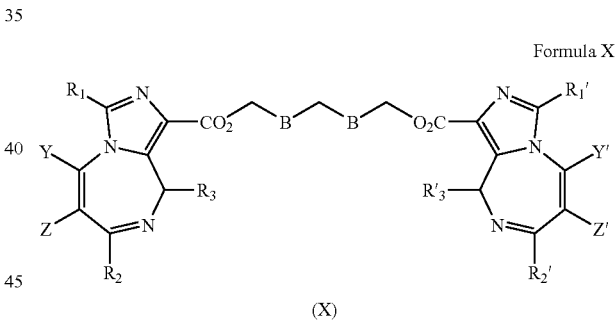

Formula X (X)

where Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent C≡C—R', where R' is H, Si (CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$ or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); B is O or NH and wherein —BCH$_2$B— is optionally replaced with —N(R$_7$)—N(R$_7$)—, where R$_7$ is one of H, CH$_3$, alkyl, or cycloalkyl and R$_3$ or R'$_3$(R and/or S) is one of CH$_3$, OH, OAc, ON(CH$_3$)$_2$, COOCH$_3$ or COOC$_2$H$_5$.

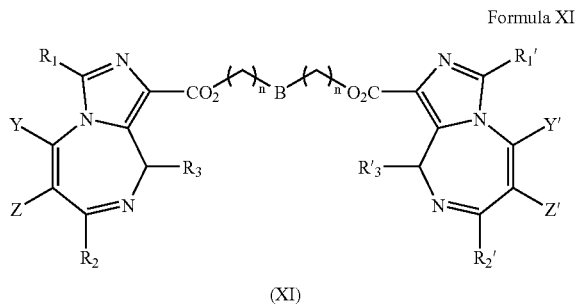

Formula XI (XI)

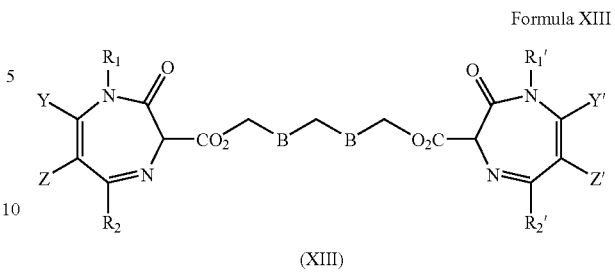

Formula XIII (XIII)

where n is 1 or 2; Y and Z are taken together with the two intervening carbon atoms to form a ring selected from phenyl and thienyl, which ring is substituted at the C(8) position with at least the substituent —C≡C—R, where R is H, Si $(CH_3)_3$, t-butyl, isopropyl, methyl, or cyclopropyl;

Y' and Z' are taken together with the two intervening carbon atoms to form a ring selected from phenyl and thienyl, which ring is substituted at the C(8)' position with at least the substituent —C≡C—R', where R' is H, Si $(CH_3)_3$, t-butyl, isopropyl, methyl, or cyclopropyl; $R_1$ and $R_1$' are independently one of H, $CH_3$, $CF_3$, $CH_2CH_3$, $CH_2CF_3$ or cyclopropyl; $R_2$ and $R_2$' are independently a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl); B is O, NH, or —N($R_7$)—N($R_7$)—, where $R_7$ is one of H, $CH_3$, alkyl, or cycloalkyl and $R_3$ or $R'_3$ (R and/or S) is one of $CH_3$, OH, OAc, $OCON(CH_3)_2$, $COOCH_3$ or $COOC_2H_5$.

where Y and Z are taken together with the two intervening carbon atoms to form a ring selected from phenyl and thienyl, which ring is substituted at the C(7) position with at least the substituent —C≡C—R, where R is H, Si $(CH_3)_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent C≡C—R', where R' is H, Si $(CH_3)_3$, t-butyl, isopropyl, methyl, or cyclopropyl; $R_1$ and $R_1$' are independently one of H, $CH_3$, $CF_3$, $CH_2CH_3$, $CH_2CF_3$ or cyclopropyl; $R_2$ and $R_2$' are independently a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl); B is O or NH and wherein —$BCH_2B$— is optionally replaced with —N($R_7$)—N($R_7$)—, where $R_7$ is one of H, $CH_3$, alkyl, or cycloalkyl. This invention also includes the pure RR, RS, SR, SS isomers as well as the (±) mixtures.

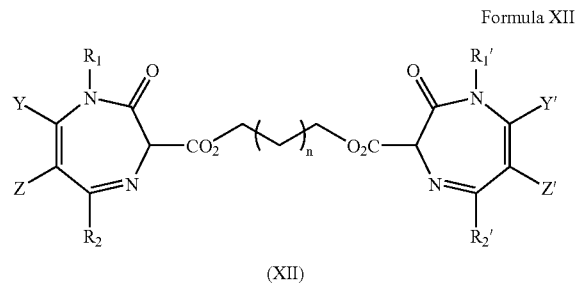

Formula XII (XII)

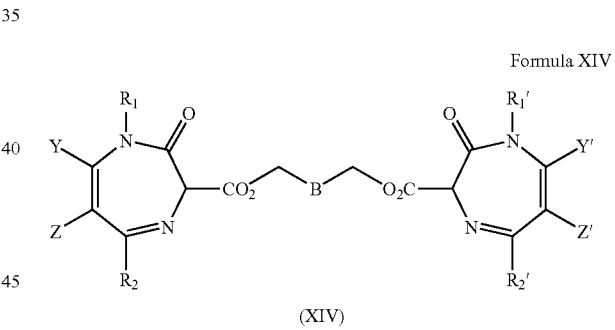

Formula XIV (XIV)

where n is 0 to 4; Y and Z are taken together with the two intervening carbon atoms to form a ring selected from phenyl and thienyl, which ring is substituted at the C(7) position with at least the substituent ≡C—R, where R is H, Si $(CH_3)_3$, t-butyl, isopropyl, methyl, or cyclopropyl;

Y' and Z' are taken together with the two intervening carbon atoms to form a ring selected from phenyl and thienyl, which ring is substituted at the C(7)' position with at least the substituent —C≡C—R', where R' is H, Si $(CH_3)_3$, t-butyl, isopropyl, methyl, or cyclopropyl; $R_1$ and $R_1$' are independently one of H, $CH_3$, $CF_3$, $CH_2CF_3$, $CH_2CH_3$, or cyclopropyl; $R_2$ and $R_2$' are independently a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl). This invention also includes the pure RR, RS, SR, SS isomers as well as the (±) mixtures.

where Y and Z are taken together with the two intervening carbon atoms to form a ring selected from phenyl and thienyl, which ring is substituted at the C(7) position with at least the substituent —C≡C—R, where R is H, Si $(CH_3)_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si $(CH_3)_3$, t-butyl, isopropyl, methyl, or cyclopropyl; $R_1$ and $R_1$' are independently one of H, $CH_3$, $CF_3$, $CH_2CH_3$, $CH_2CF_3$ or cyclopropyl; $R_2$ and $R_2$' are independently a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl); B is O, NH, or —N($R_7$)—N($R_7$)—, where $R_7$ is one of H, $CH_3$, alkyl, or cycloalkyl; the invention includes the RS, SR, SS, RR isomers as well as (±) mixtures.

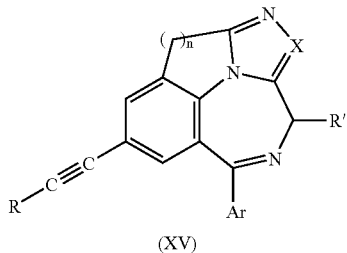

(XV)

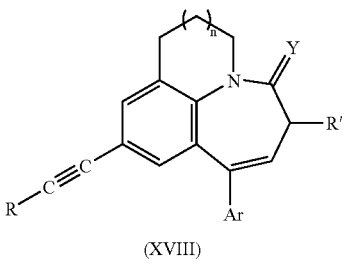

(XVIII)

where n is 1 or 2; R is H, SiMe₃, tBu, CH₃, methyl cyclopropyl, CF₃, CCl₃, CBr₃; Ar is phenyl, 2'-fluorophenyl, 2'-chlorophenyl, 2'-thienyl, 3'-thienyl, 2'-pyridyl, 2'-pyridyl N—O; X is N or CH; R' (R and/or S) is one of CH₃, OH, OAc, OCON(CH₃)₂, COOCH₃ or COOC₂H₅ where n is 0 or 1; R is H, SiMe₃, tBu, CH₃, methyl cyclopropyl, CF₃, CCl₃, CBr₃; Ar is phenyl, 2'-fluorophenyl, 2'-chlorophenyl, 2'-thienyl, 3'-thienyl, 2'-pyridyl, 2'-pyridyl N—O; Y is O, S, NHCH₃; R' (R and/or S) is one of CH₃, OH, OAc, OCON(CH₃)₂, COOCH₃ or COOC₂H₅.

The invention further provides a method of reducing anxiety or convulsant disorders in a subject in need thereof. The method includes administering an effective amount of at least one benzodiazepine analog resulting in reduced muscle relaxant, hypnotic, sedative or ataxic effects in said subject, wherein the analog consists of a compound, a salt or prodrug having a structure represented by any one of Formula I-XVIII, and combinations thereof. The compound, salt or prodrug further is capable of reducing alcoholism in the subject.

The invention also provides a pharmaceutical composition for reducing anxiety or treating convulsant disorders in subjects in need thereof. The pharmaceutical composition includes (a) an effective amount of a compound having a chemical structure represented by any one of Formula I-XVIII; and (b) a pharmaceutically-acceptable carrier.

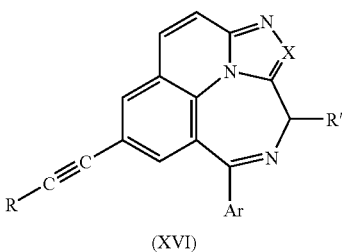

(XVI)

where R is H, SiMe₃, tBu, CH₃, methyl cyclopropyl, CF₃, CCl₃, CBr₃; Ar is phenyl, 2'-fluorophenyl, 2'-chlorophenyl, 2'-thienyl, 3'-thienyl, 2'-pyridyl, 2'-pyridyl N—O; X is N or CH; R' (R and/or S) is one of CH₃, OH, OAc, OCON(CH₃)₂, COOCH₃ or COOC₂H₅.

The invention further provides a pharmaceutical composition for reducing anxiety or treating convulsant disorders in subjects in need thereof, comprising: (a) an effective amount of a prodrug of a compound having a chemical structure represented by any one of Formula I-XVIII; and (b) a pharmaceutically-acceptable carrier.

The invention also provides a pharmaceutical composition for reducing anxiety or treating convulsant disorders in subjects in need thereof, comprising: (a) an effective amount of a salt of a compound having a chemical structure represented by any one of Formula I-XVIII; and (b) a pharmaceutically-acceptable carrier.

Other objects, features and advantages of the present invention will become apparent after review of the specifications, claims and drawings.

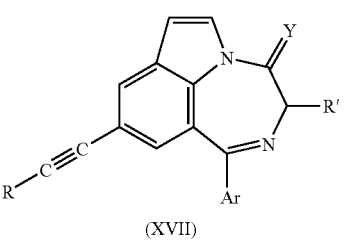

(XVII)

where R is H, SiMe₃, tBu, CH₃, methyl cyclopropyl, CF₃, CCl₃, CBr₃; Ar is phenyl, 2'-fluorophenyl, 2'-chlorophenyl, 2-thienyl, 3-thienyl, 2-pyridyl, 2-pyridyl N—O; Y is O, S, NHCH₃; R' (R and/or S) is one of CH₃, OH, OAc, OCON (CH₃)₂, COOCH₃ or COOC₂H₅.

Figure 2:
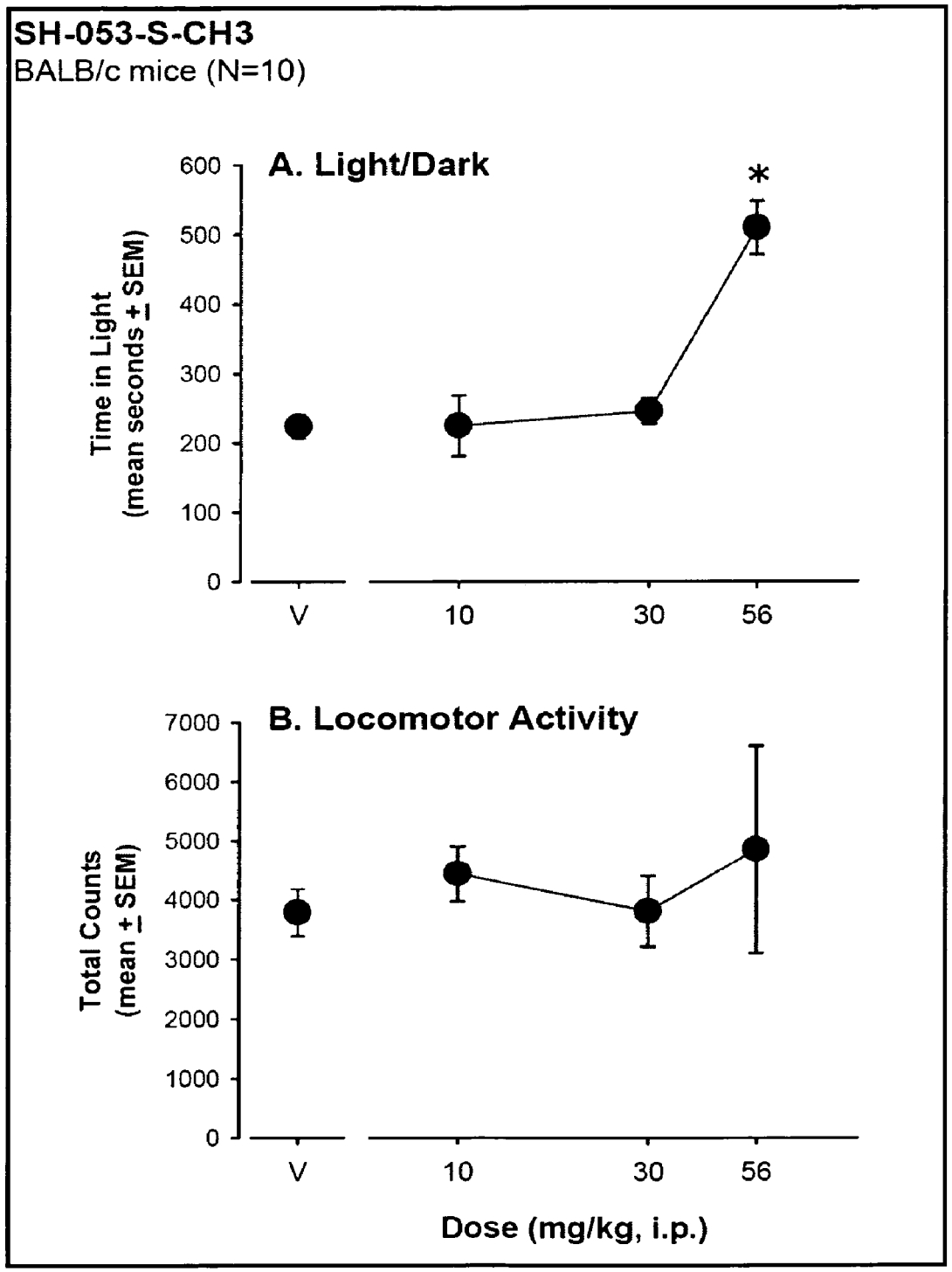

FIG. 2 is a graphical presentation of the results of the light/dark test for anxiolytic-like effects (panel A) and locomotor activity (panel B) following SH-053-S-CH₃ administration in mice. Note that *$p<0.05$ vs. vehicle, Bonferroni t-tests. SH-053-S-CH₃ increased time spent in the lighted chamber in the light/dark test; a classical predictor of anxiolytic activity. No effects on locomotor activity were observed. For all groups, n=10, except for 56.0 mg/kg S-053 in locomotor activity=n=9 for 56.0 mg/kg R-053 locomotor activity is n=5.

DETAILED DESCRIPTION OF THE INVENTION

In preferred embodiments, the present invention provides sterospecific benzodiazepine derivative compounds that are useful for the treatment of anxiety, convulsant disorders, neurosis, general anxiety disorder, panic disorder, phobias, obsessive-compulsive disorders, schizophrenia, post-cardiac trauma stress disorders, depression disorders, psychosomatic disorders, and other psychoneurotic disorders, post-traumatic stress disorders, eating disorders, menopausal disorders, infantile autism, alcoholism, emesis and other disorders, with fewer side effects. The compounds of the present invention can be synthesized as substantially pure enantiomers as described herein or resolved from racemic mixtures produced by methods disclosed herein or known in the art. Generally, such methods produce the separation of diastereomers obtained from combination of the enantiomers and an optically active resolving agent. The resolution of racemic mixtures can be accomplished by methods known in the art, such as formation of chiral diasteromeric salts, such as by the addition of D- or L-tartaric acid, or by capillary electrophoresis using chiral reagents such as highly sulfated cyclodextrins (Beckman Coulter, Fullerton, Calif.).

The present inventors engaged in repeated extensive studies to develop a superior medication free from the above problems. They found that the compounds of the present invention, that is, the novel benzodiazepine derivatives and their salts, have beneficial pharmacological and behavioral effects, that is, the compounds of the present invention show anxiolytic and anticonvulsant activity with greatly decreased or no sedative/hypnotic/muscle relaxant/ataxic side effects.

The compounds described in the present invention have been synthesized based on a modified version of the computer modeling disclosed in Cook, et al *J. Med. Chem.*, 1996, 39, 1928-1934. These compounds obtained by modifying elements, described herein, of the known benzodiazepine agents, have increased binding selectivity for the $GABA_A/\alpha 2$, $GABA_A/\alpha 3$, and/or $GABA_A/\alpha 5$ receptors described above, and/or altered efficacy at one or more $GABA_A$ receptors described above, and/or altered selectivity at one or more ion channels. These compounds, which have been tested in animal models of anxiety in rats and seizures in mice, and side effect models in rats, have been found to be orally active and have anxiolytic and anticonvulsant activity, with reduced severity and/or incidence of side effects.

One object of the present invention is to identify medications containing these benzodiazepine derivatives or their pharmaceutically acceptable salts as essential ingredients that are usable for the treatment of anxiety or convulsant disorders, neurosis, phobias, obsessive-compulsive disorders, panic disorder, generalized anxiety disorder, schizophrenia, post-cardiac trauma stress disorders, post-traumatic stress disorders, depression disorders, psychosomatic disorders, and other psychoneurotic disorders, eating disorders, menopausal disorders, infantile autism, alcoholism, emesis and other disorders.

The present invention describes a class of benzodiazepine derivatives which possess desirable enhanced agonist efficacy at various $GABA_A$ receptors and desirable behavioral profile with respect to anxiolytic and anticonvulsant efficacy and reduced side effect efficacy. The compounds in accordance with the present invention have agonist efficacy at the $GABA_A/\alpha 2$, $GABA_A/\alpha 3$, and $GABA_A/\alpha 5$ receptors. The compounds of this invention have anxiolytic and anticonvulsant effects with decreased sedative-hypnotic, muscle relaxant and ataxic side effects.

The method comprises administering an effective amount of at least one benzodiazepine analog resulting in anxiolytic and anticonvulsant activity with reduced alcohol cravings, reduced sedative effects and reduced ataxic effects. In the most preferred embodiments, the benzodiazepine analog consists of a compound, a salt or prodrug of said compounds described in Formula I through XVIII.

The present invention provides a method of using benzodiazepine analogs, including compounds of formula I through XVIII, a pharmaceutically acceptable salt or prodrug thereof to reduce alcohol cravings and reduce alcohol consumption in human alcoholics.

The present invention provides compositions which are described as compounds, salt or prodrug for the following chemical structures described by formula I through XVIII, as shown below:

Compound with Formula I is described as follows:

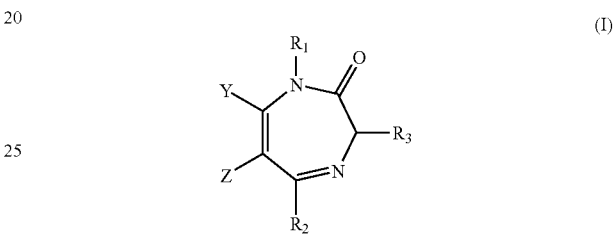

(I)

where Y and Z are taken together with the two intervening carbon atoms to form a ring selected from phenyl and thienyl, which ring is substituted at the C(7) position with at least the substituent —C≡C—R, where R is H, Si $(CH_3)_3$, t-butyl, isopropyl, methyl, or cyclopropyl; $R_1$ is one of H, $CH_3$, $C_2H_4N(C_2H_5)_2$, $CH_2CF_3$, $CH_2C≡CH$, or an alkyl cyclopropyl; $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl); and $R_3$ (R and/or S) is $CH_3$, OH, OAc, $OCON(CH_3)_2$, $COOCH_3$ or $COOC_2H_5$.

Preferred compounds according to Formula I include:

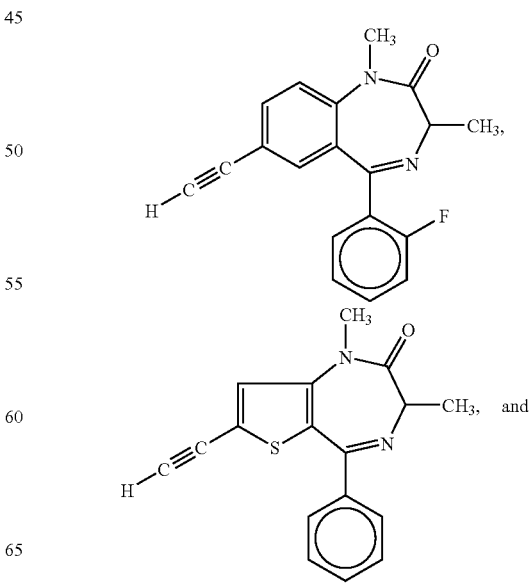

-continued

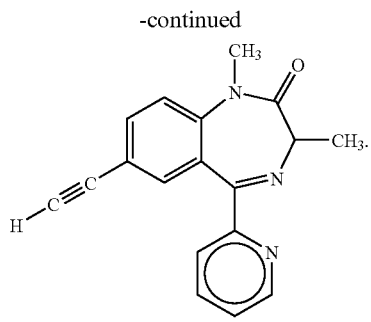

Compound with Formula II is described as follows:

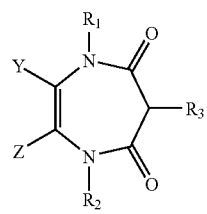

(II)

wherein Y and Z are taken together with the two intervening carbon atoms to form a ring selected from phenyl and thienyl, which ring is substituted at the C(7) position with at least the substituent —C≡C—R, where R is H, Si (CH$_3$)$_3$, t-butyl, isopropyl, methyl, or cyclopropyl; R$_1$ is one of H, CH$_3$, C$_2$H$_4$N(C$_2$H$_5$)$_2$, CH$_2$CF$_3$, CH$_2$C≡CH, or an alkyl cyclopropyl; and R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl), and R$_3$ (R and/or S) is one of CH$_3$, OH, OAc, OCON(CH$_3$)$_2$, COOCH$_3$ or COOC$_2$H$_5$. Preferred compounds according to formula II include:

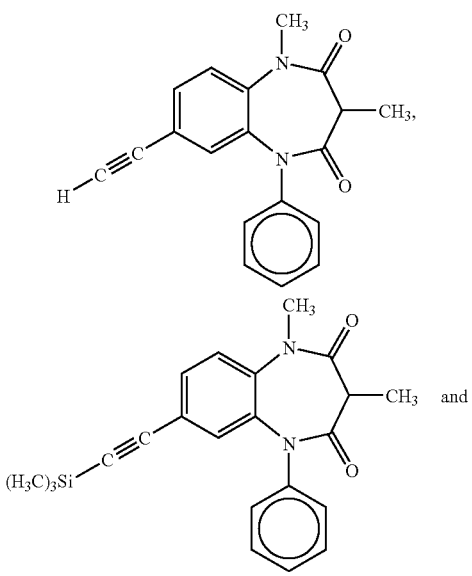

and

-continued

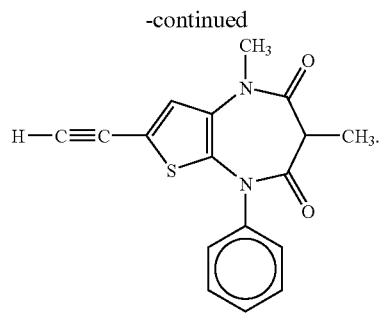

Compounds of Formula III can be described as follows:

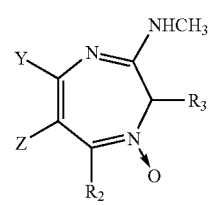

(III)

where Y and Z are taken together with the two intervening carbon atoms to form a ring selected from phenyl and thienyl, which ring is substituted at the C(7) position with at least the substituent —C≡C—R, where R is H, Si (CH$_3$)$_3$, t-butyl, isopropyl, methyl, or cyclopropyl; and R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ (R and/or S) is one of CH$_3$, OH, OAc, OCON(CH$_3$)$_2$, COOCH$_3$ or COOC$_2$H$_5$. Preferred compounds according to the formula III include:

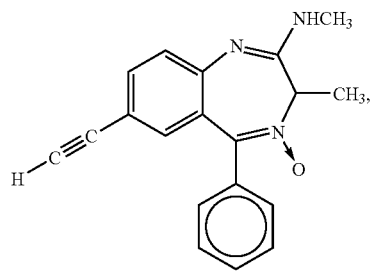

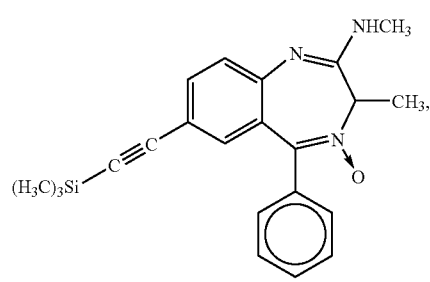

-continued

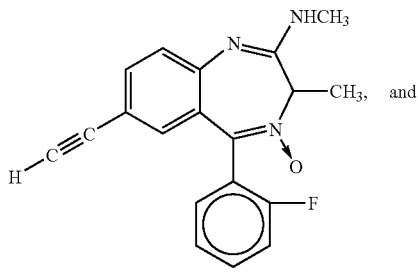

and

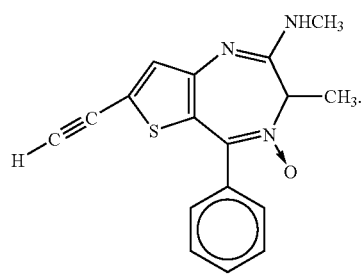

Compound with Formula IV is described as follows:

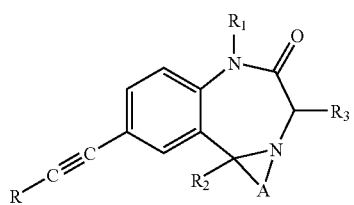
(IV)

where R is H, Si (CH$_3$)$_3$, t-butyl, isopropyl, methyl, or cyclopropyl; R$_1$ is one of H, CH$_3$, C$_2$H$_4$N(C$_2$H$_5$)$_2$, CH$_2$CF$_3$, CH$_2$C≡CH, or an alkyl cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); and A is an ethoxide or a propoxide; R$_3$ (R and/or S) is one of CH$_3$, OH, OAc, OCON(CH$_3$)$_2$, COOCH$_3$ or COOC$_2$H$_5$. Preferred compounds according to the formula IV include:

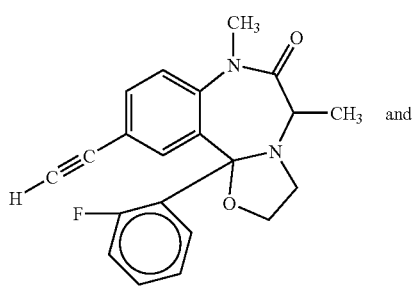

-continued

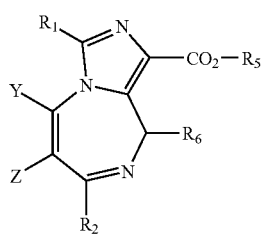

Compound with Formula V is described as follows:

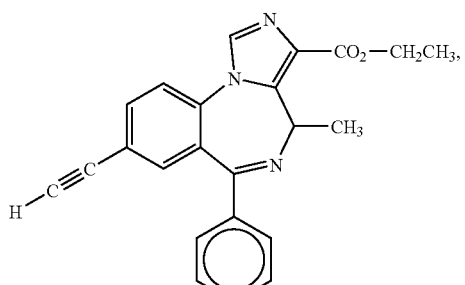
(V)

where Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; R$_1$ is one of H, CH$_3$, CF$_3$, CH$_2$CH$_3$, CH$_2$CF$_3$, CH$_2$C≡CH, an alkyl, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); and R$_5$ is a branched or straight chain C$_1$ to C$_4$ halogenated or unhalogenated alkyl or a methyl cyclopropyl; R$_6$ (R and/or S) is one of CH$_3$, OH, OAc, OCON(CH$_3$)$_2$, COOCH$_3$ or COOC$_2$H$_5$. Preferred compounds according to formula V include:

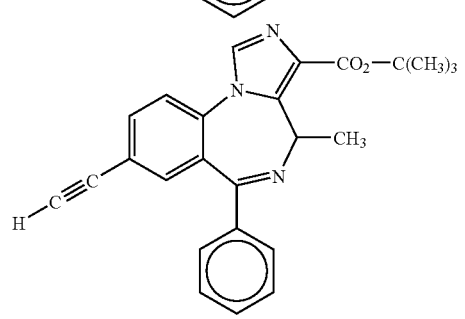

-continued

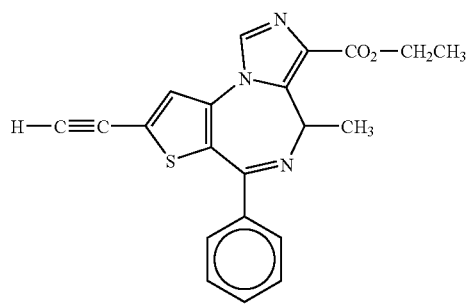

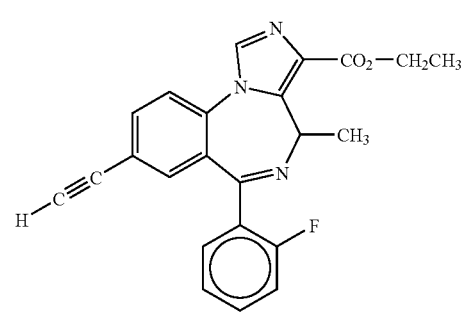

Compound with Formula VI is described as follows:

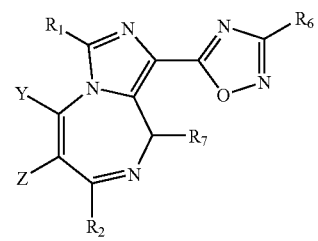

(VI)

wherein Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; R$_1$ is one of H, CH$_3$, CF$_3$, CH$_2$CH$_3$, CH$_2$CF$_3$, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); and R$_6$ is a branched or straight chain C$_1$ to C$_4$ alkyl or a methyl cyclopropyl while R$_7$ (R and/or S) is one of CH$_3$, OH, OAc, OCON(CH$_3$)$_2$, COOCH$_3$ or COOC$_2$H$_5$. Preferred compounds according to formula VI include:

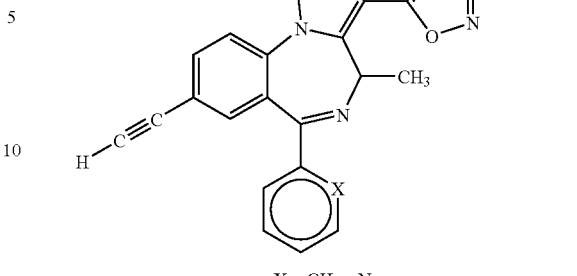

X = CH or N

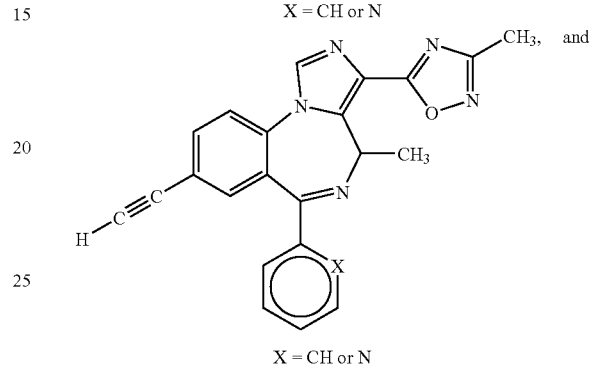

X = CH or N

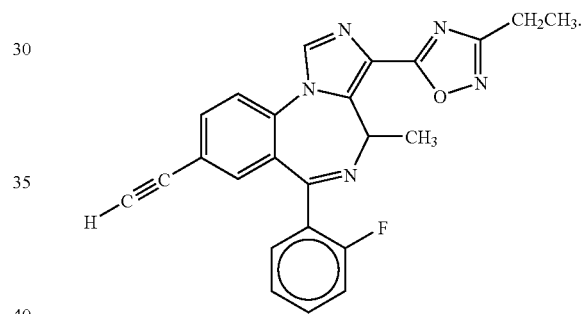

Compound with Formula VII is described as follows:

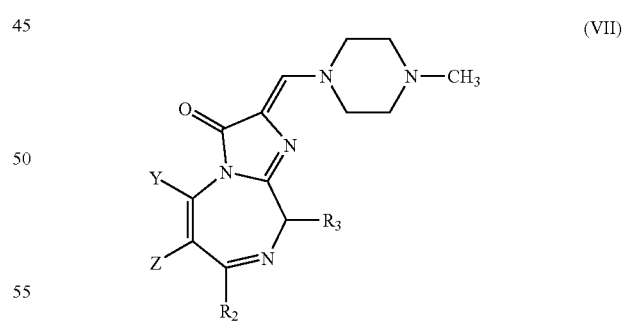

(VII)

the compound has E and Z isomers; and wherein Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; and R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and $R_3$ (R and/or S) is one of $CH_3$, OH, OAc, $OCON(CH_3)_2$, $COOCH_3$ or $COOC_2H_5$. Preferred compounds according to formula VII include:

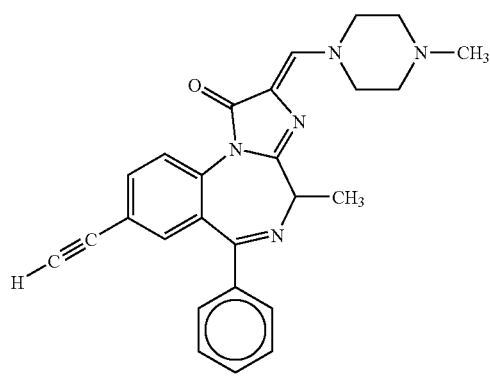

and

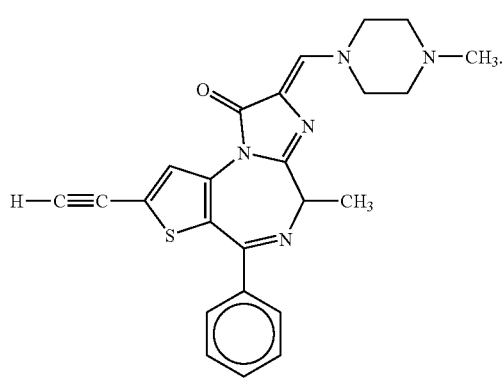

Compound with Formula VIII is described as follows:

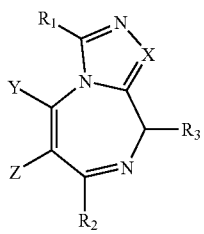

(VIII)

where Y and Z are taken together with the two intervening carbon atoms to form a ring selected from phenyl and thienyl, which ring is substituted at the C(8) position with at least the substituent —C≡C—R, where X is N or CH, where R is H, Si$(CH_3)_3$, t-butyl, isopropyl, methyl, or cyclopropyl; $R_1$ is H, $CH_3$, $CF_3$, $CH_2CH_3$, $CH_2CF_3$, or cyclopropyl; $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl) and $R_3$ (R and/or S) is one of $CH_3$, OH, OAc, $OCON(CH_3)_2$, $COOCH_3$ or $COOC_2H_5$. Preferred compounds according to formula VIII include:

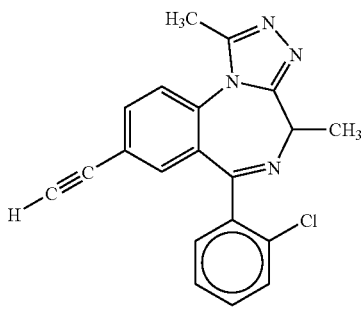

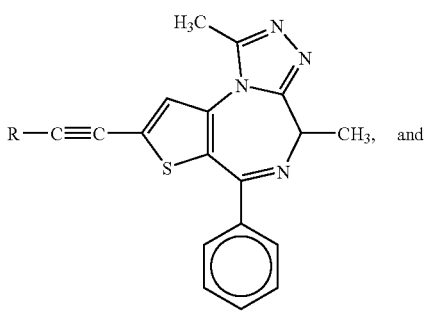

X = CH or N and

Compound with Formula IX is described as follows:

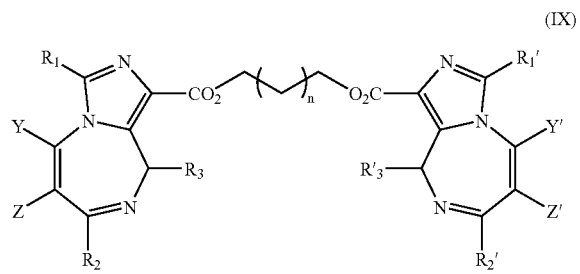

where n is 0 to 4; Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, Si (CH$_3$)$_3$, t-butyl, isopropyl, methyl, or cyclopropyl; R$_1$ and R$_1$' are independently one of H, CH$_3$, CF$_3$, CH$_2$CF$_3$, CH$_2$CH$_3$, or cyclopropyl; and R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl) and R$_3$ and R'$_3$ (R and/or S) is one of CH$_3$, OH, OAc, OCON(CH$_3$)$_2$, COOCH$_3$ or COOC$_2$H$_5$. Preferred compounds according to formula IX include:

Compound with Formula X is described as follows:

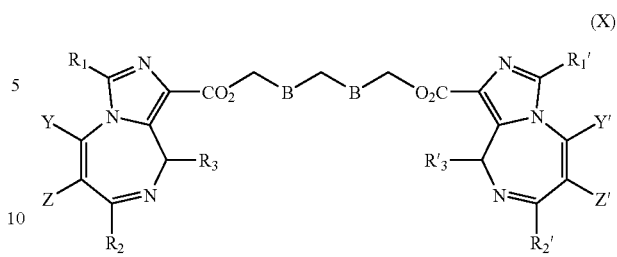

where Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R' where R' is H, Si (CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl); and B is O or NH and wherein —BCH$_2$B— is optionally replaced with —N(R$_7$)—N(R$_7$)—, where R$_7$ is one of CH$_3$, alkyl, or cycloalkyl and R$_3$ or R'$_3$ (R and/or S) is one of CH$_3$, OH, OAc, OCON(CH$_3$)$_2$, COOCH$_3$ or COOC$_2$H$_5$. Preferred compounds according to formula X include:

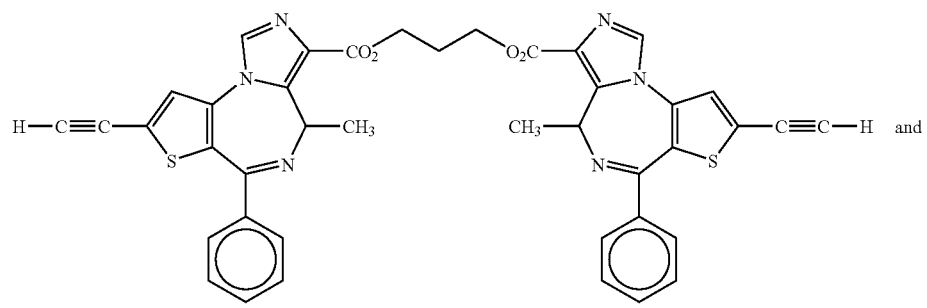

and

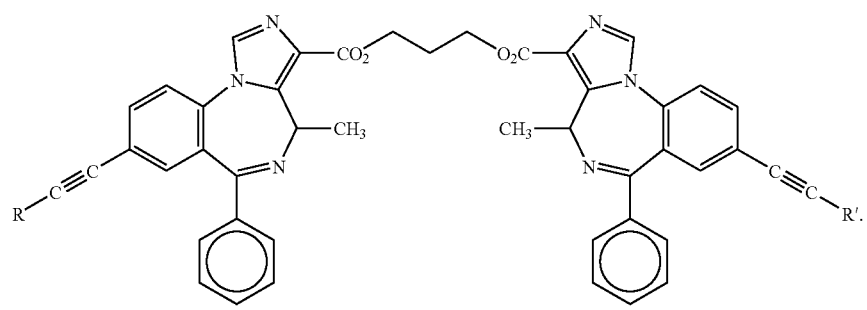

R is H or Si(CH$_3$)$_3$
R' is H or Si(CH$_3$)$_3$

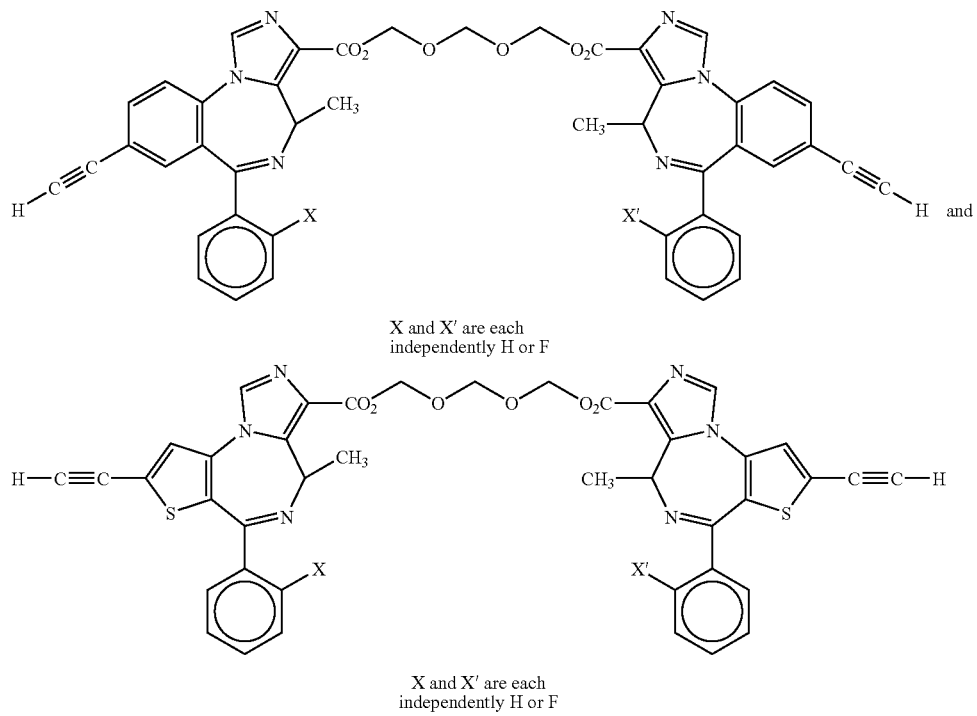

X and X' are each independently H or F

X and X' are each independently H or F

Compound with Formula XI is described as follows:

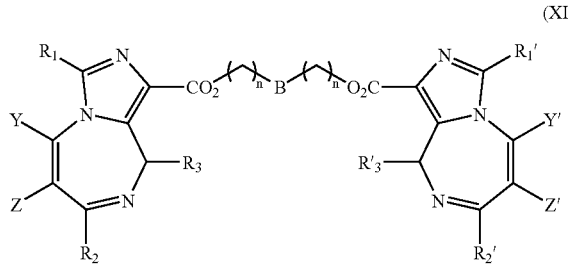

(XI)

where n is 1 or 2; wherein Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, Si (CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N (2-pyridyl); and B is O, NH, or —N(R$_7$)—N(R$_7$)—, where R$_7$ is one of H, CH$_3$, alkyl, or cycloalkyl and R$_3$ or R'$_3$ (R and/or S) is one of CH$_3$, OH, OAc, OCON(CH$_3$)$_2$, COOCH$_3$ or COOC$_2$H$_5$. Preferred compounds according to formula XI include:

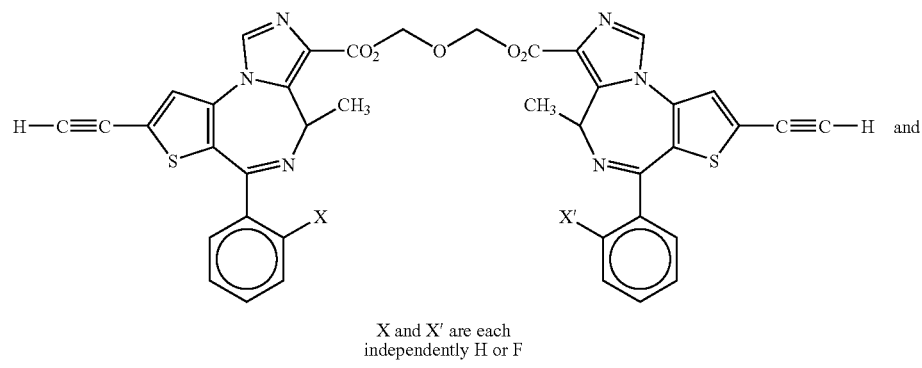

X and X' are each independently H or F

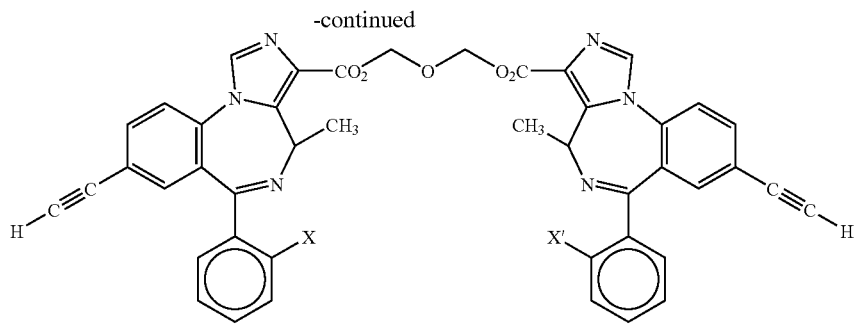

X and X' are each independently H or F

Compound with Formula XII is described as follows:

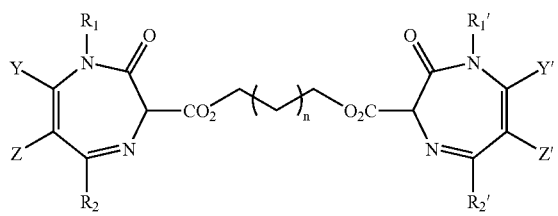

wherein n is 0 to 4; Y and Z are taken together with the two intervening carbon atoms to form a ring selected from phenyl and thienyl, which ring is substituted at the C(7) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si (CH$_3$)$_3$, t-butyl, isopropyl, methyl, or cyclopropyl; R$_1$ and R$_1$' are independently one of H, CH$_3$, CF$_3$, CH$_2$CF$_3$, CH$_2$CH$_3$, or cyclopropyl; and R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position, as well as 2'-N(2-pyridyl). This invention includes the pure RS, RR, SS, SR isomers as well as the (±) mixtures. Preferred compounds according to formula XII include:

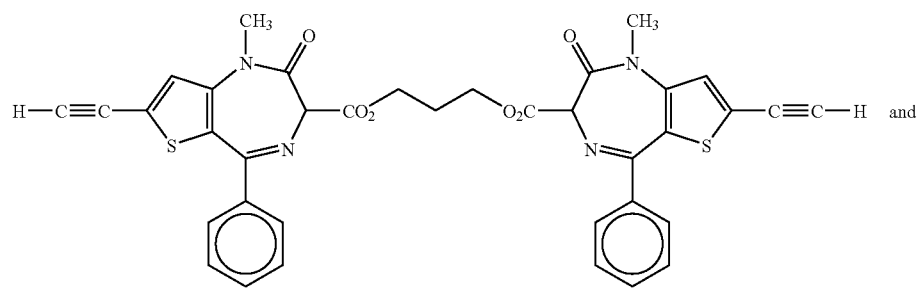

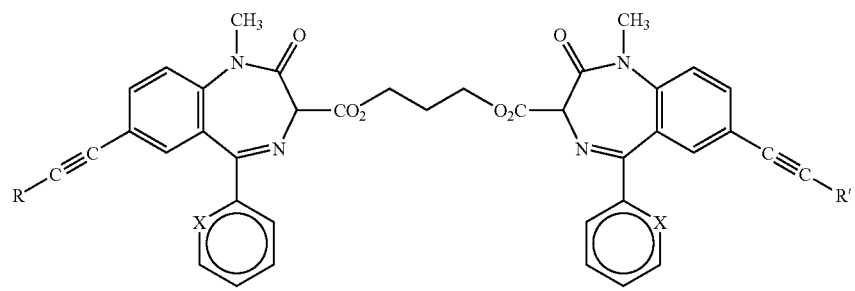

R is H or Si(CH$_3$)$_3$
R' is H or Si(CH$_3$)$_3$
H = CH or N

Compound with Formula XIII is described as follows:

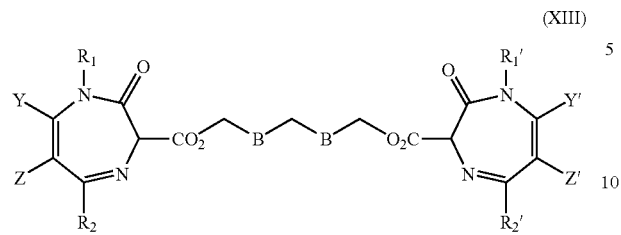
(XIII)

where Y and Z are taken together with the two intervening carbon atoms to form a ring selected from phenyl and thienyl, which ring is substituted at the C(7) position with at least the substituent —C≡C—R, where R is H, Si $(CH_3)_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si $(CH_3)_3$, t-butyl, isopropyl, methyl, or cyclopropyl; $R_1$ and $R_1'$ are independently one of H, $CH_3$, $CF_3$, $CH_2CH_3$, $CH_2CF_3$, or cyclopropyl; $R_2$ and $R_2'$ are independently a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl); and B is O or NH and wherein —$BCH_2B$— is optionally replaced with —N($R_7$)—N($R_7$)—, where $R_7$ is one of H, $CH_3$, alkyl, or cycloalkyl. This invention includes the pure RS, RR, SS, SR isomers as well as the (±) mixtures. Preferred compounds according to formula XIII include:

Compound with Formula XIV is described as follows:

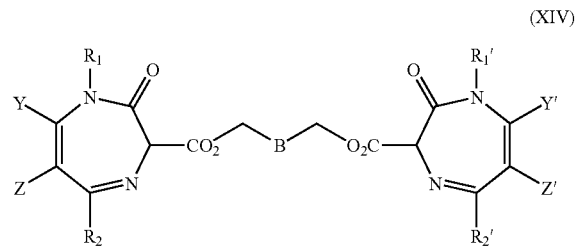
(XIV)

where Y and Z are taken together with the two intervening carbon atoms to form a ring selected from phenyl and thienyl, which ring is substituted at the C(7) position with at least the substituent —C≡C—R, where R is H, Si $(CH_3)_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si $(CH_3)_3$, t-butyl, isopropyl, methyl, or cyclopropyl; $R_1$ and $R_1'$ are independently one of H, $CH_3$, $CF_3$, $CH_2CH_3$, $CH_2CF_3$, or cyclopropyl; $R_2$ and $R_2'$ are independently a substituted or unsubstituted at least partially unsaturated 5 or 6 membered cyclic or heterocyclic ring, wherein if substituted the substituent is one or more of F, Cl, Br, or $NO_2$ at the 2'-position, as well as 2'-N(2-pyridyl); and B is O, NH, or —N($R_7$)—N($R_7$)—, where $R_7$ is one of H, $CH_3$, alkyl, or cycloalkyl. This invention includes the pure RS, RR, SS, SR isomers as well as the (±) mixtures. Preferred compounds according to formula XIV include:

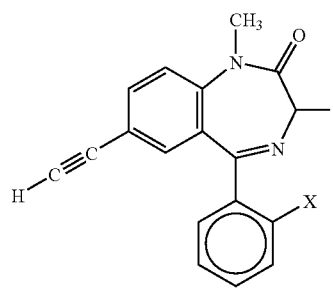 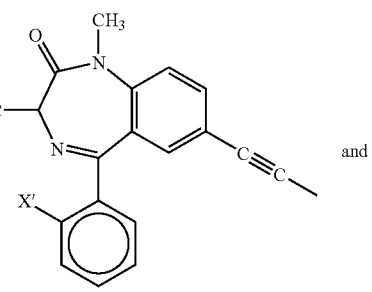 and

X and X' are each independently H or F

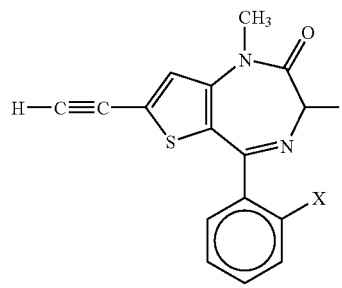 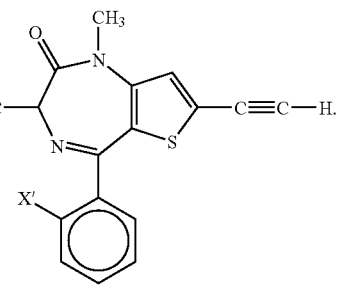.

X and X' are each independently H or F

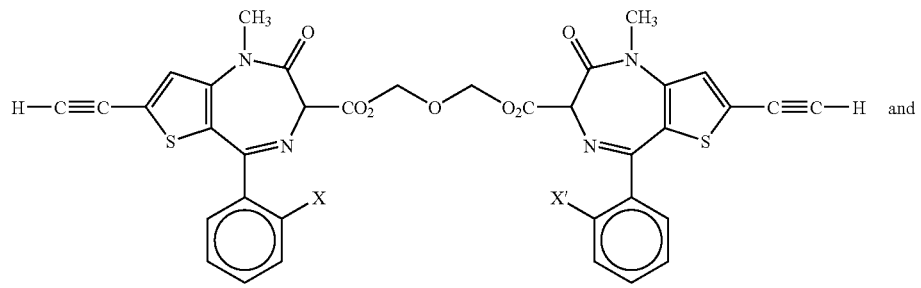

X and X' are each independently H or F

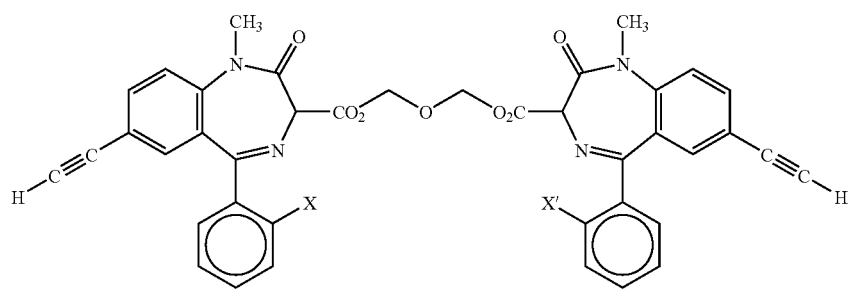

X and X' are each independently H or F

Compound with Formula XV is described as follows:

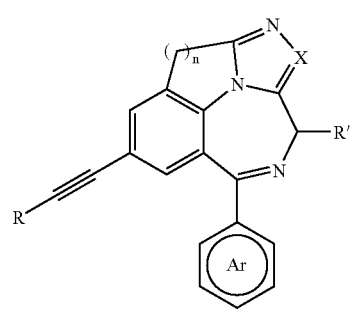

n=1, n=2; R═H, SiMe₃, tBu, CH₃,

—◁ ;

Ar=phenyl, 2'-fluorophenyl, 2'-chlorophenyl, 2'-thienyl, 3'thienyl, 2'-pyridyl, 2'-pyridyl N—O; X═N or CH; R'(R and/or S) is one of CH₃, OH, OAc, OCON(CH₃)₂, COOCH₃ or COOC₂H₅.

Compound with Formula XVI is described as follows:

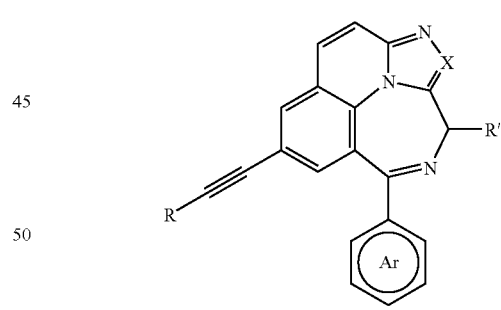

R═H, SiMe₃, tBu, CH₃,

—◁ ;

Ar=phenyl, 2'-fluorophenyl, 2'-chlorophenyl, 2'-thienyl, 3'thienyl, 2'-pyridyl, 2'-pyridyl N—O; Y═O, S, NHCH₃, R'(R and/or S) is one of CH₃, OH, OAc, OCON(CH₃)₂, COOCH₃ or COOC₂H₅.

Compound with Formula XVII is described as follows:

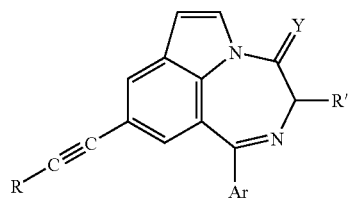

R=H, SiMe3, tBu, CH3,

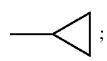;

Ar=phenyl, 2'-fluorophenyl, 2'-chlorophenyl, 2'-thienyl, 3'thienyl, 2'-pyridyl, 2'-pyridyl N—O; Y=O, S, NHCH$_3$, R'(R and/or S) is one of CH$_3$, OH, OAc, OCON(CH$_3$)$_2$, COOCH$_3$ or COOC$_2$H$_5$.

Compound with Formula XVIII is described as follows:

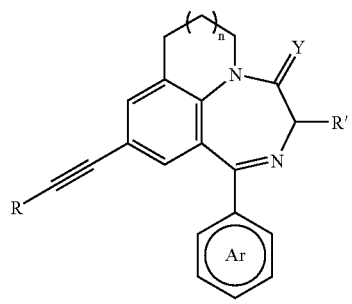

n=0, n=1; R=H, SiMe$_3$, tBu, CH$_3$,

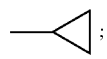;

Ar=phenyl, 2'-fluorophenyl, 2'-chlorophenyl, 2'-thienyl, 3'thienyl, 2'-pyridyl, 2'-pyridyl N—O; Y=O, S;NHCH$_3$. R'(R and/or S) is one of CH$_3$, OH, OAc, OCON(CH$_3$)$_2$, COOCH$_3$ or COOC$_2$H$_5$.

Compounds (XV) to (XVIII) above can also have R as CF$_3$, CCl$_3$, or CBr$_3$. Compounds (I), (II), (III), (IV), (V), (VI), (VII), (VIII), (XV), (XVI), (XVII) and (XVIII) are all stereospecific based on the chiral center at position depicted by R$_3$ [(I), (II), (III), (IV), (VII), (VIII)], R$_6$ [(V)], R$_7$ [(VI)] and R' [(XV), (XVI), (XVII)]. Compounds (IX), (X) and (XI), all have a chiral centers at R$_3$ and R'$_3$. Therefore, compounds (IX), (X), (XI), (XII), (XIII) and (XIV) are capable of metabolizing into chiral centered compounds if introduced into in vivo environments. Availability of the chiral center may be useful in stereospecifically selecting compounds for specific GABA receptors and targeting such receptors. Furthermore, various combinations of diastereomers and stereospecific compounds as shown by compounds (I) through (XVIII) may also be used to alter the kinetic profile of a resulting pharmaceutical compound.

The invention further provides a method of reducing anxiety or convulsant disorders in a subject in need thereof. The method includes administering an effective amount of at least one benzodiazepine analog resulting in reduced muscle relaxant, hypnotic, sedative or ataxic effects in said subject, wherein the analog consists of a compound, a salt or prodrug having a structure represented by any one of Formula I-XVIII, and combinations thereof. The compound, salt and prodrug is further capable of reducing alcoholism in said subject.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable carrier" as used herein means a chemical composition with which a biologically active ingredient can be combined and which, following the combination, can be used to administer the active ingredient to a subject.

A "pharmaceutically acceptable" ester or salt as used herein means an ester or salt form of the active ingredient which is compatible with any other ingredients of the pharmaceutical composition and which is not deleterious to the subject to which the composition is to be administered. The terms "pharmaceutically acceptable salts" or "prodrugs" includes the salts and prodrugs of compounds that are, within the scope of sound medical judgment, suitable for use with subjects without undue toxicity, irritation, allergic response, and the like, commensurate with a reasonable benefit/risk ratio, and effective for their intended use, as well as the zwitterionic forms, where possible, of the compounds.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a subject for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

The form in which the active compound is administered to the cell is not critical; the active compound need only reach the cell, directly or indirectly. The invention encompasses preparation and use of medicaments and pharmaceutical compositions comprising a compound described herein as an active ingredient.

A compound of the present invention is administered to a subject in a therapeutically effective amount. A compound of the present invention can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A compound of the present invention can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition, a compound of the present invention can be administered alone, in combination with other compound of the present inventions, or with other pharmaceutically active compounds. The other pharmaceutically active compounds can be selected to treat the same disease as the compound of the present invention or a different disease. If the subject is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. For example, a kit may comprise two separate pharmaceutical compositions comprising respectively a first composition comprising a compound of the present invention or a compound of the present invention agonist and a pharmaceutically acceptable carrier; and composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc . . . Second Week, Monday, Tuesday," etc. Other variations of memory aids will be readily apparent. A "daily dose" can be a single tablet or capsule or several pills or capsules to be taken on a given day. Also, a daily dose of a compound of the present invention composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention also provides a pharmaceutical composition for reducing anxiety or treating convulsant disorders in subjects in need thereof. The pharmaceutical composition includes (a) an effective amount of a compound having a chemical structure represented by any one of Formula I-XVIII; and (b) a pharmaceutically-acceptable carrier.

The invention further provides a pharmaceutical composition for reducing anxiety or treating convulsant disorders in subjects in need thereof, comprising: (a) an effective amount of a prodrug of a compound having a chemical structure represented by any one of Formula I-XVIII; and (b) a pharmaceutically-acceptable carrier.

The invention also provides a pharmaceutical composition for reducing anxiety or treating convulsant disorders in subjects in need thereof, comprising: (a) an effective amount of a salt of a compound having a chemical structure represented by any one of Formula I-XVIII; and (b) a pharmaceutically-acceptable carrier. Such pharmaceutically acceptable carriers are well known in the art.

Another aspect of the invention provides a method for the treatment and/or prevention of anxiety or convulsant disorders which comprises administering to a subject in need of such treatment an effective amount of a compound of the above kinds, or a pharmaceutically acceptable salt thereof or a prodrug thereof.

As used herein, "alkyl" means straight or branched halogenated or unhalogenated alkyl group having 1-6 carbon atoms. As used herein, "cycloalkyl" means one containing 3-7 carbon atoms. In preferred embodiments having a "cyclic" group, a preferred cyclic group is a phenyl group. In preferred embodiments having "heterocyclic" groups, preferred heterocyclic groups include a 2-pyridine or a 2- or 3-thiophene.

The compounds of the present invention are $GABA_A$ receptor ligands which exhibit anxiolytic activity due to increased agonist efficacy at $GABA_A/\alpha2$, $GABA_A/\alpha3$ and/or $GABA_A/\alpha5$ receptors. The compounds in accordance with this invention may possess at least 2-fold, suitably at least 5-fold, and advantageously at least a 10-fold, selective efficacy for the $GABA_A/\alpha2$, $GABA_A/\alpha3$, and/or $GABA_A/\alpha5$ receptors relative to the $GABA_A/\alpha1$ receptors. However, compounds which are not selective in terms of their agonist efficacy for the $GABA_A/\alpha2$, $GABA_A/\alpha3$, and/or $GABA_A/\alpha5$ receptors are also encompassed within the scope of the present invention. Such compounds will desirably exhibit functional selectivity by demonstrating anxiolytic activity with decreased sedative-hypnotic/muscle relaxant/ataxic activity due to decreased efficacy at $GABA_A/\alpha1$ receptors.

For use in medicine, the salts of the compounds of formulas (I)-(XVIII) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, ftimarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Compounds having N-oxides of amino groups, such as produced by reaction with hydrogen peroxide, are also encompassed.

The present invention includes within its scope prodrugs of the compounds of formulas (I)-(XVIII) above. In general, such prodrugs will be functional derivatives of the compounds of formulas (I)-(XVIII) which are readily convertible in vivo into the required compound of formulas (I)-(XVIII). Conventional procedures for the selection and preparation of suitable prodrug derivatives are described, for example, in *Design of Prodrugs*, ed. H. Bundgaard, Elsevier, 1985.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. For example, metabolism of the pro-drug may take place by hydrolysis in blood. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. For example, if a compound contains a carboxylic acid functional group, a pro-drug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl) aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl.

Similarly, if a compound comprises an alcohol functional group, a pro-drug can be formed by the replacement of the hydrogen atom of the alcohol group with a group such as ($C_1$-$C_6$)alkanoyloxymethyl, 1-($C_1$-$C_6$)alkanoyloxy)ethyl, 1-methyl-1-($C_1$-$C_6$)alkan-oyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound comprises an amine functional group, a pro-drug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural alpha-aminoacyl or natural alpha-aminoacyl-, —C(OH)C(O)OY wherein Y is H, ($C_1$-$C_6$)alkyl or benzyl, —C(OY$_0$)Y$_1$ wherein Y$_0$ is ($C_1$-$C_4$) alkyl and Y$_1$ is (($C_1$-$C_6$)alkyl, carboxy($C_1$-$C_6$)alkyl, amino($C_1$-$C_4$)alkyl or mono-N- or di-N,N-($C_1$-$C_6$)alkylaminoalkyl, —C(Y$_2$) Y$_3$ wherein Y$_2$ is H or methyl and Y$_3$ is mono-N- or di-N,N-($C_1$-$C_6$)- alkylamino, morpholino, piperidin-1-yl or pyrrolidin-1-yl.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The compounds according to the present invention exhibit anxiolytic or anticonvulsant activity, as may be demonstrated in rats by a positive response in a preclinical test for antianxiety efficacy (e.g., situational anxiety or defensive withdrawal). Moreover, the compounds of the invention are substantially non-sedating and non-ataxic as may be confirmed by an appropriate result obtained from the locomotor activity test and rotorod paradigm, respectively.

The compounds according to the present invention may also exhibit anticonvulsant activity. This can be demonstrated by the ability to block pentylenetetrazole-induced seizures in rodents.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

A compound of the present invention composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrastemal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of an active agent selected from the group consisting of a compound of the present invention, a compound of the present invention agonist and a compound of the present invention antagonist and a biodegradable polymer. In preferred embodiments, a suitable biodegradable polymer can be selected from the group consisting of a polyaspartate, polyglutamate, poly(L-lactide), a poly(D,L-lactide), a poly (lactide-co-glycolide), a poly(ε-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pregelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfiiryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups. The polypeptide compositions described herein are preferably not exposed to high cooking temperatures for extended periods of time, in order to minimize degradation of the compounds.

Compositions for rectal or vaginal administration can be prepared by mixing a compound of the present invention and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the compound of the present invention. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a compound of the present invention include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmalmically administrable formulations comprise the active ingredient in microcrystalline form or in a liposomal preparation.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration can, for example, comprise from about as little as 0.1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compound or compounds may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The compound of the present invention, the stereoisomers and prodrugs thereof, and the pharmaceutically acceptable salts of the peptides, stereoisomers, and prodrugs, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compound is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to kill cancer cells arrives, directly or indirectly at the cell. The minimum amount varies with the identity of the compound of the present invention. In some embodiments, the minimum amount is generally in the range from $10^{-9}$ to $10^{-5}$ molar. In other embodiments, the minimum amount is typically in the range from $10^{-7}$ to $10^{-5}$ molar.

In preferred embodiments, a pharmaceutical composition comprising a compound of the present invention can be administered to a patient at dosage levels in the range of about 0.1 to about 7,000 mg per day. A preferred dosage range is about 1 to about 100 mg per day. In other embodiments, a pharmaceutical composition comprising a compound of the present invention can be administered to deliver a dose of between 1 nanogram per day per kilogram body weight and 100 milligrams per day per kilogram body weight, preferably from about 0.1 to about 10 mg/kg body weight of the individual per day, and preferably to deliver of between 100 milligrams and 2 grams, to a human patient.

The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to have the desired effect on the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

In some embodiments, a compound of the present invention, a stereoisomer or prodrug thereof, or a pharmaceutically acceptable salt of the stereoisomer or prodrug; or a compound of the present invention, a stereoisomer or prodrug thereof is administered to a subject in need of treatment therewith, preferably in the form of a pharmaceutical composition. It is generally preferred that such administration be oral or pulmonary. However, if the subject being treated is unable to swallow, or oral administration is otherwise impaired or undesirable, parenteral or transdermal administration will be appropriate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

In certain embodiments for the treatment of anxiety or convulsant disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day, or on a continuous basis via, for example, the use of a transdermal patch.

Following are schemes and methods for producing the benzodiazepine analogs. In general, synthetic methods are based on those known in the art. See Sternbach, L. H., et al., (1962) J Org Chem 27:3788-3796; Liu, R., et al., (1996) J Med Chem 39: 1928-1934; Austin, W. B., et al. (1981) J Org Chem 46:2280-2286; Sternbach, L. H., et al., (1963) J Org Chem 28: 2456-2459; He, X., (2000) Ph. D. Thesis, University of Wisconsin-Milwaukee Ning, R. Y., et al., J Org Chem 41: 2724-2727; Bogatskii A V, et al., (1977) Pharm Chem J (Engl Transl) 11:1520-1525; Gu, Q., et al., (1993) J Med Chem 36: 1001-1006; Hester J B, et al., (1989) J Med Chem 32:1157-1163; Archer G A, Sternbach L H (1964) J Org Chem 29:231; Fryer R I, et al., (1993) Synth Commun 23: 985-992; U.S. Pat. No. 3,886,141; Bradley, R., et al., (2000) J. Am. Chem. Soc. 122: 460-465.

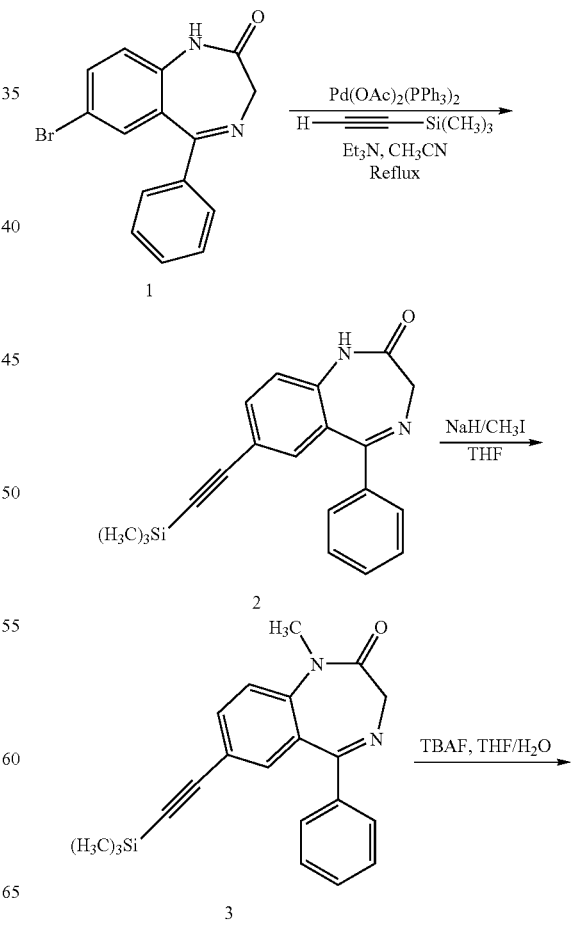

Scheme 1 (QHII-066)

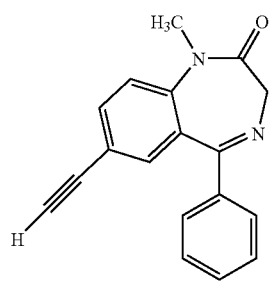

4 (QHII-066)

The bromide 1 (Sternbach, et al., 1962) was reacted with trimethylsilyacetylene in the presence of a palladium catalyst to provide trimethylsilyl analog 2 (Liu, et al., 1996; Austin, et al., 1981; Sternbach, L. H., et al., 1963). This product was methylated with methyl iodide/sodium hydride to give the N-methyl benzodiazepine 3. This was subjected to fluoride-mediated desilylation to furnish 4 (QHII-066).

Procedure for QHII-066

7-Trimethylsilylacetyleno-5-phenyl-1,3-dihydrobenzo[e]-1,4-diazepin-2-one 2. A mixture of 1 (1 g, 3.17 mmole Sternbach, et al., 1962) in triethyl amine (30 mL) and $CH_3CN$ (20 mL) with trimethylsilylacetylene (622.7 mg, 6.34 mmole) and bis(tri-phenylphosphine)-palladium (II) acetate (118 mg, 0.16 mmol) was heated to reflux under nitrogen. After 12 hours, the reaction mixture was cooled to room temperature and filtered. The filtrate was concentrated in vacuum and the residue was treated with a saturated aqueous solution of $NaHCO_3$ (30 mL), and extracted with $CH_2Cl_2$ (3×50 mL). The organic layers were combined and washed with brine and dried ($Na_2SO_4$). After removal of solvent under reduced pressure, the residue was purified via flash chromatography (silica gel, EtOAc/hexanes: 1/1) to furnish 3 as a yellow powder (791 mg, 75%): mp: 190-191.5° C.; IR (KBr) 3011, 2281, 1686, 1610, 1486, 1325, 1249, 839, 700 cm$^{-1}$; $^1$H NMR (CDCl$_3$) δ 0.21 (s, 9H), 4.31 (s,2H), 7.09 (d,1H, J=8.25 Hz), 7.21-7.61 (br,7H), 10.17 (s,1H); MS (CI) m/e (relative intensity) 333 (M$^+$+1,100). This material was used in the next step.

1-Methyl-7-trimethylsilylacetyleno-5-phenyl-1,3-dihydrobenzo[e]-1,4-diazepin-2-one 3. A mixture of 2 (485 mg, 1.46 mmol) was dissolved in dry THF (20 mL) at 0° C. and NaH (60% in mineral oil, 70 mg, 1.75 mmol) was added to the solution in one portion. See Xe, (2000). The slurry was then stirred for 20 min at 0° C. and CH$_3$I (311 mg, 2.19 mmol) was added to the mixture and it was warmed up to room temperature. After the mixture stirred for 3 hours at room temperature, the THF was then removed under reduced pressure. The residue was purified by flash chromatography [hexanes/EtOAc (1:4)] to provide the title compound 3 (303 mg, 60%) as a white solid: mp: 177-178° C.; IR (KBr) 2954, 2147, 1687, 1612, 1491, 1382, 1115, 1075, 839, 700 cm$^{-1}$; $^1$H NMR (CDCl$_3$) δ 3.18 (s, 3H), 3.54 (d, 1H, J=10.8 Hz), 4.60 (d, 1H, J=10.8 Hz), 7.05 (s, 1H), 7.07 (d, 1H, J=8.58 Hz), 7.20-7.27 (m, 3H), 7.37-7.42 (m, 3H); MS (EI) m/e 346 (M$^+$, 90), 318 (100), 303(19), 165(22), 151(20). Anal. Calcd. for $C_{21}H_{22}N_2OSi$: C, 72.79; H, 6.40; N, 8.08; Found: C, 72.50; H, 6.68; N, 8.04.

1-Methyl-7-acetyleno-5-phenyl-1,3-dihydro-benzo [e]-1,4-diazepin-2-one 4 (QHII-066). A solution of 3 (100 mg) in THF (30 mL) was treated with tetrabutylammonium fluoride (1M in THF). See Xe, (2000). The mixture was stirred for 20 minutes at room temperature before water (30 mL) was added. The mixture was then extracted with EtOAc (3×30 mL). The combined organic extracts were washed with brine and dried ($Na_2SO_4$). The solvent was removed under vacuum and the residue which resulted was passed through a wash column (silica gel, EtOAc/hexanes: 4/1) to give 4 (QHII-066) as light yellow crystals (71 mg, 90%): mp: 163-165° C.; IR (KBr) 2965, 1680, 1605, 1387, 1121, 833, 747 cm$^{-1}$; $^1$H NMR (CDCl$_3$) δ 3.38 (s, 3H), 3.75 (d, 1H, J=10.8Hz), 4.80 (d, 1H, J=10.9Hz), 5.28 (s, 1H), 7.29 (d, 1H,J=8.5Hz), 7.35-7.45 (m, 4H), 7.55-7.59 (m, 2H), 7.62 (dd, 1H,J=8.5Hz and 2.0Hz); MS (EI) m/e (relative intensity) 274 (M$^+$, 100), 259 (12), 246 (100), 189 (12), 122(19), 105 (42). Anal. Calcd. for $C_{18}H_{14}N_2O\cdot\frac{2}{3}H_2O$, Calculated: C, 75.51; H, 4.89; N, 9.78. Found: C, 75.59; H, 5.17; N, 9.62.

Scheme 2 (XHeII-053)

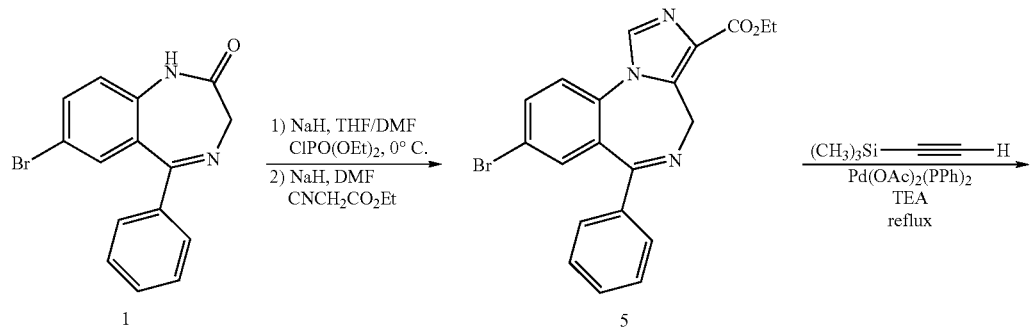

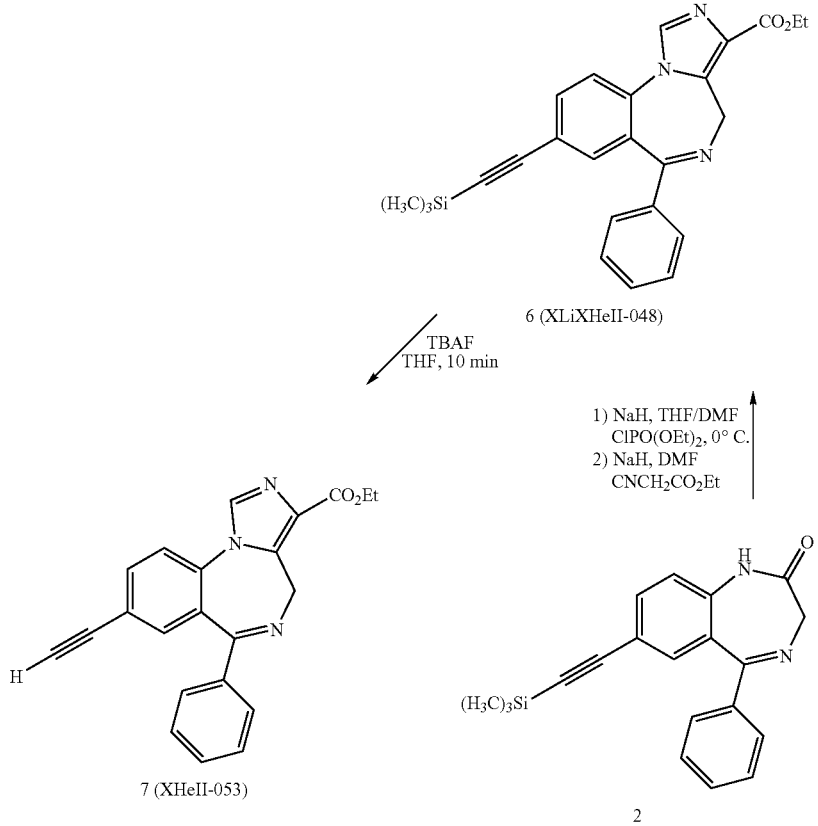

The bromide 1 was reacted with diethylphosphorochloridate in the presence of sodium hydride, followed by addition of ethyl isocyanoacetate to provide the ester 5. This was converted into the trimethylsilylacetyleno compound 6 (XLiXHeII-048) under standard conditions (Pd-mediated, Heck-type coupling; Heck R F, Palladium Reagents in Organic Synthesis; Academic Press, Orlando, Fla.: Academic Press, 1985). Treatment of 6 with fluoride gave the title compound 7 (XHeII-053).

Procedure for XHeII-053

Ethyl 8-bromo-6-phenyl-4H-benzo[f]imidazo[1,5-a][1,4]diazepine-3-carboxylate 5. This benzodiazepine 5 was obtained in 45% yield from 1[1] analogous to the literature procedure[2] as a white solid 2: mp: 174-175° C.; IR (KBr) 2978, 1712, 1609, 1491 cm$^{-1}$; $^1$H NMR (CDCl$_3$) δ 1.44 (t, 3H, J=7.1 Hz), 4.09 (d, 1H, J=12.1 Hz), 4.38-4.49 (m, 2H), 6.08 (d, 1H, J=12.3 Hz), 7.40-7.53 (m, 6H), 7.60 (d, 1H, J=2.2 Hz), 7.82 (dd, 1H, J=8.6 Hz and 2.2 Hz), 7.95 (s, 1H); MS (EI) m/e (relative intensity) 411 (34), 410 (M$^+$,8), 409 (34), 365 (61), 363 (61), 337 (100), 335 (100), 285 (21), 232, (17). Anal. Calcd. for C$_{20}$H$_{16}$BrN$_3$O$_2$: C, 58.55; H, 3.93; N, 10.24. Found: C, 58.30, H, 3.91; N, 9.90.

Ethyl 8-trimethylsilylacetylenyl-6-phenyl-4H-benzo[f]imidazo[1,5-a][1,4]diazepine-3-carboxylate 6 (XLiXHeII-048). A mixture of bromide 5 (0.3 g, 0.73 mmol), trimethylsilylacetylene (0.143 g, 1.46 mmol) and bis(triphenylphosphine)-palladium-(II) acetate (55 mg, 0.073 mmol) in a mixed solvent system of toluene (20 mL) and anhydrous TEA (50 mL) was heated to reflux under argon. See, Liu, et al., 1996; Austin, et al., 1981; Heck, 1985. After stirring for 12 hours at reflux, the mixture was cooled to room temperature and the precipitate which formed was removed by filtration. The filtrate was concentrated under reduced pressure and the residue was treated with a saturated aqueous solution of NaHCO$_3$ (20 mL), and extracted with CHCl$_3$ (3×25 mL). The combined extracts were washed with brine and dried (Na$_2$SO$_4$). After removal of solvent under reduced pressure, the residue was purified by flash chromatography (silica gel, EtOAc) to afford 6 (XLiXHeII-048) as a white solid (0.29 g, 93%). This benzodiazepine can also be obtained from 2 in 45% yield by following the same procedure 6 (XLiXHeII-048): mp: 170-172° C.; IR (KBr) 2958, 2152, 1718 cm$^{-1}$; $^1$H NMR (CDCl$_3$) δ 0.23 (s, 9H), 1.42 (t, 3H, J=7.2 Hz), 4.04 (d, 1H, J=12.6 Hz), 4.41 (m, 2H, J=7.2 Hz), 6.23 (d, 1H, J=12.6 Hz), 7.35-7.55 (m, 7H), 7.73 (dd, 1H, J=8.3 Hz and 1.9 Hz), 7.93 (s, 1H); MS (EI) m/e (relative intensity) 427 (M$^+$, 76), 412 (5), 381 (55), 353 (100) 303 (10), 287 (7). Anal. Calcd. for C$_{25}$H$_{25}$N$_3$O$_2$Si.⅓EtOAc: C, 69.22; H, 6.01; N, 9.20. Found: C, 68.87; H, 5.81; N, 9.37.

Ethyl 8-acetylenyl-6-phenyl-4H-benzo[f]imidazo[1,5-a][1,4]diazepine-3-carboxylate 7 (XHeII-053). A solution of 6 (XLiXHeII-048) (0.17 g, 0.41 mmol), in THF (15 mL) was treated with Bu$_4$NF.H$_2$O (0.16 g, 0.62 mmol). The mixture which resulted was allowed to stir for 30 min at room temperature after which the mixture was added to H$_2$O (10 mL) and extracted with EtOAc (3×25 mL). See Xe, (2000). The combined organic extracts were washed with brine (25 mL) and dried (Na$_2$SO$_4$). After removal of solvent under reduced pressure, the residue was purified by a wash column (silica gel, EtOAc) to furnish 7 (XHeII-053) (0.12 g, 85%) as a white solid: mp: 237-239° C.; IR (KBr) 3159, 3107, 2092, 1721, 1606 cm$^{-1}$; $^1$H NMR (CDCl$_3$) δ 1.44 (t, 3H, J=7.1 Hz), 3.20

(s, 1H), 4.13 (d, 1H, J=10.22 Hz), 4.41-4.48 (m, 2H), 6.11 (d, 1H, J=12 Hz), 7.42-7.63 (m, 7H), 7.81 (dd, 1H, J=8.3 Hz and 1.8 Hz), 8.03 (s, 1H); MS (EI) m/e (relative intensity) 355 (M$^+$, 83), 309 (70), 281 (100), 253 (12), 231 (18), 178 (20). Anal. Calcd. for $C_{22}H_{17}N_3O_2 \cdot \frac{3}{4}H_2O$: C, 71.63; H, 5.05; N, 11.39. Found: C, 71.27; H, 4.71; N, 11.03.

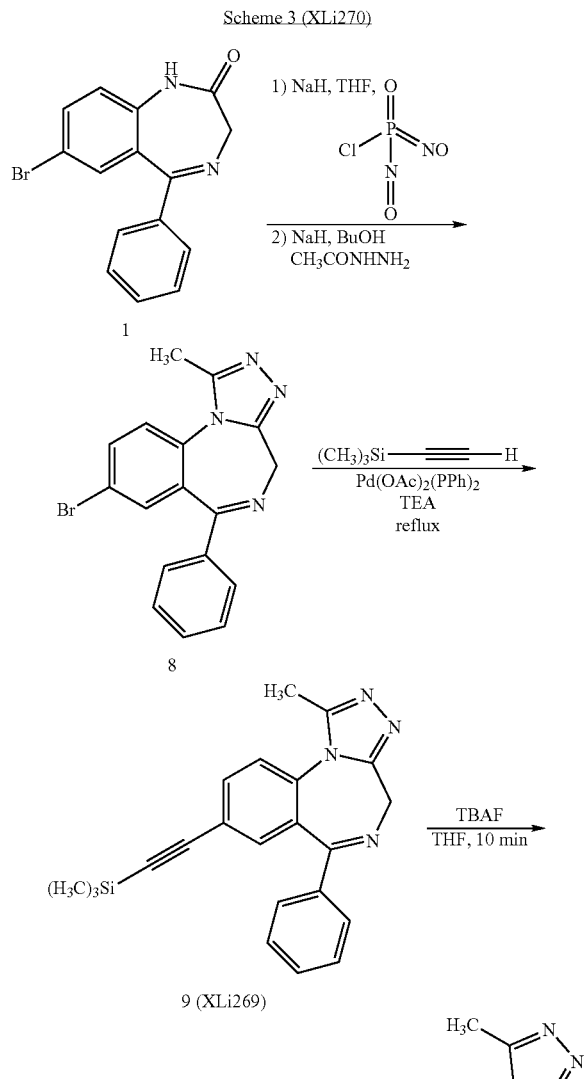

The bromide 1, obtained as in Scheme 1, above, was stirred with the di-4-morpholino-phosphinic chloride, followed by addition of acetylhydrazide to furnish triazolo-benzodiazepine 8. This material 8 was subjected to a Heck-type coupling reaction (TMS-C≡CH, Pd-mediated, See, Liu, et al., 1996; Austin, et al., 1981; Heck, 1985) to furnish ligand 9.

This analog was converted into 10 (XLi270) on stirring with fluoride anion as shown in Scheme 3.

Procedure for XLi 270

8-Bromo-1-methyl-6-phenyl-4H-s-triazolo[4,3-a][1,4] benzodiazepine 8.$^3$ A solution of 1 (1 g, 3.07 mmol of 7-bromo-5-phenyl-1,4-benzodiazepine-2-one) in dry THF (20 mL) was cooled in an ice-water bath and a 60% dispersion of sodium hydride (152.2 mg) was added in one portion. After 20 minutes, di-4-morpholinylphosphinic chloride (943.9 mg, 4.76 mmol) was added at 0° C. and this was stirred for 30 minutes and allowed to warm to room temperature (Ning, R Y., et al., (1976) J Org Chem 41: 2724-2727). The mixture was stirred for 1.5 hours. To this mixture was then added a solution of acetylhydrazide (521.9 mg, 7.14 mmol) in dry butanol (5 mL) and stirring was continued at room temperature for 10 min. The solvents were evaporated and the residue was dissolved in butanol (10 mL) and heated to reflux for 5 hours. Butanol was removed under reduced pressure and the residue was partitioned between $CH_2Cl_2$ (50 mL) and water (50 mL). The water layer was extracted by $CH_2Cl_2$ (3×30 mL). The combined organic layer was washed by brine (30 mL). The organic layer was dried ($Na_2SO_4$) and the solvent was removed under vacuum. The residue was purified by flash chromatography (silica gel) to provide pure 8 [539.5 mg (40% yield)] as a white solid: mp 268.5-270° C.; IR (KBr) 2358, 1607, 1538, 1484, 1311, 1000, 801, 697 cm$^{-1}$; $^1$H NMR (CDCl$_3$) δ 2.82(s, 3H), 4.11(d,1H, J=12.8Hz), 5.49 (d,1H, J=12.8Hz), 7.21-7.68(m, 7H), 7.75 (dd, 1H, J=0.58 Hz and 1.5Hz); MS (EI) m/e (relative intensity) 354 (34), (M$^+$, 16), 352 (34), 325(33), 323 (34), 273 (63), 245 (31), 232 (19), 204 (100), 183(23), 177 (36), 151 (24). Anal. Calcd. for $C_{17}H_{13}BrN_4$: C, 57.81; H, 3.71; N, 15.86. Found C, 57.57; H,3.64: N, 15.70.

8-Trimethylsilylacetylenyl-1-methyl-6-phenyl-4H-s-triazolo[4,3-a][1,4]-benzodiazepine 9. (XLi269). A mixture of 8 (8-bromo-1-methyl-6-phenyl-4-H-s-triazolo-[4,3-a][1,4] benzodiazepine, 300 mg, 0.85 mmol), trimethylsilylacetylene (208.5 mg, 2.12 mmol) and bis(triphenylphosphine)-palladium(II) acetate in a mixed solvent system of EtN$_3$ (5 mL) and CH$_3$CN (8mL) was heated to reflux under nitrogen. See, Liu, et al., 1996; Austin, et al., 1981; Heck, 1985. After stirring for 6 hours at reflux, the mixture was cooled to room temperature. The mixture was concentrated under reduced pressure and H$_2$O (30 mL) was added. The mixture was extracted with CH$_2$Cl$_2$ (3×50 mL). The combined extracts were washed with brine and dried (Na$_2$SO$_4$). After removal of solvent under reduced pressure, the residue was purified by flash chromatography (silica gel, EtOH/EtOAc) to afford benzodiazepine 9 (185 mg, 60% yield) as a white solid: mp 229-233° C.; IR (KBr) 2957, 2156, 1609, 1537, 1491, 1424, 1315, 1249, 881, 844, 750 cm$^{-1}$; $^1$H NMR (CDCl$_3$) δ 0.23 (s, 9H), 2.68 (s, 3H), 4.11 (d, 1H, J=12.5Hz), 5.49 (d, 1H, J=13.0Hz), 7.21-7.68(m,7H), 7.75(dd, 1H, J=8.5Hz, J=1.5Hz); MS (EI) m/e (relative intensity) 370 (M$^+$, 80), 355 (44), 341 (60), 286 (34), 177 (51), 163 (52) 143 (100), 129 (19), 115 (28). Anal. Calcd. for $C_{22}H_{22}N_4Si$: C, 71.31; H, 5.98; N, 15.12. Found: C, 70.90; H, 5.93; N, 15.08.

8-Acetylenyl-1-methyl-6-phenyl-4H-s-triazolo[4,3-a][1,4]benzodiazepine 10 (Xli-270). A solution of 9 [trimethylsilylacetylenyl-1-methyl-6-phenyl-4H-s-triazolo-[4,3-a]-[1,4]-benzodiazepine (106.4 mg, 0.288 mmol)] in dry THF (20 mL) was treated with Bu$_4$NF (1.0 M in THF, 112.8 mg, 0.431 mmol). See Xe, (2000). The mixture which resulted was allowed to stir for 5 min at room temperature after which the mixture was added to H$_2$O (10 mL) and extracted with CH$_2$Cl$_2$ (3×25 mL). The combined organic extracts were washed with brine (25 mL) and dried (Na$_2$SO$_4$). After removal of solvent under reduced pressure, the residue was crystallized from EtOAc to provide benzodiazepine 10 (XLi270) (66.8 mg, 80% yield) as a white solid: mp>250° C. (dec); IR (KBr) 3198, 2158, 1609, 1538, 1491, 1425, 1317, 1002, 838, 748, 695 cm$^{-1}$; $^1$H NMR (CDCl$_3$) δ 2.78 (s, 3H), 3.15 (s, 1H), 4.11 (d, 2H, J=12.8 Hz), 5.91 (d, 1H, J=12.8 Hz), 7.35-7.85 (m, 8H); MS (EI) (relative intensity) 298 (M$^+$, 100), 269 (78), 230 (48), 228 (65), 201 (20), 127 (65), 115 (42), 101 (54). Anal. Calcd. for C$_{19}$H$_{14}$N$_4$·½CH$_3$OH: C, 74.50; H, 5.13; N, 17.82. Found: C, 74.33; H, 4.83; N, 17.77,

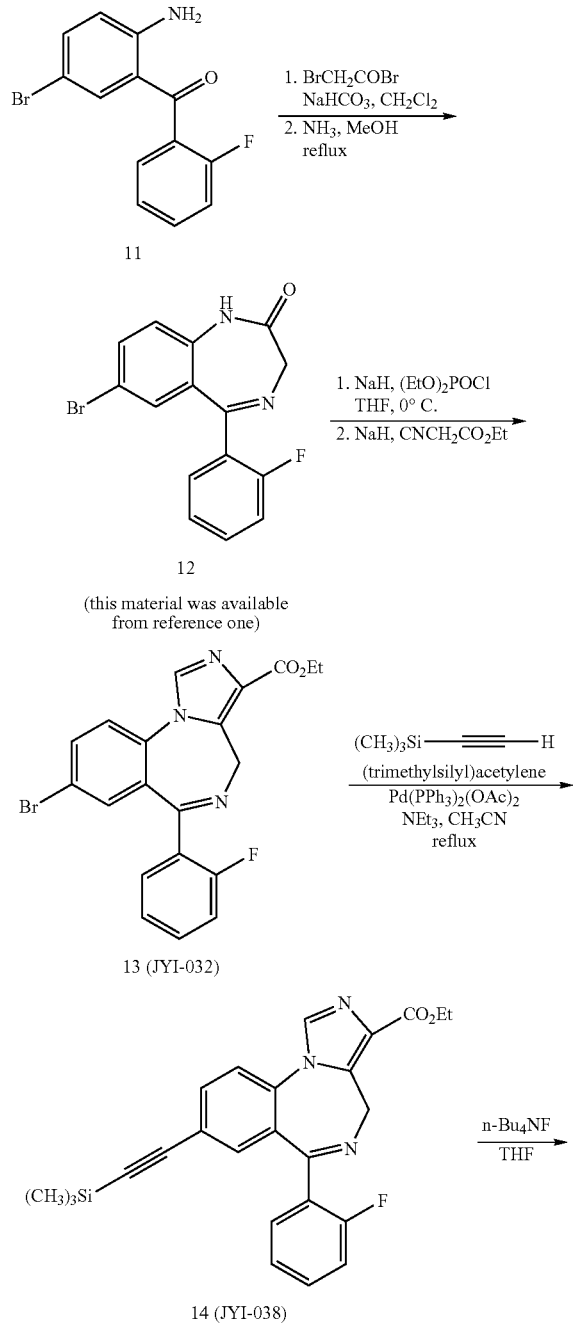

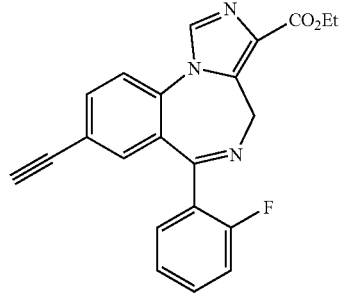

The 7-bromo-2'-fluorobenzodiazepine 12 (Sternbach, et al., 1962) was reacted with sodium hydride and diethylphosphorochloridate and this was followed by addition of ethyl isocyanoacetate to provide benzimidazo intermediate 13 (JYI-032),[2] as illustrated in Scheme 4. This material was heated with trimethysilylacetylene in a Heck-type coupling reaction[8] to provide the trimethylsilyl analog 14 (JYI-038). The silyl group was removed from 14 on treatment with fluoride anion to furnish 15, a 2'-fluoro analog of XHeII-053, in excellent yield.

Procedure:

Ethyl 8-bromo-6-(2'-fluorophenyl)-4H-benzo[f]imidazo[1,5-a][1,4]diazepine-3-carboxylate 13 (JYI-032). A solution of 12' (7.0 g, 21.0 mmol; Sternbach, et al., 1962) in THF (50 mL) was cooled in ice-water, and sodium hydride (1.0 g, 25.2 mmol) was added in one portion. After 30 min, diethyl phosphorochloridate (5.62 g, 31.5 mmol) was added dropwise, and the solution which resulted was stirred continuously for 30 min with cooling from an ice bath. A solution of ethyl isocyanoacetate (4.22 g, 25.2 mmol) and sodium hydride (1.17 g, 29.4 mmol) in THF (10 mL), which had stirred for 30 min with ice-bath cooling, was added slowly via a cannula. After stirring for another 30 min with cooling, the reaction mixture was allowed to stir at room temperature overnight. The mixture was then added to H$_2$O (10 mL) and extracted with EtOAc (3×50 mL). The combined organic extracts were washed with brine (2×50 mL) and dried (Na$_2$SO$_4$). The solvent was evaporated under reduced pressure and the residue was purified by flash chromatography (silica gel, hexanes/EtOAc: 2/1) to afford 13 (JYI-032, 5.2 g, 58%) as a white solid: mp: 200-201.5° C.; IR (KBr) 2977, 1718, 1610, 1491, 1450 cm$^{-1}$; $^1$H NMR (DMSO-d$_6$) δ 1.30 (t, 3H, J=4.2 Hz), 4.28 (bs, 1H), 4.30 (q, 2H, J=4.2 Hz), 5.75 (bs, 1H), 7.20 (t, 1H, J=5.6 Hz), 7.30 (t, 1H, J=4.5 Hz), 7.40 (s, 1H), 7.54 (m, 2H), 7.85 (d, 1H, J=5.2 Hz), 7.96 (dd, 1H, J=5.2 Hz and 1.3 Hz), 8.44 (s, 1H); MS (EI) m/e (relative intensity) 428 (7), 381 (58), 355 (100), 303 (37), 274 (36), 247 (35), 234 (52), 154 (71), 127 (62). Anal Calcd. for C$_{20}$H$_{15}$N$_3$O$_2$FBr: C, 56.09; H, 3.53; N, 9.81. Found: C, 56.02; H, 3.51; N, 9.58.

Ethyl 8-trimethylsilylacetylenyl-6-(2'-fluorophenyl)-4H-benzo[f]-imidazo[1,5a][1,4]diazepine-3-carboxylate 14 (JYI-038). A mixture of bromide 13 (JYI-032, 1.40 g, 3.3 mmol), trimethylsilylacetylene (0.65 g, 6.6 mmol) and bis(triphenylphosphine)-palladium (II) acetate (0.25 g, 0.33 mmol) in a mixed solvent system of CH$_3$CN (80 mL) and anhydrous triethylamine (50 mL) was heated to reflux under argon. After stirring for 2 h at reflux, the mixture was cooled to room temperature and the precipitate which formed was removed by filtration. The filtrate was concentrated under reduced pressure and the residue was treated with a saturated aqueous solution of NaHCO$_3$ (40 mL), and extracted with CHCl₃ (3×50 mL). The combined organic extracts were washed with brine (2×20 mL) and dried (Na₂SO₄). After removal of solvent under reduced pressure, the residue was purified by flash chromatography (silica gel, hexanes/EtOAc: 3/1) to afford 14 (JYI-038, 1.2 g, 82%) as a white solid: mp 196-197.5° C.; IR (KBr) 2959, 2157, 1709, 1613, 1494, 1451, 1252 cm⁻¹; ¹H NMR (DMSO-d₆) δ 0.20 (s, 9H), 1.32 (t, 3H, J=7.1 Hz), 4.18 (bs, 1H), 4.32 (q, 2H, J=7.1 Hz), 5.78 (bs, 1H), 7.25 (t, 1H, J=11.5 Hz), 7.30-7.35 (m, 4H), 7.81 (d, 1H, J=6.6 Hz), 7.93 (d, 1H, J=8.4 Hz), 8.49 (s, 1H); MS (EI) m/e (relative intensity) 445 (37), 399 (51), 371 (100), 235 (71), 192 (66), 178 (75). Anal. Calcd. for C₂₅H₂₄N₃O₂FSi: C, 67.39; H, 5.42; N, 9.43. Found: C, 66.98; H, 5.46; N, 9.19.

Ethyl-8-acetyleno-6-(2'-fluorophenyl)-4H-benzo[f]imidazo[1,5-a][1,4]diazepine-3-carboxylate 15 (JY-XHE-053). A solution of 14 (JYI-038, 80 mg, 0.18 mmol) in THF (5 mL) was treated with Bu₄NF (0.5 mL, 1.0M solution in THF). The mixture which resulted was allowed to stir for 5 min at room temperature after which the mixture was added to H₂O (5 mL) and extracted with EtOAc (3×10 mL). The combined organic extracts were washed with brine (2×10 mL) and dried (Na₂SO₄). The solvent was removed under reduced pressure and the residue was purified by flash chromatography (silica gel, EtOAc) to afford 15 (JY-XHE-053, 67 mg, 80%) as a white solid: mp 223.5-224.5° C.; IR (KBr) 3288, 2979, 1712, 1621, 1491, 1255, 1190 cm⁻¹; ¹H NMR (DMSO-d₆) δ 1.34 (t, 3H, J=7.1 Hz), 4.27 (bs, 1H), 4.36 (q, 2H, J=7.1 Hz), 4.47 (s, 1H), 5.80 (bs, 1H), 7.22 (t, 1H, J=8.4 Hz), 7.30-7.60 (m, 4H), 7.85 (d, 1H, J=6.6 Hz), 7.92 (d, 1H, J=8.4 Hz), 8.83 (s, 1H); MS (EI) m/e (relative intensity) 373 (28), 327 (47), 299 (100), 249(22), 178 (50). Anal. Calcd. for C₂₂H₁₆N₃O₂F.½H₂O: C, 69.10; H, 4.48; N, 10.99. Found: C, 69.19; H, 4.39; N, 10.68.

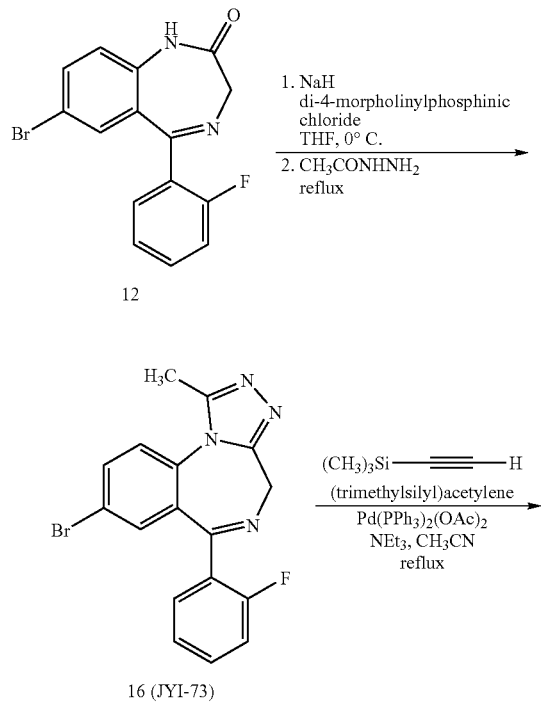

Scheme 5

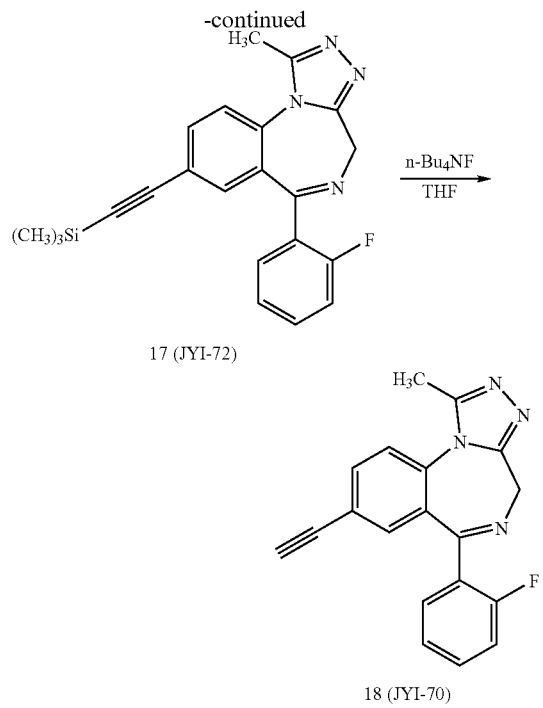

17 (JYI-72)

18 (JYI-70)

The 7-bromo-2'-fluorobenzodiazepine 12 was stirred with sodium hydride and di-4-morpholinylphosphinic chloride, followed by addition of acetic hydrazide, according to the published procedure (Ning, R. Y., et al., J Org Chem 41: 2724-2727) to provide triazolobenzodiazepine 16 (JYI-73), as illustrated in Scheme 5. This compound 16 underwent the palladium-mediated Heck-type coupling reaction as described above with trimethylsilylacetylene to furnish the 8-trimethylsilyl substituted analog 17 (JYI-72). Removal of the silyl group from 17 furnished the 8-acetyleno triazolobenzodiazepine 18 (JYI-70).

Procedure:

8-Bromo-1-methyl-6-(2'-fluorophenyl)-4H-s-triazolo[4,3-a][1,4]benzodiazepine 16 (JYI-73). A solution of 12 (JYI-032, 7.0 g, 21.0 mmol) in THF (50 mL) was cooled in ice-water, and sodium hydride (0.72 g, 18 mmol) was added in one portion. After 1 hour, di-4-morpholinylphosphinic chloride (4.84 g, 22.5 mmol) was added, and the solution which resulted was stirred continuously for 2 hours at room temperature. To this mixture was then added a solution of acetic hydrazide (2.47 g, 30 mmol) in n-BuOH (20 mL) and stirring was continued at room temperature for 15 min. The solvents were evaporated and the residue was dissolved in n-BuOH (25 mL) and heated to reflux for 2 hours. n-Butanol was evaporated and the residue was partitioned between CH₂Cl₂ and brine. The CH₂Cl₂ layer was dried and removed under reduced pressure after which the residue was purified by flash chromatography (silica gel, EtOAc) to afford 16 (JYI-73, 2.2 g, 40%) as a white solid: mp 213-214° C.; IR (KBr) 1610, 1484, 1426, 1314 cm⁻¹; ¹H NMR (DMSO-d₆) δ 2.56 (s, 3H), 4.28 (d, 1H, J=12.9 Hz), 5.26 (d, 1H, J=12.9 Hz), 7.24 (t, 1H, J=8.3 Hz), 7.29 (t, 1H, J=7.2 Hz), 7.35 (s,1H), 7.43-7.60 (m, 2H), 7.83 (d, 1H, J=8.7 Hz), 7.98 (dd, 1H, J=8.7 Hz and 2.3 Hz); MS (EI) m/e (relative intensity) 371 (5), 341 (34), 222 (100), 195 (19), 181 (28), 111 (72). Anal. Calcd. for C₁₇H₁₂N₄FBr: C, 55.01; H, 3.26; N, 15.09. Found: C, 54.76; H, 3.29; N, 14.74.

8-Trimethylsilylacetylenyl-1-methyl-6-(2'-fluorophenyl)-4H-s-triazolo[4,3-a][1,4]-benzodiazepine 17 (JYI-72). A mixture of bromide 16 (JYI-73, 1.40 g, 3.8 mmol), trimethylsilylacetylene (0.65 g, 6.6 mmol) and bis(triphenylphosphine)palladium (II) acetate (0.25 g, 0.33 mmol) in a mixed solvent system of $CH_3CN$ (80 mL) and anhydrous triethylamine (50 mL) was heated to reflux under argon. After stirring for 2 hours at reflux, the mixture was cooled to room temperature and the precipitate which formed was removed by filtration. The filtrate was concentrated under reduced pressure and the residue was treated with a saturated aqueous solution of $NaHCO_3$ (40 mL), and extracted with $CHCl_3$ (3×50 mL). The combined organic extracts were washed with brine (2×10 mL) and dried ($Na_2SO_4$). After removal of solvent under reduced pressure, the residue was purified by flash chromatography (silica gel, EtOAc) to afford 17 (JYI-72, 1.15 g, 77%) as a gray solid: mp 218-219° C.; IR (KBr) 2958, 2157, 1612, 1537, 1493, 1452, 1317, 1249 $cm^{-1}$; $^1H$ NMR (DMSO-$d_6$) δ 0.21 (s, 9H), 2.56 (s, 3H), 4.23 (s, 1H, J=12.9 Hz), 7.26 (t, 1H, J=8.4 Hz), 7.29-7.83 (m, 6H); MS (EI) m/e (relative intensity) 388 (65), 373 (14), 359 (77), 304 (44), 152 (100). Anal. Calcd. for $C_{22}H_{21}N_4SiF \cdot 0.7H_2O$: C, 65.87; H, 5.62; N, 13.94. Found: C, 65.88; H, 5.34; N, 13.94.

8-Acetyleno-1-methyl-6-(2'-fluorophenyl)-4H-s-triazolo[4,3-a][1,4]benzodiazepine 18 (JYI-70). A solution of 17 (JYI-72, 2.0 g, 5 mmol) in THF (20 mL) was treated with $Bu_4NF$ (4 mL, 1.0M solution in THF). The mixture which resulted was allowed to stir for 5 min at room temperature after which the mixture was added to $H_2O$ (20 mL) and extracted with $CH_2Cl_2$ (3×50 mL). The combined organic extracts were washed with brine (2×15 mL) and dried ($Na_2SO_4$). After removal of solvent under reduced pressure, the residue was purified by flash chromatography (silica gel, EtOAc/MeOH: 100/1) to afford 18 (JYI-70, 1.1 g, 70%) as a pale yellow solid: mp>250° C. (dec); IR (KBr) 3205, 1612, 1493, 1426, 1317 $cm^{-1}$; $^1H$ NMR (DMSO-$d_6$) δ 2.54 (s, 3H), 4.22 (d, 1H, J=12.9 Hz), 4.39 (s, 1H), 5.26 (d, 1H, J=12.9 Hz), 7.22 (t, 1H, J=8.3 Hz), 7.32-7.55 (m, 4H), 7.97 (m, 2H); MS (EI) m/e (relative intensity) 316 (72), 287 (100), 246 (69), 153 (16), 127 (62). Anal. Calcd. for $C_{19}H_{13}N_4F \cdot 0.6$ $CH_3OH$: C, 70.16; H, 4.37; N, 16.55. Found: C, 69.98; H, 4.31; N, 16.70.

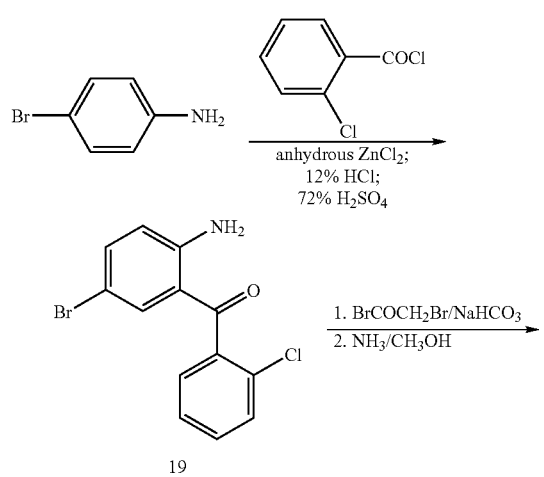

Scheme 6

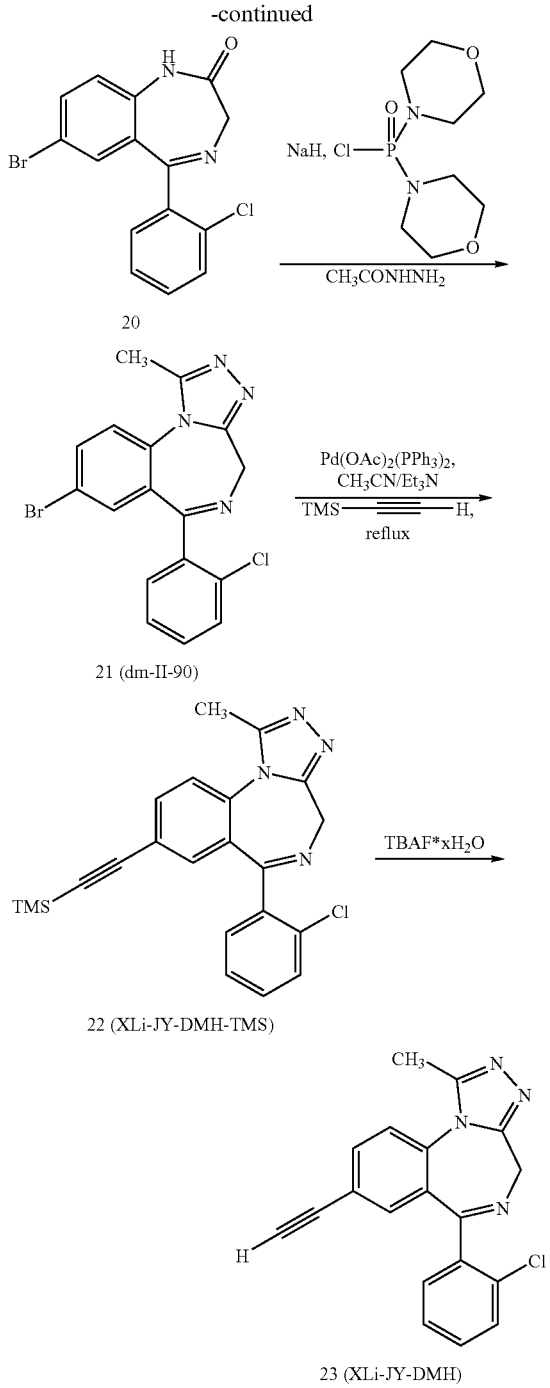

20

21 (dm-II-90)

22 (XLi-JY-DMH-TMS)

23 (XLi-JY-DMH)

2-Amino-5-bromo-2'-chlorobenzophenone 19 was obtained from simple starting materials, 4-bromoaniline and 2-chlorobenzoyl chloride, according to the improved conditions in the literature (Bogatskii A V, et al., (1977) Pharm Chem J (Engl Transl) 11: 1520-1525). The benzodiazepine 20 (Sternbach, et al., 1962) was stirred with sodium hydride and di-4-morpholinophosphinic chloride, followed by addition of acetylhydrazide to furnish triazolobenzodiazepine 21 (dm-II-90). The ligand 22 (XLi-JY-DMH-TMS) was obtained by a Heck coupling reaction as described above of 21 (dm-II-90) with trimethylsilylacetylene. This compound was converted into acetylene 23 (XLi-JY-DMH) (He, 2000) on stirring with fluoride anion as shown in Scheme 6.

2-Amino-5-bromo-2'-chlorobenzophenone 19

2-Chlorobenzoyl chloride (177 mL, 1.4 mol) was cooled in a 2-L flask equipped with a condenser and a thermometer to 0° C. with an ice-water bath and 4-bromoaniline (100 g, 0.58 mol) was added to the cooled solution. The mixture was heated to 120° C. and kept at this temperature for 1 h until analysis by TLC indicated 4-bromoaniline had been consumed (EtOAc:hexane, 1:4). The solution was heated to 160° C. and anhydrous $ZnCl_2$ (95 g, 0.70 mol, flamed dried) was added in one portion. The temperature was increased to 195° C. and stirring was maintained at this temperature for 3 hr until no more bubbles were evolved. The mixture was cooled to 120° C. and aq HCl (12%, 350 mL) was added dropwise slowly. The mixture was kept at reflux for 20 min, after which the aq layer was poured off. This procedure with aq HCl was repeated 4 times. Water (350 mL) was then added, and the mixture held at reflux for 20 min and then the water was poured off. This was repeated several times until the solid was not a block any more. Then $H_2SO_4$ (72%, 700 mL) was added to the residue and the mixture was heated to reflux for about 1 hr until the reaction mixture became a homogeneous dark colored solution. The hot acidic solution was poured into a mixture of ice and water with stirring. The precipitate which resulted was filtered and washed with a large amount of cold water until the pH value of the solid was about 6. The solid was then suspended in ice water and aq NaOH (40%, 290 mL) was added carefully. The mixture which-resulted was stirred for 2 hrs. The solid was filtered and washed with ice water. The suspension of the solid in ice water was adjusted carefully to approximately pH=3 with aq $H_2SO_4$ (40%) dropwise. The solid which remained was filtered and washed with water to neutrality. The yellow solid 19 (66.1 g, 37.0%) was dried and used directly in the next step without further purification. $^1$H NMR (300 MHz, $CDCl_3$) δ 6.49 (s, br, 2H), 6.65 (d, 1H, J=8.82 Hz), 7.26-7.8 (m, 6H).

8-Bromo-5-(2'-chlorophenyl)-1-methyl-4H-s-triazolo[4,3-a]-1,4-benzodiazepine 21 (dm-II-90)

A solution of benzodiazepine 20 (20 g, 57 mmol, prepared from 19, following Sternbach, et al., 1962) in dry THF (250 mL) was cooled to −5° C. and a 60% dispersion of sodium hydride (3.66 g, 92 mmol) was added in one portion. The mixture was allowed to warm to rt with stirring and the stirring was continued at rt until no more bubbles were evolved. The suspension was cooled to −5° C. after which di-4-morpholinylphosphinic chloride (21.8 g, 86 mmol) was added and this mixture was stirred for 30 min and allowed to warm to rt. The mixture was stirred for an additional 1.5 hr. To the mixture was then added a solution of acetylhydrazide (9.42 g, 114 mmol) in butanol (60 mL) and stirring was continued at rt for 10 min. The solvent was removed under reduced pressure and the residue was taken up in butanol (100 mL) and held at reflux for 2 hr. Butanol was removed under reduced pressure and the residue was partitioned between $CH_2Cl_2$ (200 mL) and $H_2O$ (100 mL). The aq layer was extracted 4 times and the organic layers combined. The organic layer was washed with brine and dried ($Na_2SO_4$). After the solvent was removed under reduced pressure, the residue was crystallized from $EtOAc-Et_2O$ to provide the pure triazolobenzodiazepine 21 (dm-II-90, 14 g, 63.2%) as a yellow solid: mp 265-267° C. [lit 274-275° C.][10]; IR (KBr) 3120 (br.), 1686, 1479, 1386, 1014, 827, 747 cm$^{-1}$; $^1$H NMR (300 MHz, $CDCl_3$) δ 2.42 (s, 1H), 4.18 (d, 1H, J=12.9 Hz), 5.56 (d, 1H, J=12.9 Hz), 7.36 (m, 3H), 7.43 (m, 2H), 7.61 (m, 1H), 7.80 (dd, 1H, J=2.1 Hz and 8.7 Hz); MS (EI) m/e (rel intensity) 386 (M$^+$, 45), 357 (100); Anal. Calcd. For $C_{17}H_{12}N_4BrCl.0.5H_2O$: C, 51.65; H, 3.32; N, 14.18; Found C, 51.95; H, 2.97; N, 13.91.

8-Trimethylsilylacetylenyl-5-(2'-chlorophenyl)-1-methyl-4H-s-triazolo-[4,3-a]-1,4-benzodiazepine 22 (XLi-JY-DMH-TMS)

A mixture of 21 (7.75 g, 20 mmol), acetonitrile (600 mL), triethylamine (500 mL) and bis(triphenylphosphine)-palladium (II) acetate (1.2 g, 1.6 mmol) was degassed under vacuum. Tri-methylsilylacetylene (5.65 mL, 40 mmol) was then added and the solution was degassed again. The solution was then heated to reflux for 4 hr until analysis by TLC indicated the starting material had disappeared. The mixture was cooled to rt and concentrated under reduced pressure. The residue was partitioned between $H_2O$ (50 mL) and EtOAc (2×200 mL). The combined organic layer was washed with brine and dried ($Na_2SO_4$). The residue was purified by flash chromatography on silica gel ($CHCl_3$) to furnish the trimethylsilyl analogue 22 (XLi-JY-DMH-TMS, 3 g, 37.0%) as a white solid: mp: 265-267° C.; IR (KBr) 2930, 1618, 1554, 1497, 1429, 1316, 885, 847 cm$^{-1}$; $^1$H NMR (300 MHz, $CDCl_3$) δ 0.24 (s, 9H), 2.65 (s, 3H), 4.15 (d, 1H, J=12.9 Hz), 5.52 (d, 1H, J=12.9 Hz), 7.35-7.45 (m, 5H), 7.61 (m, 1H), 7.72 (dd, 1H, J=1.8 Hz and 8.4 Hz); MS (EI) m/e (rel intensity) 404 (M+, 90), 375 (100); Anal. Calcd. For $C_{22}H_{21}N_4SiCl$: C, 65.33; H, 5.24; N, 13.86. Found: C, 64.99; H, 4.98; N, 13.79.

8-Acetyleno-5-(2'-chlorophenyl)-1-methyl-4H-s-triazolo-[4,3-a]-1,4-benzodiazepine 23 (XLi-JY-DMH)

A solution of benzodiazepine 22 (1.25 g, 31 mmol) in THF (250 mL) was cooled to −30° C. and treated with $Bu_4NF.xH_2O$ (0.97 g, 37 mmol) in THF. After the mixture was stirred for 5 min, analysis by TLC (silica gel; EtOAc: EtOH 4:1) indicated starting material had disappeared. Water (70 mL) was then added and the mixture was allowed to warm to rt. The mixture was then extracted with EtOAc (2×200 mL). The organic layer was washed with brine and dried ($Na_2SO_4$). After removal of the solvent under reduced pressure, the residue was washed successively with ethyl ether, ethyl acetate and chloroform. After drying, the title compound 23 (XLi-JY-DMH) was obtained (1.0 g, 97.3%) as a white solid: mp>250° C. (dec); IR (KBr) 3185, 1623, 1543, 1497, 1429, 756 cm$^{-1}$; $^1$H NMR (300 MHz, $CDCl_3$) δ 2.65 (s, 3H), 3.17 (s, 1H), 4.18 (d, 1H, J=12.9 Hz), 5.54 (d, 1H, 12.9 Hz), 7.34(m, 2H), 7.41-7.45 (m, 3H), 7.6 (m, 1H), 7.75 (dd, 1H, J=1.8 Hz, 8.4 Hz); MS (EI) m/e (rel intensity) 332 (M$^+$, 78) 303 (100). Anal. Calcd. For $C_{19}H_{13}N_4Cl.0.18 CHCl_3$: C, 65.14; H, 3.76; N, 15.85. Found: C, 65.29; H, 3.80; N, 15.40.

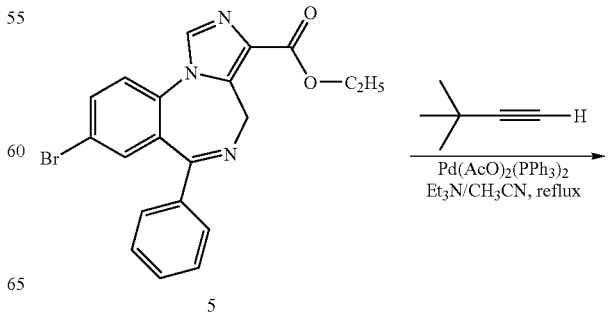

Scheme 7 (t-butylacetylene analogs)

-continued

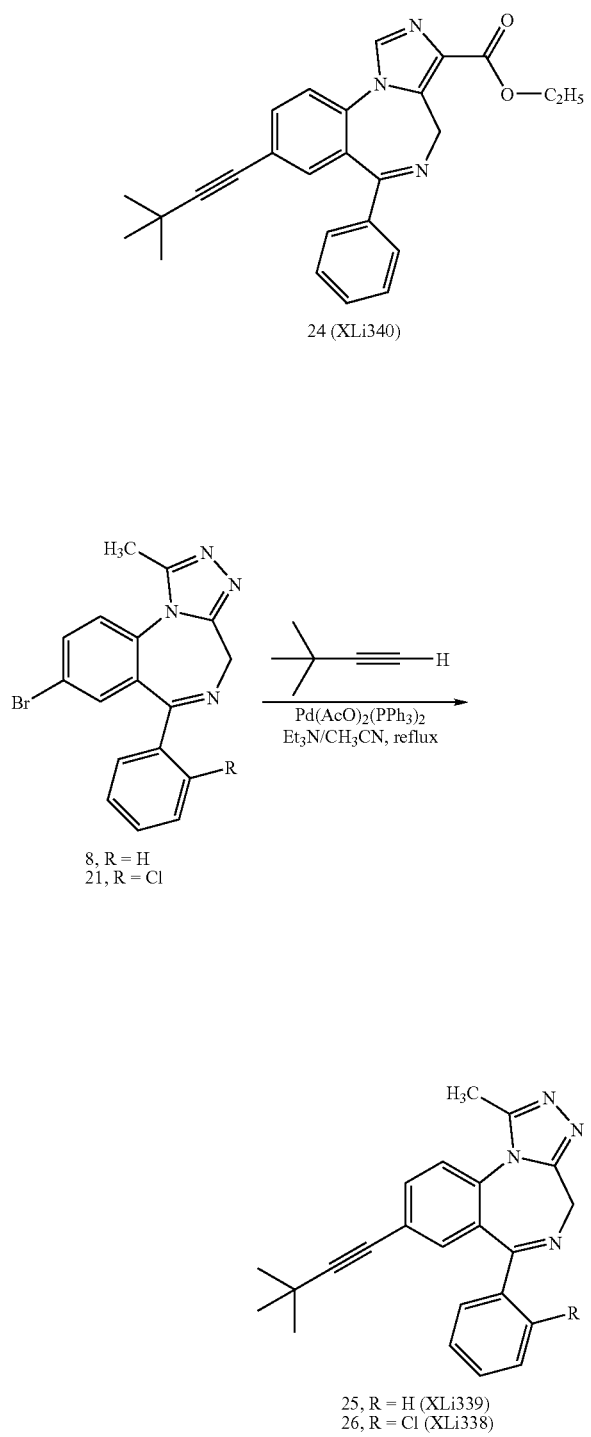

24 (XLi340)

8, R = H
21, R = Cl

Pd(AcO)₂(PPh₃)₂
Et₃N/CH₃CN, reflux

25, R = H (XLi339)
26, R = Cl (XLi338)

Based on the binding affinity of RY080, RY079 and XLiX-HeII-048, it was decided to replace the trimethylsilylacetylene functional group of previous targets at C (7) or C (8) with a t-butylacetylene derivative. The targets 24 (XLi340), 25 (XLi339), and 26 (XLi338) can be made by chemistry previously executed by the present inventors. The 3,3-dimethyl-1-butyne was added by a Heck coupling reaction in excellent yield. The chemistry followed that illustrated in Scheme 7.

Procedure for t-butylactylene Analogs.

Ethyl-8-t-butylacetylenyl-6-phenyl-4H-benzo[f]imidazo[1,5-a][1,4]-diazepine-3-carboxylate 24 (XLi340). A mixture of 5 (300 mg, 0.732 mmol) available from procedure [0051] in triethyl amine (5 mL) and $CH_3CN$ (8 mL) was stirred with 3,3-dimethyl-1-butyne (12.3 mg, 0.15 mmol) and bis(triphenylphosphine)palladium (II) acetate (38.3 mg, 0.051 mmol) and heated to reflux under nitrogen. After 5 hours, the reaction mixture was cooled to rt and filtered. The filtrate was concentrated under vacuum and the residue was treated with $H_2O$ (10 mL), and extracted with $CH_2Cl_2$ (3×10 mL). The organic layers were combined and washed with brine and dried ($Na_2SO_4$). After removal of solvent under reduced pressure, the residue was purified via flash chromatography (silica gel, EtOAc/hexanes: 1/1) to furnish the t-butylacetylene 24(XLi340) as a yellow powder (271 mg, 90%): mp: 155-156° C.; IR (KBr) 2358, 1717, 1489, 1248, 1074, 803, 668 $cm^{-1}$; ¹HNMR ($CDCl_3$) δ 1.25 (s, 9H), 1.45 (t, 3H, J=7.1 Hz), 4.05 (d, 1H, J=12.3), 4.45 (2H, J=7.1 Hz), 5.95 (d, 1H, J=12.3 Hz), 7.3-7.7 (m, 8H), 7.95 (s, 1H); MS (EI) m/e (relativity intensity) 412 ($M^+$, 46), 365 (46), 337 (100), 322 (8), 277 (16), 219 (14). Anal. Calcd. For $C_{26}H_{25}N_3O_2 \cdot \frac{1}{2}H_2O$, C 74.26, H 6.23, N 9.99. Found. C, 74.50; H, 6.29; N, 9.89.

8-t-Butylacetylenyl-1-methyl-6-phenyl-4H-s-triazolo[4,3-a][1,4]-benzodiazepine 25 (XLi339). This t-butylacetyleno benzodiazepine 25 (XLi339) was obtained in 80% yield from 8 analogous to the procedure used to produce compound 24 as a yellow solid: mp: 184-186° C.; IR (KBr) 2966, 2357, 1618, 1524, 1505, 1498, 1425, 1398, 799, 698 $cm^{-1}$; ¹H NMR ($CDCl_3$) δ 1.3 (s, 9H), 2.6 (s, 3H), 4.12 (d, 1H, J=12.8), 5.51 (d, 1H, J=12.8), 7.18 (s, 1H), 7.21-7.75 (m, 7H); MS (EI) m/e (relativity intensity) 354 ($M^+$, 100), 353 (42), 339 (19), 325 (59), 298 (7), 270 (16), 255 (12). Anal. Calcd. For $C_{23}H_{22}N_4 \cdot \frac{1}{3}EtOAc$, C, 76.26; H, 6.57; N, 14.42. Found. C, 76.29; H, 6.44; N, 14.61.

8-t-Butylacetylenyl-1-methyl-6-(2'-chlorophenyl)-4H-s-triazolo[4,3-a][1,4] benzodiazepine 26 (XLi338). This t-butylacetyleno benzodiazepine 26 (XLi338) was obtained in 95% yield from 21 analogous to the conditions of the procedure used to produce compound 24 as a white solid: mp: >268° C. dec.; IR (KBr) 2966, 1616, 1534, 1497, 1319, 914, 832, 732 $cm^{-1}$; ¹H NMR ($CDCl_3$) δ 1.29 (s, 9H), 2.61 (s, 3H), 4.08 (d, 1H, J=12.9 Hz), 4.48 (d, 1H, J=12.8 Hz), 7.15-7.55 (m, 6H), 7.65 (dd, 1H, J=1.9 Hz, J=8.4 Hz); MS (EI) m/e (relativity intensity) 389 ($M^+$, 35), 388 (100), 359 (97), 345 (7), 325 (13), 284 (16), 269 (21). Anal. Calcd. For $C_{23}H_{21}N_4 \cdot \frac{1}{3}H_2O$, C 70.08, H 5.54, N 14.18. Found. C, 70.52; H, 5.62; N, 13.81.

Scheme 8

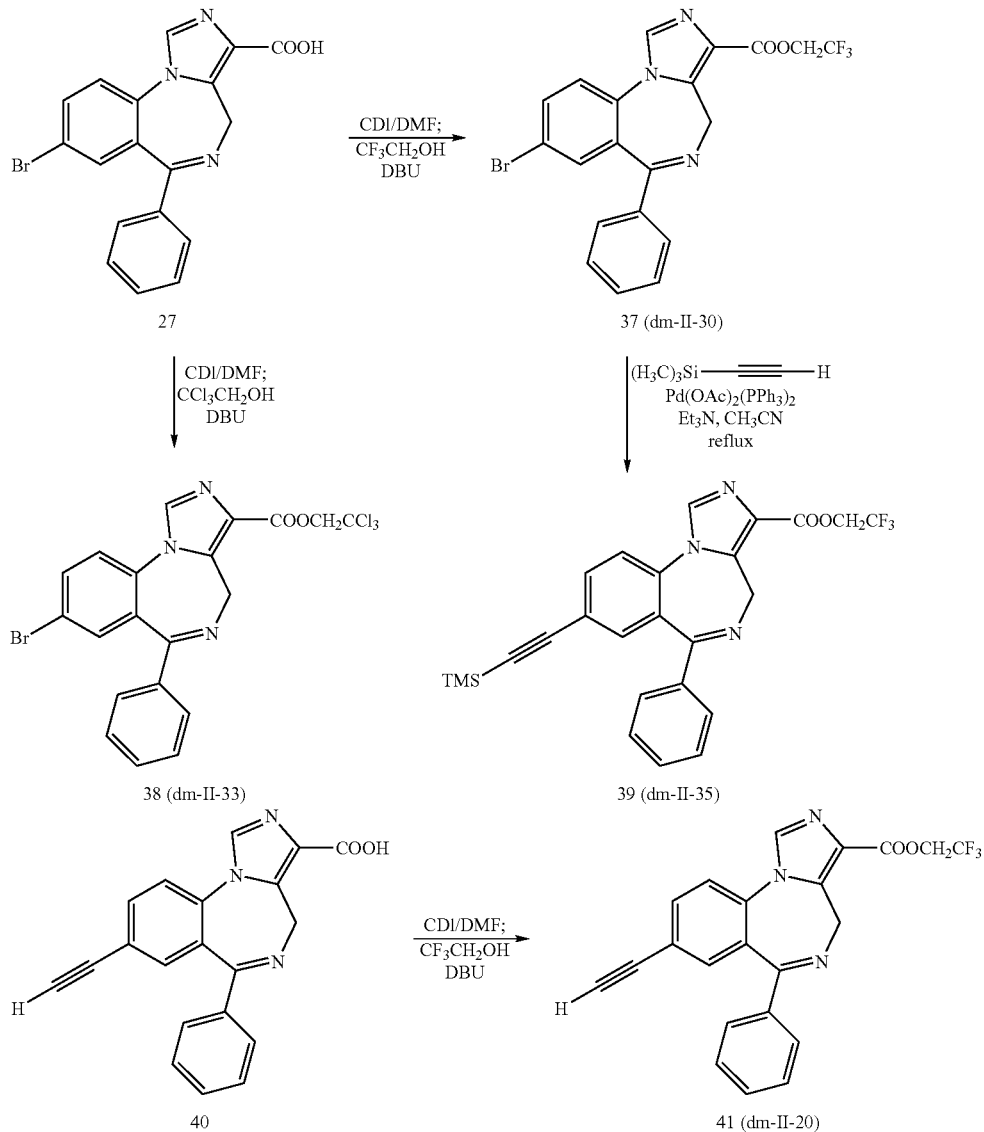

Esters 37 (dm-II-30), 38(dm-II-33) and 41 (dm-II-20) were prepared according to the general procedure described in the above paragraph from the starting acids and different alcohols, respectively. The bromide 37 was converted into the trimethylsilylacetylenyl compound 39 (dm-II-35) under standard conditions (Pd-mediated, Heck-type coupling) (Scheme 8).

General Procedure for Preparing the Esters.

The acid 27 was dissolved in DMF (10 mL/mmol S.M.) and CDI (1.2 eq) was added. The reaction mixture was stirred at room temperature for 3 h followed by addition of the alcohol (10 eq) and DBU (1 eq). The stirring was maintained until the disappearance of all the starting material as determined by TLC (EtOAc:EtOH 4:1). The reaction mixture was then quenched by adding water. The solid which precipitated was filtered and washed with ethyl ether. It was purified by flash chromatography (EtOAc) on silica gel or neutral aluminum oxide for ester 38.

2,2,2-Trifluoroethyl 8-bromo-6-phenyl-4H-benzo[f]imidazo[1,5-a][1,4]diazepine-3-carboxylate 37 (dm-II-30). A white solid (69.1%) was obtained from acid 27 and 2,2,2-trifluoroethanol with CDI, 37: mp 202-204° C.; IR (KBr) 3114, 1711, 1608, 1495, 1368, 1288, 1158 cm$^{-1}$; $^1$H NMR (300 MHz, CDCl$_3$) δ 4.10 (d, 1H, J=12.6 Hz), 4.68 (m, 1H), 4.85 (m, 1H), 6.02 (d, 1H, J=12.6 Hz), 7.41-7.54 (m, 6H), 7.62 (d, 1H, J=2.1 Hz), 7.83 (dd, 1H, J=2.1 Hz, 8.4 Hz), 7.97 (s, 1H); MS (EI) m/e (rel intensity) 463 (M$^+$, 14), 465 (14).

2,2,2-Trichloroethyl 8-bromo-6-phenyl-4H-benzo[f]imidazo[1,5-a][1,4]diazepine-3-carboxylate 38 (dm-II-33). A white solid (90.9%) was obtained from acid 27 and 2,2,2-trichloroethanol with CDI, 38: mp 113-116° C.; IR (KBr) 3434, 1728, 1610, 1493, 1270, 1146, 1128 cm$^{-1}$; $^1$H NMR (300 MHz, CDCl$_3$) δ 4.11 (d, 1H, J=12.6 Hz), 4.91 (d, 1H, J=12.0 Hz), 5.19 (d, 1H, J=12.0 Hz), 6.12 (d, 1H, J=12.6 Hz), 7.41-7.54 (m, 6H), 7.61 (d, 1H, J=2.1 Hz), 7.83 (dd, 1H, J=2.1 Hz, 8.4 Hz); MS (EI) m/e (rel intensity) 511 (M$^+$, 45).

2,2,2-Trifluoroethyl 8-trimethylsilylacetylenyl-6-phenyl-4H-benzo[f]imidazo[1,5-a][1,4]diazepine-3-carboxylate 39 (dm-II-35). A white solid (49.8%) 39: mp 107-110° C.; IR (KBr) 2961, 1734, 1611, 1560, 1497, 1251, 1159, 1120, 846 cm$^{-1}$; $^1$H NMR (300 MHz, CDCl$_3$) δ 0.25 (s, 9H), 4.08 (d, 1H, J=12.3 Hz), 4.69 (m, 1H), 4.84 (m, 1H), 5.98 (d, 1H, J=12.3 Hz), 7.39-7.57 (m, 7H), 7.76 (dd, 1H, J=1.8 Hz, 8.4 Hz); MS (EI) m/e (rel intensity) 481 (M$^+$, 100).

2,2,2-Trifluoroethyl 8-acetylenyl-6-phenyl-4H-benzo[f]imidazo[1,5-a][1,4]diaze-pine-3-carboxylate 41 (dm-II-20). A white solid (36.9%) was obtained from acid 40 and 2,2,2-trifluoroethanol with CDI, 41: mp 188-190° C.; IR (KBr) 3443, 3277, 1710, 1600, 1492, 1366, 1280, 1156 cm$^{-1}$; $^1$HNMR (500 MHz, CDCl$_3$) δ 3.18 (s, 1H), 4.08 (d, 1H, J=12.5 Hz), 4.67 (m, 1H), 4.82 (m, 1H), 5.98 (d, 1H, J=12.5 Hz), 7.37-7.40 (m, 2H), 7.44-7.51 (m, 3H), 7.56-7.59 (m, 2H), 7.78 (dd, 1H, J=1.5 Hz, 8.5 Hz); MS (EI) m/e (rel intensity) 409 (M$^+$, 28). Anal. Calcd. For C$_{22}$H$_{14}$N$_3$O$_2$F$_3$.0.25H$_2$O: C, 63.82; H, 3.72; N, 10.16. Found: C, 63.89; H, 3.37; N, 9.94.

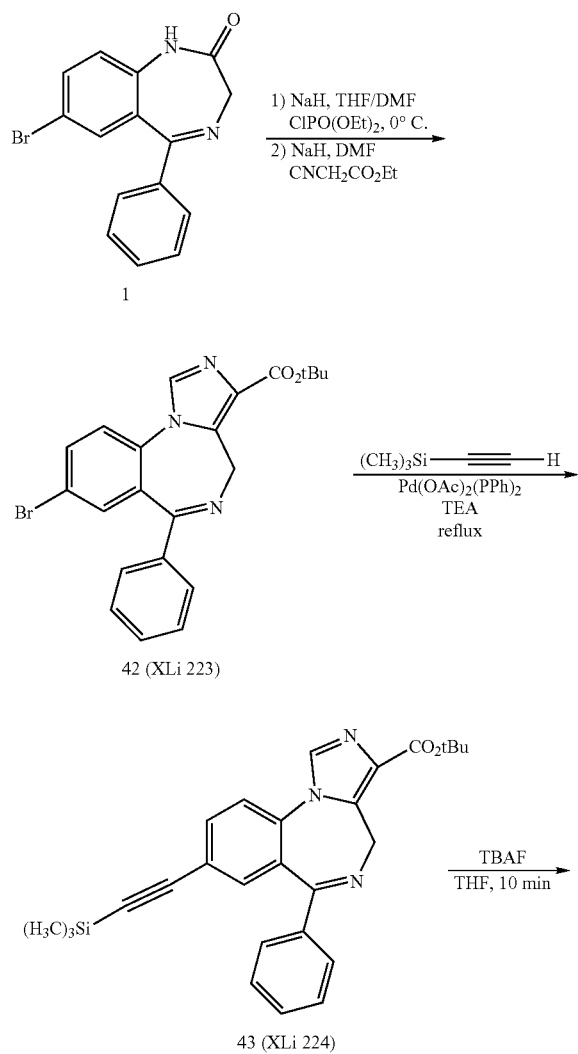

Scheme 9

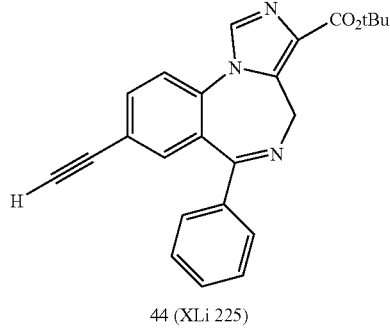

44 (XLi 225)

The bromide 1 was reacted with diethylphosphorochloridate in the presence of sodium hydride, followed by addition of t-butyl isocyanoacetate to provide the ester 42. This was converted into the trimethylsilylacetyleno compound 43 under standard conditions (Pd-mediated, Heck-type coupling). Treatment of 43 with fluoride gave the title compound 44.

Procedure for XLi225 t-Butyl 8-bromo-6-phenyl-4H-benzo[f]imidazo[1,5-a][1,4]diazepine-3-carboxylate 42. This benzodiazepine 42 was obtained in 40% yield from 1 (Sternbach, et al., 1962) analogous to the literature procedure (Gu, Q., et al., (1993) J Med Chem 36: 1001-1006) as a white solid. 42 (XLi223): mp: 222°-223° C.; IR (KBr) 2975, 2358, 1717, 1608, 1557, 1277, 1073, 908, 696, 652 cm$^{-1}$; $^1$H NMR (CDCl$_3$) δ 1.60 (s, 9H), 4.03 (d, 1H, J=12.5 Hz), 6.08 (d, 1H, J=12.4 Hz), 7.35-7.52 (m, 7H), 7.58 (d, 1H, J=2.2 Hz), 7.80 (dd, 1H, J=2.22 Hz and 8.55 Hz), 7.93 (s, 1H).

t-Butyl-8-trimethylsilylacetylenyl-6-phenyl-4H-benzo[f]imidazo[1,5-a][1,4]-diazepine-3-carboxylate 43 (XLi 224). A mixture of bromide 42 (1 g, 2.28 mmol, trimethylsilylacetylene (559 mg, 5.69 mmol) and bis(triphenylphosphine)-palladium-(II) acetate (55 mg, 0.073 mmol) in a mixed solvent system of CH$_3$CN (15 mL) and anhydrous TEA (25 mL) was heated to reflux under argon. After stirring for 6 hours at reflux, the mixture was cooled to room temperature and the precipitate which formed was removed by filtration. The filtrate was concentrated under reduced pressure and the residue was treated with a saturated aqueous solution of NaHCO$_3$ (20 mL), and extracted with CHCl$_3$ (3×25 mL). The combined extracts were washed with brine and dried (Na$_2$SO$_4$). After removal of solvent under reduced pressure, the residue was purified by flash chromatography (silica gel, EtOAc) to afford 43 (XLi224) as a white solid (710 mg, 68.9%): mp: 234°-236° C.; IR (KBr) 2973, 2357, 2154, 1719, 1611, 1493, 1366, 1250, 1152, 1075, 946, 880 cm$^{-1}$; $^1$H NMR (CDCl$_3$) δ 0.23 (s, 9H), 1.64 (s, 9H), 4.05 (d, 1H, J=12.7 Hz), 6.06 (d, 1H, J=12.4), 7.37-7.53 (m, 7H), 7.73 (dd, 1H, J=1.95 and 8.25 Hz), 7.92 (s, 1H); MS (EI) m/e (relative intensity) 427 (M$^+$, 76), 412 (5), 381 (55), 353 (100) 303 (10), 287 (7).

t-Butyl 8-acetylenyl-6-phenyl-4H-benzo[ ]imidazo[1,5-a][1,4]diazepine-3-carboxylate 44 (XLi 225). A solution of 43 (128 mg, 0.281 mmol) in THF (15 mL) was treated with Bu$_4$NF.H$_2$O (100.04 mg, 0.38 mmol). The mixture which resulted was allowed to stir for 5 min at room temperature after which the mixture was added to H$_2$O (10 mL) and extracted with EtOAc (3×15 mL). See Xe, (2000). The combined organic extracts were washed with brine (15 mL) and dried (Na$_2$SO$_4$). After removal of solvent under reduced pressure, the residue was purified by a wash column (silica gel, EtOAc) to furnish 44 (XLi225) (92 mg, 85.4%) as a white solid: mp: 221°-223° C.; IR (KBr) 3159, 3107, 2092, 1721, 1606 cm$^{-1}$; $^1$H NMR (CDCl$_3$) δ 1.62 (s, 9H), 3.21 (s, 1H), 4.12 (d, 1H, J=10.2 Hz), 6.07 (d, 1H, J=12.5 Hz), 7.35-7.53 (m, 7H), 7.73 (dd, 1H, J=1.8 Hz and 8.3 Hz), 7.92 (s, 1H).

Scheme 10

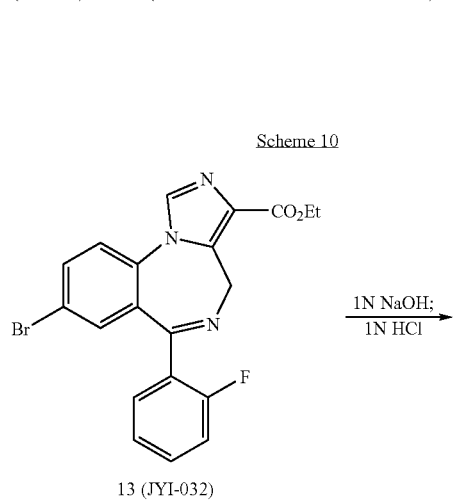

13 (JYI-032)

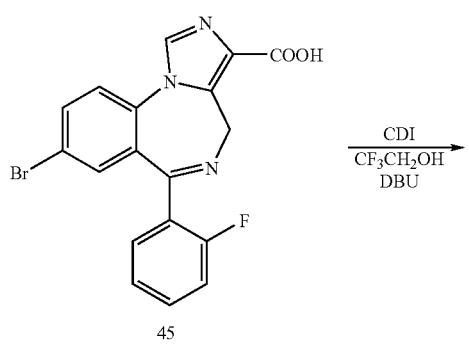

45

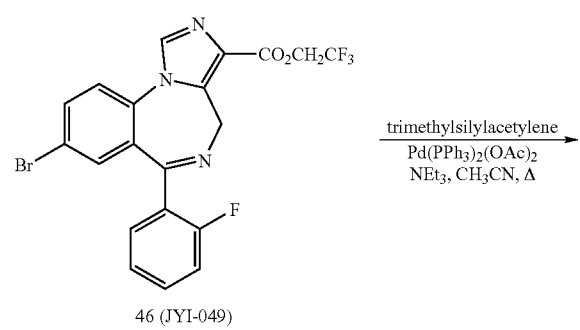

46 (JYI-049)

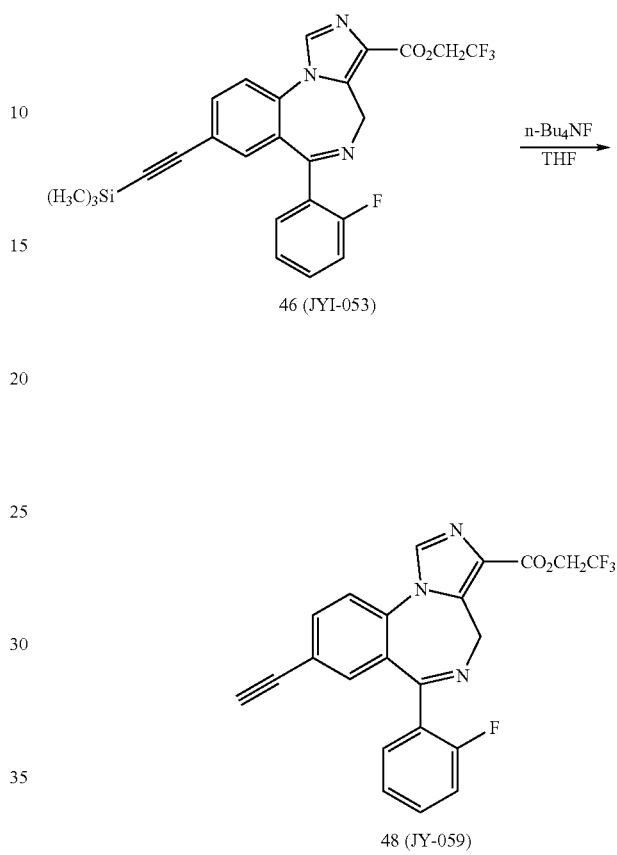

7-Bromo-2'-fluorobenzodiazepine 13 was hydrolyzed with aq 2 N sodium hydroxide in EtOH and acidified to pH 4 by adding 1 N HCl to afford the acid 45. The acid, obtained from the ester 13, was stirred with CDI in DMF, followed by stirring with trifluoroethanol and DBU to provide the ester 46 (JYI-049). This material 46 was heated with trimethysilylacetylene in a Heck-type coupling reaction to provide the trimethylsilyl analog 47 (JYI-053). The silyl group was removed from 47 on treatment with tetrabutylammonium fluoride to furnish 48 (JYI-059) in 70% yield.

Procedure:

8-Bromo-6-(2'-fluorophenyl)-4H-benzo[f]imidazo[1,5-a][1,4]diaze-pine-3-carboxylic acid 45. The ester 13 (1.0 g, 2.36 mmol) was dissolved in EtOH (80 mL) and 2 N aq NaOH (8 mL) was added to the solution. The mixture was stirred at rt for 4 hours. After the EtOH was removed under reduced pressure, the solution was allowed to cool. The pH value was adjusted to 4 by adding 1 N HCl dropwise. The mixture was filtered and the solid was washed with cold water and ethyl ether. The solid was dried to afford 45 (0.96 g, 97%) as a white solid: mp 280° C. (dec); IR (KBr) 3419, 1740, 1611, 1491 cm$^{-1}$; $^1$H NMR (DMSO-d$_6$) δ 4.11 (bs, 1H), 5.99 (bs, 1H), 7.20 (t, 1H, J=8.5 Hz), 7.32 (t, 1H, J=7.5 Hz), 7.38 (d, 1H, J=1.8 Hz), 7.55 (m, 2H), 7.84 (d, 1H, J=8.7 Hz), 7.95 (dd, 1H, J=8.6, 1.9 Hz), 8.35 (s, 1H). MS (EI) m/e (relative intensity) 400 (72), 399 (85), 381 (100), 355 (82).

2,2,2-Trifluoroethyl-8-bromo-6-(2'-fluorophenyl)-4H-benzo[f]imidazo[1,5-a][1,4]diazepine-3-carboxylate 46 (JYI-049). The carboxylic acid 45 (0.89 g, 2.23 mmol) was dissolved in dry DMF (20 mL), after which CDI (0.72 g, 4.45 mmol) was added at rt and the mixture was stirred for 12 hours. The trifluoroethanol (0.49 mL, 6.68 mmol) in DMF (1 mL) and DBU (0.37 mL, 2.45 mmol) in DMF (1 mL) were then added to the mixture and stirring continued overnight. The solvent was evaporated under reduced pressure and the residue was purified by flash chromatography (silica gel, hexanes/EtOAc: 3/1) to afford 46 (JYI-049, 0.81 g, 76%) as a white solid: mp: 223-224° C.; IR (CHCl$_3$) 3063, 1732, 1611, 1492 cm$^{-1}$; $^1$H NMR (CDCl$_3$) δ 4.16 (bs, 1H), 4.80 (bs, 2H), 6.07 (bs, 1H), 7.06 (dt, 1H, J=8.3, 0.9 Hz), 7.30 (m, 2H), 7.48 (m, 2H), 7.68 (dt, 1H, J=7.6, 1.8 Hz), 7.80 (dd, 1H, J=8.6, 2.1 Hz), 8.11 (s, 1H). MS (EI) m/e (relative intensity) 483 (38), 383 (64), 355 (100). Anal. Calcd. for C$_{20}$H$_{12}$N$_3$O$_2$F$_4$Br: C, 49.81; H, 2.51; N, 8.71. Found: C, 49.97; H, 2.44; N, 8.68.

2,2,2-Trifluoroethyl-8-trimethylsilylacetylenyl-6-(2'-fluorophenyl)-4H-benzo[f]imidazo[1,5-a][1,4]diazepine-3-carboxylate 47 (JYI-053). A mixture of bromide 46 (JYI-049, 482 mg, 1.0 mmol), trimethylsilylacetylene (0.28 mL, 2.0 mmol) and bis(triphenylphosphine)palladium (II) acetate (75 mg, 0.1 mmol) in a mixed solvent system of CH$_3$CN (25 mL) and anhydrous triethylamine (25 mL) was heated to reflux under argon. After stirring for 12 h at reflux, the mixture was cooled to room temperature and the precipitate which formed was removed by filtration. The filtrate was concentrated under reduced pressure and the residue was treated with a saturated aq solution of NaHCO$_3$ (40 mL), and extracted with CHCl$_3$ (3×100 mL). The combined organic extracts were washed with brine (2×50 mL) and dried (Na$_2$SO$_4$). After removal of solvent under reduced pressure, the residue was purified by flash chromatography (silica gel, hexanes/EtOAc: 3/1) to afford 47 (JYI-053, 360 mg, 76%) as a gray solid: mp 220-221° C.; IR (CHCl$_3$) 2960, 1741, 1612, 1496 cm$^{-1}$; $^1$H NMR (CDCl$_3$) δ 0.25 (s, 9H), 4.12 (bs, 1H), 4.82 (bs, 2H), 6.10 (bs, 1H), 7.06 (t, 1H, J=8.3 Hz), 7.30 (m, 1H), 7.48 (m, 2H), 7.56 (d, 1H, J=8.3 Hz), 7.67 (m, 1H), 7.73 (dd, 1H, J=8.3, 1.8 Hz), 8.02 (s, 1H); MS (EI) m/e (relative intensity) 499 (52), 399 (45), 371 (100), 235 (21), 178 (36). Anal. Calcd. for C$_{25}$H$_{21}$N$_3$O$_2$F$_4$Si: C, 60.11; H, 4.24; N, 8.41. Found: C, 60.27; H, 4.22; N, 8.33.

Trifluoroethyl-8-acetyleno-6-(2'-fluorophenyl)-4H-benzo[f]imidazo-[1,5-a][1,4]diazepine-3-carboxylate 48 (JYI-059). A solution of 47 (JYI-053, 475 mg, 1.0 mmol) in THF (15 mL) was treated with Bu$_4$NF (2 mL, 1.0M solution in THF). The mixture, which resulted, was allowed to stir for 5 min at room temperature after which the mixture was added to H$_2$O (5 mL) and extracted with EtOAc (3×10 mL). The combined organic extracts were washed with brine (2×10 mL) and dried (Na$_2$SO$_4$). The solvent was removed under reduced pressure and the residue was recrystallized from ethyl acetate/hexanes to afford 48 (JYI-059, 299 mg, 70%) as a pale yellow solid: mp: 192-193° C.; IR (CHCl$_3$) 3295, 3052, 1741, 1612, 1494, 1277, 1159 cm$^{-1}$; $^1$H NMR (CDCl$_3$) δ 3.14 (s, 1H), 4.17 (bs, 1H), 4.78 (bs 2H), 4.47 (s, 1H), 6.05 (bs, 1H), 7.05 (dt, 1H, J=8.3, 0.8 Hz), 7.30 (m, 1H), 7.48 (m, 2H), 7.60 (d, 1H, J=8.3 Hz), 7.68 (dt, 1H, J=7.6, 1.8 Hz), 7.76 (dd, 1H, J=10.1, 1.8 Hz), 8.02 (s, 1H); MS (EI) m/e (relative intensity) 427 (37), 327 (26), 299 (100), 178 (50). Anal. Calcd. for C$_{22}$H$_{13}$N$_3$O$_2$F$_4$: C, 61.83; H, 3.07; N, 9.83. Found: C, 61.94; H, 3.03; N, 9.68.

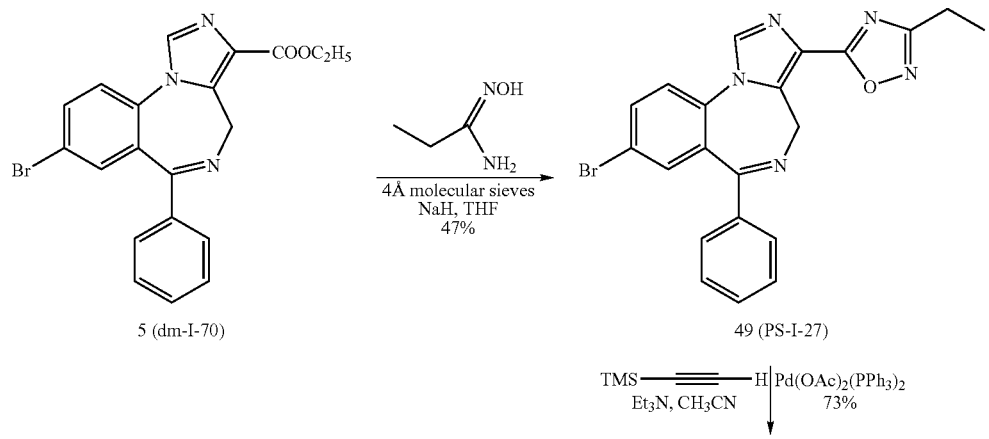

Scheme 11

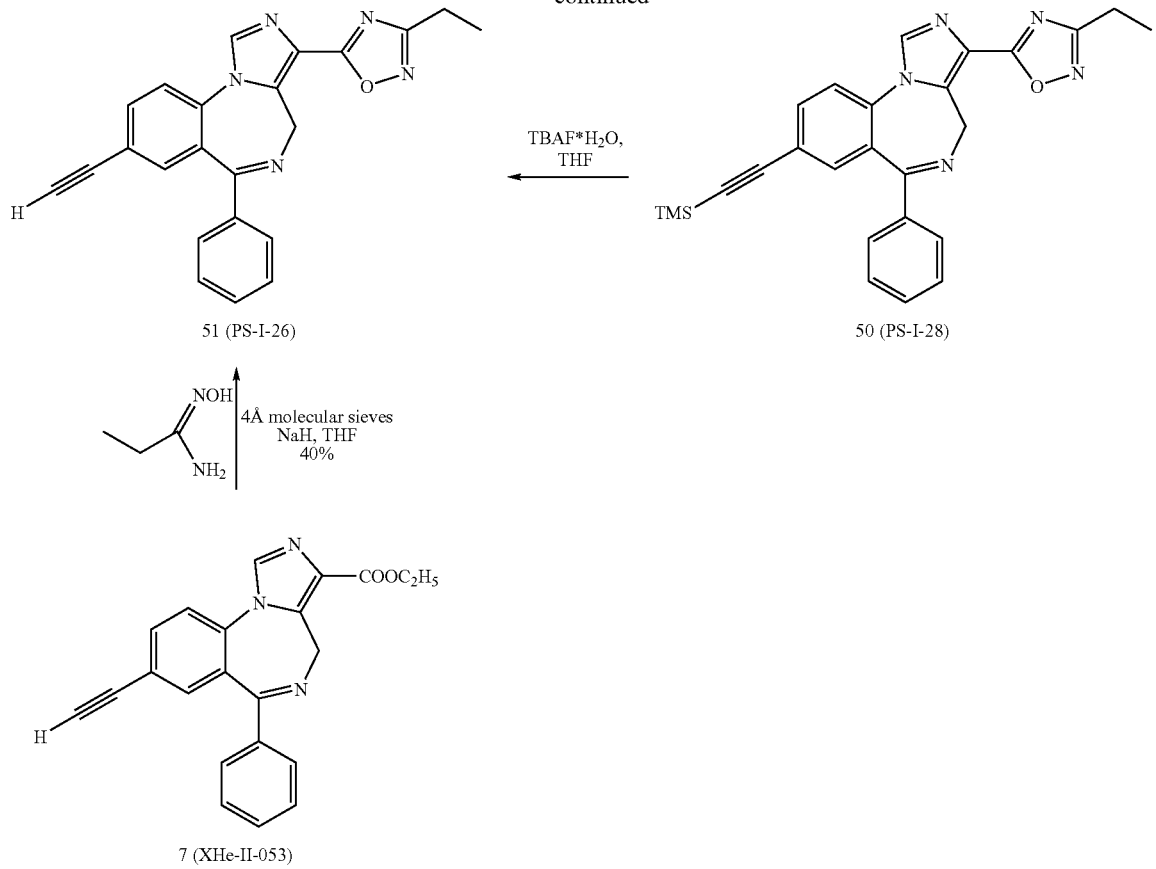

Ethyl amido oxime (59.5 mg, 0.676 mmol) was added to a stirred suspension of powdered 4 Å molecular sieves (75 mg) in anhydrous THF (15 mL) under nitrogen. After the mixture was stirred at rt for 10 min, NaH (27 mg of 60% in mineral oil, 0.676 mmol) was added to the mixture. After the mixture was stirred for a further 30 min, a solution of the forgoing ester 7 (XHeII-053, 120 mg, 0.338 mmol) in THF (20 mL) was added. The mixture which resulted was heated to reflux for 8 hr. It was cooled to rt, after which acetic acid (40.6 mg, 0.676 mmol) was added. After the solution was stirred for 10 min, the mixture was filtered through celite. The filtrate was diluted with $CH_2Cl_2$ (50 mL) and washed with water, brine and dried ($K_2CO_3$). Evaporation of the solvent under reduced pressure afforded a pale yellow solid, which was purified by flash column chromatography (silica gel, EtOAc/hexane, 2:3) to furnish 51 as a white solid (PS-I-26, 52 mg, 40%). mp: 221-222° C.; IR (KBr) 3297, 3105, 1631, 1570, 1495, 1310, 938 cm$^{-1}$; $^1$H NMR (CDCl$_3$) δ 8.07 (s, 1H), 7.80 (dd, 1H, J=8.4 Hz, J=1.8 Hz), 7.64-7.60 (m, 2H), 7.53-7.37 (m, 5H), 6.12 (d, 1H, J=12.9 Hz), 4.21 (d, 1H, J=12.9 Hz), 3.20 (s, 1H), 2.88 and 2.83 (ABq, 2H, J=7.6 Hz), 1.41 (t, 3H, J=7.6 Hz); $^{13}$C NMR (CDCl$_3$) δ 171.8, 170.6, 168.8, 139.1, 136.6, 135.8, 135.4 (2C), 135.1, 130.7, 129.3 (2C), 128.3 (2C), 128.1, 124.7, 122.7, 121.6, 81.2, 80.0, 44.7, 19.7, 11.5; MS (m/z) 379 (100).

This compound 49 (PS-I-27) was obtained in 47% yield from 5 (dm-I-70) analogous to the procedure employed in [00125] as a white solid. mp: 210° C.; IR (KBr) 3106, 1631, 1563, 1493, 1147, 931, 698 cm$^{-1}$; $^1$H NMR (CDCl$_3$) δ 8.06 (s, 1H), 7.84 (dd, 1H, J=8.6 Hz, J=2.25 Hz), 7.63-7.38 (m, 7H), 6.13 (d, 1H, J=12.9 Hz), 4.21 (d, 1H, J=12.9 Hz), 3.20 (s, 1H), 2.88 and 2.83 (ABq, 2H, J=7.6 Hz), 1.41 (t, 3H, J=7.6 Hz); MS (m/z) 435 (100). Anal. Calcd. for $C_{21}H_{16}N_5OBr$: C, 58.23; H, 3.71; N, 15.99. Found: C, 58.08; H, 3.71; N, 16.13.

To the suspension of compound 49 (PS-I-27, 0.5 g, 1.15 mmol) in acetonitrile (30 mL) and triethylamine (80 mL) was added bis(triphenylphosphine)palladium (II) acetate (0.086 g, 0.115 mmol). The solution was degassed and trimethylsilylacetylene (0.33 mL, 2.3 mmol) added. The mixture was heated to reflux and stirred overnight. After removal of the solvent, the residue was dissolved in $CH_2Cl_2$ and washed with a saturated aqueous solution NaHCO$_3$ and brine. The organic layer was dried (Na$_2$SO$_4$) filtered and concentrated under vacuum. The residue was purified by flash column chromatography (EtOAc:hexane 2:3) to furnish the trimethylsilyl analog 50 (PS-I-28, 380 mg, 73%) as a pale yellow solid: mp: 193-194° C.; IR (KBr) 3106, 2960, 2149, 1630, 1567, 1493, 938, 851, 701 cm$^{-1}$; $^1$H NMR (300 Hz, CDCl$_3$) δ 8.07 (s, 1H), 7.78 (dd, 1H, J=1.86 Hz and 8.34 Hz), 7.61-7.38 (m, 7H), 6.11 (d, J=12.78 Hz), 4.19 (d, J=12.78 Hz), 2.88 and 2.83 (ABq, 2H, J=7.56 Hz), 1.41 (t, 3H, J=7.56 Hz), 0.25 (s, 9H). Anal. Calcd. for $C_{26}H_{27}N_5OSi \cdot 0.1H_2O$: C, 68.43; H, 5.64; N, 15.17. Found: C, 68.57; H, 6.02; N, 15.37.

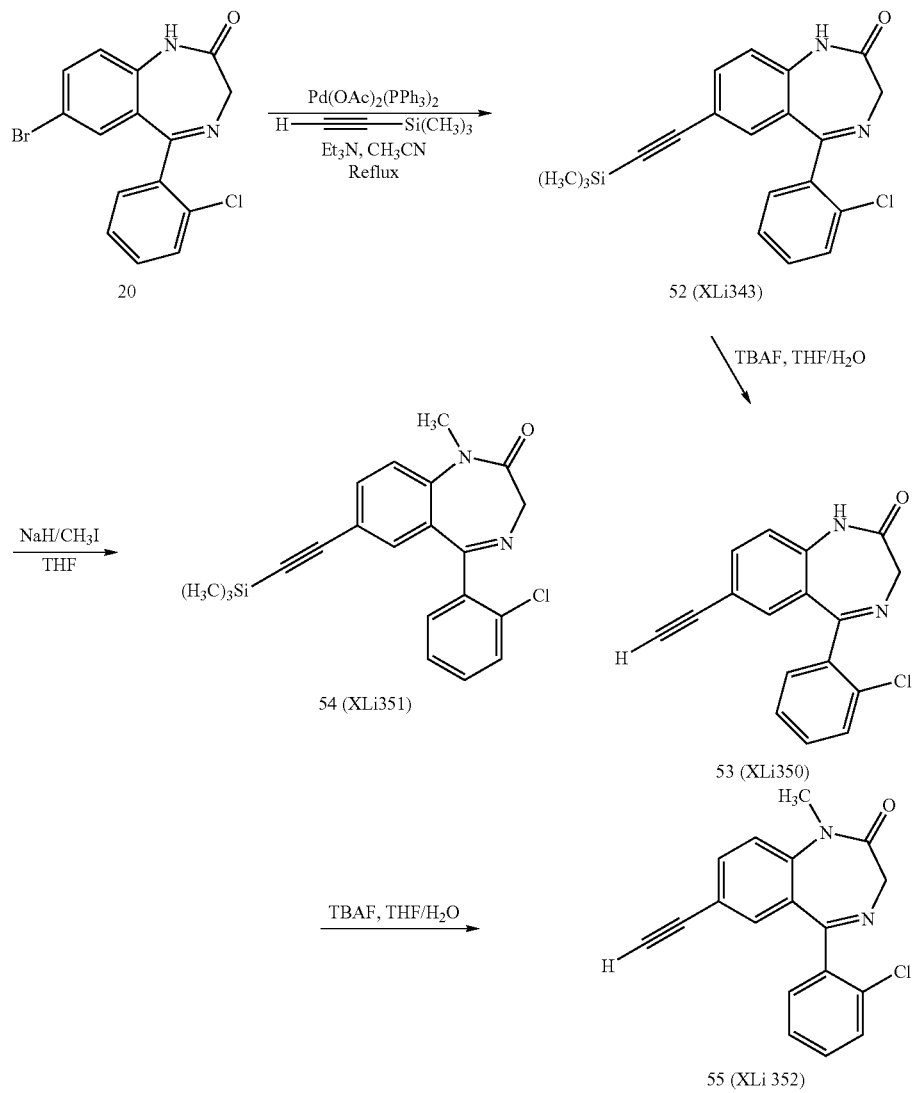

Scheme 12

The bromide 20 (Bogatskii A V, et al., (1977) Pharm Chem J (Engl Transl) 11:1520-1525; Vejdelek Z, Protiva M (1983) Collect Czech Chem Commun 48:1477-1482) was reacted with trimethylsilyacetylene in the presence of a palladium catalyst to provide trimethylsilyl analog 52. This product was methylated with methyl iodide/sodium hydride to give the N-methyl benzodiazepine 54 (XLi 351). This was subjected to fluoride-mediated desilylation to furnish 53 (XLi 350) from 53 and 55 (XLi 352) from 54.

Procedure for XLi 350 and XLi 352

7-Trimethylsilylacetyleno-5-phenyl-(2'-chlorophenyl)1,3-dihydrobenzo[e]-1,4-diazepin-2-one 52 (XLi 343). A mixture of 20 (500 mg, 1.43 mmole) available from references 9 and 10 in triethyl amine (10 mL) and $CH_3CN$ (16 mL) with trimethyl-silylacetylene (126 mg, 1.28 mmole) and bis(triphenylphosphine)palladium (II) acetate (64.3 mg, 0.086 mmol) was heated to reflux under nitrogen. After 6 hours, the reaction mixture was cooled to room temperature and filtered. The filtrate was concentrated under vacuum and the residue was treated with a saturated aqueous $NaHCO_3$ solution (15 mL), and extracted with $CH_2Cl_2$ (3×20 mL). The organic layers were combined and washed with brine and dried ($Na_2SO_4$). After removal of solvent under reduced pressure, the residue was purified via flash chromatography (silica gel, EtOAc/hexanes: 1/1) to furnish 52 as a yellow powder (310 mg, 59%): mp: 225.8-228.2° C.; IR (KBr) 2953, 2358, 1685, 1616, 1490, 1328, 1248, 1058, 1011, 841, 746 $cm^{-1}$, $^1H$ NMR ($CDCl_3$) δ 0.21 (s, 9H), 4.38 (s, 2H), 7.41 (d. 1H, J=8.37 Hz), 7.19-7.52 (br, 7H), 8.11 (s,1H); MS (EI) m/e (relative intensity) 366 ($M^+$, 100), 331(59), 229(18), 161(26).

7-Acetyleno-5-phenyl-(2-chlorophenyl)-1,3-dihydrobenzo [e]-1,4-diazepin-2one 53 (XLi 350):[7] A solution of 52 (150 mg, 0.408 mol) in THF (30 mL) was treated with tetrabutylammonium fluoride (1M in THF). The mixture was stirred for 20 minutes at room temperature before water (30 mL) was added. The mixture was then extracted with EtOAc (3×30 mL). The combined organic extracts were washed with brine and dried over ($Na_2SO_4$). The solvent was removed under vacuum and the residue which resulted was passed through a wash column (silica gel, EtOAc/hexanes: 4/1) to give 55 as light yellow crystals (110 mg, 95.2%); mp: 215° C.; IR (KBr) 3290, 1685, 1615, 1491, 1328, 731 cm$^{-1}$, $^1$H NMR (CDCl$_3$) δ 3.06 (s, 1H), 4.40 (s, 3H), 7.03-7.61 (m, 7H), 7.58-7.86 (m, 2H), 7.99 (s, 1H); MS (EI) m/e (relative intensity) 294 (M$^+$, 100), 266(75), 265(87), 259(83), 231(40), 201(24), 176(23).

1-Methyl-7-trimethylsilylacetyleno-5-phenyl-(2-chlorophenyl)-1,3-dihydro-benzo[e]-1,4-diazepin-2-one 54 (XLi 351). A sample of 52 (300 mg, 0.82 mmol) was dissolved in dry THF (40 mL) at 0° C. and NaH (60% in mineral oil, 50 mg, 1.25 mmol) was added to the solution in one portion. See Xe, (2000). The slurry was then stirred for 20 min at 0° C. and CH$_3$I (139 mg, 0.98 mmol) was added to the mixture and it was allowed to warm to room temperature. After the mixture stirred for 3 hours at room temperature, the THF was then removed under reduced pressure. The residue was purified by flash chromatography [hexanes/EtOAc (1:4)] to provide the title compound 54 (260 mg, 83%) as a white solid: mp: 196.9-198° C.; IR (KBr) 2953, 1676, 1611, 1489, 1346, 1125, 1078, 913, 742 cm$^{-1}$; $^1$HNMR (CDCl$_3$) δ(ppm) 0.21(s, 9H) 3.46 (s, 3H), 3.54 (d, 1H, J=10.9 Hz), 4.60 (d, 1H. J=10.8 Hz), 7.20-7.43 (m, 5H), 7.58-7.65 (m, 3H). MS (EI) m/e (relative intensity) 380(M$^+$, 8), 366(10), 308(100), 280(88), 273(97), 245(61).

1-Methyl-7-acetyleno-5-phenyl-(2-chlorophenyl)-1,3-dihydro-benzo[e]-1,4diazepin-2-one 55 (XLi 352). A solution of 54 (100 mg, 0.262) in THF (30 mL) was treated with tetrabutylammonium fluoride (1M in THF). The mixture was stirred for 20 minutes at room temperature before water (30 mL) was added. The mixture was then extracted with EtOAc (3×30 mL). See Xe, (2000). The combined organic extracts were washed with brine and dried (Na$_2$SO$_4$). The solvent was removed under vacuum and the residue which resulted was passed through a wash column (silica gel, EtOAc/hexanes: 4/1) to give 55 as light yellow crystals (71 mg, 90%): mp: 95.6-98.1° C.; IR (KBr) 2953, 1677, 1489, 1346, 1091, 791, 749 cm$^{-1}$, $^1$H NMR (CDCl$_3$) δ 3.05(s, 1H), 3.46 (s, 3H), 3.83 (d, 1H, J=10.5 Hz), 4.87 (d, 1H, J=9.33 Hz), 5.28 (s, 1H), 7.20-7.43 (m, 5H), 7.58-7.86 (m, 2H); MS (EI) m/e (relative intensity) 308(M$^+$, 100), 294(19), 280(82), 273(99), 249(28), 245(61), 229(29), 201(32), 189(43).

Scheme 13

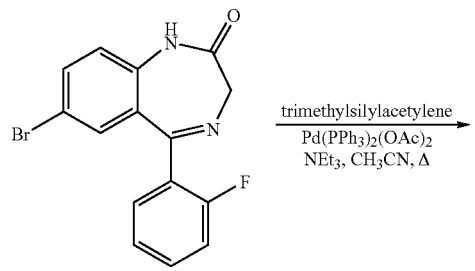

12

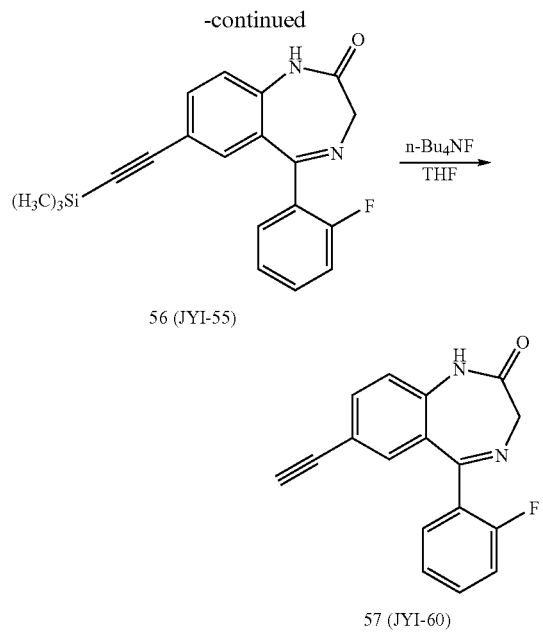

56 (JYI-55)

57 (JYI-60)

7-Trimethylsilylacetyleno-5-(2'-fluorophenyl)-1,3-dihydrobenzo[e]-1,4diazepine-2-one 56 (JYI-55). A mixture of bromide 12 (1.6 g, 5.0 mmol), trimethylsilyl-acetylene (3.0 mL, 21.0 mmol) and bis(triphenylphosphine)palladium (II) acetate (375 mg, 0.5 mmol) in a mixed solvent system of CH$_3$CN (60 mL) and anhydrous triethylamine (40 mL) was heated to reflux under argon. After stirring for 3 h at reflux, the mixture was cooled to room temperature and the precipitate which formed was removed by filtration. The filtrate was concentrated under reduced pressure and the residue was treated with a saturated aq solution of NaHCO$_3$ (100 mL), and extracted with CHCl$_3$ (3×200 mL). The combined organic extracts were washed with brine (2×100 mL) and dried (Na$_2$SO$_4$). After removal of solvent under reduced pressure, the residue was purified by flash chromatography (silica gel, hexanes/EtOAc: 2/1) to afford 56 (JYI-55, 794 mg, 47%) as a gray solid: mp: 168.5-169.5° C.; IR (CHCl$_3$) 3202, 3113, 2955, 1686, 1612, 1490 cm$^{-1}$; $^1$H NMR (CDCl$_3$) δ 0.22 (s, 9H), 4.38 (s, 2H), 7.04-7.33 (m, 3H), 7.34 (s, 1H), 7.45-7.53 (m, 1H), 7.56-7.62 (m, 2H), 8.73 (bs, 1H). MS (EI) m/e (relative intensity) 350 (94), 322 (100), 167 (41), 153 (37). Anal. Calcd. for C$_{20}$H$_{19}$N$_2$OFSi: C, 68.54; H, 5.46; N, 7.99. Found: C, 68.23; H, 5.40; N, 8.34.

7-Acetyleno-5-(2'-fluorophenyl)-1,3-dihydrobenzo[e]1,4-diazepine-2-one 57 (JYI-60). A solution of 56 (JYI-55, 700 mg, 2.0 mmol) in THF (200 mL) was treated with Bu$_4$NF (2 mL, 1.0M solution in THF). The mixture, which resulted, was allowed to stir for 5 min at room temperature after which the mixture was added to H$_2$O (5 mL) and extracted with EtOAc (3×10 mL). The combined organic extracts were washed with brine (2×10 mL) and dried (Na$_2$SO$_4$). After the solvent was removed under reduced pressure, the residue was purified by flash chromatography (silica gel, hexanes/EtOAc: 2/1) to afford 57 (JYI-60, 400 mg, 72%) as a pale yellow solid: mp: 208-209.5° C.; IR (CHCl$_3$) 3290, 3110, 2930, 1685, 1612, 1489 cm$^{-1}$; $^1$H NMR (CDCl$_3$) δ 3.04 (s, 1H), 4.40 (s, 2H), 7.06-7.28 (m, 3H), 7.38 (s, 1H), 7.44-7.51 (m, 1H), 7.59-7.62 (m, 2H), 9.43 (bs, 1H). MS (EI) m/e (relative intensity) 278 (80), 250 (100). Anal. Calcd. for C$_{17}$H$_{11}$N$_2$OF. C, 73.37; H, 3.98; N, 10.07. Found: C, 73.64; H, 3.92; N, 9.78.

Scheme 14

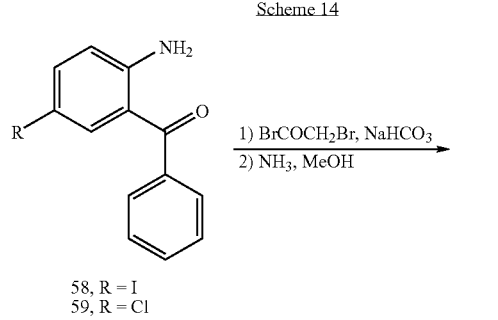

58, R = I
59, R = Cl

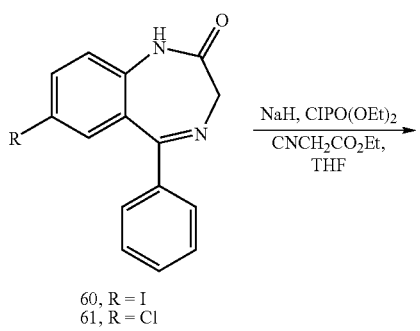

60, R = I
61, R = Cl

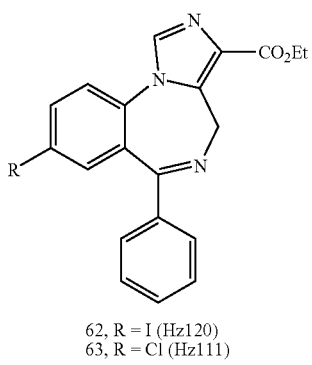

62, R = I (Hz120)
63, R = Cl (Hz111)

2-Amino-5-iodo-benzophenone was prepared from p-iodonitrobenzene and phenylacetonitrile according to Hester J B, et al., (1989) J Med Chem 32:1157-1163. 2-Amino-5-chloro-benzophenone was obtained commercially from Acros. The benzodiazepine 60 was reacted with diethylphosphorochloridate in the presence of sodium hydride, followed by the addition of ethyl isocyanoacetate to provide the ester 62 (Hz120), as shown in Scheme 14.

Ethyl 8-iodo-6-phenyl-4H-benzo[f]imidazo[1,5-a][1,4]diazepine-3carboxylate 62. A solution of benzodiazepine 60 (3 g, 8.3 mmol) in dry THF (36 mL) was cooled to 0° C. and a 60% dispersion of sodium hydride (0.70 g, 17.4 mmol) was added in one portion. The mixture was allowed to warm to rt with stirring and the stirring was continued at rt until no more bubbles were evolved. The suspension was cooled to 0° C. after which diethylphosphorochloridate (2.29 g, 13.3 mmol) was added and this mixture was stirred for 30 min and allowed to warm to rt. The mixture was stirred for an additional 1.5 hr. In another flask, a 60% dispersion of sodium hydride (0.70 g, 17.4 mmol) in mineral oil was added in dry THF (36 mL) and cooled to 0° C. Ethyl isocyanoacetate (1.13 g, 9.94 mmol) was added and the stirring was continued until no more bubbles were evolved. This mixture was transferred to the above mixture at 0° C. The mixture was then stirred at rt for 6 h and quenched with HOAc (3.2 mL). The mixture was partitioned between EtOAc (200 mL) and $H_2O$ (50 mL). The organic layer was washed with brine and dried ($Na_2SO_4$). After the solvent was removed under reduced pressure, the residue was purified by flash chromatography (silica gel, gradient elution, EtOAc:hexane 1:4, 1:1, 4:1) to provide the ester 62 (Hz120) in 43% yield as a light brown solid. mp: 221-222° C.; IR (KBr) 2977, 1717, 1608, 1489 cm$^{-1}$; $^1$H NMR (DMSO-$d_6$) δ 1.31 (t, 3H, J=7.1 Hz), 4.10 (d, 1H, J=12.5 Hz), 4.29 (q, 2H, J=6.7 Hz), 5.75 (d, 1H, J=12.4 Hz), 7.40-7.50 (m, 5H), 7.63 (d, 1H, J=1.8 Hz), 7.69 (d, 1H, J=8.5 Hz), 8.13 (dd, 1H, J=1.9, 8.5 Hz), 8.36 (s, 1H); MS (EI) m/e (relative intensity) 458 (23), 457 (M$^+$, 100), 411 (62), 384 (29), 383 (100), 257 (29). Anal. Calcd. for $C_{20}H_{16}IN_3O_2$: C, 52.53; H, 3.53; N, 9.19. Found: C, 52.57, H, 3.73; N, 8.64.

Ethyl 8-chloro-6-phenyl-4H-benzo[f]imidazo[1,5-a][1,4]diazepine-3-carboxylate 63. This ester 63 was obtained in 52% yield from 61 analogous to the procedure employed in [00129] as a white solid: mp: 174-175° C. (lit.$^{12}$ 174-175° C.); $^1$H NMR (DMSO-$d_6$) δ 1.32 (t, 3H, J=7.1 Hz), 4.13 (d, 1H, J=12.3 Hz), 4.32 (q, 2H, J=6.7 Hz), 5.76 (d, 1H, J=12.3 Hz), 7.37-7.50 (m, 6H), 7.86-8.38 (m, 2H), 8.74 (s, 1H).

Scheme 15

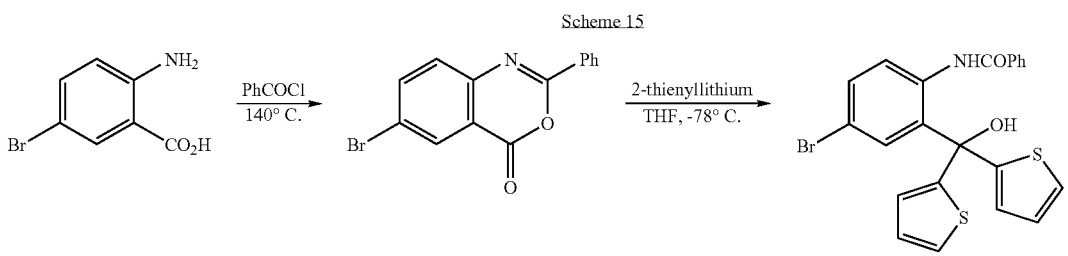

64

65

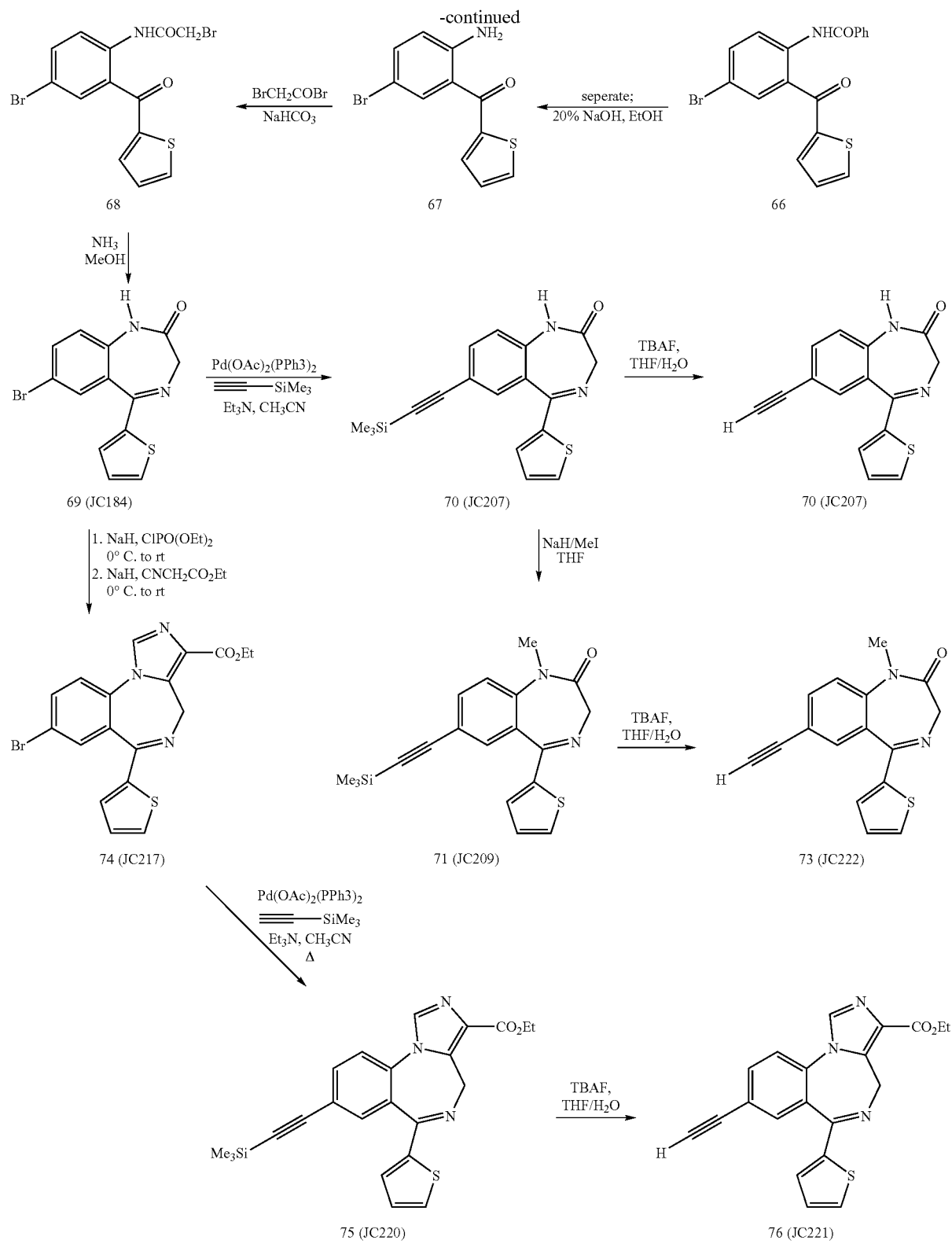
6-Bromo-2-phenyl-4H-benzo[2,3-d]-1,3-oxazin-4-one 64. The 2-amino-5-bromobenzoic acid (5 g, 23.1 mmol) was treated with benzoyl chloride (237 mL, 2.04 mol) at 140° C. for 3 h. After the reaction mixture was cooled to rt, the crystals that formed were collected by filtration and were washed with hexanes to provide 64 as light brown needles (6.8 g, 97%): mp: 199-201° C.; $^1$H NMR (CDCl$_3$) δ 7.51-7.2 (m, 4H), 7.9 (dd, 1H, J=2.3, 8.6 Hz), 8.30-8.33 (m, 2H), 8.8 (d, 1H, J=2.2

Hz); $^{13}$C NMR (CDCl$_3$) δ 158.19, 157.35, 145.75, 139.58, 132.82, 130.97, 129.77, 128.82, 128.73, 128.29, 121.37, 118.27; MS (EI) m/e (relative intensity) 303 (M$^+$, 36), 301 (M$^+$, 36), 259 (14), 257 (14), 226 (6), 224 (6), 178 (9), 170 (9), 168 (9), 151 (4), 105 (100).

4-Bromo-2-(2'-thienylcarbonyl)-N-benzoylaniline 66 and bis-(2'-thienyl)-[5-bromo-2-(N-benzoyl)-amino]phenyl-methanol 65. The benzoxazinone 64 (5.0 g, 16.6 mmol) was dissolved in dry THF (250 mL) and cooled to −78° C. for 45 min. The 2-thienyllithium (18.21 mL of 1M solution in THF) was added dropwise over 35 min and the reaction was stirred at −78° C. for 1.2 h. Saturated aq NH$_4$Cl solution (25 mL) and Et$_2$O (30 mL) were then added. The organic layer was separated, washed with brine and dried (MgSO$_4$). The solvent was removed under reduced pressure, and the residue was purified via flash chromatography (silica gel, hexanes/EtOAc: 1:0, 49:1, 20:1, 11:1, 5:1) to provide 66 as yellow crystals and the alcohol 65. 66: $^1$H NMR (CDCl$_3$) δ 7.23 (dd, 1H), 7.52-7.56 (m, 3H), 7.66 (dd, 1H, J=0.99, 3.8 Hz), 7.82 (d, 1H, J=5.0 Hz), 7.99-8.02 (m, 3H), 7.75 (d, 1H, J=9.0 Hz), 11.2 (s, 1H); $^{13}$C NMR (CDCl$_3$) δ 188.82, 165.45, 143.24, 138.79, 136.57, 135.90, 135.51, 134.25, 134.03, 132.17, 128.81, 128.31, 127.26, 125.65, 123.45, 114.95; MS (EI) m/e (relative intensity) 387 (M$^+$, 12), 385 (M$^+$, 12), 276 (18), 274 (18), 201 (7), 172 (7), 105 (100). 65: mp: 124-127° C.; $^1$H NMR (CDCl$_3$) δ 4.20 (s, 1H), 6.82 (s, 2H), 6.96-7.01 (m, 3H), 7.33-7.38 (m, 7H), 7.65 (d, 2H, J=7.23 Hz), 8.43 (d, 1H, J=8.8 Hz), 9.92 (s, 1H); $^{13}$C NMR (CDCl$_3$) δ 165.04, 148.94, 136.44, 135.49, 134.49, 132.34, 131.59, 131.40, 128.40, 127.20, 126.89, 126.58, 124.18, 116.00, 79.35, 76.92, 76.50; MS (EI) m/e (relative intensity) 471 (M$^+$, 54), 469 (M$^+$, 51), 453 (100), 451 (93), 348 (98), 346 (92), 316 (54), 314 (58), 282 (20), 280 (19), 267 (88), 235 (12), 234 (12), 223 (15), 222 (17), 201 (56), 173 (20), 172 (12), 158 (10), 129 (10).

5-Bromo-2-(2'-thienylcarbonyl) aniline 67. The amide 66 (2 g, 635 mmol) was dissolved in EtOH (150 mL) and 20% NaOH solution (30 mL) was added. The mixture was heated to reflux for 5 h and the EtOH was removed under reduced pressure. The mixture was extracted with EtOAc and the organic phases were combined, washed with brine and dried (Na$_2$SO$_4$). The solvent was removed under reduced pressure, and the residue was purified via a wash column (silica gel, hexanes/EtOAc: 11:1 to 4:1) to provide 67 as a bright yellow solid: mp: 101-103° C.; $^1$H NMR (DMSO-d$_6$) δ 6.28 (br s, 2H), 6.82 (s, 1H), 6.90 (s, 1H), 7.26 (dd, 1H, J=3.8, 5.0 Hz), 7.42 (dd, 1H, J=2.4, 8.9 Hz), 7.61 (dd, 1H, J=1.1, 3.8 Hz), 7.69 (dd, 1H, J=2.4 Hz), 8.04 (dd, 1H, J=1.1, 5.0 Hz); $^{13}$C NMR (DMSO) δ 187.42, 150.09, 143.87, 136.46, 134.75, 134.41, 133.93, 128.78, 119.36, 119.17, 104.95; MS (EI) m/e (relative intensity) 283 (M$^+$, 59), 282 (M$^+$, 87), 281 (M$^+$, 59), 280 (M$^+$, 79), 250 (23), 248 (23), 201 (13), 199 (49), 197 (48), 172 (25), 170 (23), 145 (13), 140 (1), 111 (100), 101 (33).

4-Bromo-2-(2'-thienylcarbonyl)-N-bromoacetylaniline 68. The thienylaniline 67 (3.3 g, 11.7 mmol) and NaHCO$_3$ (2.9 g, 34.5 mmol) were suspended in dry CHCl$_3$ (180 mL) and cooled to 0° C. A solution of bromoacetyl bromide (1.12 mL, 12.9 mmol) in dry CHCl$_3$ (30 mL) was added dropwise over 20 min at 0° C. and the mixture was stirred at rt for 3 h. The CHCl$_3$ solution was then washed with aq NaHCO$_3$ (5%) and dried (Na$_2$SO$_4$). The CHCl$_3$ was removed under reduced pressure, and Et$_2$O was added to the flask. The solution was sonicated and filtered to provide 68 as a light solid: mp: 144.0-146.5° C.; $^1$H NMR (CDCl$_3$) δ 4.01 (s, 2H), 7.23-7.26 (m, 1H), 7.24 (d, 1H), 7.65 (d, 1H), 7.74 (d, 1H), 7.84 (d, 1H), 8.46 (d, 1H), 10.85 (br s, 1H); MS (EI) m/e (relative intensity) 405 (M$^+$, 69), 404 (40), 403 (M$^+$, 100), 401 (M$^+$, 66), 324 (39), 322 (38), 310 (33), 308 (33), 292 (32), 283 (65), 282 (72), 281 (65), 280 (67), 266 (10), 264 (10), 250 (34), 248 (35), 226 (55), 224 (55), 201 (43), 199 (27), 197 (27), 173 (32), 111 (73).

7-Bromo-5-(2'-thienyl)-1,3-dihydrobenzo[e][1,4]diazepine 69 (JC184). The bromoacetyl amide 68 (0.236 g, 0.586 mmol) was dissolved in a saturated solution of anhydrous ammonia in MeOH (50 mL) and the mixture was heated to reflux for 6 h. After the MeOH was removed under reduced pressure, EtOAc was added to the residue. The solution was sonicated and then filtered to provide 69 (JC184) as a light solid: mp: 208-211° C.; MS (EI) m/e (relative intensity) 322 (M$^+$, 54), 320 (M$^+$, 53), 294 (100), 292 (98), 211 (24), 185 (31), 140 (21). The material was used directly in the next step.

7-Trimethylsilylacetylenyl-5-(2'-thienyl)-1,3-dihydrobenzo[e][1,4]diazepine 70 (JC207). A mixture of 69 (1 g, 3.12 mmol) in CH$_3$CN (20 mL) and Et$_3$N (30 mL) was degassed and heated to reflux under nitrogen. Bis(triphenylphosphine)-palladium (II) acetate (0.26 g, 0.347 mmol) was then quickly added, followed by the addition of TMS acetylene (0.76 g, 7.78 mmol). The mixture was stirred at reflux for 4 h and the solvent was removed under reduced pressure. Water (25 mL) and EtOAc (25 mL) were added to the residue and the mixture was filtered through celite to remove the organometallic species. The filtrate was then extracted with EtOAc and the organic phases were combined, washed with brine and dried (Na$_2$SO$_4$). The solvent was removed under reduced pressure and the residue was purified via flash chromatography (silica gel, hexanes/EtOAc: 11:1, 5:1) to provide 70 (JC207) as a light yellow solid: mp: 198.5-201° C.; MS (EI) m/e (relative intensity) 338 (M$^+$, 68), 337 (M$^+$, 28), 310 (100), 295 (13), 161 (13), 147 (33), 105 (17). The material was used directly in the next step.

7-Acetylenyl-5-(2'-thienyl)-1,3-dihydrobenzo[e][1,4]diazepine 72 (JC208). A solution of 70 (150 mg, 0.457 mmol) in THF (30 mL) was treated with tetrabutylammonium fluoride (1M in THF) at 0° C. for 5 minutes. Water (20 mL) was subsequently added to quench the reaction and the THF was removed under reduced pressure. The remaining aq solution was then extracted with EtOAc and the organic phases were combined, washed with brine and dried (Na$_2$SO$_4$). Upon removal of the solvent, Et$_2$O was added to the residue which was sonicated and then filtered to provide the title compound 72 (JC208, 111 mg, 91%) as an ivory colored solid: mp: 214-216° C.; MS (EI) m/e (relative intensity) 266 (M$^+$, 61), 265 (M$^+$, 30), 238 (100), 237 (49), 210 (13), 209 (10), 164 (6), 153 (7), 139 (7). This material was used in the next step.

1-N-methyl-7-trimethylsilylacetylenyl-5-(2'-thienyl)-1,3-dihydrobenzo [e][1,4]diazepine 71 (JC209). Thiophere 70 (500 g, 1.52 mmol) was dissolved in dry THF (25 mL) at 0° C. and NaH (60% in mineral oil, 76 mg, 1.50 mmol) was added to the solution in one portion. After the mixture was stirred at 0° C. for 30 min, MeI (0.14 mL, 2.25 mmol) was added and the ice bath was allowed to warm to rt. The mixture was allowed to stir for 3 h and the THF was then removed under reduced pressure. The residue was purified via flash chromatography (silica gel, hexanes/EtOAc 8:1, 4:1) to provide the title compound 71 (JC209) as a white solid: mp: 171.3-173.6° C.; $^1$H NMR (CDCl$_3$) δ 0.26 (br s, 9H), 3.38 (s, 3H), 4.71 (d, 1H), 7.09 (dd, 1H, J=3.7, 5.0 Hz), 7.17 (dd, 1H, J=1.1, 3.7 Hz), 7.30 (s, 1H), 7.49 (dd, 1H, J=1.1, 5.0 Hz), 7.65 (dd, 1H, J=2.0, 8.5 Hz), 7.75 (d, 1H); $^{13}$C NMR (CDCl$_3$) δ 170.12, 163.22, 143.65, 143.14, 134.69, 133.12, 131.38, 130.14, 127.77, 127.47, 121.01, 119.10, 103.01, 95.66, 56.38, 34.67; MS (EI) m/e (relative intensity) 352 (M$^+$, 71), 351 (M$^+$, 60), 337 (10), 324 (100), 309 (24), 168 (28), 154 (38).

1-N-methyl-7-acetyleno-5-(2'-thienyl)-1,3-dihydrobenzo [e][1,4]diazepine 73 (JC222). The same procedure for preparing 72 (JC208) was applied to 73 (JC222) and a very light brown solid resulted: mp: 218.3-220.4° C.; $^1$H NMR (CDCl$_3$) δ 3.16 (s, 1H), 3.39 (s, 3H), 3.78 (d, 1H, J=11.07 Hz), 4.72 (d, 1H, J=5.9 Hz), 7.08 (dd, 1H, J=3.8, 5.0 Hz), 7.31 (d, 1H, J=8.6 Hz), 7.49 (dd, 1H, J=1.0, 5.0 Hz), 7.67 (dd, 1H, J=2.0, 8.5 Hz), 7.79 (d, 1H, J=1.9 Hz); $^{13}$C NMR (CDCl$_3$) δ 171.04, 170.07, 163.12, 143.49, 134.79, 133.50, 131.34, 130.25, 127.85, 127.46, 121.16, 117.99, 81.83, 78.30, 56.34, 34.69. MS (EI) m/e (relative intensity) 281 (13), 280 (M$^+$, 60), 279 (51), 253(19), 252 (100), 251(2), 235 (11), 209(10).

Ethyl 8-bromo-6-(2'-thienyl)-4H-benzo[f]imidazo[1,5-a][1,4]diazepine-3-carboxylate 74 (JC217). Dry THF (30 mL) was added to a flask containing the benzodiazeoine 69 (1.27 g, 3.96 mmol) and the solution was allowed to cool to 0° C. and NaH (60% in mineral oil, 0.191 g, 4.76 mmol) was quickly added. The mixture was stirred for 30 min at 0° C. and then removed from an ice bath to stir another 1 h at rt. Prior to adding ClPO(OEt)$_2$ (1.06 g, 6.35 mmol), the mixture was again pre-cooled to 0° C. The solution was stirred another 3 h as the ice bath warmed to rt. Meanwhile, dry THF (10 mL) was added to a second flask containing NaH (60% in mineral oil, 0.229 g, 5.72 mmol). After the second mixture was cooled to 0° C., CNCH$_2$CO$_2$Et was added dropwise and the solution continued to stir for 30 min at 0° C. After both reaction mixtures were again pre-cooled to 0° C., the two solutions were combined under Ar via cannula and the solution stirred at rt overnight. The reaction was quenched with ice water and worked up with EtOAc, and the combined organic phases were washed with brine and dried (Na$_2$SO$_4$). The solvent was removed under reduced pressure and the residue was purified via flash chromatography (silica gel, hexanes: EtOAc 4:1, 1:1, 1:3) to provide the title compound 74 (JC217) as an ivory solid (500 mg, 30% yield): mp: 204.0-205.3° C.; $^1$H NMR (CDCl$_3$) δ 1.45 (t, 3H, J=7.1, 14.3 Hz), 4.07 (d, 1H, J=8.8 Hz), 4.44 (dd, 2H, J=3.8, 4.7 Hz), 5.98 (d, 1H, J=12.8 Hz), 7.05 (d, 1H, J=1.0 Hz), 7.07 (s, 1H), 7.46-7.49 (m, 2H), 7.83 (dd, 1H, J=2.2, 8.5 Hz), 7.91 (s, 1H), 7.96 (d, 1H, J=2.2 Hz): MS (EI) m/e (relative intensity) 418 (M$^+$, 15), 417 (M$^+$, 68), 416 (M$^+$, 15), 415 (M$^+$, 64), 407 (22), 344 (26), 343 (100), 342 (30), 341 (93), 293 (15), 291 (21), 262 (18), 235 (15), 211 (12), 154 (10), 127 (11).

Ethyl 8-trimethylsilylacetylenyl-6-(2-thienyl)-4H-benzo[f]imidazo[1,5-a][1,4]diazepine-3-carboxylate 75 (JC220). The same procedure for preparing 70 (JC207) was applied to 75 (JC220) and an ivory colored solid resulted: mp: 124-127° C.; $^1$H NMR (CDCl$_3$) δ 0.29 (s, 9H), 1.45 (t, 3H, J=7.1, 14.3 Hz), 4.0 (d, 1H, J=18.1 Hz), 4.45 (dd, 2H, J=7.2, 8.5 Hz), 5.97 (d, 1H, J=12.8 Hz), 7.06-7.11 (m, 2H), 7.49 (dd, 1H, J=1.2, 5.0 Hz), 7.52 (d, 1H, J=8.3 Hz), 7.77 (dd, 1H, J=1.9, 8.3 Hz), 7.90 (d, 1H, J=1.8 Hz), 7.93 (s, 1H). MS (EI) m/e (relative intensity) 433 (M$^+$, 74), 387 (49), 359 (100), 277 (28), 262 (19), 235 (24), 172 (19), 129(17).

Ethyl 8-acetyleno-6-(2'-thienyl)-4H-benzo[f]imidazo[1,5-a][1,4]diazepine-3-carboxylate 76 (JC221). The same procedure for preparing 72 (JC208) was applied to 76 (JC221) and an ivory colored solid resulted: mp: >198° C. dec.; $^1$H NMR (CDCl$_3$) δ 1.43 (t, 3H, J=4.3, 11.4 Hz), 3.25 (s, 1H), 4.10 (d, 1H, J=12.8 Hz), 4.40-4.49 (m, 2H), 5.99 (d, 1H, J=12.9 Hz), 7.50 (d, 1H, J=5.0 Hz), 7.56 (d, 1H, J=8.3 Hz), 7.81 (dd, 1H, J=1.8, 8.3 Hz), 7.95 (s, 1H); MS (EI) m/e (relative intensity) 361 (M$^+$, 24), 315 (35), 287 (100), 237 (26), 178 (30), 153 (21), 126 (18).

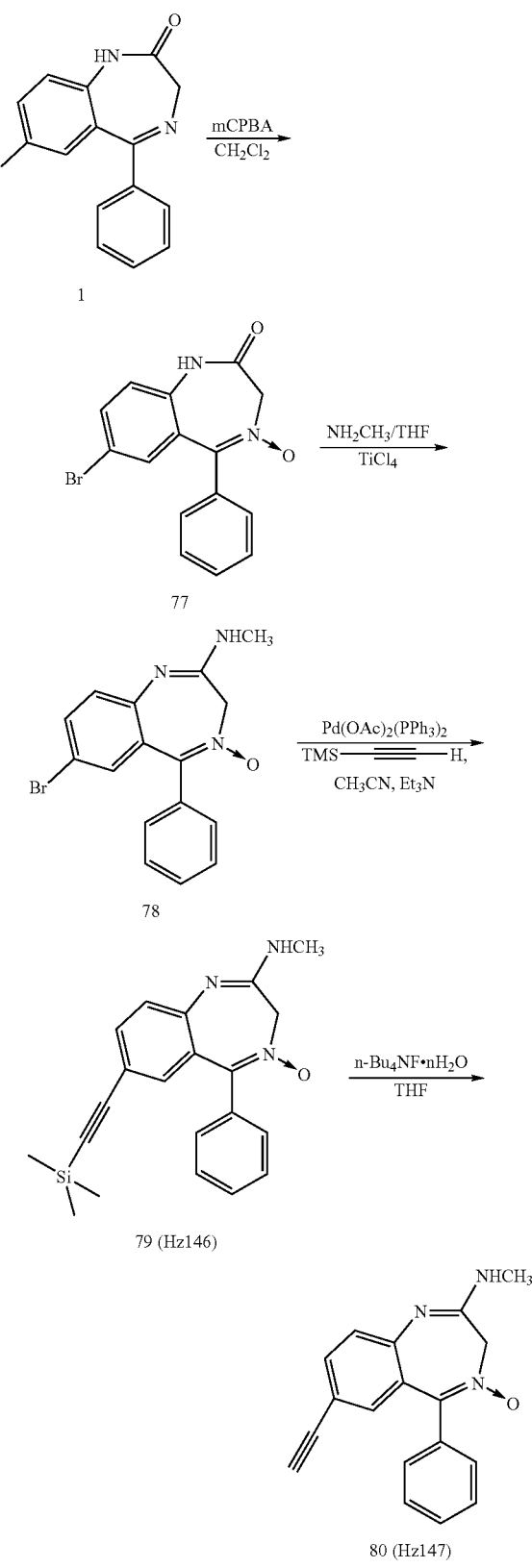

87

Scheme 17

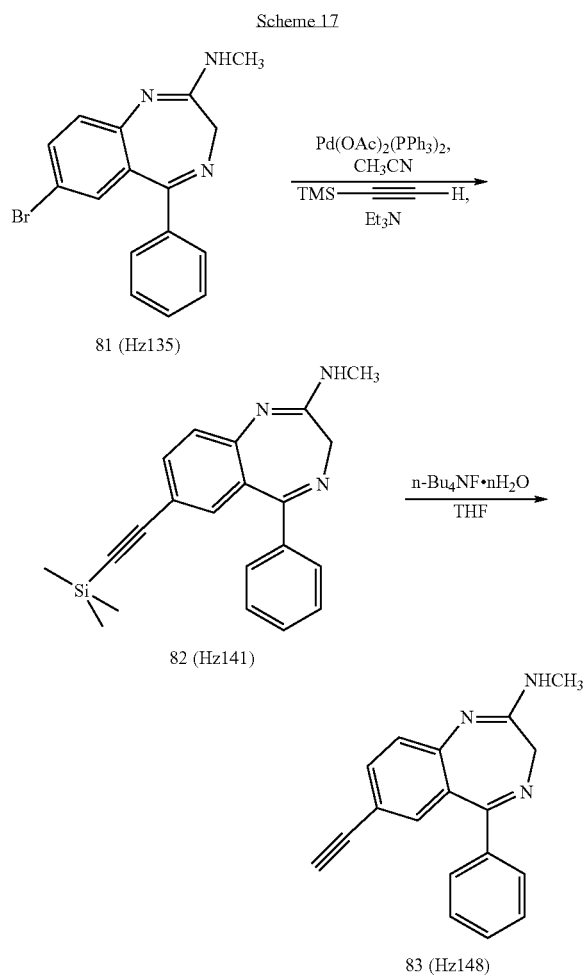

The benzodiazepine 1 was oxidized with 3-chloroperoxybenzoic acid (mCPBA) to form 77, followed by the addition of methylamine to afford amidine 78. N-Oxide 78 was reacted with trimethylsilyacetylene in the presence of a palladium catalyst to provide the trimethylsilyl analog 79 (Hz146) which was subjected to fluoride-mediated desilylation to afford 80 (Hz147), as shown in Scheme 15. In a related route, bromide 81 was converted into the trimethylsilylacetylene 82 (Hz141). This analog was then transformed into target 79 (Hz146) with mCPBA or the key target (Hz148) on treatment with fluoride (Scheme 17).

7-Bromo-4-oxy-5-phenyl-1,3-dihydro-benzo[e][1,4]diazepin-2-one 77. Bromide 1 (1.88 g, 5.95 mmol) was dissolved in $CH_2Cl_2$ (50 mL) and mCPBA (77% max) (1.76 g) was added at rt. The reaction mixture was stirred overnight. The mixture was diluted with $CH_2Cl_2$ (80 mL) and washed with a sat. solution of $NaHCO_3$ (50 mL), water (50 mL) and brine (40 mL). The organic layer was dried ($Na_2SO_4$) and concentrated. The residue was purified by flash chromatography (silica gel, EtOAc) to afford compound 77 in 90% yield as a white solid. mp: 230-231° C. (lit.[13] 230-231° C.); $^1$H NMR (CDCl$_3$) δ 4.69 (s, 2H), 7.16 (d, 1H, J=8.7 Hz), 7.24 (d, 1H, J=2.1 Hz), 7.45 (m, 3H), 7.54 (dd, 1H, J=8.6, 2.2 Hz), 7.64 (dd, 2H, J=7.3, 3.6 Hz), 10.02 (s, 1H).

(7-Bromo-4-oxy-5-phenyl-3H-benzo[e][1,4]diazepin-2-yl)-methyl-amine 78. Methylamine (50 mL, 2 M in THF) was added to 77 (1.9 g, 5.7 mmol) in a 100 mL round-bottom flask.

88

The mixture was cooled to 0° C. after which TiCl$_4$ (0.54 g, 2.86 mmol) was added dropwise. The reaction mixture was allowed to warm to rt and stirred for 4 h. The mixture was quenched with water (5 mL), diluted with EtOAc (100 mL) and washed with dilute $NH_4OH$. The organic layer was washed with water, brine and dried ($Na_2SO_4$). After the solvent was removed under reduced pressure, the residue was purified by flash chromatography (silica gel, gradient elution, EtOAc, EtOAc:MeOH 10:1) to provide 78 in 86% yield as a white solid. mp: 236-237° C. (lit.[14] 242-243° C.); $^1$H NMR (300 MHz, CDCl$_3$) δ 0.21 (s, 9H), 2.91 (s, 3H), 4.17 (s, 1H), 4.85 (s, 1H), 7.13-7.66 (m, 9H).

(7-Trimethylsilylacetylenyl-4-oxy-5-phenyl-3H-benzo[e][1,4]diazepin-2-yl)-methyl-amine 79 (Hz146). Trimethylsilylacetylenyl analog 79 (Hz146) was obtained in 58% yield from 78 analogous to the procedure described above for the synthesis of compound 6 as a light gray solid. mp: 239-240° C.; IR (KBr) 3229, 3060, 2952, 2149, 1616, 1593, 1462, 1238, 868 cm$^{-1}$; $^1$H NMR (300 MHz, CDCl$_3$) δ 2.89 (d, 3H, J=4.4 Hz), 4.14 (d, 1H, J=10.6 Hz), 4.78 (d, 1H, J=10.4 Hz), 7.15 (d, 1H, J=1.7 Hz), 7.24-7.28 (m, 2H), 7.45 (m, 4H), 7.66 (m, 2H); MS (EI) m/e (relative intensity) 361 (M$^+$, 48), 344 (100), 303 (31), 165(33).

(7-Acetylenyl-4-oxy-5-phenyl-3H-benzo[e][1,4]diazepin-2-yl)-methyl-amine 80 (Hz147). The 7-acetyleno target 80 was obtained in 90% yield from 79 analogous to the procedure described above for the synthesis of compound 6 as a light yellow solid. mp: 213-214° C.; IR (KBr) 3242, 3068, 2977, 1619, 1589, 1460, 1414 cm$^{-1}$; $^1$H NMR (300 MHz, CDCl$_3$) δ 2.89 (d, 2H, J=3.7 Hz), 2.98 (s, 1H), 4.13 (bs, 1H), 4.78 (bs, 1H), 7.18-7.71 (m, 9H); MS (EI) m/e (relative intensity) 289 (M$^+$, 47), 272 (100), 231 (42).

(7-Bromo-5-phenyl-3H-benzo[e][1,4]diazepin-2-yl)-methyl-amine 81 (Hz135). Bromide 81 was obtained in 70% yield from 1 analogous to the procedure described above for the synthesis of compound 79 as a white solid. mp: 234-235° C.; IR (KBr) 3253, 3076, 1609, 1571, 1415, 1326, 1230 cm$^{-1}$; $^1$H NMR (300 MHz, CDCl$_3$) δ 2.62 (s, 3H), 3.56 (bs, 1H), 4.68 (bs, 1H), 6.34 (s, 1H), 7.17 (d, 1H, J=8.7 Hz), 7.36-7.81 (m, 7H); MS (EI) m/e (relative intensity) 329 (80), 328 (M$^+$, 100), 327 (82), 326 (92), 220 (38), 219(48), 218(46), 205 (38).

(7-Trimethylsilylacetylenyl-5-phenyl-3H-benzo[e][1,4] diazepin-2-yl)-methyl-amine 82 (Hz141). Trimethylsilylacetylenyl analog 82 (Hz141) was obtained in 73% yield from 81 analogous to the procedure described above for the synthesis of compound 6 as a light yellow solid. mp: 210-211° C.; IR (KBr) 3257, 3079, 2956, 2150, 1619, 1610, 1580, 1416, 1237, 880, 843 cm$^{-1}$; $^1$H NMR (300 MHz, CDCl$_3$) δ 0.22 (s, 9H), 2.59 (d, 3H, J=3.5 Hz), 3.56 (bs, 1H), 4.66 (bs, 1H), 6.39 (s, 1H), 7.21 (d, 1H, J=8.4 Hz), 7.39-7.65 (m, 7H); MS (EI) m/e (relative intensity) 345 (M$^+$, 100), 344 (98), 164(50).

(7-Acetylenyl-4-oxy-5-phenyl-3H-benzo[e][1,4]diazepin-2-yl)-methylamine 83 (Hz148). The 7-acetyleno analog 83 (Hz148) was obtained in 92% yield from 82 analogous to the procedure described above for the synthesis of compound 14 as a white solid. mp: 226-227° C.; IR (KBr) 3275, 3245, 3075, 2102, 1618, 1599, 1580, 1467, 1416, 1333, 1235 cm$^{-1}$; $^1$H NMR (300 MHz, CDCl$_3$) δ 2.65 (d, 3H, J=4.4 Hz), 2.97 (s, 1H), 3.57 (bs, 1H), 4.65 (bs, 1H), 6.20 (d, 1H, J=3.7 Hz), 7.22 (d, 1H, J=8.4 Hz), 7.42-7.58 (m, 7H). MS (EI) m/e (relative intensity) 273 (M$^+$, 100), 272 (98).

Scheme 18

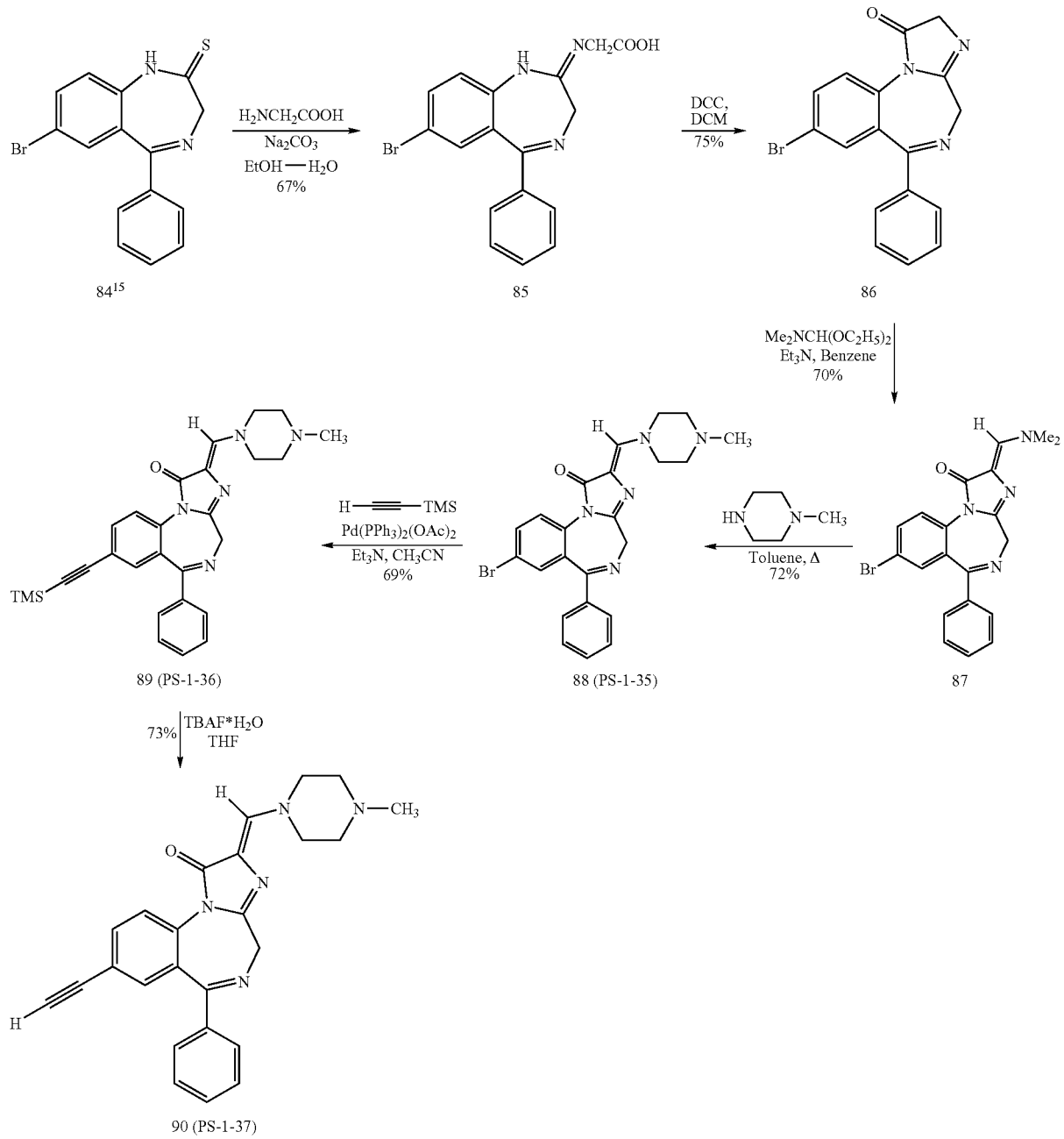

A suspension of 7-bromo-1,3-dihydro-5-phenyl-2H-1,4-benzodiazepin-2-thione 84 (1.6 g, 4.83 mmol), glycine (1.81 g, 24.2 mmol) and Na$_2$CO$_3$ (1.84 g, 17.4 mmol) in EtOH (38 mL)-H$_2$O (16 mL) was stirred at reflux for 5 h, poured into water (100 mL), and then filtered to remove a small amount of 7-bromo-1,3-dihydro-5-phenyl-2H-1,4-benzodiazepin-2-one which remained. See Archer G A, Sternbach L H (1964) J Org Chem 29:231. The filtrate was extracted with CHCl$_3$. The CHCl$_3$ extract was discarded; the aqueous layer was adjusted to pH 4 with 2N HCl and then extracted with CHCl$_3$ (3×25 mL). Evaporation of the CHCl$_3$ solution gave pure acid 85 (1.2 g, 67%) as a yellow solid. Acid 85 (350 mg, 0.941 mmol) was suspended in dry CH$_2$Cl$_2$ (10 mL) and DCC (223 mg, 1.08 mmol) was added. The suspension which resulted was stirred at 40° C. for 2 h and then cooled to 0° C. It was filtered, and the solvent was removed under vacuum to give 8-bromo-2,4-dihydro-6-phenyl-1H-imidazo[1,2-a][1,4]benzodiazepin-1-one 86 as a brown oil. The cyclized product 86 (ca. 250 mg) was dissolved in dry benzene (6 mL), dimethylformamide diethylacetal (130 mg, 0.883 mmol) and triethylamine (89 mg, 0.883 mmol) were added. The solution which resulted was stirred at room temperature for 1 h and the solvent was removed under vacuum, The residue was then crystallized from EtOAc-MeOH to give 87 (200 mg, 70%). A solution of 87 (180 mg, 0.440 mmol) in dry toluene (5 mL) was treated with 1-methyl piperazine (1 mL) and heated to reflux for 5 h. The solvent was removed in vacuum to give a gum which crystallized from $CH_2Cl_2$-$Et_2O$ to furnish 88 (PS-I-35, 146 mg, 72%). mp>250° C.; IR (KBr) 3324, 2932, 2787, 1692, 1624, 1475, 1402, 1297, 1137, 933 cm$^{-1}$; $^1$H NMR (CDCl$_3$) δ 7.95 (d, 1H, J=8.8 Hz), 7.72 (dd, 1H, J=2.3 Hz, J=8.8 Hz), 7.58-7.55 (m, 2H), 7.49-7.37 (m, 4H), 7.17 (s, 1H), 5.01 (d, 1H, J=12 Hz), 4.50-4.60 (m, 1H), 4.20-4.30 (m, 1H), 4.16 (d, 1H, J=12 Hz), 3.50-3.58 (m, 2H), 2.40-2.60 (m, 4H), 2.34 (s, 3H); MS (m/z) 465 (100). Anal. Calcd. for $C_{23}H_{22}N_5OBr\cdot\frac{1}{3}H_2O$: C, 58.79; H, 4.95; N, 14.89. Found: C, 58.73; H, 4.86; N, To the suspension of compound 88 (PS-I-35, 140 mg, 0.302 mmol) in acetonitrile (4 mL) and triethylamine (3 mL) was added bis(triphenylphosphine)-palladium (II) acetate (22.6 mg, 0.03 mmol). The solution was degassed under vacuum and trimethylsilylacetylene (0.1 mL, 0.7 mmol) was added. The mixture was heated to reflux and stirred overnight. After removal of the solvent under vacuum, the residue was dissolved in $CH_2Cl_2$ and washed with a saturated aqueous solution of NaHCO$_3$ and brine. The organic layer was dried (Na$_2$CO$_3$), filtered and concentrated under vacuum. The residue was purified by flash column chromatography (EtOAc: MeOH 9:1) to furnish the trimethylsilyl analogue 89 (PS-I-36, 100 mg, 69%) as a pale yellow solid. mp>250° C.; IR (KBr) 3436, 2936, 2794, 2154, 1682, 1625, 1489, 1136, 847 cm$^{-1}$; $^1$H NMR (CDCl$_3$) δ 8.0 (d, 1H, J=8.5 Hz), 7.68 (dd, 1H, J=1.9 Hz and 8.5 Hz), 7.55-7.59 (m, 2H), 7.37-7.49 (m, 4H), 7.16 (s, 1H), 4.99 (d, 1H, J=12 Hz), 4.50-4.60 (m, 1H), 4.20-4.30 (m, 1H), 4.13 (d, 1H, J=12.4 Hz), 3.48-3.58 (m, 2H), 2.4-2.6 (m, 4H), 2.35 (s, 3H), 0.23 (s, 9H); MS (m/z) 482 (100). Anal. Calcd. for $C_{28}H_{31}N_5OSi\cdot H_2O$: C, 67.60; H, 6.54; N, 13.59. Found: C, 67.30; H, 6.66; N, 14.01.

A solution of the trimethylsilyl analog 89 (PS-I-36, 65 mg, 0.135 mmol) in THF (15 mL) was stirred with tetrabutylammonium fluoride hydrate (45 mg, 0.175 mmol) at −5° C. for 5 min. After this, H$_2$O (5 mL) was added to the solution to quench the reaction and stirring continued at low temperature for one half hour. The solution was extracted with EtOAc (3×40 mL), and the organic layer was washed with water. After removal of the solvent under reduced pressure, ethyl ether was added to the residue to precipitate a solid. The mixture was filtered and the solid was washed with CHCl$_3$-Et$_2$O (ca 1:15) to provide the acetyl target 90 (PS-I-37, 40 mg, 73%). mp 223-224° C.; IR (KBr) 3298, 2935, 2786, 1695, 1628, 1364, 1136, 1002, 778 cm$^{-1}$; $^1$H NMR (CDCl$_3$) δ 8.04 (d, 1H, J=8.5 Hz), 7.71 (dd, 1H, J=1.9 Hz, J=8.5 Hz), 7.55-7.58 (m, 2H), 7.36-7.48 (m, 4H), 7.17 (s, 1H), 5.0 (d, 1H, J=12.1 Hz), 4.5-4.6 (m, 1H), 4.2-4.3 (m, 1H), 4.16 (d, 1H, J=12.1 Hz), 3.5-3.6 (m, 2H), 3.08 (s, 1H), 2.4-2.6 (m, 4H), 2.35 (s, 3H); MS (m/z) (100).

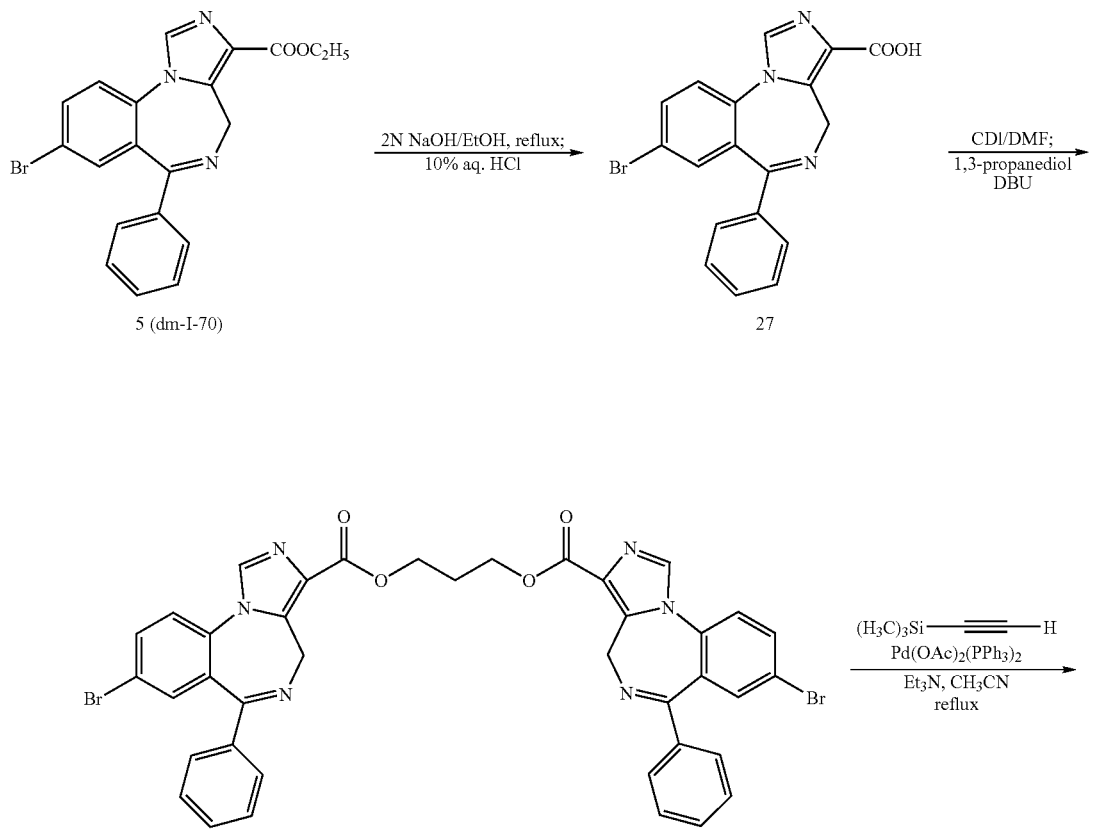

Scheme 19

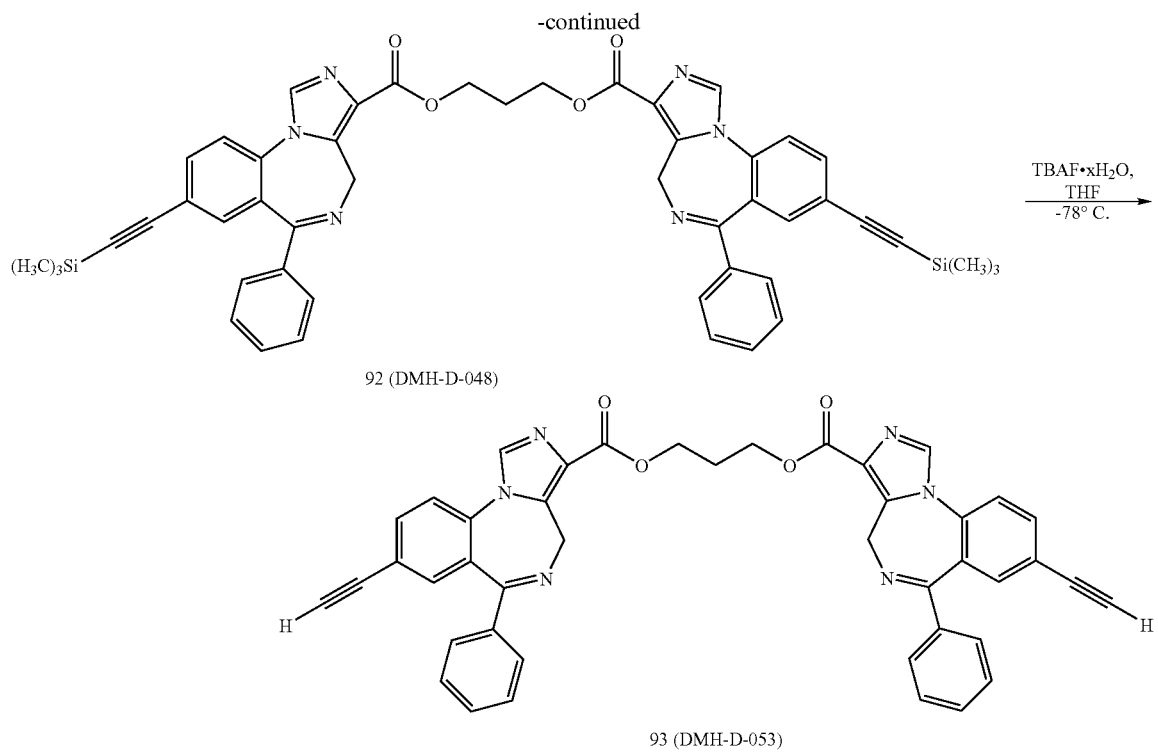

92 (DMH-D-048)

93 (DMH-D-053)

The acid 27, obtained from the ester 5 (dm-1-70), was stirred with CDI in DMF, followed by stirring with 1,3-propanediol and DBU to provide 91 (DMH-D-070, the dimer of dm-I-70). This was converted into the trimethylsilylacetylenyl compound 92 (DMH-D-048, the dimer of XLiXHe048) under standard conditions (Pd-mediated, Heck-type coupling). The bisacetylene 93 (DMH-D-053, the dimer of XHeII-053) was easily obtained by treatment of trimethylsilyl compound 92 with fluoride anion as shown in Scheme 19. See Xe, (2000).

8-Bromo-6-phenyl-4H-benzo[f]imidazo[1,5-a][1,4]diazepine-3-carboxylic acid 27. The ester 5 (2 g) was dissolved in EtOH (50 mL) and aq sodium hydroxide (10 mL, 2N) was added to the solution. The mixture was heated to reflux for half an hour. After the EtOH was removed under reduced pressure, the solution was allowed to cool. The pH value was adjusted to 4 by adding 10% aq HCl dropwise. The mixture was filtered and the solid was washed with water and ethyl ether. The solid was dried to provide 27 (1.8 g, 96.6%): mp>250° C.; IR (KBr) 3450 (b), 2844, 1707, 1615, 1493, 1166, 700 cm$^{-1}$; $^1$H NMR (300 MHz, DMSO-d$_6$) δ 4.14 (d, 1H, J=12.6 Hz), 5.79 (d, 1H, 12.6 Hz), 7.41-7.54 (m, 6H), 7.88 (d, 1H, J=8.7 Hz), 8.03 (dd, 1H, J=8.7 Hz, J=2.1 Hz), 8.47 (s, 1H); MS (EI) m/e (rel intensity) 381 (M$^+$, 20), 383 (19).

1,3-Bis(8-bromo-6-phenyl-4H-benzo[f]imidazo[1,5-a][1,4]diazepine-3-carboxy) propyl diester 91 (DMH-D-070). The carboxylic acid 27 (2 g, 5.2 mmol) was dissolved in DMF (20 mL), after which CDI (1.02 g, 6.3 mmol) was added at rt and the mixture was stirred for 2 h. Then 1,3-propanediol (0.19 mL, 2.6 mmol) and DBU (0.78 mL, 5.2 mmol) were added to the mixture and stirring continued overnight. The reaction solution was then cooled with an ice-water bath, after which water was added to precipitate a solid. This material was purified further by flash chromatography on silica gel (gradient elution, EtOAc:EtOH 20:1, 15:1, 10:1) to provide the bisbromide 91 (DMH-D-070) as a white solid (1.3 g, 61.9%): mp 187.5-189° C.; IR (KBr) 3112, 2968, 1708, 1610, 1559, 1491, 1269, 1160, 1123, 1073 cm$^{-1}$; $^1$H NMR (300 MHz, CDCl$_3$) δ 2.35 (m, 2H), 4.08 (d, 2H, J=12.6 Hz), 4.55 (m, 4H), 6.05 (d, 2H, J=12.6 Hz), 7.37-7.53 (m, 12H), 7.6 (d, 2H, J=2.1 Hz), 7.81 (dd, 2H, J=2.1 Hz, 8.6 Hz), 7.93 (s, 2H); $^{13}$C NMR (75.5 MHz, CDCl$_3$) δ 28.2, 44.9, 61.4, 120.7, 124.2, 128.3, 129.0, 129.3, 129.6, 130.6, 134.1, 134.4, 134.7, 135.0, 138.9, 138.9, 162.6, 167.9; MS (FAB, NBA) m/e (rel intensity) 803 (M$^+$+1, 15); Anal. Calcd. For C$_{39}$H$_{28}$N$_6$O$_4$Br$_2$: C, 58.23; H, 3.51; N, 10.45. Found: C, 57.92; H, 3.43; N, 10.29.

1,3-Bis(8-trimethylsilylacetylenyl-6-phenyl-4H-benzo[f]imidazo[1,5-a][1,4]-diazepine-3-carboxy) propyl diester 92 (DMH-D-048). To a suspension of bisbromide 91 (1.005 g, 1.25 mmol) in acetonitrile (50 mL) and triethylamine (65 mL), was added bis(triphenylphosphine)-palladium (II) acetate (0.15 g, 0.2 mmol). The solution was degassed and trimethylsilylacetylene (0.7 mL, 5 mmol) was added after which it was degassed again. The mixture was heated to reflux and stirring maintained overnight. After removal of the solvent under reduced pressure, the residue was dissolved in CH$_2$Cl$_2$ and washed with water. 3-Mecaptopropyl functionalized silica gel (0.6 g) was added into the organic layer and stirring continued for 1 hour. The silica gel/Pd complex was removed by filtration and the filtrate was concentrated under reduced pressure. The residue was purified by flash column chromatography on silica gel (gradient elution, EtOAc:EtOH 20:1, 15:1, 10:1) to furnish the bistrimethylsilyl dimer 92 (DMH-D-048, 680 mg, 60.8%) as a white solid: mp 169-172° C.; IR (KBr) 3449, 2950, 1725, 1720, 1715, 1496, 1250, 1160, 1080, 847 cm$^{-1}$; $^1$H NMR (300 MHz, CDCl$_3$) δ 0.25 (s, 18H), 2.35 (m, 2H), 4.05 (d, 2H, J=12.6 Hz), 4.55 (m, 4H), 6.02 (d, 2H, J=12.6 Hz), 7.37-7.55 (m, 14H), 7.75 (dd, 2H, J=1.8 Hz, 8.4 Hz), 7.94 (s, 2H); $^{13}$C NMR (75.5 MHz, CDCl$_3$) δ −0.3, 28.3, 44.9, 61.4, 97.4, 102.3, 122.4, 122.6, 128.0, 128.3, 129.0, 129.4, 130.5, 134.1, 134.9, 135.1, 139.0, 139.2, 139.2, 162.6, 168.5; MS (FAB, NBA) m/e (rel intensity) 839 (M$^+$+1, 100); Anal. Calcd. For C$_{49}$H$_{46}$N$_6$O$_4$Si$_2$: C, 70.14; H, 5.53; N, 10.02. Found: C, 69.97; H, 5.35; N, 9.77.

1,3-Bis(8-acetylenyl-6-phenyl-4H-benzo[f]imidazo[1,5-a][1,4]diazepine-3-carboxy) propyl diester 93 (DMH-D-053). A solution of bistrimethylsilyl dimer 92 (330 mg, 0.4 mmol) in THF (70 mL) was stirred with tetrabutylammonium fluoride hydrate (250 mg, 0.96 mmol) at −78° C. for 5 min. After this, H$_2$O (35 mL) was added to the solution to quench the reaction and stirring continued at low temperature for one half hour. The solution was extracted with EtOAc (3×100 mL), and the organic layer was washed with water. After removal of the solvent under reduced pressure, ethyl ether was added to the residue to precipitate a solid. See Xe, (2000). The mixture was filtered and the solid was washed with CHCl$_3$-Et$_2$O (ca 1:15), the bisacetylenyl dimer 93 (DMH-D-053, 220 mg, 80%) was obtained as a yellow solid: mp: 172-175° C.; IR (KBr) 3450, 3280, 2950, 1720, 1715, 1495, 1250, 1120, 1050 cm$^{-1}$; $^1$H NMR (300 MHz, CDCl$_3$) δ 2.35 (m, 2H), 3.18 (s, 2H), 4.08 (d, 2H, J=12.3 Hz), 4.56 (m, 4H), 6.04 (d, 2H, J=12.6 Hz), 7.36-7.59 (m, 14H), 7.78 (dd, 2H, J=8.4 Hz, 1.7 Hz), 7.95 (s, 2H); $^{13}$C NMR (75.5 MHz, CDCl$_3$) δ 28.8, 45.4, 61.9, 80.2, 81.3, 121.4, 122.7, 128.1, 128.3, 129.0, 129.3, 130.5, 134.2, 135.2, 135.3, 135.6, 138.9, 139.2, 162.6, 168.5; MS (FAB, NBA) m/e (rel intensity) 695 (M$^+$+1, 100). Anal. Calcd. For C$_{43}$H$_{30}$N$_6$O$_4$·0.5 EtOAc: C, 73.15; H, 4.64; N, 11.38. Found: C, 72.82; H, 4.32; N, 11.66.

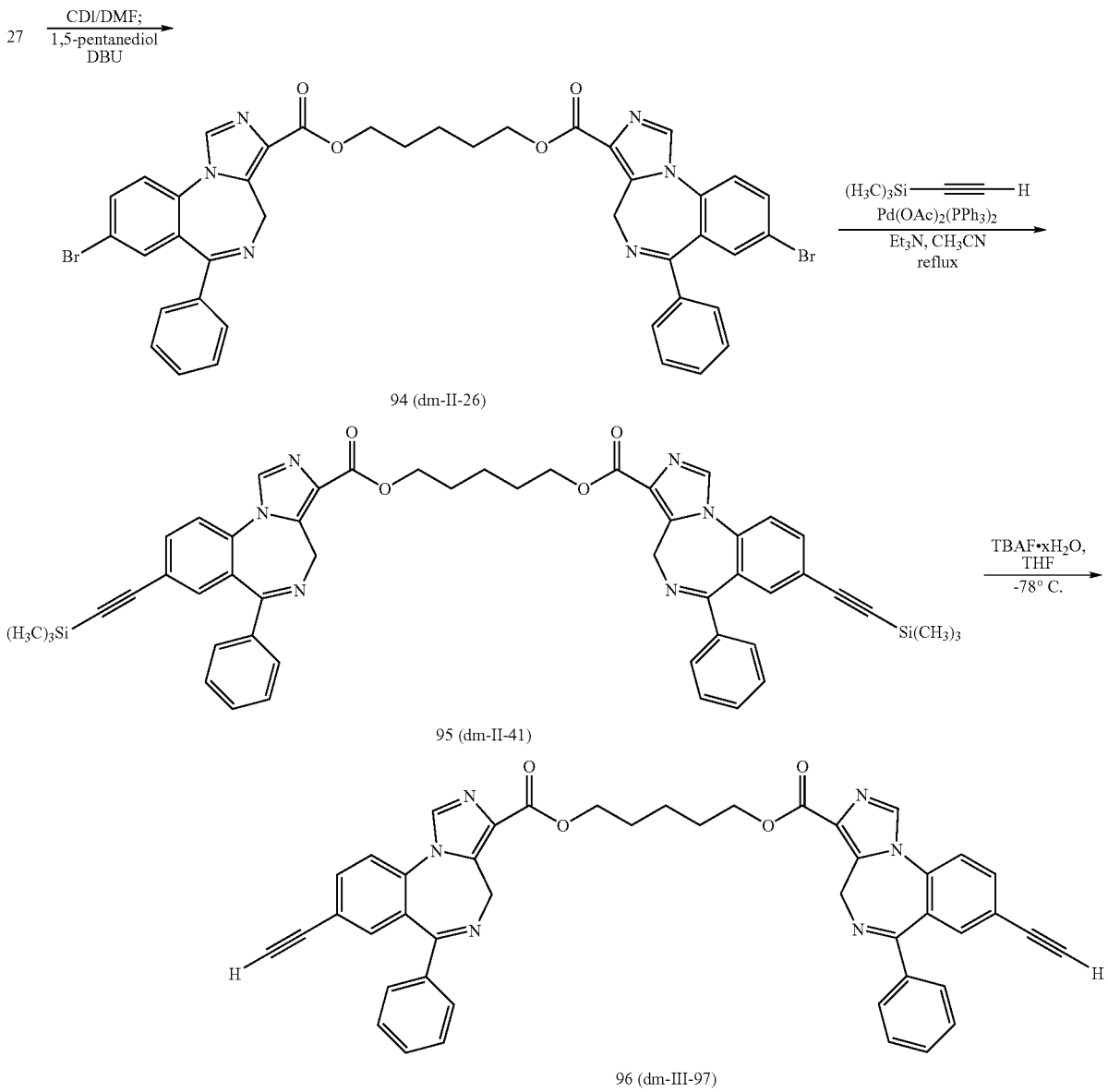

Scheme 20

The 5-carbon linker bisbromide 94 (dm-II-26), bis-trimethylsilylacetylenyl dimer 95 (dm-II-41) and bisacetylene dimer 96 (dm-II-97), which are analogues of dimers DMH-D-070, DMH-D-048 and DMH-D-053, respectively, were prepared from acid 27 under the same conditions employed for preparing dimers 91 (DMH-D-070), 92 (DMH-D-048) and 93 (DMH-D-053), respectively, by using 1,5-pentanediol in place of 1,3-propanediol (Scheme 20).

1,5-Bis(8-bromo-6-phenyl-4H-benzo[f]imidazo[1,5-a][1,4]diazepine-3-carboxy) pentyl diester 94 (dm-II-26)

A yellow powder (63.2%): mp 172-175° C.; IR (KBr) 3112, 2970, 1721, 1609, 1490, 1267, 1158, 1075, 754, 697 cm$^{-1}$; $^1$H NMR (300 MHz, CDCl$_3$) δ 1.62 (m, 2H), 1.90 (m, 4H), 4.07 (d, 2H, J=12.6 Hz), 4.39 (m, 4H), 6.05 (d, 2H, J=12.6 Hz), 7.37-7.53 (m, 12H), 7.58 (d, 2H, J=2.1 Hz), 7.78 (dd, 2H, J=2.1 Hz, 8.6 Hz), 7.92 (s, 2H); $^{13}$C NMR (75.5 MHz, CDCl$_3$) δ 22.5, 28.4, 44.9, 64.5, 120.7, 124.2, 128.3, 129.2, 129.3, 129.6, 130.6, 134.0, 134.5, 134.6, 135.0, 138.8, 138.9, 162.8, 167.9; MS (FAB, NBA) m/e (rel intensity) 831 (M$^+$+1, 5). Anal. Calcd. For C$_{41}$H$_{32}$N$_6$O$_4$Br$_2$·0.25H$_2$O: C, 58.95; H, 3.89; N, 10.07; Found: C, 58.69; H, 3.74; N, 9.70.

1,5-Bis(8-trimethylsilylacetylenyl-6-phenyl-4H-benzo[f]imidazo[1,5-a][1,4]-diazepine-3-carboxy) pentyl diester 95 (dm-II-41)

A yellow solid (58.1%): mp 154-156° C.; IR (KBr) 3426, 2955, 1727, 1720, 1612, 1495, 1251, 1174, 1076, 846 cm$^{-1}$; $^1$H NMR (300 MHz, CDCl$_3$) δ 0.25 (s, 18H), 1.63(m, 2H), 1.90 (m, 4H), 4.05 (d, 2H, J=12.6 Hz), 4.39 (m, 4H), 6.03 (d, 2H, J=12.6 Hz), 7.40-7.54 (m, 14H), 7.75 (dd, 2H, J=1.8 Hz, 8.4 Hz), 7.93 (s, 2H); $^{13}$C NMR (75.5 MHz, CDCl$_3$) δ −0.3, 22.5, 28.4, 44.9, 64.5, 97.4, 102.3, 122.4, 122.6, 128.0, 128.3, 129.2, 129.4, 130.5, 134.1, 135.0, 135.1, 135.1, 138.9, 139.3, 162.8, 168.5; MS (FAB, NBA) m/e (rel intensity) 867 (M$^+$+1, 100).

1,5-Bis(8-acetylenyl-6-phenyl-4H-benzo[f]imidazo[1,5-a][1,4]diazepine-3-carboxy) pentyl diester 96 (dm-III-97). A yellow solid: mp 150-153° C.; IR (KBr) 3290, 2953, 1718, 1611, 1493, 1253, 1172, 1120, 1076 cm$^{-1}$; $^1$H NMR (300 MHz, CDCl$_3$) δ 1.62 (m, 2H), 1.90 (m, 4H), 3.18 (s, 2H), 4.07 (d, 2H, J=12.3 Hz), 4.38 (m, 4H), 6.04 (d, 2H, J=12.3 Hz), 7.36-7.58 (m, 14H), 7.77 (dd, 2H, J=8.4 Hz, 1.6 Hz), 7.94 (s, 2H); $^{13}$C NMR (75.5 MHz, CDCl$_3$) δ 22.5, 28.4, 44.9, 64.5, 79.8, 81.3, 121.3, 122.7, 128.1, 128.3, 129.2, 129.3, 130.5, 134.1, 135.2, 135.3, 135.6, 138.8, 139.2, 162.8, 168.5; MS (FAB, NBA) m/e (rel intensity) 723 (M$^+$+1, 13).

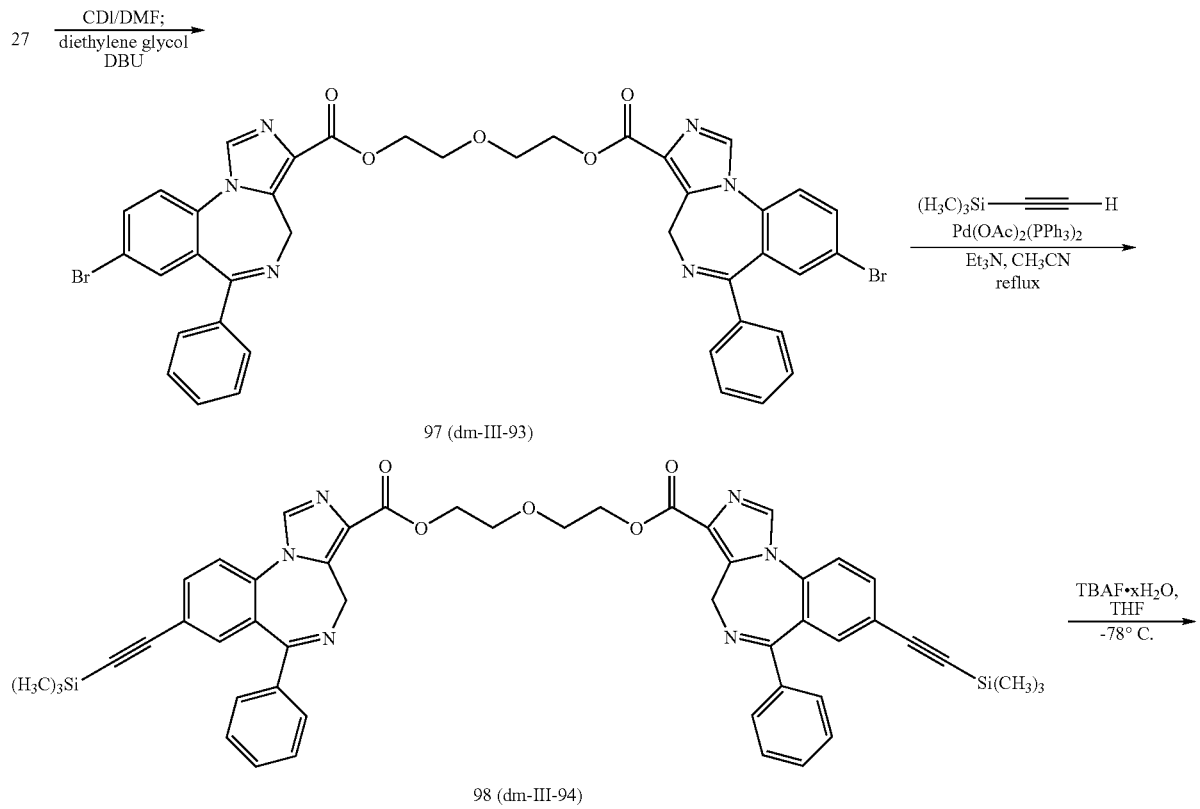

Scheme 21

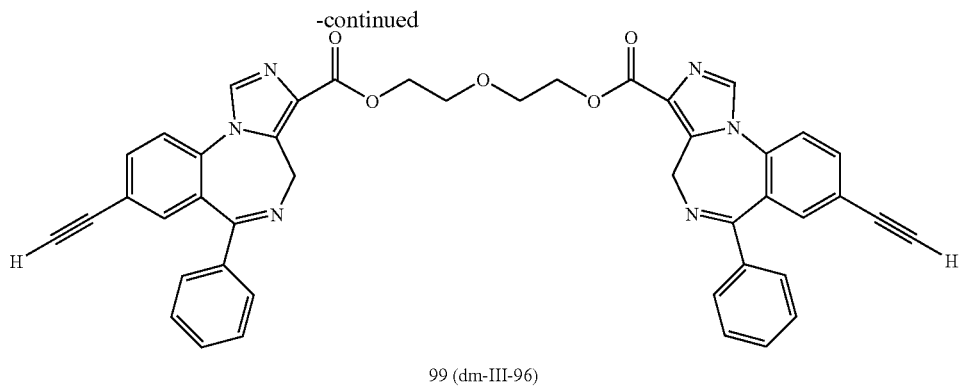

99 (dm-III-96)

In order to improve the water solubility of the dimers, the oxygen-containing 5-atom linked dimers 97 (dm-III-93), 98 (dm-II-94) and 99 (dm-III-96), were designed and prepared from acid 27 under the same conditions employed for preparation of dimers DMH-D-070, DMH-D-048 and DMH-D-053, respectively, by replacing 1,3-propanediol with diethylene glycol (Scheme 21).

Bis(8-bromo-6-phenyl-4H-benzo [f]imidazo[1,5-a][1,4]diazepine-3-carboxy) diethylene glycol diester 97 (dm-III-93)

A yellow solid (93.7%): mp 165-168° C.; IR (KBr) 3060, 2956, 1725, 1610, 1558, 1491, 1267, 1161, 1123, 1074 cm$^{-1}$; $^1$H NMR (300 MHz, CDCl$_3$) δ 3.93 (t, 4H, J=4.8 Hz), 4.06 (d, 2H, J=12.6 Hz), 4.54 (m, 4H), 6.05 (d, 2H, J=12.6 Hz), 7.39-7.50 (m, 12H), 7.57 (d, 2H, J=2.7 Hz), 7.80 (dd, 2H, J=2.1 Hz, 8.4 Hz), 7.90 (s, 2H); $^{13}$C NMR (75.5 MHz, CDCl$_3$) δ 44.9, 63.6, 69.0, 120.7, 124.2, 128.3, 129.0, 129.3, 129.6, 130.6, 134.1, 134.4, 134.6, 135.0, 138.9, 139.0, 162.5, 167.9; MS (FAB, NBA) m/e (rel intensity) 833 (M$^+$+1, 5).

Bis(8-trimethylsilylacetylenyl-6-phenyl-4H-benzo[f]imidazo[1,5-a][1,4]diazepine-3-carboxy) diethylene glycol diester 98 (dm-III-94)

A yellow solid (49.5%): mp 205-208° C.; IR (KBr) 3433, 2960, 1730, 1700, 1612, 1493, 1255, 1169, 1120, 1071, 847 cm$^{-1}$; $^1$H NMR (300 MHz, CDCl$_3$) δ 0.25 (s, 18H), 3.93 (t, 4H, J=5.4 Hz), 4.04 (d, 2H, J=12.6 Hz), 4.55 (m, 4H), 6.04 (d, 2H, J=12.6 Hz), 7.37-7.53 (m, 14H), 7.74 (dd, 2H, J=1.2 Hz, 8.4 Hz), 7.91 (s, 2H); $^{13}$C NMR (75.5 MHz, CDCl$_3$) δ −0.3, 45.0, 63.6, 69.0, 97.5, 102.4, 122.5, 122.7, 128.1, 128.3, 129.0, 129.4, 130.5, 134.2, 135.0, 135.1, 135.2, 139.1, 139.3, 162.7, 168.6; MS (FAB, NBA) m/e (rel intensity) 869 (M$^+$+1, 100).

Bis(8-acetylenyl-6-phenyl-4H-benzo[f]imidazo[1,5-a][1,4]diazepine-3-carboxy) diethylene glycol diester 98 (dm-III-96)

A yellow solid (81.6%): mp 173-177° C.; IR (KBr) 3432, 3280, 1720, 1715, 1496, 1254, 1175, 1120, 1074 cm$^{-1}$; $^1$H NMR (300 MHz, CDCl$_3$) δ 3.12 (s, 2H), 3.93 (t, 4H, J=4.5 Hz), 4.06 (d, 2H, J=12.6 Hz), 4.55 (m, 4H), 6.05 (d, 2H, J=12.6 Hz), 7.38-7.56 (m, 14H), 7.75 (dd, 2H, J=8.4 Hz, 1.8 Hz), 7.91 (s, 2H); $^{13}$C NMR (75.5 MHz, CDCl$_3$) δ 45.0, 63.6, 69.0, 79.8, 81.3, 121.3, 122.7, 128.1, 128.3, 129.0, 129.3, 130.5, 134.2, 135.2, 135.3, 135.6, 139.0, 139.1, 162.6, 168.4; MS (FAB, NBA) m/e (rel intensity) 725 (M$^+$+1, 63).

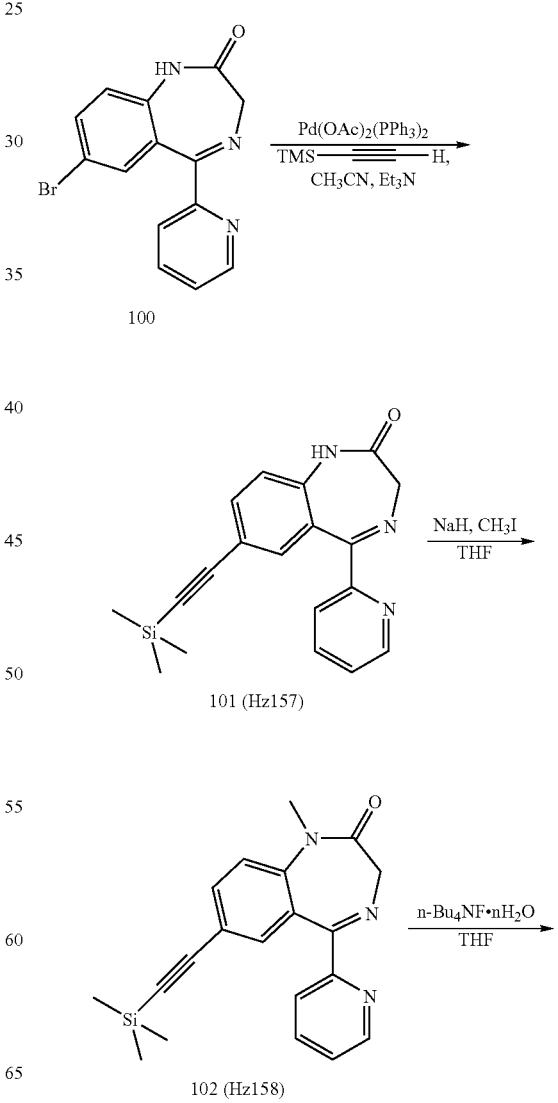

Scheme 22

-continued

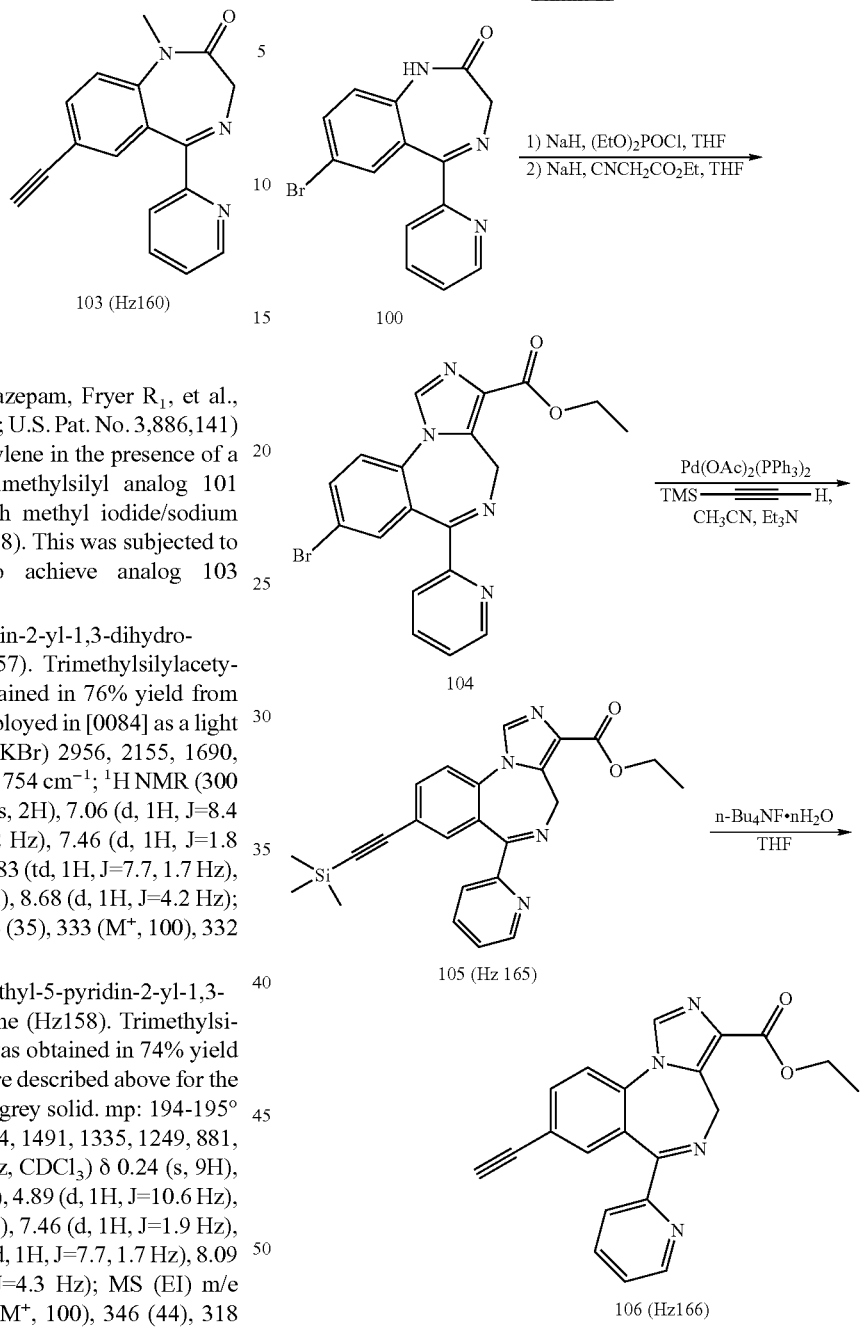

Scheme 23

The benzodiazepine 100 (bromazepam, Fryer R₁, et al., (1993) Synth Commun 23: 985-992; U.S. Pat. No. 3,886,141) was reacted with trimethylsilylacetylene in the presence of a palladium catalyst to provide trimethylsilyl analog 101 (Hz157) that was methylated with methyl iodide/sodium hydride to afford analog 102 (Hz158). This was subjected to fluoride-mediated desilylation to achieve analog 103 (Hz160).

Trimethylsilylacetylenyl-5-pyridin-2-yl-1,3-dihydro-benzo[e][1,4]diazepin-2-one (Hz157). Trimethylsilylacetylenyl analog 101 (Hz157) was obtained in 76% yield from 100 analogous to the procedure employed in [0084] as a light gray solid. mp: 242-243° C.; IR (KBr) 2956, 2155, 1690, 1616, 1492, 1332, 1248, 1018, 842, 754 cm$^{-1}$; $^1$H NMR (300 MHz, CDCl₃) δ 0.23 (s, 9H), 4.39 (s, 2H), 7.06 (d, 1H, J=8.4 Hz), 7.41 (ddd, 1H, J=7.5, 4.8, 1.2 Hz), 7.46 (d, 1H, J=1.8 Hz), 7.57 (dd, 1H, J=8.4, 1.9 Hz), 7.83 (td, 1H, J=7.7, 1.7 Hz), 7.97 (d, 1H, J=7.9 Hz), 8.41 (bs, 1H), 8.68 (d, 1H, J=4.2 Hz); MS (EI) m/e (relative intensity) 334 (35), 333 (M⁺, 100), 332 (57), 318 (21), 304 (31).

7-Trimethylsilylacetylenyl-1-methyl-5-pyridin-2-yl-1,3-dihydro-benzo[e][1,4]diazepin-2-one (Hz158). Trimethylsilylacetylenyl analog 102 (Hz158) was obtained in 74% yield from 101 analogous to the procedure described above for the synthesis of compound 6 as a light grey solid. mp: 194-195° C.; IR (KBr) 2956, 2154, 1682, 1614, 1491, 1335, 1249, 881, 844, 747 cm$^{-1}$; $^1$H NMR (300 MHz, CDCl₃) δ 0.24 (s, 9H), 3.42 (s, 3H), 3.84 (d, 1H, J=10.6 Hz), 4.89 (d, 1H, J=10.6 Hz), 7.29 (d, 1H, J=7.6 Hz), 7.40 (m, 1H), 7.46 (d, 1H, J=1.9 Hz), 7.63 (dd, 1H, J=8.5, 1.9 Hz), 7.84 (td, 1H, J=7.7, 1.7 Hz), 8.09 (d, 1H, J=7.9 Hz), 8.68 (d, 1H, J=4.3 Hz); MS (EI) m/e (relative intensity) 348 (28), 347 (M⁺, 100), 346 (44), 318 (34), 291 (23).

7-Acetylenyl-1-methyl-5-pyridin-2-yl-1,3-dihydro-benzo[e][1,4]diazepin-2-one (Hz160). The 7-acetyleno analog 103 (Hz160) was obtained in 63% yield from 102 analogous to the procedure described above for the synthesis of compound 6 as a white solid. mp: 190-191° C.; IR (KBr) 3286, 3233, 1678, 1614, 1491, 1344, 1126,750 cm$^{-1}$; $^1$H NMR (300 MHz, CDCl₃) δ 3.07 (s, 1H), 3.86 (d, 1H, J=10.6 Hz), 4.93 (d, 1H, J=10.2 Hz), 7.32 (d, 1H, J=8.6 Hz), 7.39 (m, 1H), 7.51 (d, 1H, J=1.8 Hz), 7.65 (dd, 1H, J=8.5, 1.9 Hz), 7.83 (td, 1H, J=7.7, 1.7 Hz), 8.11 (d, 1H, J=7.9 Hz), 8.65 (d, 1H, J=4.7 Hz); MS (EI) m/e (relative intensity) 275 (M⁺, 100), 274 (35), 246 (43), 219 (30).

The benzodiazepine 100 (bromazepam) was reacted with diethylphosphorochloridate, followed by the addition of ethyl isocyanoacetate to provide the ester 104. This was then reacted with trimethylsilyacetylene in the presence of a palladium catalyst to provide trimethylsilyl analog 105 (Hz165) which was subjected to fluoride-mediated desilylation to furnish analog 106 (Hz166).

8-Trimethylsilylacetylenyl-6-pyridin-2-yl-4H-benzo[f]imidazo[1,5-a][1,4]diazepine-3-carboxylic acid ethyl ester 105 (Hz165). Trimethylsilyacetylenyl analog 105 (Hz165) was obtained in 73% yield from 104 analogous to the procedure employed in [0085] as a white solid. mp: 205-206° C.; $^1$H NMR (300 MHz, CDCl₃) δ 0.25 (s, 9H), 1.44 (t, 3H, J=7.1

Hz), 4.14 (d, 1H, J=11.0 Hz), 4.44 (m, 2H), 6.11 (d, 1H, J=10.9 Hz), 7.38 (ddd, 1H, J=7.5, 4.8, 1.1 Hz), 7.51 (s, 1H), 7.54 (d, 1H, J=8.4 Hz), 7.74 (dd, J=8.3, 1.8 Hz), 7.83 (td, 1H, J=7.7, 1.7 Hz), 7.93 (s,1H), 8.05 (m, 1H), 8.61 (m, 1H).

8-Acetylenyl-6-pyridin-2-yl-4H-benzo[f]imidazo[1,5-a][1,4]diazepine-3-carboxylic acid ethyl ester 106 (Hz166). The 7-acetyleno analog 106 (Hz166) was obtained in 98% yield from 105 analogous to the procedure described above for the synthesis of compound 6 as a white solid. mp: 243-244° C.; $^1$H NMR (300 MHz, CDCl$_3$) δ 1.45 (t, 3H, J=7.1 Hz), 3.17 (s, 1H), 4.17 (d, 1H, J=10.0 Hz), 4.45 (m, 2H), 6.13 (d, 1H, J=10.4 Hz), 7.38 (ddd, 1H, J=7.5, 4.8, 1.1 Hz), 7.56 (d, 1H, J=8.2 Hz), 7.58 (s, 1H), 7.77 (dd, 1H, J=8.6, 1.8 Hz), 7.83 (td, 1H, J=7.7, 1.8 Hz), 7.93 (s, 1H), 8.08 (m, 1H), 8.59 (m, 1H).

Scheme 24 (SH-053-S-CH$_3$)

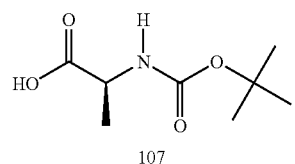

107

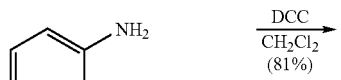

DCC
CH$_2$Cl$_2$
(81%)

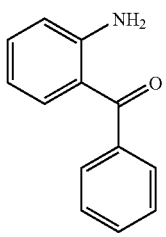

108

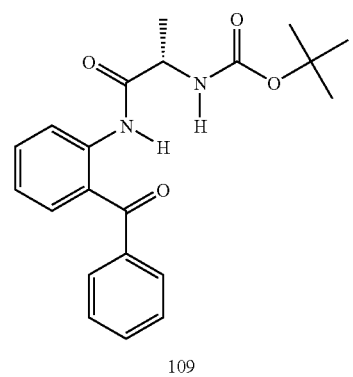

109

1) HCl (g)
2) MeOH/H$_2$O (pH 8.5)
(83%)

-continued

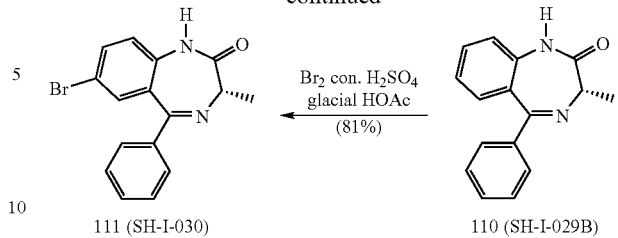

111 (SH-I-030)    110 (SH-I-029B)

Br$_2$ con. H$_2$SO$_4$
glacial HOAc
(81%)

1) NaH, THF/DMF
ClPO(OEt)$_2$, -10° C.
2) NaH, DMF
CNCH$_2$CO$_2$Et, -10° C.
(40%)

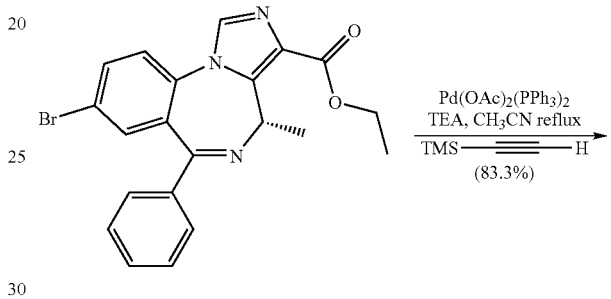

112 (SH-I-036)

Pd(OAc)$_2$(PPh$_3$)$_2$
TEA, CH$_3$CN reflux
TMS≡H
(83.3%)

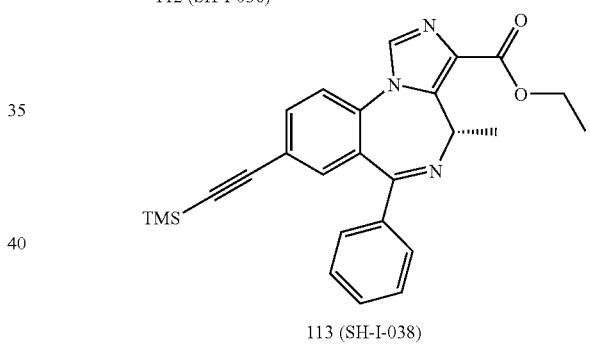

113 (SH-I-038)

TBAF
THF
10 min
(85%)

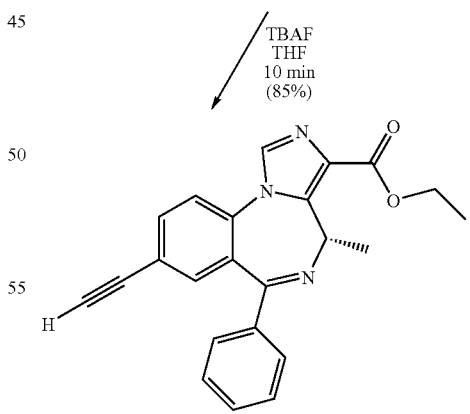

114 (SH-053-S-CH$_3$)

The benzophenone 108 was reacted with N-BOC-L-alanine 107 to give [1-(2-benzoyl-phenylcarbamoyl)-ethyl]-carbamic acid tert-butyl ester 109. See Bradley, R., et al., (2000) J. Am. Chem. Soc. 122: 460-465. This ester was treated with HCl(g) in CHCl₃ and then cyclized under basic conditions to give benzodiazepine 110. This amide 110 was regioselectively brominated at position-7 to give bromide 111. The bromide 111 was stirred with diethylphosphorochloridate in the presence of sodium hydride, followed by addition of ethyl isocyanoacetate to provide the ethyl ester 112 (SH-1-036). This was converted into the trimethylsilylacetylene analog 113 (SH-1-038) under standard conditions (Pd-mediated, Heck-type coupling). Treatment of 113 with fluoride anion gave the title compound 114 (SH-053-S—CH₃). The other analogs were prepared via the same process.

Procedure for SH-053-S—CH₃ (113)

[1-(2-Benzoyl-phenylcarbamoyl)-ethyl]-carbamic acid tert-butyl ester 109. To a stirred solution of 2-amino-5-bromobenzophenone 108 (5.73 g, 29.07 mmol) and the N-Boc-L-alanine 107 (5 g, 26.43 mmol) in CH₂Cl₂ (200 mL) was added dicyclohexylcarbodiimide (DCC) (5.99 g, 29.07 mmol) in CH₂Cl₂ (100 mL) dropwise, over 30 min at 0° C. The reaction mixture was stirred an additional 8 h at rt. The dicyclohexyl urea which formed was filtered off and the filtrate concentrated under reduced pressure. The crude solid 109 was purified by recrystallization from hexane to afford 109 (7.88 g, 81%). mp 127-129° C.; IR (KBr, cm⁻¹) 3288, 2475, 2352, 1684, 1636, 1576, 1507, 1447, 1264, 1165, 700; ¹H NMR (CDCl₃) δ 11.48 (s, 1H), 8.67 (d, J=8.22 Hz, 1H), 7.71-7.43 (m, 7H), 7.13-7.08 (m, 1H) 5.06 (br s, 1H), 4.36 (br s, 1H), 1.50 (d, J=7.1 Hz, 3H), 1.44 (s, 9H); MS (EI) m/e (relative intensity) 368 (M⁺, 6), 295 (10), 225 (27), 224 (79), 197 (83), 196 (77), 167 (15), 145 (46), 144 (88), 126 (17), 105 (38), 88 (94), 77(37), 57 (100); $[\alpha]^{26}_D$=−67.7 (c 0.88, EtOAc).

3-Methyl-5-phenyl-1,3-dihydro-benzo[e][1,4]diazepin-2-one 110. To a stirred solution of the benzophenone 109 (10.65 g, 29.38 mmol) in CHCl₃ (400 mL) at rt, hydrogen chloride gas was added in slowly. After 20 min, the addition was stopped and the solution was stirred overnight at rt. The reaction mixture was washed with a saturated solution of sodium bicarbonate (2×50 mL) and water (2×50 mL). The organic layer was concentrated under reduced pressure. The residual oil was dissolved in methanol-water (2:1, 500 mL) and the pH was adjusted to 8.5 by the addition of aqueous sodium hydroxide (1 N). The reaction mixture was stirred for 10 h at rt. The solution was concentrated under reduced pressure and water (100 mL) was added. The solution was extracted with CH₂Cl₂ (3×100 mL) and concentrated under reduced pressure. The crude solid 110 was purified by recrystallization from methanol/water to provide 110 (6.10 g, 83%). mp 160-162° C.; IR (KBr, cm⁻¹) 3215, 3059, 2974, 2932, 1681, 1574, 1478, 1445, 1372, 1321, 1242, 1160, 1131; ¹H NMR (CDCl₃) δ 9.65 (s, 1H), 7.54-7.13 (m, 9H), 3.78 (q, J=6.5 Hz, 1H), 1.78 (d, J=7.1 Hz, 3H); MS (EI) m/e (relative intensity) 250 (M⁺, 40), 249 (83), 234 (15), 209 (75), 208 (76), 207 (100), 180 (17), 152 (19) 103 (23), 77 (40); $[\alpha]^{26}_D$=290.2 (c 0.78, EtOAc).

7-Bromo-3-methyl-5-phenyl-1,3-dihydro-benzo[e][1,4]diazepin-2-one 111. To a stirred solution of 110 (66.5 g, 265 mmol) in glacial acetic acid (400 mL), sulfuric acid (80 mL) was added to the solution. Bromine (28 mL, 530 mmol) dissolved in acetic acid (150 mL) was added dropwise into the mixture. The reaction mixture was allowed to stir until NMR spectroscopy indicated that all of the starting material 110 had been consumed. The solution was concentrated under reduced pressure and then neutralized by addition of 1N NaOH solution and then extracted with EtOAc. The crude product 111 was purified by recrystallization from CH₂Cl₂ to afford 5 (70.4 g, 81%). mp 210-212° C.; IR (KBr, cm⁻¹) 2931, 1692, 1603, 1563, 1475, 1445, 1375, 1259, 1235, 1130, 1090; ¹H NMR (CDCl₃) δ 9.36 (s, 1H), 7.63 (dd, J=2.22, 8.58 Hz, 1H), 7.54-7.39 (m, 6H), 7.12 (d, J=8.611H), 3.76 (q, J=6.3 Hz, 1H), 1.76 (d, J=6.45 Hz, 3H). MS (EI) m/e (relative intensity) 330 (M⁺+1, 21), 329 (M⁺, 50), 328 (22), 327 (48), 289 (44), 288 (46), 287 (100), 286 (45), 285 (60) 205 (25), 77 (49); $[\alpha]^{26}_D$=313.1 (c 0.34, EtOAc).

8-Bromo-4-methyl-6-phenyl-4H-2,5,10b-triaza-benzo[e]azulene-3-carboxylic acid ethyl ester 112. 7-Bromo-3-methyl-5-phenyl-1,3-dihydro-benzo[e][1,4]diazepin-2-one 111 (16.6 g, 0.052 mol) was suspended in dry THF (250 mL) and cooled to −10° C. Sodium hydride (60% dispersion in mineral oil, 4.36 g, 0.109 mol) was added into the suspension in one portion. The reaction mixture was allowed to stir and warm to rt over a 3 h period. The reaction mixture was again cooled to −10° C. and diethyl chlorophosphate (12.7 ml, 0.09 mol) was added. The cooling bath was then removed and stirring continued for 3 h. At this time, sodium hydride (60% dispersion in mineral oil, 4.2 g, 0.1 mol) was suspended in dry THF (250 mL) at −10° C. in another flask. Ethyl isocyanoacetate (6.78 mL, 0.06 mol) was added to the NaH/THF suspension, the solution which resulted was allowed to stir for 3 h. After 3 h the first flask was cooled to −30° C. and the solution in the 2nd reaction flask was added to the first flask via a cannula. The reaction mixture was allowed to stir for 24 h, and then cooled with an ice-water bath and slowly quenched with acetic acid (10 mL). Water was added to the reaction mixture after which it was extracted with EtOAc. The EtOAc layers were combined, washed with aq NaHCO₃, brine and dried (Na₂SO₄). After removal of the solvent under reduced pressure, the solid was purified by flash chromatography (silica gel, EtOAc:hexane, gradient elution 1:2, 1:1, 2:1). The ester 112 was a white solid (8.76 g, 40%). mp 164-165° C.; IR (KBr, cm⁻¹) 2925, 1706, 1622, 1557, 1495, 1266, 1185; ¹H NMR (CDCl₃) δ 7.89 (s, 1H), 7.73 (dd, J=1.73 Hz, 1H), 7.51-7.36 (m, 7H), 6.66 (q, J=7.30, 1H), 4.45-4.30 (m, 2H), 1.40 (t, J=7.11, 3H), 1.25 (d, J=7.38 Hz, 3H). MS (EI) m/e (relative intensity) 426 (M⁺+2, 15), 425 (M⁺+1, 58), 424 (M⁺, 15), 423 (58), 380 (24), 379 (71), 378 (35), 377 (69), 352 (50), 351(100), 350 (67), 349 (92), 270 (38), 229 (16); $[\alpha]^{26}_D$=−38.0 (c 0.45, EtOAc).

4-Methyl-6-phenyl-8-trimethylsilanylethynyl-4H-2,5,10b-triaza-benzo[e]azulene-3-carboxylic acid ethyl ester 113. A mixture of ester 112 (3.0 g, 7.07 mmol) and bis(triphenylphosphine)palladium(II) acetate (0.42 g, 0.57 mmol) was dissolved in a mixed solvent system of acetonitrile (80 mL) and TEA (120 mL). The mixture was degassed under vacuum and argon gas was added, after which trimethylsilylacetylene (2 mL, 14.14 mmol) was added into the mixture. The mixture was degassed again under vacuum (argon) and heated to reflux. The mixture was heated at reflux until analysis by TLC (EtOAc) indicated that all of the starting material 112 had been consumed. The mixture was cooled to rt and the precipitate which formed was removed by filtration through celite. The filtrate was concentrated under reduced pressure and partitioned between H₂O and EtOAc. The combined layers of EtOAc were washed with brine and dried (Na₂SO₄), after which the solvent was removed under reduced pressure and the residue was purified by flash chromatography (silica gel, EtOAc:hexane 1:1). Conditions for TLC were EtOAc. A white solid 113 (2.60 g, 83.3%) was obtained. mp 160-162° C.; IR (KBr, cm⁻¹) 3365, 2925, 1706, 1616, 1553, 1498; ¹H NMR (CDCl₃) δ 7.89 (s, 1H), 7.73 (dd, J=1.73 Hz, 1H), 7.51-7.36 (m, 7H), 6.66 (q, J=7.30, 1H), 4.45-4.30(m, 2H), 1.40 (t, J=7.11, 3H), 1.25 (d, J=7.38 Hz, 3H), 0.15 (s, 9H). MS (EI) m/e (relative intensity) 441 (M⁺, 15), 369 (25), 323 (55), 295 (100), 267 (15).

8-Ethynyl-4-methyl-6-phenyl-4H-2,5,10b-triaza-benzo[e]azulene-3-carboxylic acid ethyl ester 114 (SH-053-S—CH₃). The trimethylsilylacetylene intermediate 113 (SH—I-038) (2.8 g, 6.3 mmol) was dissolved in THF (60 mL) and was then treated with Bu₄NF.H₂O (1.9 g, 7.56 mmol). The mixture was allowed to stir for 30 min at rt, after which H₂O (10 mL) was added and the mixture was extracted with EtOAc (3×50 mL). The combined organic extracts were washed with brine (25 mL) and dried (Na₂SO₄). After removal of the solvent under reduced pressure, the residue was purified by a wash column (silica gel, EtOAc) to furnish 114 (SH-053-S—CH₃) (1.9 g, 85%) as a white solid: mp 197-199° C.; IR (KBr, cm⁻¹) 3285, 2928, 1708, 1616, 1553, 1498, 1445, 1374; $^1$H NMR (CDCl₃) δ 7.92 (s, 1H), 7.73 (dd, J=1.72, 8.32 Hz, 1H), 7.58-7.36 (m, 7H), 6.67 (q, J=7.35, 1H), 4.46-4.34 (m, 2H), 3.16 (s, 1H), 1.41 (t, J=7.11, 3H), 1.25 (d, J=7.38, 3H); MS (EI) m/e (relative intensity) 369 (M⁺, 30), 323 (55), 295 (100), 267 (15). Anal. Calcd. for $C_{23}H_{19}N_3O_2$: C, 74.78; H, 5.18; N, 11.37. Found: C, 74.22; H, 5.11; N, 11.41. $[\alpha_D]^{26}$=−74.8 (c 0.8, EtOAc).

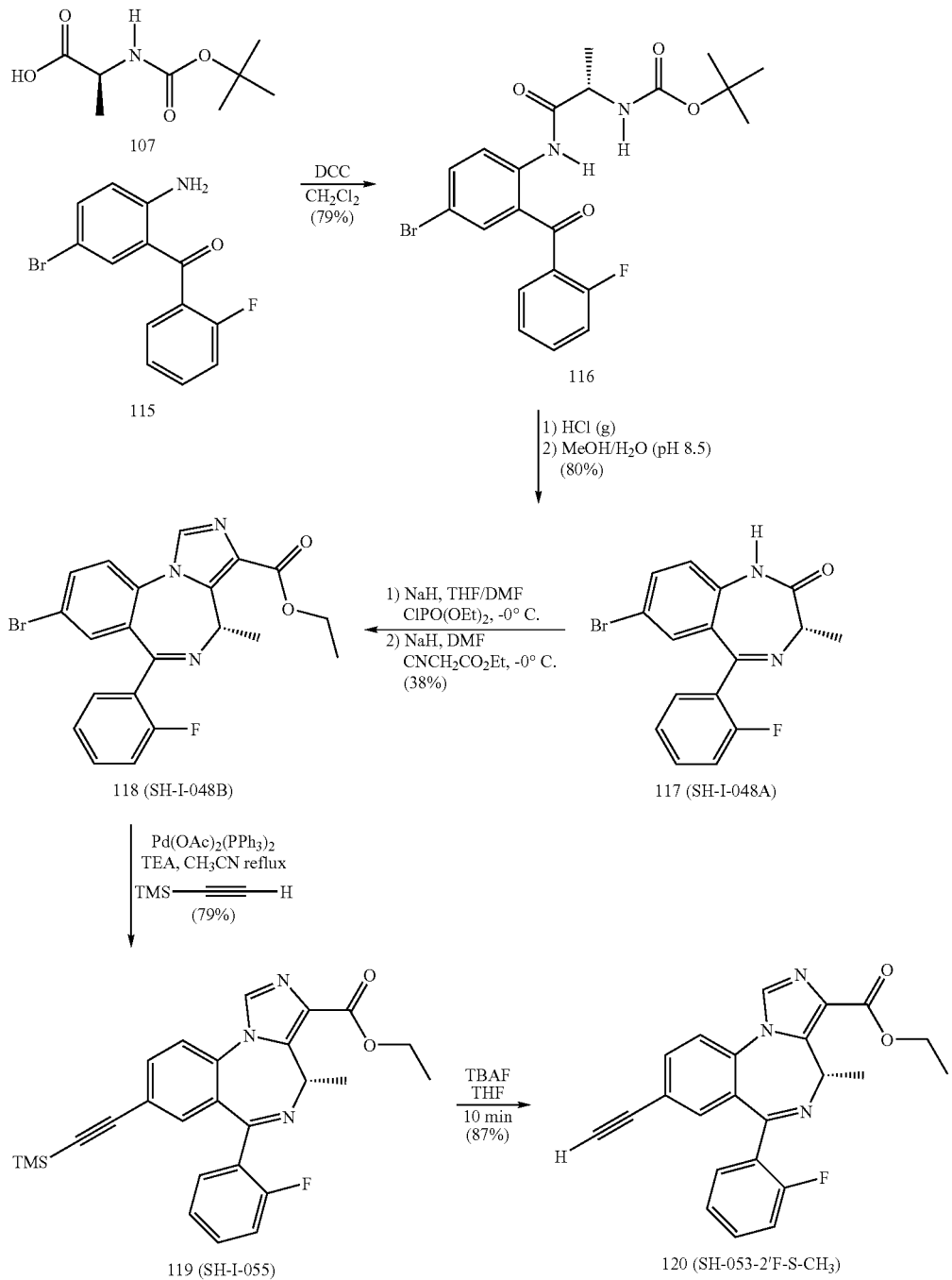

Scheme 25 (SH-053-2'F-S-CH₃)

Procedure for SH-053-2'F—S—CH$_3$

{1-[4-Bromo-2-(2-fluoro-benzoyl)-phenylcarbamoyl]-ethyl}-carbamic acid tert-butyl ester 116. To a stirred solution of (2-amino-5-bromophenyl)-(2-fluoro-phenyl)-methanone (60 g, 204 mmol) 115 and the N-Boc-L-alanine 107 (38.59 g, 204 mmol) in CH$_2$Cl$_2$ (500 mL) was added dicyclohexylcarbodiimide (DCC) (42.09 g, 204 mmol) in CH$_2$Cl$_2$ (200 mL) dropwise, over a 30 min period at 0° C. The reaction mixture was allowed to stir an additional 8 h at rt. The dicyclohexyl urea which formed was filtered off and the filtrate concentrated under reduced pressure. The crude solid residue 116 was purified by recrystallization from hexane and EtOAc to afford 116 (74.9 g, 79%). mp 158-159° C.; IR (KBr, cm$^{-1}$) 3332, 2931, 255, 1694, 1643, 1613, 1582, 1537, 1450; $^1$H NMR (CDCl$_3$) δ 11.68 (s, 1H), 8.71 (d, J=9.0 Hz, 1H), 7.69 (dd, J=9.0, 2.3 Hz, 1H), 7.55-7.62 (m, 2H), 7.46 (td, J=7.6, 1.4 Hz, 1H), 7.30 (t, J=7.5 Hz, 1H), 7.21 (t, J=9.1 Hz, 1H), 5.13 (b, 1H), 4.37 (b, 1H), 1.51 (d, J=7.2 Hz, 3H), 1.45 (S, 9H). MS (EI) m/e (relative intensity) 467 (M$^+$+2, 14), 466 (M$^+$+1, 44), 465 (M$^+$, 14), 464 (42), 329 (15), 321 (60), 295 (100), 224 (26); $[α]^{26}_D$=−59.1 (c 0.51, EtOAc).

7-Bromo-5-(2-fluoro-phenyl)-3-methyl-1,3-dihydro-benzo[e][1,4]diazepin-2-one 117. To a stirred solution of the benzophenone 116 (30 g, 64.4 mmol) in CHCl$_3$ (300 mL) at rt, hydrogen chloride gas was added slowly. After 20 min, the addition was stopped and the solution was allowed to stir overnight at rt. The reaction mixture was washed with a saturated solution of sodium bicarbonate solution (2×70 mL) and water (2×70 mL). The organic layer was concentrated under reduced pressure. The residual oil was dissolved in methanol-water (1:1, 300 mL) and the pH was adjusted to 8.5 by the addition of aq sodium hydroxide (1 N). The reaction mixture was allowed to stir for 10 h at rt. The solution was then concentrated under reduced pressure and water (100 mL) was added. The solution was extracted with CH$_2$Cl$_2$ (3×50 mL), the organic layer was dried (Na$_2$SO$_4$) and concentrated under reduced pressure. The crude solid 11 was purified by recrystallization from methanol/water to provided 117 (17.8 g, 80%). mp 183-185° C.; IR (KBr, cm$^{-1}$) 2928, 1694, 1611, 1479, 1450, 1377, 1315; $^1$H NMR (CDCl$_3$) δ 9.50 (bs, 1H), 7.62-7.65 (m, 2H), 7.50 (q, J=6.5 Hz, 1H), 7.40 (d, J=2.0 Hz, 1H), 7.29 (t, J=7.5 Hz 1H) 7.15 (d, J=8.6 Hz, 1H), 7.11 (t, J=8.9 Hz, 1H), 3.84 (q, J=6.5 Hz, 1H), 1.82 (d, J=6.5 Hz, 3H); MS (EI) m/e (relative intensity) 348 (M$^+$+1, 23), 347 (M$^+$, 38), 346 (24), 345 (36), 329 (19), 327 (20), 307 (40), 306 (41), 305(100), 304 (37), 303 (63); $[α]^{26}_D$=168.8 (c 0.73, EtOAc).

8-Bromo-6-(2-fluorophenyl)-4-methyl-4H-2,5,10b-triaza-benzo[e]azulene-3-carboxylic acid ethyl ester 118. 7-Bromo-5-(2-fluorophenyl)-3-methyl-1,3-dihydro-benzo[e][1,4]diazepin-2-one 117 (3.78 g, 10.88 mmol) was suspended in dry THF (150 mL) and cooled to −10° C. Sodium hydride (60% dispersion in mineral oil, 0.52 g, 13.07 mol) was added into the suspension in one portion. The reaction mixture was allowed to stir and then warm to rt over a 3 h period. The reaction mixture was again cooled to −10° C. and diethyl chlorophosphate (2.65 mL, 17.42 mmol) was added. The cooling bath was then removed and stirring continued for 3 h. During this time, sodium hydride (60% dispersion in mineral oil, 0.61 g, 15.24 mmol) was suspended in dry THF (60 mL) at −10° C. in another flask. Ethyl isocyanoacetate (1.43 ml, 13.07 mmol) was added to the NaH/THF suspension and this mixture allowed to stir for 3 h. After 3 h the first flask was cooled to −30° C. with a cooling bath and the mixture in the second reaction flask was added to the first flask via a cannula. The reaction mixture was allowed to stir for 24 h, after which it was cooled to 0° C. with an ice-water bath and slowly quenched with acetic acid (5 mL). Water was then added to the reaction mixture and this was extracted with EtOAc. The EtOAc layers were combined, washed with aq NaHCO$_3$, brine and dried (Na$_2$SO$_4$). After removal of the solvent under reduced pressure, the solid was purified by flash chromatography (silica gel, EtOAc:hexane: gradient elution 1:2, 1:1, 2:1). The ethyl ester 118 was a white solid (1.82 g, 38%). mp 190-192° C.; IR (KBr, cm$^{-1}$) 3316, 2925, 1693, 1621, 1485, 1448, 1371; $^1$H NMR (CDCl$_3$) δ 7.92 (s, 1H), 7.72 (dd, J=8.5, 1.5 Hz, 1H), 7.6 (t, J=6.9 Hz, 1H), 7.48 (d, J=8.5 Hz, 1H), 7.42-7.49 (m, 2H), 7.23-7.29 (m, 1H), 7.05 (t, J=9.3 Hz, 1H), 6.71 (q, J=7.3 Hz, 1H), 4.41 (m, 2H), 1.42 (t, J=7.1 Hz, 3H), 1.29 (d, J=7.2, 3H). MS (EI) m/e (relative intensity) 442 (M$^+$, 5), 428 (7), 381 (58), 355 (100), 303 (37); $[α]^{26}_D$=10.6 (c 0.53, EtOAc).

6-(2-Fluorophenyl)-4-methyl-8-trimethylsilanylethynyl-4H-2,5,10b-triaza-benzo[e]azulene-3-carboxylic acid ethyl ester 119. A mixture of 118 (69.3 mg, 0.16 mmol) and bis(triphenylphosphine) palladium(II) acetate (11.68 mg, 0.015 mmol) was dissolved in a mixed solvent system of acetonitrile (120 mL) and TEA (80 mL). The mixture was degassed under vacuum and argon gas was added, after which trimethylsilylacetylene (0.044 mL, 0.31 mmol) was added into the mixture. The mixture was degassed again under vacuum (argon) and heated to reflux. The mixture was heated at reflux until analysis by TLC (EtOAc) indicated that all of the starting material 118 had been consumed. The mixture was cooled to rt and the precipitate which formed was removed by filtration through celite. The filtrate was concentrated under reduced pressure and partitioned between H$_2$O and EtOAc. The combined layers of EtOAc were washed with brine and dried (Na$_2$SO$_4$), after which the solvent was removed under reduced pressure and the residue was purified by flash chromatography (silica gel, EtOAc:hexane 1:1). The conditions for TLC were EtOAc on silica gel. A white solid 119 (58.1 mg, 79%) was obtained. mp 186-187° C.; IR (KBr, cm$^{-1}$) 2410, 2358, 1716, 1497, 1253; $^1$H NMR (CDCl$_3$) δ 7.92 (s, 1H), 7.72 (dd, J=8.5, 1.5 Hz, 1H), 7.6 (t, J=6.9 Hz, 1H), 7.48 (d, J=8.5 Hz, 1H), 7.42-7.49 (m, 2H), 7.23-7.29 (m, 1H), 7.05 (t, J=9.3 Hz, 1H), 6.71 (q, J=7.3 Hz, 1H), 4.41 (m, 2H), 1.42 (t, J=7.1 Hz, 3H), 1.29 (d, J=7.2, 3H), 0.24 (s, 9H). MS (EI) m/e (relative intensity) 459 (M$^+$, 28), 445 (32), 399 (51), 371 (100), 235 (71), 178 (75); $[α]^{26}_D$=−27.8 (c 0.46, EtOAc).

8-Ethynyl-6-(2-fluorophenyl)-4-methyl-4H-2,5,10b-triaza-benzo[e]azulene-3-carboxylic acid ethyl ester 110 (SH-053-2'F—S—CH$_3$). The trimethylsilylacetylene intermediate 119 (SH—I-055) (0.17 g, 0.37 mmol) was dissolved in THF (30 mL) and was then treated with Bu$_4$NF.H$_2$O (0.114 g, 0.44 mmol). The mixture was allowed to stir for 30 min at rt, after which H$_2$O (10 mL) was added and the mixture was extracted with EtOAc (3×25 mL). The combined organic extracts were washed with brine (25 mL) and dried (Na$_2$SO$_4$). After removal of the solvent under reduced pressure, the residue was purified by a wash column (silica gel, EtOAc) to furnish 120 (SH-053-2'F—S—CH$_3$) (0.12 g, 87%) as a white solid: mp 212-214° C.; IR (KBr, cm$^{-1}$) 3288, 2979, 1716, 1497, 1257, 1255; $^1$H NMR (CDCl$_3$) δ 7.98 (s, 1H), 7.72 (d, J=8.3 Hz, 1H), 7.63 (d, J=8.5 Hz, 1H), 7.59 (d, J=8.3 Hz, 1H), 7.42-7.49 (m, 1H), 7.42 (s, 1H), 7.23-7.28 (m, 1H), 7.05 (t, J=9.2 Hz, 1H), 6.71 (q, J=7.2, 1H), 4.41 (m, 2H), 3.16 (s, 1H), 1.42 (t, J=7.1 Hz, 3H) 1.29 (d, J=7.3 Hz, 3H). MS (EI) m/e (relative intensity) 387 (M$^+$, 20), 373 (21), 327 (47), 299 (100); $[α]^{26}_D$=−0.95 (c 0.84, EtOAc).

Scheme 26 (SH-053-2'N-S-CH3)
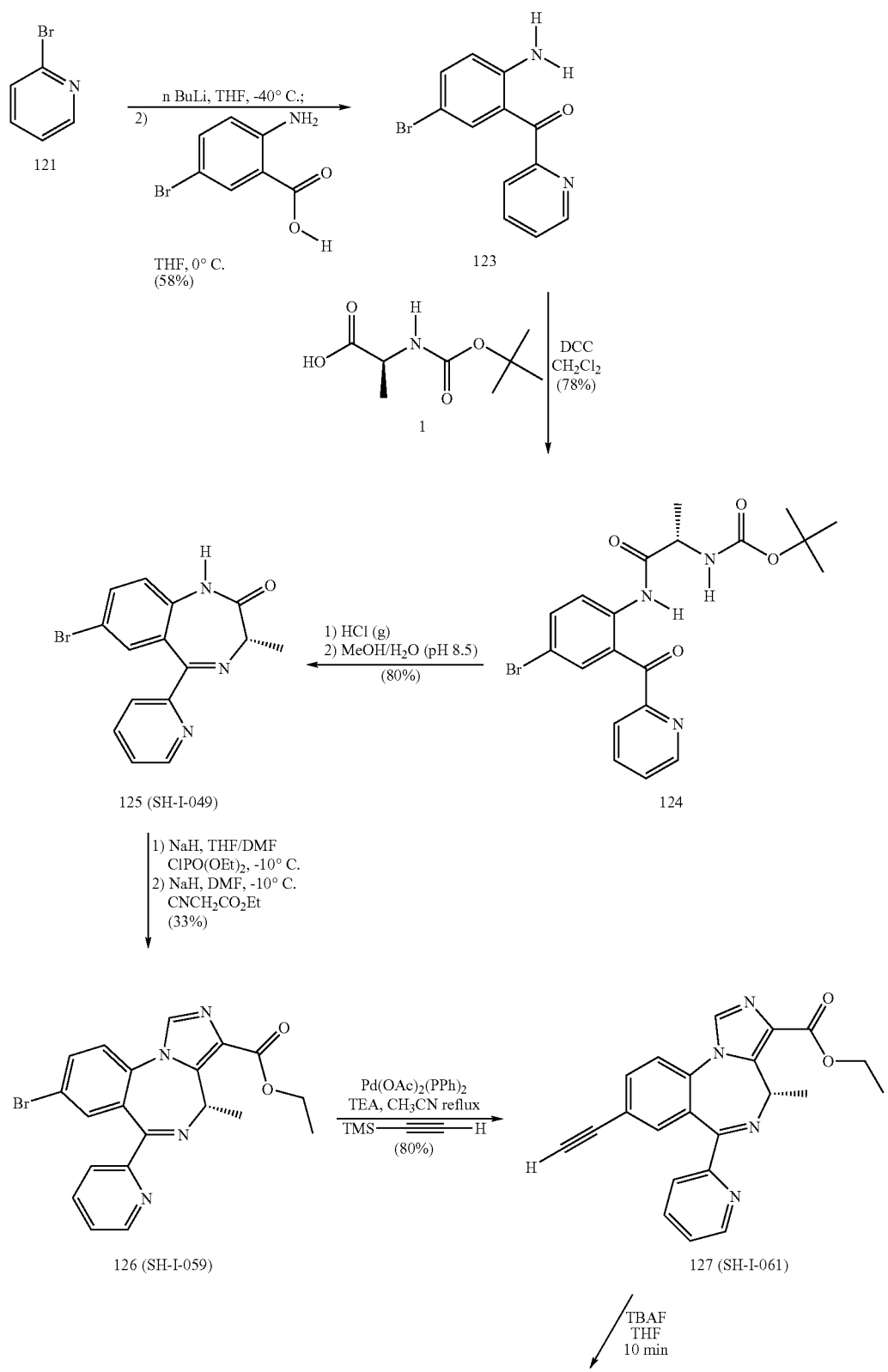

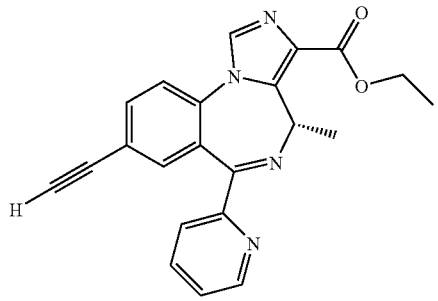

128 (SH-053-2'N-S-CH₃)

Procedure for SH-053-2'N-S—CH₃ (128)

(2-Amino-5-bromo-phenyl)-pyridin-2-yl-methanone 123

The anion of 2-bromo-pyridine 121 and 2-amino-5-bromobenzoic acid 122 were condensed to provide the 2'-pyridylketone 123.

{1-[4-Bromo-2-(pyridine-2-carbonyl)-phenylcarbamoyl]-ethyl}-carbamic acid tert-butyl ester 124

To a stirred solution of (2-amino-5-bromophenyl)-pyridin-2-yl-methanone 123 (16 g, 57.33 mmol) and the N-Boc-L-alanine 107 (10.92 g, 57.73 mmol) in $CH_2Cl_2$ (100 mL) was added dicyclohexylcarbodiimide (DCC) (11.91 g, 57.73 mmol) in $CH_2Cl_2$ (60 mL) dropwise, over a 30 min period at 0° C. The reaction mixture was allowed to stir an additional 8 h at rt. The dicyclohexyl urea which formed was filtered off and the filtrate concentrated under reduced pressure. The crude solid 124 was purified by recrystallization from hexane and EtOAc to afford 124 (7.88 g, 81%). mp 208-210° C.; IR (KBr, cm$^{-1}$) 3332, 2931, 1694, 1507, 1287, 1163; $^1$H NMR (CDCl$_3$) δ 11.68 (s, 1H), 8.71 (d, J=9.0 Hz, 1H), 7.69 (dd, J=9.0, 2.3 Hz, 1H), 7.55-7.62 (m, 2H), 7.46 (td, J=7.6, 1.4 Hz, 1H), 7.30 (t, J=7.5 Hz, 1H), 7.21 (t, J=9.1 Hz, 1H), 5.13 (b, 1H), 4.37 (b, 1H), 1.51 (d, J=7.2 Hz, 3H), 1.45 (S, 9H). MS (EI) m/e (relative intensity) 449 (M$^+$+1, 5), 448 (M$^+$, 5), 376 (10), 329 (20), 304 (100), 228 (25); $[\alpha]^{26}_D$=−36.1 (c 0.61, EtOAc).

7-Bromo-3-methyl-5-pyridin-2-yl-1,3-dihydro-benzo [e][1,4]diazepin-2-one 125

To a stirred solution of ester 124 (16 g, 35.69 mmol) in CHCl$_3$ (300 mL) at rt, hydrogen chloride gas was added in slowly. After 20 min, the addition was stopped and the solution was allowed to stir overnight at rt. The reaction mixture was washed with a saturated solution of sodium bicarbonate (2×50 mL) and water (2×50 mL). The organic layer was concentrated under reduced pressure. The residual oil was dissolved in methanol-water (3:1, 300 mL) and the pH was adjusted to 8.5 by the addition of aq sodium hydroxide (1 N). The reaction mixture was stirred for 10 h at rt. The solution was concentrated under reduced pressure and water (80 mL) was added. The solution was extracted with $CH_2Cl_2$ (3×70 mL) and concentrated under reduced pressure. The crude solid 125 was purified by recrystallization from methanol/water to provide pure 125 (9.42 g, 80%). mp 227-229° C.; IR (KBr, cm$^{-1}$) 2928, 1684, 1611, 1476; $^1$H NMR (CDCl$_3$) δ 9.47 (bs, 1H), 8.62 (d, J=4.7 Hz, 1H), 8.0 (d, J=7.90 Hz, 1H), 7.81 (td, J=7.7, 1.6 Hz, 1H), 7.56 (dd, J=8.6, 2.2 Hz 1H), 7.50 (dd, J=2.1 Hz, 1H), 7.36 (dd, J=7.4 Hz, 1H), 7.06 (d, J=8.6 Hz, 1H), 3.85 (q, J=6.5 Hz, 1H), 1.76 (d, J=6.5 Hz, 3H); MS (EI) m/e (relative intensity) 330 (M$^+$, 50), 329 (50), 314 (52), 288 (100), 250 (30), 208 (32), 179(50), 88(72); $[\alpha]^{26}_D$=403.2 (c 0.50, EtOAc).

8-Bromo-4-methyl-6-pyridin-2-yl-4H-2,5,10b-triaza-benzo [e]azulene-3-carboxylic acid ethyl ester 126

The 7-bromo-3-methyl-5-pyridin-2-yl-1,3-dihydro-benzo [e][1,4]diazepin-2-one 125 (3.3 g, 10 mmol) was suspended in dry THF (200 mL) and cooled to −10° C. Sodium hydride (60% dispersion in mineral oil, 0.48 g, 12 mmol) was added into the suspension in one portion. The reaction mixture was allowed to stir and warm to rt over a 3 h period. The reaction mixture was again cooled to −10° C. and diethyl chlorophosphate (2.31 mL, 16 mmol) was added. The cooling bath was then removed and stirring continued for 3 h. At this time, sodium hydride (60% dispersion in mineral oil, 0.56 g, 14 mmol) was suspended in dry THF (150 mL) at −10° C. in another flask. Ethyl isocyanoacetate (1.31 mL, 12 mmol) was added to the NaH/THF suspension, the solution which resulted was allowed to stir for 3 h. After 3 h, the first flask was cooled to −30° C. and the solution in the 2nd reaction flask was added to the first flask via a cannula. The reaction mixture was allowed to stir for 24 h, and then cooled with an ice-water bath and slowly quenched with acetic acid (10 mL). Water was added to the reaction mixture after which it was extracted with EtOAc. The EtOAc layers were combined, washed with aq NaHCO$_3$, brine and dried (Na$_2$SO$_4$). After removal of the solvent under reduced pressure, the solid was purified by flash chromatography (silica gel, EtOAc:hexane, gradient elution 1:1, 2:1, 3:1). The ester 126 was a white solid (1.40 g, 33%). mp 193-195° C.; IR (KBr, cm$^{-1}$) 2962, 1719, 1260, 1021; $^1$H NMR (CDCl$_3$) δ 7.92 (s, 1H), 7.72 (dd, J=8.5, 1.5 Hz, 1H), 7.6 (t, J=6.9 Hz, 1H), 7.48 (d, J=8.5 Hz, 1H), 7.42-7.49 (m, 2H), 7.23-7.29 (m, 1H), 7.05 (t, J=9.3 Hz, 1H), 6.71 (q, J=7.3 Hz, 1H), 4.41 (m, 2H), 1.42 (t, J=7.1 Hz, 3H), 1.29 (d, J=7.2, 3H).

4-Methyl-6-pyridin-2-yl-8-trimethylsilanylethynyl-4H-2,5,10b-triaza-benzo [e]azulene-3-carboxylic acid ethyl ester 127 (SH—I-061)

A mixture of 126 (2.73 g, 6.42 mmol) and bis(triphenylphosphine)palladium(II) acetate (0.48 g, 0.64 mmol) was dissolved in a mixed solvent system of acetonitrile (80 mL) and TEA (120 mL). The mixture was degassed under vacuum and argon gas was added, after which trimethylsilylacetylene (1.8 mL, 12.85 mmol) was added into the mixture. The mixture was degassed again under vacuum (argon) and heated to reflux. The mixture was heated at reflux until analysis by TLC (EtOAc) indicated that all of the starting material 126 had been consumed. The mixture was cooled to rt and the precipitate which formed was removed by filtration through celite. The filtrate was concentrated under reduced pressure and partitioned between H$_2$O and EtOAc. The combined layers of EtOAc were washed with brine and dried (Na$_2$SO$_4$), after which the solvent was removed under reduced pressure and the residue was purified by flash chromatography (silica gel, EtOAc:hexane 2:1). A white solid 127 (SH-1-061) (2.27 g, 80%) was obtained. mp 197-198° C.; IR (KBr, cm$^{-1}$) 3477, 2982, 2158, 1713, 1643; $^1$H NMR (CDCl$_3$) δ 7.92 (s, 1H), 7.72 (dd, J=8.5, 1.5 Hz, 1H), 7.6 (t, J=6.9 Hz, 1H), 7.48 (d, J=8.5 Hz, 1H), 7.42-7.49 (m, 2H), 7.23-7.29 (m, 1H), 7.05 (t, J=9.3 Hz, 1H), 6.71 (q, J=7.3 Hz, 1H), 4.41 (m, 2H), 1.42 (t, J=7.1 Hz, 3H), 1.29 (d, J=7.2, 3H), 0.24 (s, 9H); [α]$^{26}_D$=304.4 (c 0.41, EtOAc).

8-Ethynyl-4-methyl-6-pyridin-2-yl-4H-2,5,10b-triaza-benzo[e]azulene-3-carboxylic acid ethyl ester 128 (SH-053-2'N-S—CH$_3$)

The trimethylsilylacetylene intermediate 127 (1.5 g, 3.39 mmol) was dissolved in THF (150 mL) and was then stirred with Bu$_4$NF.H$_2$O (1.06 g, 4.06 mmol). The mixture was allowed to stir for 30 min at rt, after which H$_2$O (10 mL) was added and the mixture was extracted with EtOAc (3×50 mL). The combined organic extracts were washed with brine (25 mL) and dried (Na$_2$SO$_4$). After removal of the solvent under reduced pressure, the residue was purified by a wash column (silica gel, EtOAc) to furnish 128 (SH-053-2'N-S—CH$_3$) (1.01 g, 81%) as a white solid: mp 235-237° C.; IR (KBr, cm$^{-1}$) 3321, 2979, 2933, 1647, 1597; $^1$H NMR (CDCl$_3$) δ 8.61 (d, J=4.2 Hz, 1H), 8.01 (d, J=7.8 Hz, 1H), 7.91 (s, 1H), 7.81 (t, J=7.8 Hz, 1H), 7.72 (d, J=9.5 Hz, 1H), 7.55 (d, J=12 Hz, 1H), 7.59 (s, 1H), 7.37 (t, J=9.8 Hz, 1H), 6.71 (q, J=7.3, 1H), 4.41 (m, 2H), 3.16 (s, 1H), 1.42 (t, J=7.1 Hz, 3H) 1.28 (d, J=7.3 Hz, 3H); [α]$^{26}_D$=−85.2 (c 0.69, EtOAc).

Scheme 27 (SH-053-R-CH$_3$)

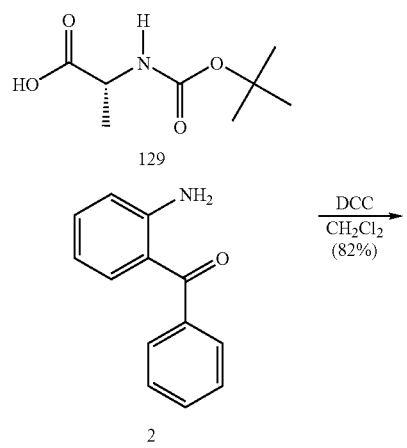

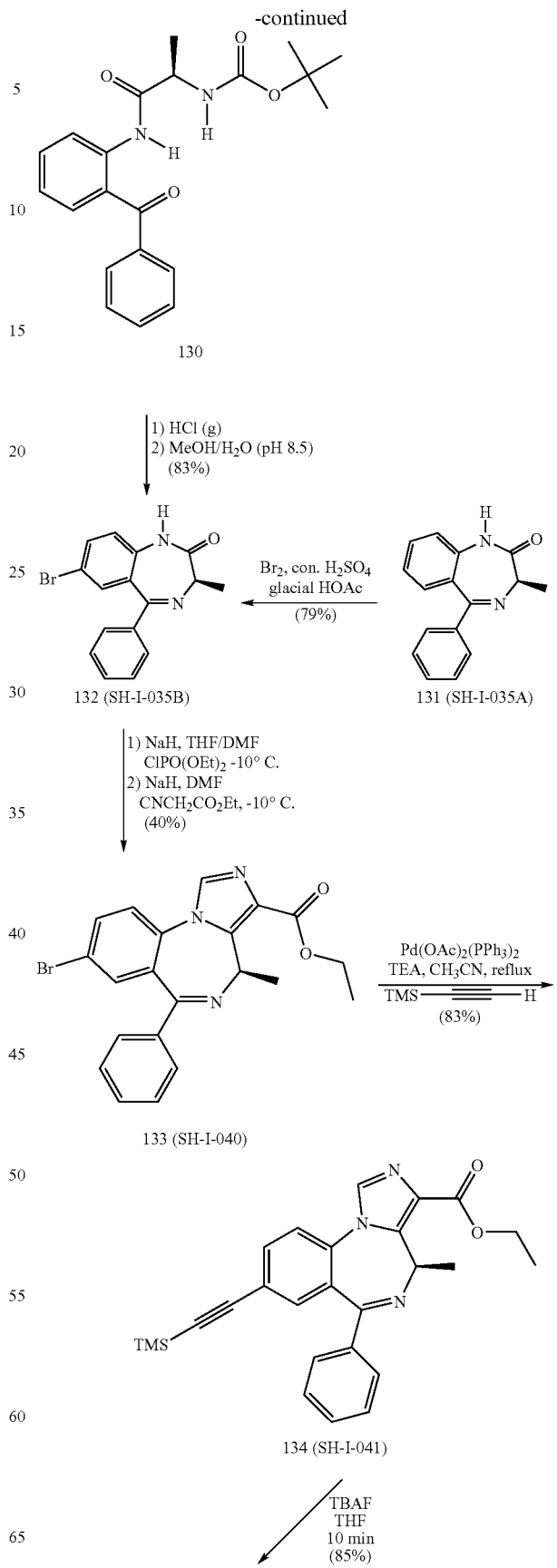

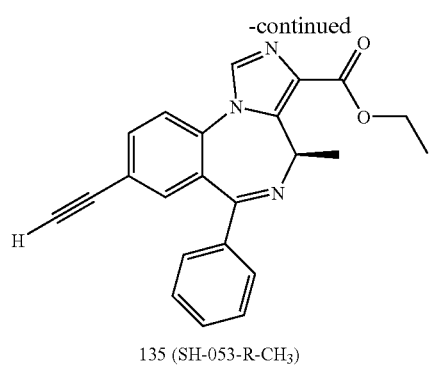

135 (SH-053-R-CH₃)

Procedure for SH-053-R-CH₃ (135)

1-(2-Benzoyl-phenylcarbamoyl)-ethyl]-carbamic acid tert-butyl ester 130

To a stirred solution of 2-amino-5-bromobenzophenone (5.73 g, 29.07 mmol) and the N-Boc-D-alanine 129 (5 g, 26.43 mmol) in CH₂Cl₂ (200 mL) was added dicyclohexyl-carbodiimide (DCC) (5.99 g, 29.07 mmol) in CH₂Cl₂ (100 mL) dropwise, over a 30 min period at 0° C. The reaction mixture was allowed to stir an additional 8 h at rt. The dicyclohexyl urea which formed was filtered off and the filtrate concentrated under reduced pressure. The crude solid 130 was purified by recrystallization from hexane to afford 130 (7.97 g, 82%). mp 127-129° C.; IR (KBr, cm⁻¹) 3288, 2475, 2352, 1684, 1636, 1576, 1507, 1447, 1264, 1165, 700; ¹H NMR (CDCl₃) δ 11.48 (s, 1H), 8.67 (d, J=8.22 Hz, 1H), 7.71-7.43 (m, 7H), 7.13-7.08 (m, J=1H) 5.06 (br s, 1H), 4.36 (br s, 1H), 1.50 (d, J=7.1 Hz, 3H), 1.44 (s, 9H); MS (EI) m/e (relative intensity) 368 (M⁺, 6), 295 (10), 225 (27), 224 (79), 197 (83), 196 (77), 167 (15), 145 (46), 144 (88), 126 (17), 105 (38), 88 (94), 77(37), 57 (100); [α]²⁶_D=67.3 (c 0.44, EtOAc).

3-Methyl-5-phenyl-1,3-dihydro-benzo[e][1,4]diazepin-2-one 131

To a stirred solution of the benzophenone 130 (10.65 g, 29.38 mmol) in CHCl₃ (400 mL) at rt, hydrogen chloride gas was added in slowly. After 20 min, the addition was stopped and the solution was allowed to stir overnight at rt. The reaction mixture was then washed with a saturated solution of sodium bicarbonate (2×50 mL) and water (2×50 mL). The organic layer was concentrated under reduced pressure. The residual oil was dissolved in methanol-water (2:1, 500 mL) and the pH was adjusted to 8.5 by the addition of aq sodium hydroxide (1 N). The reaction mixture was stirred for 10 h at rt. The solution was concentrated under reduced pressure and water (100 mL) was added. The solution was extracted with CH₂Cl₂ (3×100 mL) and concentrated under reduced pressure. The crude solid 131 was purified by recrystallization from methanol/water to provide 131(6.10 g, 83%). mp 160-162° C.; IR (KBr, cm⁻¹) 3215, 3059, 2974, 2932, 1681, 1574, 1478, 1445, 1372, 1321, 1242, 1160, 1131; ¹H NMR (CDCl₃) δ 9.65 (s, 1H), 7.54-7.13 (m, 9H), 3.78 (q, J=6.45 Hz, 1H), 1.78 (d, J=7.1 Hz, 3H); MS (EI) m/e (relative intensity) 250 (M⁺, 40), 249 (83), 234 (15), 209 (75), 208 (76), 207 (100), 180 (17), 152 (19) 103 (23), 77 (40).

7-Bromo-3-methyl-5-phenyl-1,3-dihydro-benzo[e][1,4]diazepin-2-one 132

To a stirred solution of 131 (66.5 g, 265 mmol) in glacial acetic acid (400 mL), sulfuric acid (80 mL) was added to the solution. Bromine (28 mL, 530 mmol) dissolved in acetic acid (150 mL) was added dropwise into the mixture. The reaction mixture was allowed to stir until analysis by NMR spectroscopy indicated that all of the starting material 131 had been consumed. The solution was concentrated under reduced pressure and then brought to pH 7 by addition of 1N aq NaOH solution and then extracted with EtOAc. The crude product 132 was purified by recrystallization from CH₂Cl₂ to afford 132 (68.66 g, 79%). mp 210-212° C.; IR (KBr, cm⁻¹) 2931, 1692, 1603, 1563, 1475, 1445, 1375, 1259, 1235, 1130, 1090; ¹H NMR (CDCl₃) δ 9.36 (s, 1H), 7.63 (dd, J=2.22, 8.58 Hz, 1H), 7.54-7.39 (m, 6H), 7.12 (d, J=8.611H), 3.76 (q, J=6.3 Hz, 1H), 1.76 (d, J=6.45 Hz, 3H). MS (EI) m/e (relative intensity) 330 (M⁺+1, 21), 329 (M⁺, 50), 328 (22), 327 (48), 289 (44), 288 (46), 287 (100), 286 (45), 285 (60) 205 (25), 77 (49).

8-Bromo-4-methyl-6-phenyl-4H-2,5,10b-triaza-benzo[e]azulene-3-carboxylic acid ethyl ester 133

7-Bromo-3-methyl-5-phenyl-1,3-dihydro-benzo [e][1,4] diazepin-2-one 132 (16.6 g, 0.052 mol) was suspended in dry THF (250 mL) and cooled to −10° C. Sodium hydride (60% dispersion in mineral oil, 4.36 g, 0.109 mol) was added into the suspension in one portion. The reaction mixture was allowed to stir and warm to rt over a 3 h period. The reaction mixture was again cooled to −10° C. and diethyl chlorophosphate (12.7 mL, 0.09 mol) was added. The cooling bath was then removed and stirring contined for 3 h. At this time, sodium hydride (60% dispersion in mineral oil, 4.2 g, 0.1 mol) was suspended in dry THF (250 mL) at −10° C. in another flask. Ethyl isocyanoacetate (6.78 mL, 0.06 mol) was added to the NaH/THF suspension, after which the solution which resulted was allowed to stir for 3 h. After 3 h the first flask was cooled to −30° C. and the solution in the 2nd reaction flask was added to the first flask via a cannula. The reaction mixture was allowed to stir for 24 h, and then cooled with an ice-water bath and slowly quenched with acetic acid (10 mL). Water was added to the reaction mixture after which it was extracted with EtOAc. The EtOAc layers were combined, washed with aq NaHCO₃, brine and dried (Na₂SO₄). After removal of the solvent under reduced pressure, the solid was purified by flash chromatography (silica gel, EtOAc: hexane, gradient elution 1:2, 1:1, 2:1). The ester 133 was a white solid (8.76 g, 40%). mp 164-165° C.; IR (KBr, cm⁻¹) 2925, 1706, 1622, 1557, 1495, 1266, 1185; ¹H NMR (CDCl₃) δ 7.89 (s, 1H), 7.73 (dd, J=1.73 Hz, 1H), 7.51-7.36 (m, 7H), 6.66 (q, J=7.30, 1H), 4.45-4.30 (m, 2H), 1.40 (t, J=7.11, 3H), 1.25 (d, J=7.38 Hz, 3H). MS (EI) m/e (relative intensity) 426 (M⁺+2, 15), 425 (M⁺+1, 58), 424 (M⁺, 15), 423 (58), 380 (24), 379 (71), 378 (35), 377 (69), 352 (50), 351(100), 350 (67), 349 (92), 270 (38), 229 (16); [α]²⁶_D=38.2 (c 0.45, EtOAc).

4-Methyl-6-phenyl-8-trimethylsilanylethynyl-4H-2, 5,10b-triaza-benzo[e]azulene-3-carboxylic acid ethyl ester 134 (SH—I-041)

A mixture of ester 133 (3.0 g, 7.07 mmol) and bis(triphenylphosphine) palladium(II) acetate (0.42 g, 0.57 mmol) was dissolved in a mixed solvent system of acetonitrile (80 mL) and TEA (120 mL). The mixture was degassed under vacuum and argon was added, after which trimethylsilylacetylene (2 mL, 14.14 mmol) was added into the mixture. The mixture was degassed again under vacuum (argon) and heated to reflux. The mixture was heated at reflux until analysis by TLC (EtOAc) indicated that all of the starting material 133 had been consumed. The mixture was cooled to rt and the precipitate which formed was removed by filtration through celite. The filtrate was concentrated under reduced pressure and partitioned between $H_2O$ and EtOAc. The combined layers of EtOAc were washed with brine and dried ($Na_2SO_4$), after which the solvent was removed under reduced pressure and the residue was purified by flash chromatography (silica gel, EtOAc:hexane 1:1). The conditions for TLC were EtOAc on silica gel. A white solid 134 (SH—I-041) (2.59 g, 83%) was obtained. mp 160-162° C.; IR (KBr, $cm^{-1}$) 3365, 2925, 1706, 1616, 1553, 1498; $^1H$ NMR ($CDCl_3$) δ 7.89 (s, 1H), 7.73 (dd, J=1.73 Hz, 1H), 7.51-7.36 (m, 7H), 6.66 (q, J=7.30, 1H), 4.45-4.30 (m, 2H), 1.40 (t, J=7.11, 3H), 1.25 (d, J=7.38 Hz, 3H), 0.15 (s, 9H). MS (EI) m/e (relative intensity) 441 ($M^+$, 15), 369 (25), 323 (55), 295 (100), 267 (15).

8-Ethynyl-4-methyl-6-phenyl-4H-2,5,10b-triazabenzo [e]azulene-3-carboxylic acid ethyl ester 135 (SH-053-R-$CH_3$)

The trimethylsilylacetylene intermediate 134 (2.8 g, 6.3 mmol) was dissolved in THF (20 mL) and was then treated with $Bu_4NF.H_2O$ (1.9 g, 7.56 mmol). The mixture was allowed to stir for 30 min at rt, after which $H_2O$ (10 mL) was added and the mixture was extracted with EtOAc (3×50 mL). The combined organic extracts were washed with brine (25 mL) and dried ($Na_2SO_4$). After removal of the solvent under reduced pressure, the residue was purified by a wash column (silica gel, EtOAc) to furnish 135 (SH-053-R-$CH_3$) (1.9 g, 85%) as a white solid: mp 197-199° C.; IR (KBr, $cm^{-1}$) 3285, 2928, 1708, 1616, 1553, 1498, 1445, 1374; $^1H$ NMR ($CDCl_3$) δ 7.92 (s, 1H), 7.73 (dd, J=1.72, 8.32 Hz, 1H), 7.58-7.36 (m, 7H), 6.67 (q, J=7.35, 1H), 4.46-4.34 (m, 2H), 3.16 (s, 1H), 1.41 (t, J=7.11, 3H), 1.25 (d, J=7.38, 3H); MS (EI) m/e (relative intensity) 369 ($M^+$, 30), 323 (55), 295 (100), 267 (15). Anal. Calcd. for $C_{23}H_{19}N_3O_2$: C, 74.78; H, 5.18; N, 11.37. Found: C, 74.43; H, 5.67; N, 11.39. $[\alpha_D]^{26}$=75.0 (c 0.8, EtOAc).

Scheme 28 (SH-053-2'F-R-$CH_3$)

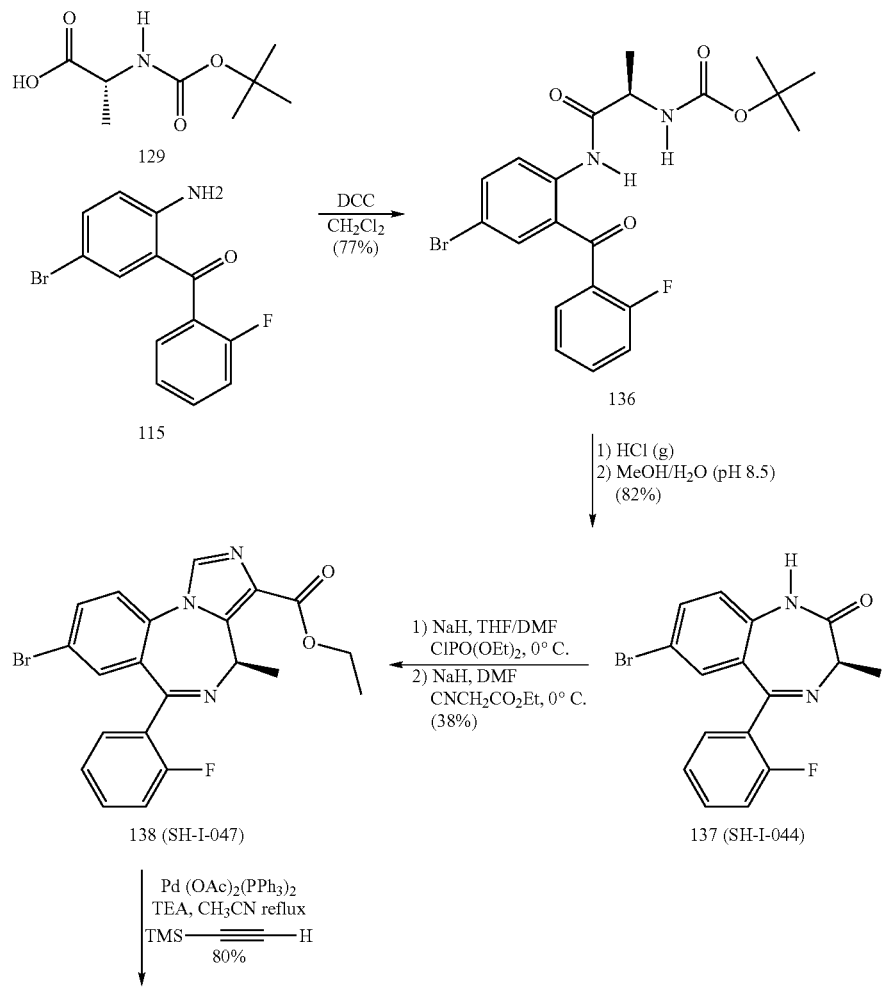

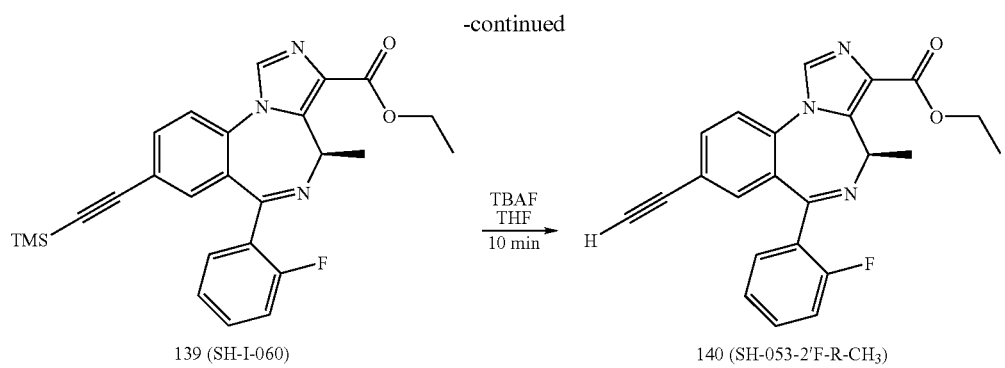

139 (SH-I-060) → 140 (SH-053-2'F-R-CH3)

TBAF / THF / 10 min

Procedure for SH-053-2'F-R-CH3 (140)

{1-[4-Bromo-2-(2-fluorobenzoyl)-phenylcarbamoyl]-ethyl}-carbamic acid tert-butyl ester 136

To a stirred solution of (2-amino-5-bromophenyl)-(2'-fluoro-phenyl)-methanone 115 (60 g, 204 mmol) and the N-Boc-D-alanine 129 (38.59 g, 204 mmol) in $CH_2Cl_2$ (500 mL) was added dicyclohexylcarbodiimide (DCC) (42.09 g, 204 mmol) in $CH_2Cl_2$ (200 mL) dropwise, over a 30 min period at 0° C. The reaction mixture was allowed to stir an additional 8 h at rt. The dicyclohexyl urea which formed was filtered off and the filtrate concentrated under reduced pressure. The crude solid product 136 was purified by recrystallization from hexane and EtoAc to afford 136 (73 g, 77%). mp 158-159° C.; IR (KBr, $cm^{-1}$) 3332, 2931, 255, 1694, 1643, 1613, 1582, 1537, 1450; $^1$H NMR ($CDCl_3$) δ 11.68 (s, 1H), 8.71 (d, J=9.0 Hz, 1H), 7.69 (dd, J=9.0, 2.3 Hz, 1H), 7.55-7.62 (m, 2H), 7.46 (td, J=7.6, 1.4 Hz, 1H), 7.30 (t, J=7.5 Hz, 1H), 7.21 (t, J=9.1 Hz, 1H), 5.13 (b, 1H), 4.37 (b, 1H), 1.51 (d, J=7.2 Hz, 3H), 1.45 (S, 9H). MS (EI) m/e (relative intensity) 467 ($M^+$+2, 14), 466 ($M^+$+1, 44), 465 ($M^+$, 14), 464 (42), 329 (15), 321 (60), 295 (100), 224 (26); $[α]^{26}{}_D$=59.6 (c 0.51, EtOAc).

7-Bromo-5-(2-fluoro-phenyl)-3-methyl-1,3-dihydro-benzo[e][1,4]diazepin-2-one 137

To a stirred solution of the benzophenone 136 (30 g, 64.4 mmol) in $CHCl_3$ (300 mL) at rt, hydrogen chloride gas was added slowly. After 20 min, the addition was stopped and the solution was allowed to stir overnight at rt. The reaction mixture was then washed with a saturated solution of sodium bicarbonate (2×70 mL) and water (2×70 mL). The organic layer was concentrated under reduced pressure. The residual oil was dissolved in methanol-water (1:1, 300 mL) and the pH was adjusted to 8.5 by the addition of aq sodium hydroxide (1 N). The reaction mixture was allowed to stir for 10 h at rt. The solution was then concentrated under reduced pressure and water (100 mL) was added. The solution was extracted with $CH_2Cl_2$ (3×50 mL), and the organic layer was dried ($Na_2SO_4$) and concentrated under reduced pressure. The crude solid 137 was purified by recrystallization from methanol/water to provided 137(18.2 g, 82%). mp 183-185° C.; IR (KBr, $cm^{-1}$) 2928, 1694, 1611, 1479, 1450, 1377, 1315; $^1$H NMR($CDCl_3$) δ 9.50 (bs, 1H), 7.62-7.65 (m, 2H), 7.50 (q, J=6.5 Hz, 1H), 7.40 (d, J=2.0 Hz, 1H), 7.29 (t, J=7.5 Hz 1H) 7.15 (d, J=8.6 Hz, 1H), 7.11 (t, J=8.9 Hz, 1H), 3.84 (q, J=6.5 Hz, 1H), 1.82 (d, J=6.5 Hz, 3H); MS (EI) m/e (relative intensity) 348 ($M^+$+1, 23), 347 ($M^+$, 38), 346 (24), 345 (36), 329 (19), 327 (20), 307 (40), 306 (41), 305(100), 304 (37), 303 (63); $[α]^{26}{}_D$=−169.1 (c 0.71, EtOAc).

8-Bromo-6-(2-fluorophenyl)-4-methyl-4H-2,5,10b-triaza-benzo[e]azulene-3-carboxylic acid ethyl ester 138

7-Bromo-5-(2'-fluorophenyl)-3-methyl-1,3-dihydro-benzo[e][1,4]diazepin-2-one 137 (3.78 g, 10.88 mmol) was suspended in dry THF (150 mL) and cooled to −10° C. Sodium hydride (60% dispersion in mineral oil, 0.52 g, 13.07 mol) was added into the suspension in one portion. The reaction mixture was allowed to stir and then warm to rt over 3 h period. The reaction mixture was again cooled to −10° C. and diethyl chlorophosphate (2.65 mL, 17.42 mmol) was added. The cooling bath was then removed and stirring continued for 3 h. During this time, sodium hydride (60% dispersion in mineral oil, 0.61 g, 15.24 mmol) was suspended in dry THF (60 mL) at −10° C. in another flask. Ethyl isocyanoacetate (1.43 mL, 13.07 mmol) was added to the NaH/THF suspension and this mixture allowed to stir for 3 h. After 3 h the first flask was cooled to −30° C. with a cooling bath and the mixture in the second reaction flask was added to the first flask via a cannula. The reaction mixture was allowed to stir for 24 h, after which it was cooled to 0° C. with an ice-water bath and slowly quenched with acetic acid (5 mL). Water was then added to the reaction mixture and this was extracted with EtOAc. The EtOAc layers were combined, washed with aq $NaHCO_3$, brine and dried ($Na_2SO_4$). After removal of the solvent under reduced pressure the solid was purified by flash chromatography (silica gel, EtOAc:hexane: gradient elution 1:2, 1:1, 2:1). The ethyl ester 138 was a white solid (1.82 g, 38%). mp 190-192° C.; IR (KBr, $cm^{-1}$) 3316, 2925, 1693, 1621, 1485, 1448, 1371; $^1$H NMR ($CDCl_3$) δ 7.92 (s, 1H), 7.72 (dd, J=8.5, 1.5 Hz, 1H), 7.6 (t, J=6.9 Hz, 1H), 7.48 (d, J=8.5 Hz, 1H), 7.42-7.49 (m, 2H), 7.23-7.29 (m, 1H), 7.05 (t, J=9.3 Hz, 1H), 6.71 (q, J=7.3 Hz, 1H), 4.41 (m, 2H), 1.42 (t, J=7.1 Hz, 3H), 1.29 (d, J=7.2, 3H). MS (EI) m/e (relative intensity) 442 ($M^+$, 5), 428 (7), 381 (58), 355 (100), 303 (37); $[α]^{26}{}_D$=−10.9 (c 0.54, EtOAc).

6-(2-Fluorophenyl)-4-methyl-8-trimethylsilanylethynyl-4H-2,5,10b-triaza-benzo[e]azulene-3-carboxylic acid ethyl ester 139

A mixture of 138 (69.3 mg, 0.16 mmol) and bis(triphenylphosphine) palladium(II) acetate (11.68 mg, 0.015 mmol) was dissolved in a mixed solvent system of acetonitrile (120 mL) and TEA (80 mL). The mixture was degassed under vacuum and argon gas was added, after which trimethylsilylacetylene (0.044 mL, 0.31 mmol) was added into the mixture. The mixture was degassed again under vacuum (argon) and heated to reflux. The mixture was heated at reflux until analysis by TLC (EtOAc) indicated that all of the starting material 138 had been consumed. The mixture was cooled to rt and the precipitate which formed was removed by filtration through celite. The filtrate was concentrated under reduced pressure and partitioned between $H_2O$ and EtOAc. The combined layers of EtOAc were washed with brine and dried ($Na_2SO_4$), after which the solvent was removed under reduced pressure and the residue was purified by flash chromatography (silica gel, EtOAc:hexane 1:1). The conditions for TLC were EtOAc on silica gel. A white solid 139 (58.8 mg, 80%) was obtained. mp 186-187° C.; IR (KBr, $cm^{-1}$) 2410, 2358, 1716, 1497, 1253; $^1$H NMR ($CDCl_3$) δ 7.92 (s, 1H), 7.72 (dd, J=8.5, 1.5 Hz, 1H), 7.6 (t, J=6.9 Hz, 1H), 7.48 (d, J=8.5 Hz, 1H), 7.42-7.49 (m, 2H), 7.23-7.29 (m, 1H), 7.05 (t, J=9.3 Hz, 1H), 6.71 (q, J=7.3 Hz, 1H), 4.41 (m, 2H), 1.42 (t, J=7.1 Hz, 3H), 1.29 (d, J=7.2, 3H), 0.24 (s, 9H). MS (EI) m/e (relative intensity) 459 ($M^+$, 28), 445 (32), 399 (51), 371 (100), 235 (71), 178 (75); $[\alpha]^{26}_D$=−28.2 (c 0.48, EtOAc).

8-Ethynyl-6-(2-fluorophenyl)-4-methyl-4H-2,5,10b-triaza-benzo [e]azulene-3-carboxylic acid ethyl ester 140 (SH-053-2'F-R-$CH_3$)

The trimethylsilylacetylene intermediate 139 was converted to 140 (SH-053-2'F-R-$CH_3$) by using the same procedure described above for the synthesis of compound 10.

Some exemplary compounds falling under the scope of the present invention are as follows:

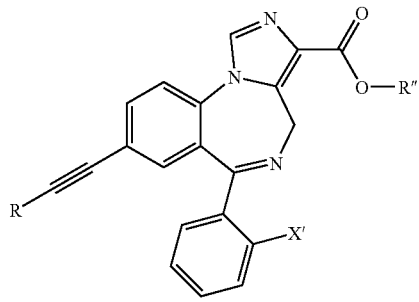

(XIX)

R = H, Si($CH_3$)$_3$
$R_3$ = (R and/or S) $CH_3$, OH, OAc, OCON($CH_3$)$_2$, COOCH$_3$ or COOC$_2$H$_5$
R" = H, $CH_3$, $CH_2CH_3$, t-butyl, iPr, isoxazole
X' = F, Cl, Br, I, $NO_2$ 113 R = Si($CH_3$)$_3$, $R_3$ = (S) $CH_3$, R" = Et, X' = X (SH-I-038)
114 R = H, $R_3$ = (S) $CH_3$, R" = Et, X' = H (SH-053-S-$CH_3$)
119 R = Si($CH_3$)$_3$, $R_3$ = (S) $CH_3$, R" = Et, X' = F (SH-I-055)
120 R = H, $R_3$ = (S) $CH_3$, R" = Et, X' = F (SH-053-S-2"F-$CH_3$)
127 R = Si($CH_3$)$_3$, $R_3$ = (S) $CH_3$, R" = Et, X' = N in place of CH (2'-pyridine (SH-I-061)
128 R = H, $R_3$ = (S) $CH_3$, R" = Et, X' = N in place of CH (2'-pyridine) (SH-053-2'N-S-$CH_3$)
134 R = Si($CH_3$)$_3$, $R_3$ = (R) $CH_3$, R" = Et, X' = H (SH-I-041)
135 R = H, $R_3$ = (R) $CH_3$, R" = Et, X' = H (SH-053-R-$CH_3$)
139 R = Si($CH_3$)$_3$, $R_3$ = (R) $CH_3$, R" = Et, X' = F (SH-I-060)
140 R = H, $R_3$ = (R) $CH_3$, R" = Et, X' = F (SH-053-2'F-R-$CH_3$)

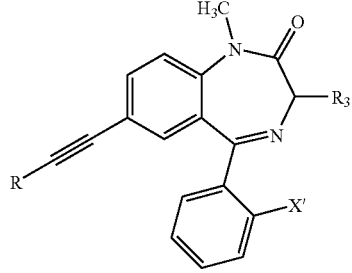

(XX)

R = H, Si($CH_3$)$_3$
$R_3$ = (R and/or S) $CH_3$, OH, OAc, OCON($CH_3$)$_2$, COOCH$_3$ or COOC$_2$H$_5$
X' = F, Cl, Br, I, $NO_2$

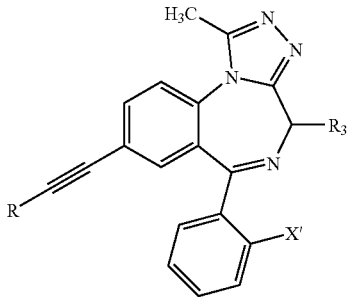

(XXI)

R = H, Si($CH_3$)$_3$
$R_3$ = (R and/or S) $CH_3$, OH, OAc, OCON($CH_3$)$_2$, COOCH$_3$ or COOC$_2$H$_5$
X' = F, Cl, Br, I, $NO_2$ In general, the present invention provides a 1,4-benzodiazepine compound with a 5-phenyl-like substituent in which C(7) has been replaced with an acetylene substituent or a trimethylsilyl acetylene substituent or a triazolo benzodiazepine that has a corresponding substituent at C(8) with a 6-phenyl group (alprazolam numbering system). In preferred embodiments, the invention provides methods of treating anxiety using the compound of the present invention. In other embodiments, the invention provides methods of treating convulsions using the compound of the present invention. In further embodiments, the invention provides methods of treating alcoholism using the compound of the present invention.

In preferred embodiments, the invention provides benzodiazepine analogs of 113, 114, 119, 120, 127 128, 134, 135, 139 and 140 above with X'=F, Cl, Br, $NO_2$ and/or R"=$CH_3$, isopropyl, t-butyl, isoxazoles, as well as all analogs of R—C≡C— with R=methyl, isopropyl, cyclopropyl. It is believed that the replacement of the halogen atom in 1,4-benzodiazepines or the related triazolo-1,4-benzodiazepines at C(7) or C(8) generally results in anxiolytic activity with greatly decreased undesirable side-effects such as sedative activity, hypnotic activity, muscle relaxant activity, ataxic activity, convulsions or alcohol consumption. In preferred embodiments, the benzodiazepine analog compounds are substantially lacking in sedative activity, hypnotic activity, muscle relaxant activity or ataxic activity compared to previously known benzodiazepine analogs. Exemplary structures of benzodiazepine analogs of the present invention are provided below.

125

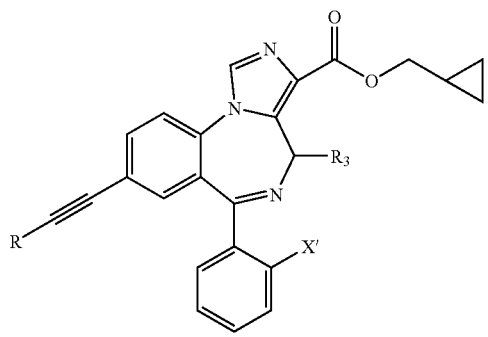

R = H, R = Si(CH₃)₃, or R = [Si(CH₃)(cyclopropyl)]

R₃ = (R and/or S) CH₃, OH, OAc,
OCON(CH₃)₂, COOCH₃ or COOC₂H₅

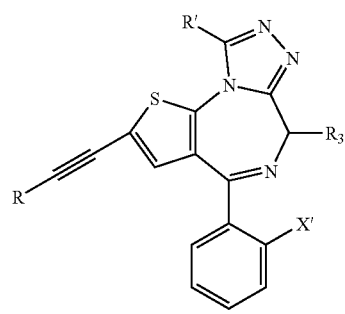

R = H, R = Si(CH₃)₃
R' = H or CH₃, X' = F, Cl, Br, NO₂

R₃ = (R and/or S) CH₃, OH,
OAc, OCON (CH₃)₂, COOCH₃ or
COOC₂H₅

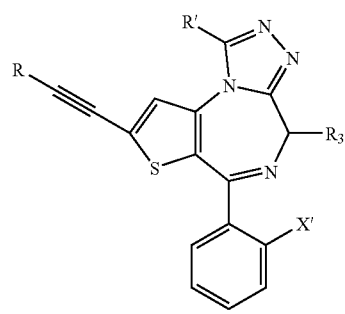

| R = H, R' = CH₃, X' = H | R = Si(CH₃)₃, R' = CH₃, X' = H |
| R = H, R' = H, X' = H | R = Si(CH₃)₃, R' = H, X' = H |
| R = H, R' = CH₃, X' = Cl | R = Si(CH₃)₃, R' = CH₃, X' = Cl |
| R = H, R' = CH₃, X' = F | R = Si(CH₃)₃, R' = CH₃, X' = F |

R₃ = (R and/or S) CH₃, OH, OAc,
OCON(CH₃)₂, COOCH₃ or COOC₂H₅

126

-continued

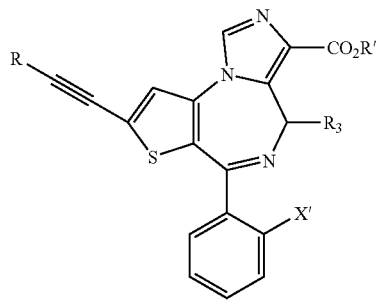

R = H, R' = Et, X' = H
R = H, R' = Et, X' = Br
R = H, R' = Et, X' = Cl
R = H, R' = Et, X' = F

R₃ = (R and/or S)
CH₃, OH, OAc,
OCON(CH₃)₂,
COOCH₃ or
COOC₂H₅

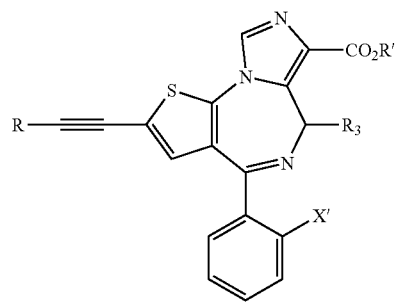

R = Si(CH₃)₃, R' = Et, X' = H
R = Si(CH₃)₃, R' = Et, X' = Br
R = Si(CH₃)₃, R' = Et, X' = Cl
R = Si(CH₃)₃, R' = Et, X' = F

R₃ = (R and/or S) CH₃,
OH, OAc,
OCON(CH₃)₂,
COOCH₃ or COOC₂H₅

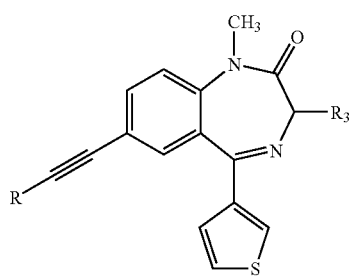

R = H
R = Si(CH₃)₃

R₃ = (R and/or S) CH₃, OH
OAc, OCON(CH₃)₂,
COOCH₃ or COOC₂H₅

127

-continued

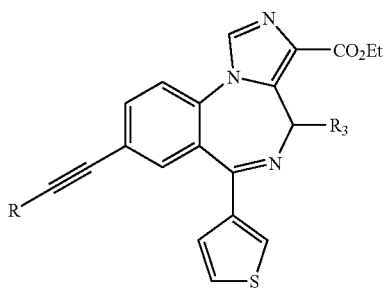

R = H, R = Si(CH₃)₃
R₃ = (R and/or S) CH₃, OH,
OAc, OCON(CH₃)₂,
COOCH₃ or COOC₂H₅

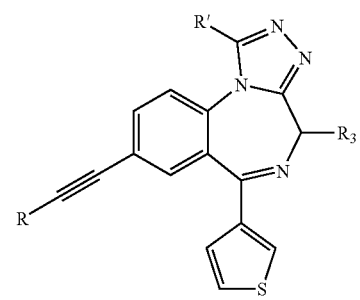

R = H, R' = CH₃       R = H, R' = H
R = Si(CH₃)₃, R' = CH₃   R = Si(CH₃)₃, R' = H

R₃ = (R and/or S) CH₃, OH, OAc,
OCON(CH₃)₂, COOCH₃ or COOC₂H₅

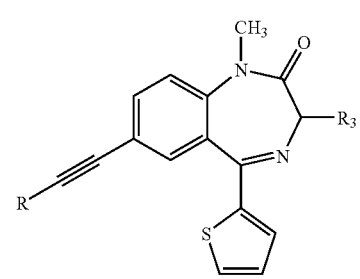

R = H
R = Si(CH₃)₃

R₃ = (R and/or S) CH₃, OH,
OAc, OCON(CH₃)₂,
COOCH₃ or COOC₂H₅

All of the above claimed also with R' =
t-butyl, isopropyl, isoxazole, CH₂—▽

All of the above claimed with this unit below
CO₂R' replaced with R'' R'' = CH₃, CH₂CH₃, iPr.

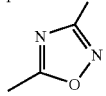

128

-continued

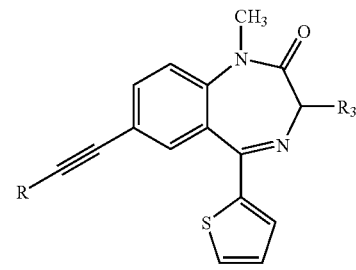

R = H, R = Si(CH₃)₃

R₃ = (R and/or S) CH₃, OH, OAc,
OCON(CH₃)₂, COOCH₃ or COOC₂H₅

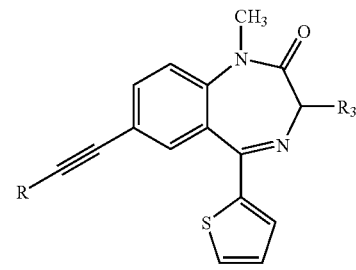

R = H, R' = CH₃       R = H, R' = H
R = Si(CH₃)₃, R' = CH₃   R = Si(CH₃)₃, R' = H

R₃ = (R and/or S) CH₃, OH, OAc,
OCON(CH₃)₂, COOCH₃ or COOC₂H₅

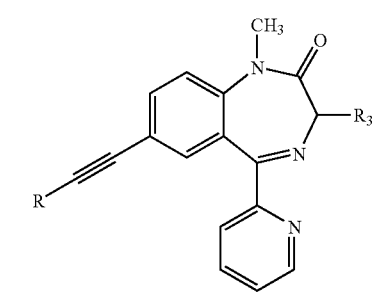

R = H
R = Si(CH₃)₃

R₃ = (R and/or S) CH₃, OH,
OAc, OCON(CH₃)₂,
COOCH₃ or COOC₂H₅

-continued
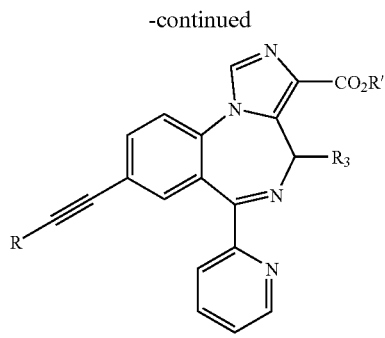
R = H, R' = Et
R = Si(CH₃)₃, R' = Et
R' = t-butyl, isopropyl, isoxazole, CH₂—
$R'' R'' = CH_3 CH_2CH_3, iPr.$
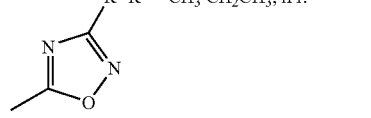
$R_3$ = (R and/or S) CH₃, OH,
OAc, OCON(CH₃)₂,
COOCH₃ or COOC₂H₅
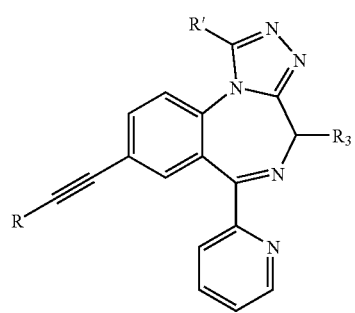
R = H, R' = CH₃          R = H, R' = H
R = Si(CH₃)₃, R' = CH₃   R = Si(CH₃)₃, R' = H
R = H, R' = CH₂CH₃       R = Si(CH₃)₃, R' = CH₂CH₃
$R_3$ = (R and/or S) CH₃, OH,
OAc, OCON(CH₃)₂,
COOCH₃ or COOC₂H₅
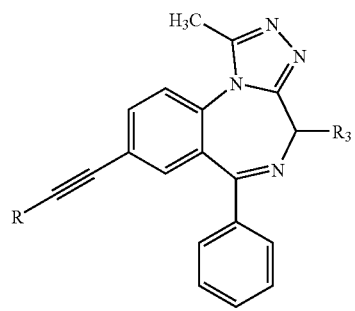
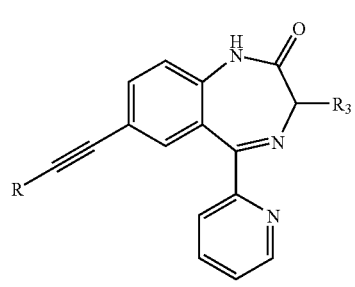
-continued
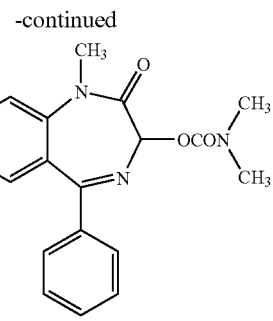
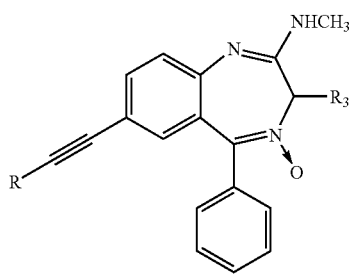
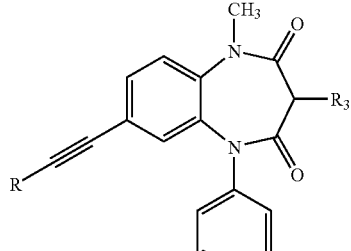
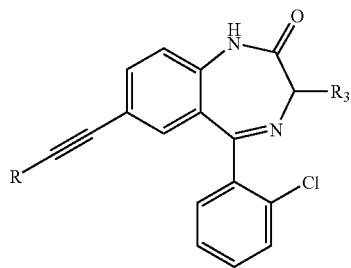
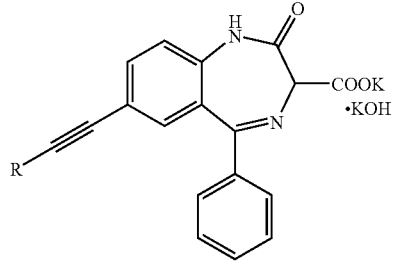
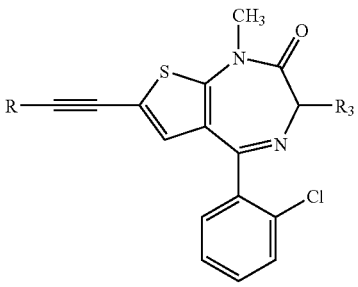

-continued
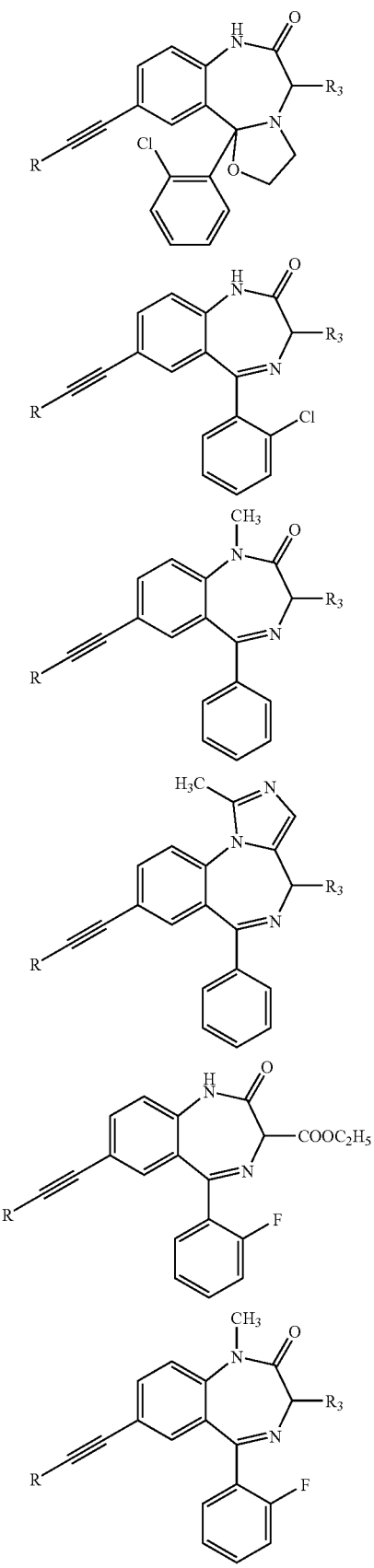
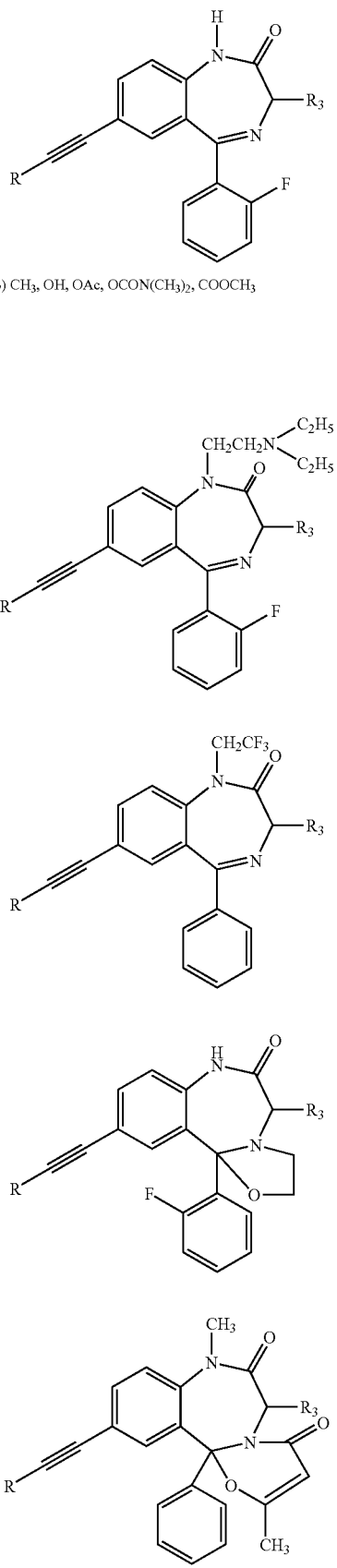
$R_3$ = (R and/or S) $CH_3$, OH, OAc, $OCON(CH_3)_2$, $COOCH_3$ or $COOC_2H_5$

133
-continued
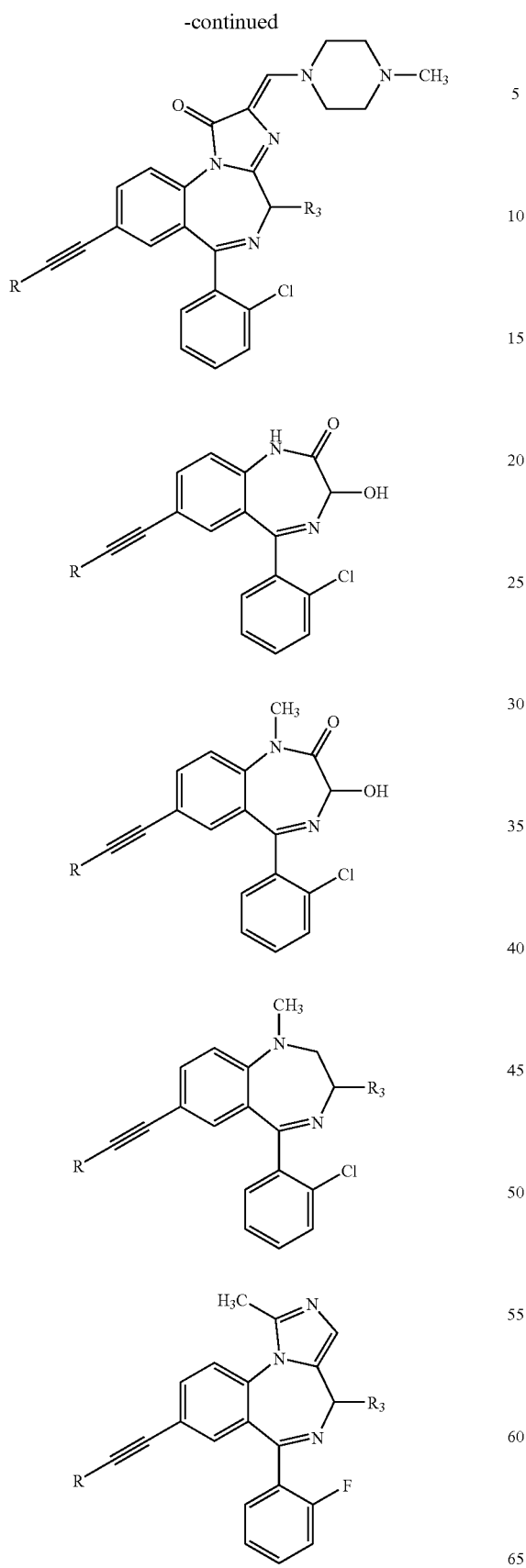
134
-continued
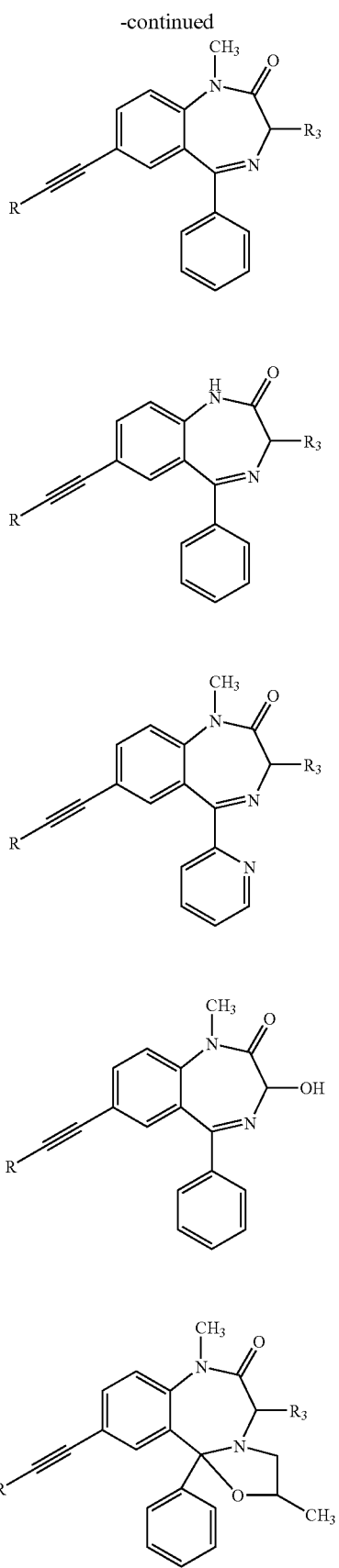

-continued

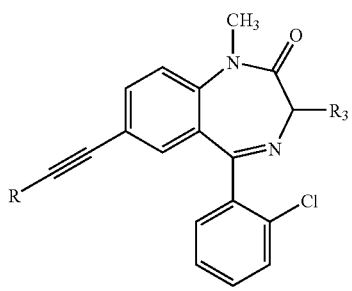

R = H or R = (CH$_3$)$_3$Si
R$_3$ = (R and/or S) CH$_3$, OH, OAc, OCON(CH$_3$)$_2$, COOCH$_3$ or COOC$_2$H$_5$ -continued

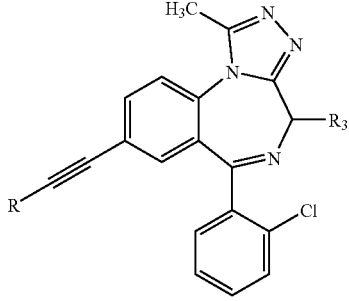

R = H or R = (CH$_3$)$_3$Si
R$_3$ = (R and/or S) CH$_3$, OH, OAc, OCON(CH$_3$)$_2$, COOCH$_3$ or COOC$_2$H$_5$

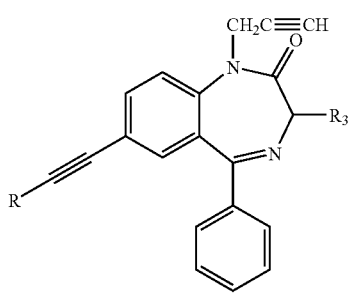

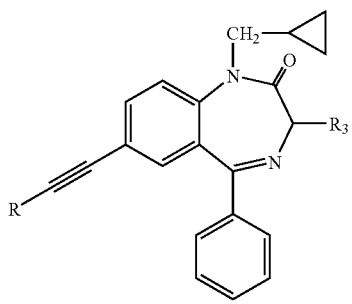

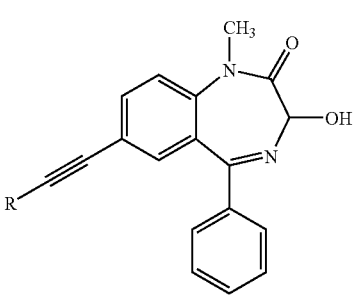

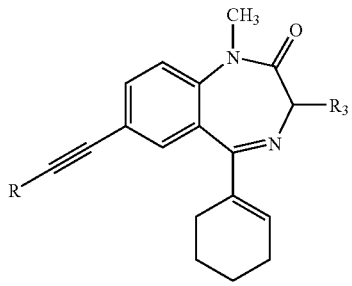

II. Experimental Methods

Situational Anxiety Model in Rats

Male Sprague-Dawley rats weighing 180-200 grams were purchased from Charles River Laboratories (Wilmington, Mass.). The rats were housed individually in suspended wire cages in a colony room maintained at constant temperature (21±2° C.) and humidity (50±10%). The room was illuminated 12 hours per day (lights on at 0600 h). The rats had ad libitum access to food and water throughout the study. Behavioral studies were conducted between 0600 and 1300 hours.

Testing: A modification of the Defensive Withdrawal procedure, as originally described by Takahashi L K, et al., (1989) Behav Neurosci 103:648-654 was employed. The testing apparatus consisted of an opaque plexiglass open field (106 cm length×92 cm width×50 cm height), containing a cylindrical galvanized chamber (14 cm length, 10 cm diameter) that was positioned lengthwise against one wall, with the open end 40 cm from the corner. The open field was illuminated by a 60 watt incandescent bulb, and illumination was titrated by a powerstat transformer to a 23 lux reading at the entrance to the cylinder. Rats were habituated to handling by gently stroking their dorsal surface for approximately one minute daily for 5-6 consecutive days before testing. To initiate testing of exploratory behavior in this unfamiliar environment, each rat was placed within the cylinder, which was then secured to the floor. Behavior was assessed for 15 minutes by a trained observer (unaware of treatment assignment) via a video monitor in an adjacent room. The latency to emerge from the cylinder, defined by the placement of all four paws into the open field, was recorded for each rat. After testing each rat, the plexiglass chamber and the cylinder were cleaned with 1.0% glacial acetic acid to prevent olfactory cues from influencing the behavior of subsequently tested rats.

Drug Administration: All drugs were administered PO 20-60 minutes prior to behavioral testing.

Data Analysis: Results were expressed as the mean±1 SEM. All data were subjected to analysis of variance (ANOVA) followed by individual mean comparisons using Fisher's Least Significant Difference Test (Kirk, 1968) where appropriate. The significance level was set at p<0.05.

Protection from Pentylenetetrazole-Induced Seizures

Male CF1 mice weighing 20-22 g at the time of the experiment were purchased from Charles River Laboratories (Wilmington, Mass.). Pentylenetetrazole (Sigma Chemical Co.) was administered at 125 mg/kg s.c. The number of animals surviving was recorded at 30 minutes and 60 minutes after administration of pentylenetetrazole.

Drug Administration: All drugs were administered PO 60 minutes before administration of pentyenetetrazole.

Data Analysis: The data are presented as the percent of animals protected from death. The data were analyzed by Chi Square statistics. The significance level was set at p<0.05.

Protection from Electroshock-Induced Seizures

Male CF1 mice weighing 20-22 g at the time of the experiment were purchased from Charles River Laboratories (Wilmington, Mass.). Electroshock is administered using a Ugo Basile ECT, Unit 7801 seizure apparatus (Ugo Basile, Italy) and corneal electrodes soaked in 0.9% saline. Mice received a shock of 30 mA for 0.3 seconds.

Drug Administration: All experimental compounds were administered PO 60 minutes before administration of electroshock.

Data Analysis: The data are presented as the percent of animals protected from the hind-limb extensor component of the seizure. The data were analyzed by Chi Square statistics. The significance level was set at p<0.05.

Open-Field Locomotor Activity in Rats

Male Sprague-Dawley rats, weighing 250-290 grams at the beginning of the experiment were purchased from Charles River Laboratories (Wilmington, Mass.). The animals were housed in groups of four in a colony room maintained at constant temperature (21±2° C.) and humidity (50±10%). The room was illuminated 12 hours per day (lights on at 0600 h). The rats had ad libitum access to food and water. The testing apparatus consisted of Plexiglas chambers (42×42×30 cm) equipped with Digiscan activity monitors (Omnitech Electronics, Columbus, Ohio) that detect interruptions of 16 photobeams spaced 2.5 cm apart and 2.5 cm above the floor. Horizontal activity was monitored for 60 minutes.

Drug Administration: All drugs were administered PO 20-60 minutes before behavioral testing.

Data Analysis: Results were expressed as the mean±1 SEM. All data were subjected to analysis of variance (ANOVA) followed by individual mean comparisons using Fisher's Least Significant Difference Test (Kirk, 1968) where appropriate. The significance level was set at p<0.05.

Rotorod Performance in Rats

Male Sprague-Dawley rats, weighing 180-200 grams at the beginning of the experiment were purchased from Charles River Laboratories (Wilmington, Mass.). The animals were housed in groups of four in a colony room maintained at constant temperature (21±2° C.) and humidity (50±10%). The room was illuminated 12 hours per day (lights on at 0600 h). The rats had ad libitum access to food and water. The degree of muscle coordination or balance (i.e., ataxia) was determined using a standard accelerating rotorod treadmill (Ugo Basile, Comerio-Varese, Italy or Columbus Instruments, Columbus, Ohio) that was 6 cm in diameter, 24 cm above the base, and run from an initial speed of 2 rpm to a maximum speed of 20 rpm. The time each animal remained on the rotating rod was automatically recorded, up to a maximum of 5 minutes. Each rat had three pretest acclimation trials, and the latency from the third trial was used to counterbalance rats for subsequent drug testing.

Drug Administration: All drugs were administered PO 20-60 minutes before behavioral testing.

Data Analysis: Results were expressed as the mean±1 SEM. All data were subjected to analysis of variance (ANOVA) followed by individual mean comparisons using Fisher's Least Significant Difference Test (Kirk, 1968) where appropriate. The significance level was set at p<0.05.

Discriminative Stimulus Effects of Chlordiazepoxide in Rats

Male Sprague-Dawley rats weighing 240 to 300 g at the start of the experiment were purchased from Charles River Laboratories (Wilmington, Mass.). Animals were housed singly in hanging wire cages in a room maintained at constant temperature (21-23° C.) and humidity (50±10%) and illuminated 12 hours per day (lights on at 0600 h). Throughout the study rats were restricted to 12 g of laboratory rodent chow pellets (Bio-Serv, Frenchtown, N.J.) per day, while access to water was unlimited. All training and testing was done Monday through Friday of each week.

Twelve model E10-10 Coulbourn operant chambers (28× 26×31 cm) were housed in light-proof, sound-attenuated, and fan-ventilated chambers. Each operant chamber was equipped with two non-retractable levers, requiring a downward force equivalent to 15 g (0.15 N), that were mounted 3 cm from the side wall, 3 cm above the metal grid floor, and 5 cm from a centrally placed dipper that delivered one 45 mg food pellet (Dustless Precision Pellets, Bio-Serv, Frenchtown, N.J.). The experimental chambers were connected to a Micro PDP11/73 computer using a LAB LINC interface. A SKED-11 operating system (State System, Kalamazoo, Mich.) was used to record and control behavior.

Discrimination training: After habituation to the operant chamber, rats were trained to alternate daily between response levers on a Fixed Ratio 1 (FR 1) schedule of reinforcement. Once lever pressing was well established, the reinforcement contingency was increased incrementally to an FR 10 schedule, while maintaining the lever alternation. Next, rats were trained to discriminate between drug (5.0 mg/kg, IP, chlordiazepoxide) and drug vehicle (0.9% saline). Half of the rats were randomly assigned the left lever as "drug-correct" and the right lever as "saline-correct." The lever assignments were reversed for the remaining animals. Every tenth response on the drug-correct lever was reinforced on days when the rats were pretreated with drug, whereas every tenth response on the opposite lever was reinforced after saline injections. In each 2-week period there were 5 drug days and 5 saline days, with the constraint that there not be more than 3 consecutive drug or vehicle days. Discrimination sessions were continued until each rat reached the criterion of no more than three incorrect responses before first food presentation in 9 out of 10 consecutive sessions.

Test sessions: Once criterion for testing was met, stimulus substitution tests were conducted on Friday of each week. Test sessions were 10 minutes in duration. During the test sessions, the lever on which the rat first responded 10 times resulted in reinforcement and subsequent FR 10 reinforcement was made contingent upon pressing this "selected" lever. The lever on which the rat first made 10 responses (the selected lever) and the total number of responses in the session were recorded. On Monday through Thursday of each week, training sessions were conducted to ensure that criterion for testing was met. If any rat failed to meet the criterion for testing, testing with that animal was postponed and discrimination training continued until the performance criterion was attained.

Data analysis: Drug discrimination results are expressed as the percentage of animals selecting the chlordiazepoxide-correct lever. Kirk R E (1968) Experimental Design: Procedures for the Behavioral Sciences. Brooks/Cole, Belmont, Calif., Experimental Results Table 1 (below) shows ratios of lowest effective anxiolytic doses in the situational anxiety (SA) assay compared with lowest effective doses producing side effects in three different models: locomotor activity (LMA), rotorod (RR), and chlordiazepoxide-like subjective effects as measured by the drug discrimination method (DD).

Table 2 (below) shows effective doses in a model of epilepsy (pentylenetetrazole-induced seizures) in mice (mg/kg, PO) for QH-ii-066, Xli-JY-DMH, and XHe-ii-053 in comparison with diazepam, triazolam, and DM-1-070.

EXAMPLE 1

Situational Anxiety in Rats

Rats were handled daily for at least 5-6 days. They were then placed in a dark cylinder in an illuminated open field. The time for the rats to exit the dark cylinder was then measured. Vehicle-treated animals remain within the dark cylinder for 10-15 minutes (total test duration is 15 minutes). This high latency to exit the dark chamber is an index of a heightened state of anxiety. Compounds with anxiolytic efficacy reduce latency to exit the dark chamber. Table 1 shows that QH-ii-066, XLi-JY-DMH, and XHe-ii-053 show anxiolytic effects in the situational anxiety test at doses >100-fold lower than doses producing sedative and ataxic effects (see Examples 2 and 3).

EXAMPLE 2

Locomotor Activity in Rats

Rats were placed in an open field and the total distance covered by the rat was measured. The test duration was 60 minutes. Compounds producing sedative effects decrease the distance covered. Table 1 shows that QH-ii-066, XLi-JY-DMH, and XHe-ii-053 are less effective in producing sedative or hypnotic effects than diazepam or triazolam.

EXAMPLE 3

Rotorod Performance in Rats

Rats were placed on a slowly rotating rod and the speed of rotation was gradually increased. The time on the rod for each rat was recorded. Compounds producing ataxia (motor incoordination) decrease the time spent on the rod compared with vehicle-treated animals. Table 1 shows that QH-ii-066, XLi-JY-DMH, and XHe-ii-053 are less potent in producing ataxia than diazepam or triazolam. Thus, they are likely better drugs clinically because they have decreased side effects [decreased sedation (Example 2) and ataxia (Example 3)].

EXAMPLE 4

Drug Discrimination in Rats

Animals are taught to emit one response if they just received drug and a different response if they just received saline. The animals learn to discriminate between a "drug state" and a "no drug state". The rats were trained to discriminate between a state induced by a typical benzodiazepine chlordiazepoxide (CDP; "drug state") and a state induced by vehicle (methocel: "no drug state"). Table 1 shows that QH-ii-066, XLi-JY-DMH, and XHe-ii-053 are less potent in producing CDP-like effects than diazepam or triazolam and thus may have reduced abuse potential compared with CDP.

EXAMPLE 5

Seizure Protection in Mice

Mice treated with certain compounds of the present invention were subjected to pentylenetetrazole (PTZ) at 125 mg/kg to induce seizures. The percent of animals protected from death within one hour of PTZ was measured. Table 2 shows that QH-ii-066 and XLi-JY-DMH have anticonvulsant effects against PTZ-induced seizures at doses comparable to those for diazepam and triazolam. Table 2 also shows that XHe-ii-053 is effective against PTZ-induced seizures.

TABLE 1

|  | Antianxiety/sedation | Antianxiety/ataxia | Antianxiety/abuse liability |
|---|---|---|---|
| Diazepam | 10 | 100 | 5 |
| QH-ii-066 | 100 | >100 | 30 |
| Triazolam | 300 | 100 | 30 |
| XLi-JY-DMH | 10000 | 10000 | 1000 |
| DM-i-070 | >100 | >100 | 10 |
| XHe-ii-053 | >300 | >300 | >300 |

TABLE 2

|  | PTZ Seizures (mg/kg, PO) |
|---|---|
| Diazepam | <10 |
| QH-ii-066 | <30 |
| Triazolam | <1.0 |
| XLi-JY-DMH | <1.0 |
| DM-i-070 | <100 |
| XHe-ii-053 | ≦100 |

Anxiolytic Activity: Experimental Methods and Results

Figure 1:
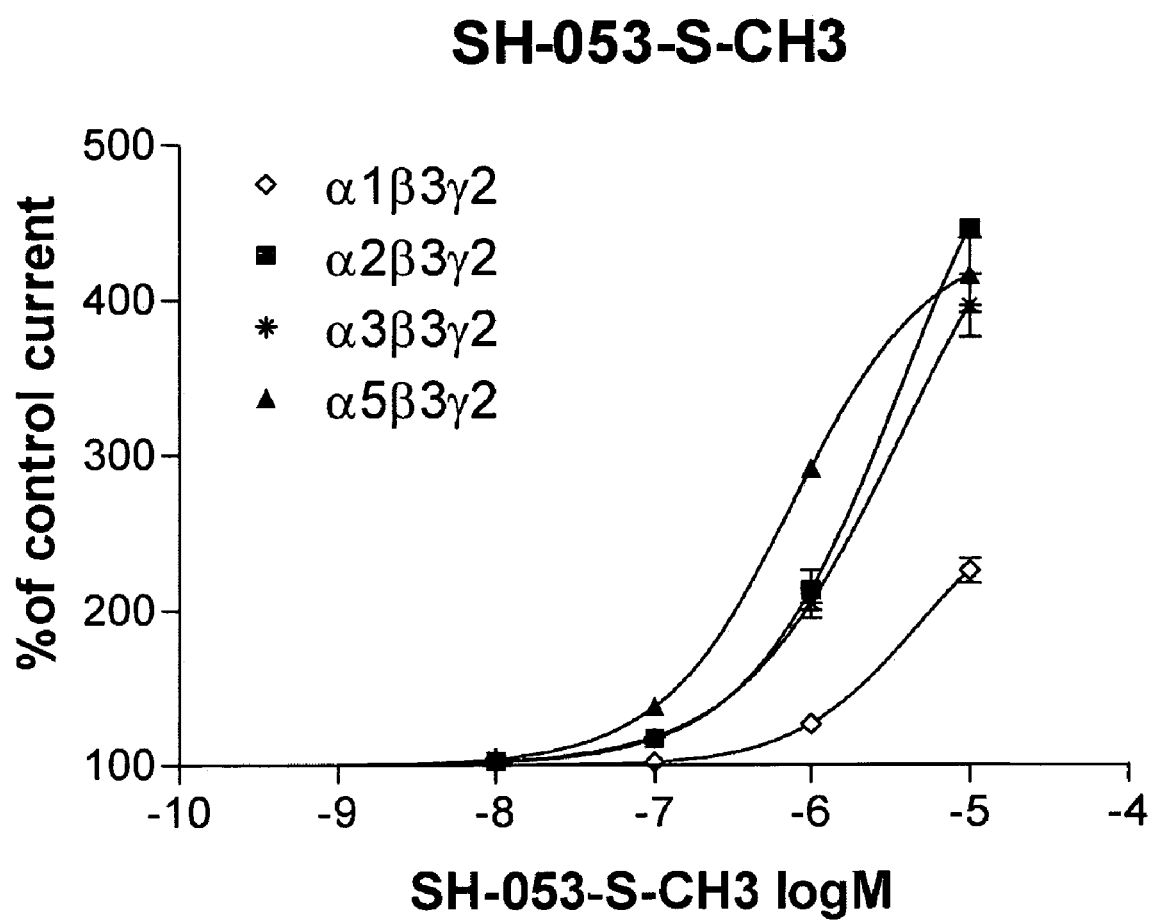
FIG. 1 is a dose-response curve presenting the results of voltage clamp study of *Xenopus* oocytes treated with compound SH-053-S-CH₃.

1. Effects of SH-053-S—CH$_3$ 8 on GABA(A) receptors were tested by two-electrode voltage clamp experiments in cRNA injected *Xenopus* oocytes that functionally expressed several subtype combinations of GABA$_A$ receptors. Analysis of the data in FIG. 1 illustrates SH-053-S—CH$_3$ 8 is an agonist at α2 and α3β3γ2 subtypes but has almost no efficacy at α1β3γ2 subtypes. This oocyte profile is indicative of an anxiolytic agent devoid of sedative, ataxic and anterograde amnestic side effects.

1.1 Experimental Procedures

The methods were based on those published previously. See Li, X., et al., (2003) J. Med. Chem. 46: 5567-5570.

1.1.1 Preparation of Cloned mRNA

Cloning of GABA$_A$ receptor subunits α1, β3 and γ2 into pCDM8 expression vectors (Invitrogen, CA) has been described elsewhere (Squires, R. F.; Braestrup, C. Benzodiazepine Receptors in Rat Brain. Nature 1977, 266, 732-734). GABA$_A$ receptor subunit α4 was cloned in an analogous way. cDNAs for subunits α2, α3 and α5 were gifts from P. Malherbe and were subcloned into pCI-vector (Li, et al., 2003). cDNA for subunit α6 was a gift from P. Seeburg and was subcloned into the vector pGEM-3Z (Promega). After linearizing the cDNA vectors with appropriate restriction endonucleases, capped transcripts were produced using the mMessage mMachine T7 transcription kit (Ambion, Tex.). The capped transcripts were polyadenylated using yeast poly(A)

polymerase (USB, OH) and were diluted and stored in diethylpyrocarbonate-treated water at −70° C. (Li, et al., 2003).

1.1.2 Functional Expression of $GABA_A$ Receptors

The methods used for isolating, culturing, injecting and defolliculating of the oocytes were identical with those described by E. Sigel (Sieghart, W. Structure and Pharmacology of γ-Aminobutyric AcidA Receptor Subtypes. Pharm. Rev. 1995, 47, 181-234; Mohler, H.; et al.,. A New Benzodiazepine Pharmacology. J. Pharmacol. Ther. 2002, 300, 2-8). Mature female *Xenopus laevis* (Nasco, Wis.) were anaesthetized in a bath of ice-cold 0.17% Tricain (Ethyl-m-aminobenzoate, Sigma, St. Louis, Mo.) before decapitation and removal of the frogs ovary. Stage 5 to 6 oocytes with the follicle cell layer around them were singled out of the ovary using a platinum wire loop (Li, et al., 2003). Oocytes were stored and incubated at 18° C. in modified Barths' Medium (MB, containing 88 mM NaCl, 10 mM HEPESNaOH (pH 7.4), 2.4 mM $NaHCO_3$, 1 mM KCl, 0.82 mM $MgSO_4$, 0.41 mM $CaCl_2$, 0.34 mM $Ca(NO_3)_2$) that was supplemented with 100 U/ml penicillin and 100 μg/ml streptomycin. Oocytes with follicle cell layers still around them were injected with 50 nl of an aqueous solution of cRNA. This solution contained the transcripts for the different alpha subunits and the beta 3 subunit at a concentration of 0.0065 ng/nl as well as the transcript for the gamma 2 subunit at 0.032 ng/nl. After injection of cRNA, oocytes were incubated for at least 36 hours before the enveloping follicle cell layers were removed. To this end, oocytes were incubated for 20 min at 37° C. in MB that contained 1 mg/ml collagenase type IA and 0.1 mg/ml trypsin inhibitor I-S (both Sigma). This was followed by osmotic shrinkage of the oocytes in doubly concentrated MB medium supplied with 4 mM Na-EGTA. Finally, the oocytes were transferred to a culture dish containing MB and were gently pushed away from the follicle cell layer which stuck to the surface of the dish. After removing of the follicle cell layer, oocytes were allowed to recover for at least four hours before being used in electrophysiological experiments.

1.1.3 Electrophysiological Experiments

For electrophysiological recordings, oocytes were placed on a nylon-grid in a bath of *Xenopus* Ringer solution (XR, containing 90 mM NaCl, 5 mM HEPES-NaOH (pH 7.4), 1 mM $MgCl_2$, 1 mM KCl and 1 mM $CaCl_2$). The oocytes were constantly washed by a flow of 6 ml/min XR which could be switched to XR containing GABA and/or drugs. Drugs were diluted into XR from DMSO-solutions resulting in a final concentration of 0.1% DMSO perfusing the oocytes. Drugs were preapplied for 30 sec before the addition of GABA, which was coapplied with the drugs until a peak response was observed. Between two applications, oocytes were washed in XR for up to 15 min to ensure full recovery from desensitization. For current measurements the oocytes were impaled with two microelectrodes (2-3 mΩ) which were filled with 2 mM KCl. All recordings were performed at room temperature at a holding potential of −60 mV using a Warner OC-725C two-electrode voltage clamp (Warner Instruments, Hamden, Conn.). Data were digitised, recorded and measured using a Digidata 1322A data acquisition system (Axon Instruments, Union City, Calif.). Results of concentration response experiments were fitted using GraphPad Prism 3.00 (GraphPad Software, San Diego, Calif.). The equation used for fitting concentration response curves was Y=Bottom +(Top-Bottom)/(1+10((LogEC50-X)*HillSlope)); X represents the logarithm of concentration, Y represents the response; Y starts at Bottom and goes to Top with a sigmoid shape. This is identical to the "four parameter logistic equation."

2.1 Experimental Methods

2.1.1 Subjects:

Male BALB/c mice approximately 8 to 10 weeks old (18-25 grams) served as subjects in the locomotor activity and light/dark assays. Animals were housed in groups of four on a 14 hour light/10 hour dark cycle and were given free access to food and water. All experiments were conducted during the animals' light cycle (0800-1700).

2.1.2 Procedure:

Behavioral testing was conducted in an illuminated open field chamber (11.0"×11.0"; Med Associates MED-OFA-510) equipped with infrared beams and sensors which was placed in a sound attenuating cubicle. Horizontal locomotor activity was measured by recording the total number of beams crossed in a 60 minute period. Anxiolytic-like behavior was assessed using the same chambers with the addition of a Plexiglas insert that is opaque to visible light creating separate darkened and illuminated sides (5.5"×11.0") of the chamber. An opening in the middle of the dark insert allowed the animals to move freely between each side of the chamber. Animals were place in the center of the illuminated side of the chamber and allowed to freely explore for 10 minutes. The amount of time (sec) that the animals spent in each side of the chamber was recorded. Data were analyzed using one-way analysis of variance and Bonferroni t-tests.

2.1.3 Drugs:

Vehicle and doses of SH-053-S—$CH_3$ 8 (10.0-100.0 mg/kg) and SH-053-R-$CH_3$ 29 (56.0 mg/kg) were tested in the light/dark and locomotor activity assays. All drugs were administered intraperitoneally (ip) 30 minutes before each test in volumes of approximately 1 ml/kg. Drugs were dissolved in varying amounts of 95% ethanol (5-10%), propylene glycol and sterile water and diluted to the desired concentration with a solution of 50% propylene glycol and 50% sterile water.

2.1.4 Results

The highest dose tested of SH-053-S—$CH_3$ 8 in the light/dark assay was 56 mg/kg. It did not suppress locomotor activity and was anxiolytic (see FIG. 2, A). At 100 mg/kg SH-053-S—$CH_3$ 8 did not suppress locomotor activity in any significant fashion.

3. The Test of Bidirectional Effects of Benzodiazepine Binding Site Ligands in the Elevated Plus-Maze

3.1 Materials and Methods

3.1.1 Animals

Except where noted, the methods used were those of Miroslav M., et al., (2004) Pharmacology, Biochemistry and Behavior 79: 279-290. Experiments were carried out on male Wistar rats (Military Farm, Belgrade, Serbia and Montenegro), weighing 200-240 g. All procedures in the study conformed to EEC Directive 86/609 and were approved by the Ethical Committee on Animal Experimentation of the Medical Faculty in Belgrade. The rats were housed in transparent plastic cages, six animals per cage, and had free access to pelleted food and tap water before and after drug administration. The temperature of the animal room was 22±1° C., the relative humidity 40-70%, the illumination 120 1× and the 12/12-h light/dark period (light on at 06:00 h). All handling and testing took place during the light portion of the cycle. Throughout the study the animals were used only once.

3.1.2 Drugs

Midazolam and flumazenil were generously donated from F. Hoffman-La Roche (Basel, Switzerland). Zolpidem was purchased from Toronto Research Chemicals (North York, Canada) and DMCM from Research Biochemicals (Natick, Mass., USA). All drugs were dissolved/suspended with the aid of sonication in a solvent containing 85% distilled water, 14% propylene glycol and 1% Tween 80™, and were administered intraperitoneally, in a volume of 1 ml/kg, 20 min before testing. Doses are expressed as the base forms of the drugs. In the cases of combined treatment, agonists were administered at separate sites, immediately after the antagonist. Each animal received a total volume of 2 ml/kg of compounds tested or appropriate vehicles, at two different injection sites.

3.1.3 Behavior on the Elevated Plus-Maze

The test apparatus was constructed of sheet metal, with a black rubber floor. It consisted of a maze elevated to a height of 50 cm with two open (50×10 cm) and two enclosed arms (50×10×40 cm), connected by junction area (central platform) measured 10×10 cm. Although the floor was rubberized, a ledge of sheet metal (0.3 cm high) surrounding the open arms was added, to avoid rats falling off. The illumination in the experimental room consisted of one red neon tube fixed on the ceiling, giving light intensity of 10 1x on the surface of the arms. The experiments were carried out during the diurnal phase (between 08:00 and 12:00 h). At the beginning of the experiment, rats were placed in the centre of the maze, facing one of the enclosed arms and observed for 5 min. The observer sat in the same room 1 m from the maze. After each trial, the maze was cleaned with dry and wet towels. Throughout the study, the number of rats per treatment group was 8-14. Each experiment was run over 4 consecutive days, with three control rats per day; as there was no difference in plus-maze activity among control subgroups, they were pooled in a single control group (n=12).

3.1.4 Statistical Analysis

All numerical data presented in the figures were given as the mean±S.E.M. Each dose-response curve (agonist or antagonist alone or agonist+antagonist) was assessed by a one-way ANOVA. If the ANOVA was significant, each treatment condition was compared with the appropriate solvent control by a Dunnett's test (a=0.05). In case of significant effect in the number of enclosed arm entries, an analysis of covariance (ANCOVA) was performed in the anxiety-related parameters using the number of enclosed arm entries as covariate. Interactions between the agonists and antagonists were analyzed separately with a two-way ANOVA [factors: agonist dose versus cotreatment (an antagonist or saline)]; pairwise comparisons for the assessment of the antagonist influence on the agonist effects were conducted by Tukey's test, one of the methods recommended even in the absence of an overall significant F-test (Wilcox R R. New designs in analysis of variance. Annu Rev Psychol 1987; 38: 29-60). Statistical analyses were performed with commercial statistical software for PC, Stat for Windows R. 5.0.

3.2 Summary of Experimental Data and Results:

The experimental results which are presented FIG. 1, FIG. 2, and in Tables 3-6, below, showed that SH-053-S—$CH_3$ has anxiolytic activity and has no measurable effects on locomotor activity at the dose tested.

The present invention is not limited to the embodiments specifically described above, but is capable of variation and modification without departure from the scope of the appended claims. Those skilled in the art will recognize, or be able to ascertain using no more then routine experimentation, numerous equivalents to the specific schemes, methods, assays and reagents described herein. Such equivalents are considered to be within the scope of this invention and covered by the following claims. All publications, patents, and patent applications cited herein are hereby incorporated by reference in their entirety for all purposes.

TABLE 3

SOLVvs[1][1].DZP
[DZP = diazepam(control), SOLV = SOL = SOLVENT = Vehicle]

| Treatment | N | Mean | SD (note 1) | Data (notes 2, 3) |
|---|---|---|---|---|
| *Total Distance Travelled (m)* | | | | |
| SOLVENT | 7 | 9.30 | ±2.09 | $5.937^{(1)}, 9.141^{(6)}, 11.205^{(10)}, 11.837^{(15)}, 9.661^{(20)}, 10.074^{(25)}, 7.251^{(31)}$ |
| DZP 1.25 mg/kg | 6 | 8.59 | ±3.64 | $5.402^{(2)}, 6.678^{(7)}, 9.352^{(11)}, 5.243^{(19)}, 14.793^{(21)}, 10.090^{(26)}$ |
| t test: t (11) = 0.4384 p = 0.670 | | | | |
| *Total Entries* | | | | |
| SOLVENT | 7 | 9.71 | ±2.14 | $6.0^{(1)}, 10.0^{(6)}, 12.0^{(10)}, 12.0^{(15)}, 10.0^{(20)}, 10.0^{(25)}, 8.0^{(31)}$ |
| DZP 1.25 mg/kg | 6 | 10.33 | ±4.37 | $5.0^{(2)}, 9.0^{(7)}, 11.0^{(11)}, 8.0^{(19)}, 18.0^{(21)}, 11.0^{(26)}$ |
| t test: t (11) = −0.3331 p = 0.745 | | | | |
| *% Open Time* | | | | |
| SOLVENT | 7 | 20.43 | ±8.89 | $9^{(1)}, 18^{(6)}, 19^{(10)}, 38^{(15)}, 20^{(20)}, 16^{(25)}, 23^{(31)}$ |
| DZP 1.25 mg/kg | 6 | 46.33 | ±27.93 | $3^{(2)}, 43^{(7)}, 57^{(11)}, 67^{(19)}, 28^{(21)}, 80^{(26)}$ |
| t test (note 4): t (11) = −2.3353 p = *0.040* | | | | |
| *% Open Entries* | | | | |
| SOLVENT | 7 | 25.57 | ±8.42 | $17^{(1)}, 30^{(6)}, 25^{(10)}, 42^{(15)}, 20^{(20)}, 20^{(25)}, 25^{(31)}$ |
| DZP 1.25 mg/kg | 6 | 47.00 | ±18.75 | $20^{(2)}, 56^{(7)}, 64^{(11)}, 50^{(19)}, 28^{(21)}, 64^{(26)}$ |
| t test (note 4): t (11) = −2.7337 p = *0.019* | | | | |
| *Closed Entries* | | | | |
| SOLVENT | 7 | 7.14 | ±1.35 | $5^{(1)}, 7^{(6)}, 9^{(10)}, 7^{(15)}, 8^{(20)}, 8^{(25)}, 6^{(31)}$ |
| DZP 1.25 mg/kg | 6 | 5.50 | ±3.67 | $4^{(2)}, 4^{(7)}, 4^{(11)}, 4^{(19)}, 13^{(21)}, 4^{(26)}$ |
| t test: t (11) = 1.1064 p = 0.292 | | | | |
| *Time in closed arms* | | | | |
| SOLVENT | 7 | 196.29 | ±32.39 | $246^{(1)}, 211^{(6)}, 225^{(10)}, 163^{(15)}, 170^{(20)}, 194^{(25)}, 165^{(31)}$ |
| DZP 1.25 mg/kg | 6 | 129.50 | ±78.92 | $263^{(2)}, 145^{(7)}, 97^{(11)}, 68^{(19)}, 160^{(21)}, 44^{(26)}$ |
| t test: t (11) = 2.0577 p = 0.064 | | | | |

TABLE 3-continued

Open Entries

| Treatment | N | Mean | SD | Data |
|---|---|---|---|---|
| SOLVENT | 7 | 2.57 | ±1.27 | 1[1], 3[6], 3[10], 5[15], 2[20], 2[25], 2[31] |
| DZP 1.25 mg/kg | 6 | 4.83 | ±2.23 | 1[2], 5[7], 7[11], 4[19], 5[21], 7[26] | t test (note 4): t (11) = −2.2941 p = _0.042_

Time in open arms

| Treatment | N | Mean | SD | Data |
|---|---|---|---|---|
| SOLVENT | 7 | 50.29 | ±23.98 | 2[10], 100[15], 42[20], 38[25], 50[31] |
| DZP 1.25 mg/kg | 6 | 104.17 | ±60.35 | 9[2], 109[7], 127[11], 136[19], 63[21], 181[26] | t test: t (11) = −2.1824 p = 0.052

Notes:
1. SD = Standard deviation.
2. The data analysed has been limited in the following way: Treatment = SOLVENT or DZP 1.25 mg/kg.
3. The numbers in parentheses next to the data values are animal numbers.
4. p ≦ 0.05 is highlighted in bold italics

TABLE 4

SOL vs SH-053-S 20 mg/kg
[SH-053-S = SH-053-S—CH$_3$, SOLV = SOL = SOLVENT = Vehicle]

| Treatment | N | Mean | SD (note 1) | Data (notes 2, 3) |
|---|---|---|---|---|

Total Distance Travelled (m)

| SOLVENT | 7 | 9.30 | ±2.09 | 5.937[1], 9.141[6], 11.205[10], 11.837[15], 9.661[20], 10.074[25], 7.251[31] |
|---|---|---|---|---|
| SH-053-S 20 mg/kg | 6 | 7.49 | ±2.04 | 6.850[3], 9.098[8], 6.669[12], 6.489[16], 5.117[22], 10.732[27] | t test: t (11) = 1.5701 p = 0.145

Total Entries

| SOLVENT | 7 | 9.71 | ±2.14 | 6.0[1], 10.0[6], 12.0[10], 12.0[15], 10.0[20], 10.0[25], 8.0[31] |
|---|---|---|---|---|
| SH-053-S 20 mg/kg | 6 | 8.33 | ±2.94 | 7.0[3], 11.0[8], 7.0[12], 6.0[16], 6.0[22], 13.0[27] | t test: t (11) = 0.9787 p = 0.349

% Open Time

| SOLVENT | 7 | 20.43 | ±8.89 | 9[1], 18[6], 19[10], 38[15], 20[20], 16[25], 23[31] |
|---|---|---|---|---|
| SH-053-S 20 mg/kg | 6 | 27.50 | ±20.61 | 6[3], 18[8], 44[12], 10[16], 28[22], 59[27] | t test (note 4): t (11) = −0.8272 p = 0.426

% Open Entries

| SOLVENT | 7 | 25.57 | ±8.42 | 17[1], 30[6], 25[10], 42[15], 20[20], 20[25], 25[31] |
|---|---|---|---|---|
| SH-053-S 20 mg/kg | 6 | 34.17 | ±17.17 | 14[3], 27[8], 43[12], 17[16], 50[22], 54[27] | t test (note 4): t (11) = −1.1754 p = 0.265

Closed Entries

| SOLVENT | 7 | 7.14 | ±1.35 | 5[1], 7[6], 9[10], 7[15], 8[20], 8[25], 6[31] |
|---|---|---|---|---|
| SH-053-S 20 mg/kg | 6 | 5.33 | ±1.75 | 6[3], 8[8], 4[12], 5[16], 3[22], 6[27] | t test: t (11) = 2.1079 p = 0.059

Time in closed arms

| SOLVENT | 7 | 196.29 | ±32.39 | 246[1], 211[6], 225[10], 163[15], 170[20], 194[25], 165[31] |
|---|---|---|---|---|
| SH-053-S 20 mg/kg | 6 | 144.67 | ±49.37 | 168[3], 183[8], 94[12], 107[16], 212[22], 104[27] | t test: : t (11) = 2.2635 p = _0.045_

Open Entries

| SOLVENT | 7 | 2.57 | ±1.27 | 1[1], 3[6], 3[10], 5[15], 2[20], 2[25], 2[31] |
|---|---|---|---|---|
| SH-053-S 20 mg/kg | 6 | 3.00 | ±2.19 | 1[3], 3[8], 3[12], 1[16], 3[22], 7[27] | t test (note 4): t (11) = −0.4400 p = 0.668

Time in open arms

| SOLVENT | 7 | 50.29 | ±23.98 | 23[1], 47[6], 52[10], 100[15], 42[20], 38[25], 50[31] |
|---|---|---|---|---|
| SH-053-S 20 mg/kg | 6 | 61.83 | ±52.90 | 11[3], 41[8], 75[12], 12[16], 81[22], 151[27] | t test: t (11) = −0.4400 p = 0.668

Notes:
1. SD = Standard deviation.
2. The data analysed has been limited in the following way: Treatment = SOLVENT or SH-053-S—CH$_3$, 20 mg/kg.
3. The numbers in parentheses next to the data values are animal numbers.
4. p ≦ 0.05 is highlighted in bold italics

TABLE 5

SOL vs SH-053-S 30 mg/kg
[SH-053-S = SH-053-S—CH$_3$, SOLV = SOL = SOLVENT = Vehicle]

| Treatment | N | Mean | SD note 1 | Data (notes 2, 3) |
|---|---|---|---|---|
| Total Distance Travelled (m) | | | | |
| SOLVENT | 7 | 9.30 | ±2.09 | 5.937$^{(1)}$, 9.141$^{(6)}$, 11.205$^{(10)}$, 11.837$^{(15)}$, 9.661$^{(20)}$, 10.074$^{(25)}$, 7.251$^{(31)}$ |
| SH-053-S 30 mg/kg | 7 | 9.48 | ±3.50 | 11.551$^{(4)}$, 10.339$^{(13)}$, 6.008$^{(17)}$, 14.660$^{(23)}$, 10.346$^{(28)}$, 4.110$^{(29)}$, 9.338$^{(32)}$ |
| t test: t (12) = −0.1154 p = 0.910 | | | | |
| Total Entries | | | | |
| SOLVENT | 7 | 9.71 | ±2.14 | 6.0$^{(1)}$, 10.0$^{(6)}$, 12.0$^{(10)}$, 12.0$^{(15)}$, 10.0$^{(20)}$, 10.0$^{(25)}$, 8.0$^{(31)}$ |
| SH-053-S 30 mg/kg | 7 | 10.86 | ±4.10 | 12.0$^{(4)}$, 12.0$^{(13)}$, 7.0$^{(17)}$, 16.0$^{(23)}$, 14.0$^{(28)}$, 4.0$^{(29)}$, 11.0$^{(32)}$ |
| t test: t (12) = −0.6539 p = 0.525 | | | | |
| % Open Time | | | | |
| SOLVENT | 7 | 20.43 | ±8.89 | 9$^{(1)}$, 18$^{(6)}$, 19$^{(10)}$, 38$^{(15)}$, 20$^{(20)}$, 16$^{(25)}$, 23$^{(31)}$ |
| SH-053-S 30 mg/kg | 7 | 36.00 | ±13.71 | 25$^{(4)}$, 22$^{(13)}$, 55$^{(17)}$, 39$^{(23)}$, 44$^{(28)}$, 20$^{(29)}$, 47$^{(32)}$ |
| t test (note 4): t (12) = −2.5215 p = *0.027* | | | | |
| % Open Entries | | | | |
| SOLVENT | 7 | 25.57 | ±8.42 | 17$^{(1)}$, 30$^{(6)}$, 25$^{(10)}$, 42$^{(15)}$, 20$^{(20)}$, 20$^{(25)}$, 25$^{(31)}$ |
| SH-053-S 30 mg/kg | 7 | 43.71 | ±8.81 | 33$^{(4)}$, 42$^{(13)}$, 57$^{(17)}$, 38$^{(23)}$, 50$^{(28)}$, 50$^{(29)}$, 36$^{(32)}$ |
| t test (note 4): t (12) = −3.9387 p = *0.002* | | | | |
| Closed Entries | | | | |
| SOLVENT | 7 | 7.14 | ±1.35 | 5$^{(1)}$, 7$^{(6)}$, 9$^{(10)}$, 7$^{(15)}$, 8$^{(20)}$, 8$^{(25)}$, 6$^{(31)}$ |
| SH-053-S 30 mg/kg | 7 | 6.29 | ±2.81 | 8$^{(4)}$, 7$^{(13)}$, 3$^{(17)}$, 10$^{(23)}$, 7$^{(28)}$, 2$^{(29)}$, 7$^{(32)}$ |
| t test: t (12) = 0.7276 p = 0.481 | | | | |
| Time in closed arms | | | | |
| SOLVENT | 7 | 196.29 | ±32.39 | 246$^{(1)}$, 211$^{(6)}$, 225$^{(10)}$, 163$^{(15)}$, 170$^{(20)}$, 194$^{(25)}$, 165$^{(31)}$ |
| SH-053-S 30 mg/kg | 7 | 164.71 | ±37.22 | 171$^{(4)}$, 197$^{(13)}$, 129$^{(17)}$, 155$^{(23)}$, 148$^{(28)}$, 228$^{(29)}$, 125$^{(32)}$ |
| t test: t (12) = −1.6928 p = 0.116 | | | | |
| Open Entries | | | | |
| SOLVENT | 7 | 2.57 | ±1.27 | 1$^{(1)}$, 3$^{(6)}$, 3$^{(10)}$, 5$^{(15)}$, 2$^{(20)}$, 2$^{(25)}$, 2$^{(31)}$ |
| SH-053-S 30 mg/kg | 7 | 4.57 | ±1.62 | 4$^{(4)}$, 5$^{(13)}$, 4$^{(17)}$, 6$^{(23)}$, 7$^{(28)}$, 2$^{(29)}$, 4$^{(32)}$ |
| t test (note 4): t (12) = −2.5704 p = *0.025* | | | | |
| Time in open arms | | | | |
| SOLVENT | 7 | 50.29 | ±23.98 | 23$^{(1)}$, 47$^{(6)}$, 52$^{(10)}$, 100$^{(15)}$, 42$^{(20)}$, 38$^{(25)}$, 50$^{(31)}$ |
| SH-053-S 30 mg/kg | 7 | 93.71 | ±38.83 | 57$^{(4)}$, 57$^{(13)}$, 158$^{(17)}$, 99$^{(23)}$, 117$^{(28)}$, 57$^{(29)}$, 111$^{(32)}$ |
| t test: t (12) = −2.5179 p = *0.027* | | | | |

Notes:
1. SD = Standard deviation.
2. The data analysed has been limited in the following way: Treatment = SOLVENT or SH-053-S—CH$_3$, 30 mg/kg.
3. The numbers in parentheses next to the data values are animal numbers.
4. p ≦ 0.05 is highlighted in bold italics

TABLE 6

SOLvsS—CH$_3$-2'F 10 mg/kg
[S—CH$_3$-2'F = SH-053-s-2'F = SH-053-2'F-S—CH$_3$, SOLV = SOL = SOLVENT = Vehicle]

| Treatment | N | Mean | SD (note 1) | Data (notes 2, 3) |
|---|---|---|---|---|
| Total Distance Travelled (m) | | | | |
| SOLVENT | 7 | 9.30 | ±2.09 | 5.937$^{(1)}$, 9.141$^{(6)}$, 11.205$^{(10)}$, 11.837$^{(15)}$, 9.661$^{(20)}$, 10.074$^{(25)}$, 7.251$^{(31)}$ |
| SH-053-2'F-S—CH$_3$, 10 mg/kg | 6 | 6.91 | ±2.38 | 9.043$^{(5)}$, 4.707$^{(9)}$, 9.904$^{(14)}$, 5.310$^{(18)}$, 8.047$^{(24)}$, 4.455$^{(30)}$ |
| t test: t (11) = 1.9285 p = 0.080 | | | | |
| Total Entries | | | | |
| SOLVENT | 7 | 9.71 | ±2.14 | 6.0$^{(1)}$, 10.0$^{(6)}$, 12.0$^{(10)}$, 12.0$^{(15)}$, 10.0$^{(20)}$, 10.0$^{(25)}$, 8.0$^{(31)}$ |
| SH-053-2'F-S—CH$_3$, 10 mg/kg | 6 | 8.00 | ±2.83 | 10.0$^{(5)}$, 7.0$^{(9)}$, 12.0$^{(14)}$, 5.0$^{(18)}$, 9.0$^{(24)}$, 5.0$^{(30)}$ |
| t test: t (11) = 1.2445 p = 0.239 | | | | |
| % Open Time | | | | |
| SOLVENT | 7 | 20.43 | ±8.89 | 9$^{(1)}$, 18$^{(6)}$, 19$^{(10)}$, 38$^{(15)}$, 20$^{(20)}$, 16$^{(25)}$, 23$^{(31)}$ |
| SH-053-2'F-S—CH$_3$, 10 mg/kg | 6 | 25.00 | ±16.38 | 32$^{(5)}$, 7$^{(9)}$, 48$^{(14)}$, 27$^{(18)}$, 31$^{(24)}$, 5$^{(30)}$ |
| t test: t (11) = −0.6396 p = 0.536 | | | | |

TABLE 6-continued

| | | % Open Entries | | |
|---|---|---|---|---|
| SOLVENT | 7 | 25.57 | ±8.42 | 17[1], 30[6], 25[10], 42[15], 20[20], 20[25], 25[31] |
| SH-053-2'F-S—CH$_3$, 10 mg/kg | 6 | 37.17 | ±17.54 | 40[5], 43[9], 67[14], 20[18], 33[24], 20[30] |
| t test: t (11) = −1.5595 p = 0.147 | | | | |
| | | Closed Entries | | |
| SOLVENT | 7 | 7.14 | ±1.35 | 5[1], 7[6], 9[10], 7[15], 8[20], 8[25], 6[31] |
| SH-053-2'F-S—CH$_3$, 10 mg/kg | 6 | 4.67 | ±1.03 | 6[5], 4[9], 4[14], 4[18], 6[24], 4[30] |
| t test (note 4): t (11) = 3.6686 p = *0.004* | | | | |
| | | Time in closed arms | | |
| SOLVENT | 7 | 196.29 | ±32.39 | 246[1], 211[6], 225[10], 163[15], 170[20], 194[25], 165[31] |
| SH-053-2'F-S—CH$_3$, 10 mg/kg | 6 | 183.33 | ±50.31 | 150[5], 251[9], 133[14], 212[18], 135[24], 219[30] |
| t test: t (11) = 0.5609 p = 0.586 | | | | |
| | | Open Entries | | |
| SOLVENT | 7 | 2.57 | ±1.27 | 1[1], 3[6], 3[10], 5[15], 2[20], 2[25], 2[31] |
| SH-053-2'F-S—CH$_3$, 10 mg/kg | 6 | 3.33 | ±2.58 | 4[5], 3[9], 8[14], 1[18], 3[24], 1[30] |
| t test: t (11) = −0.6923 p = 0.503 | | | | |
| | | Time in open arms | | |
| SOLVENT | 7 | 50.29 | ±23.98 | 23[1], 47[6], 52[10], 100[15], 42[20], 38[25], 50[31] |
| SH-053-2'F-S—CH$_3$, 10 mg/kg | 6 | 60.50 | ±40.32 | 72[5], 18[9], 121[14], 77[18], 62[24], 13[30] |
| t test: t (12) = −2.5179 p = *0.027* | | | | |

Notes:
1. SD = Standard deviation.
2. The data analysed has been limited in the following way: Treatment = SOLVENT or SH-053-S—CH$_3$, 30 mg/kg.
3. The numbers in parentheses next to the data values are animal numbers.
4. p ≦ 0.05 is highlighted in bold italics

What is claimed is:

1. A compound according to the structure

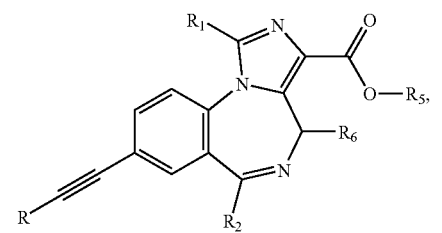

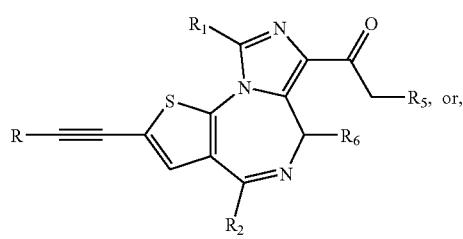

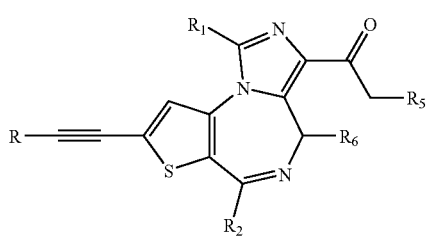

wherein R is selected from H, Si(CH$_3$)$_3$, t-butyl, isopropyl, methyl, and cyclopropyl;

wherein R$_1$ is selected from H, CH$_3$, CF$_3$, CH$_2$CF$_3$, CH$_2$CH$_3$, CH$_2$C≡CH, an alkyl, and cyclopropyl;

wherein R$_2$ is a substituted or unsubstituted, at least partially unsaturated, 5 or 6 membered cyclic or heterocyclic ring, and wherein said substitution is selected from F, Cl, Br, and NO$_2$ at the 2'-position;

wherein R$_5$ is selected from a branched or straight chain C$_1$ to C$_4$ halogenated or unhalogenated alkyl and a methyl cyclopropyl, and, wherein R$_6$ is R or S, and, wherein R$_6$ is selected from CH$_3$, OH, OAc, OCON(CH$_3$)$_2$, COOCH$_3$ and COOC$_2$H$_5$, or a salt thereof.

2. The compound of claim 1 wherein R$_2$ is a substituted or unsubstituted six membered heterocyclic ring.

3. The compound of claim 2 wherein the compound is selected from the group consisting of

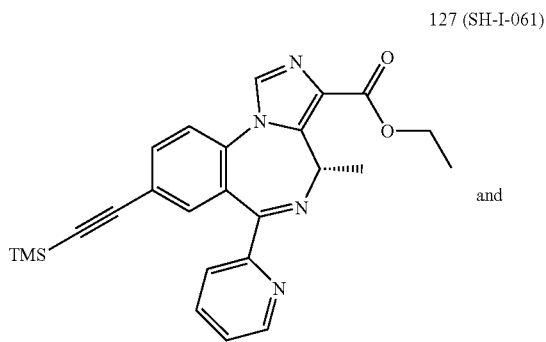

127 (SH-I-061)

and 128 (SH-053-2'N-S-CH₃)

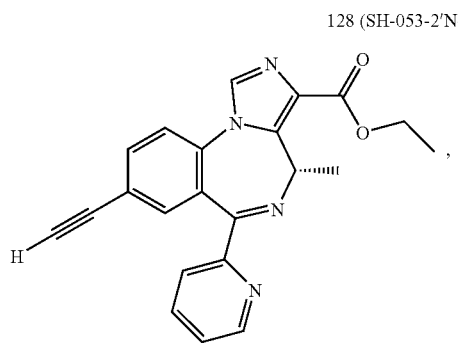

or a salt thereof.

4. A compound of formula XIX (XIX)

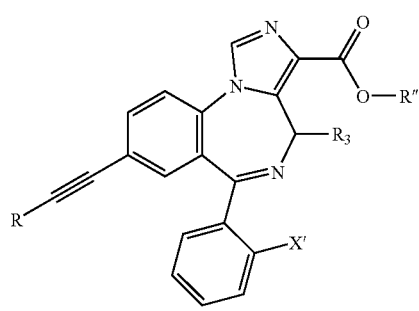

wherein R is selected from H and Si(CH₃)₃;
wherein X' is selected from F, Cl, Br, and NO₂;
wherein R" is selected from H, CH₃, CH₂CH₃, t-butyl, iPr and isoxazole, and,
wherein R₃ is R or S, and R₃ is selected from CH₃, OH, OAc, OCON(CH₃)₂, COOCH₃ and COOC₂H₅,
or a salt thereof.

5. The compound of claim 1 wherein the compound is selected from the group consisting of 113 (SH-I-038)

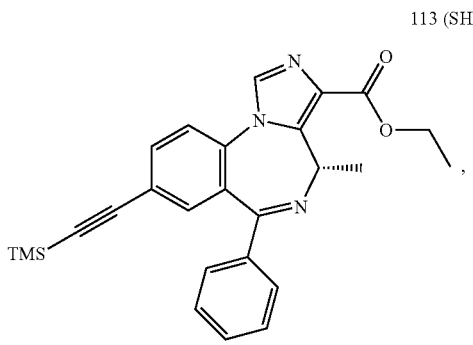

128 (SH-053-2'N-S-CH₃)

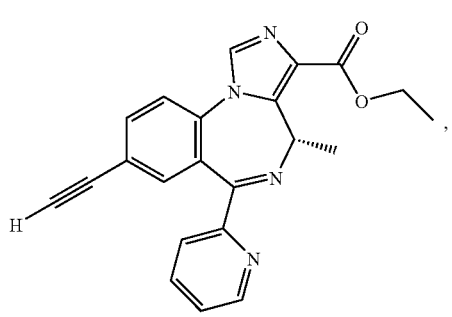

114 (SH-053-S-CH₃)

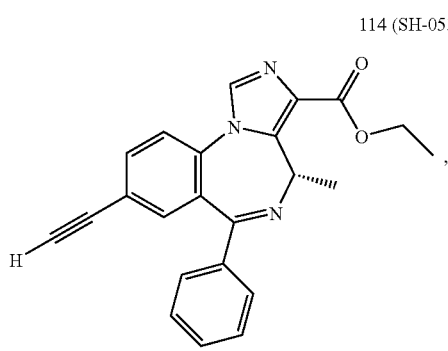

119(SH-I-055)

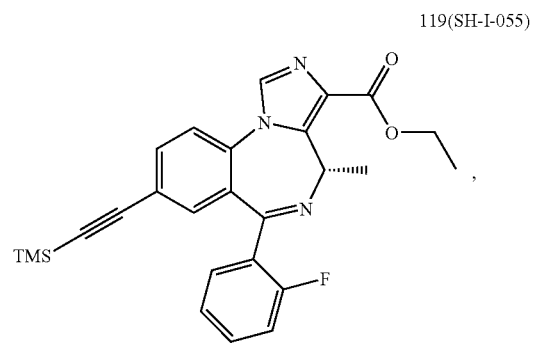

135(SH-R-CH₃)

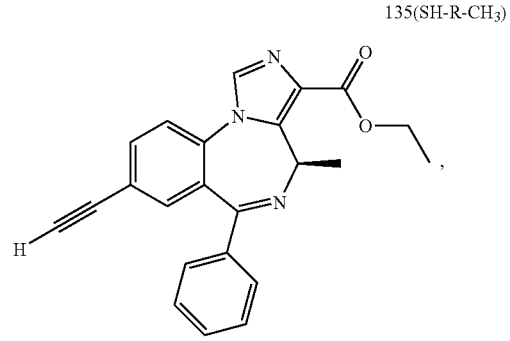

-continued

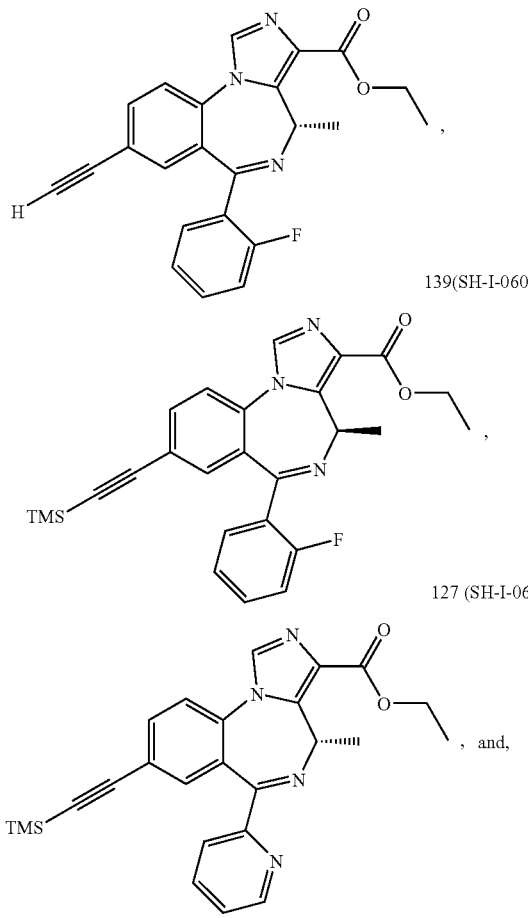

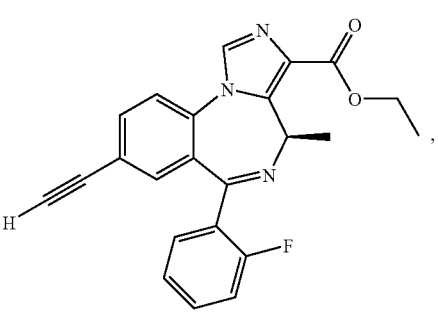

or a salt thereof.

6. A pharmaceutical composition comprising therapeutically effective amount of a compound of claims 1, 2, 3, 4, or 5; and a pharmaceutically-acceptable carrier.

7. A method of reducing anxiety in a subject in need thereof comprising administering an effective amount of a compound of claims 1, 2, 3, 4, or 5.

8. A method of reducing convulsant disorders in a subject in need thereof comprising administering an effective amount of a compound of claims 1, 2, 3, 4, or 5.

9. A method of reducing alcoholism in a subject in need thereof comprising administering an effective amount of a compound of claims 1, 2, 3, 4, or 5.

* * * * *

UNITED STATES PATENT AND TRADEMARK OFFICE
CERTIFICATE OF CORRECTION

PATENT NO. : 7,618,958 B2  Page 1 of 1
APPLICATION NO. : 11/173981
DATED : November 17, 2009
INVENTOR(S) : Cook et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 961 days.

Signed and Sealed this

Twenty-sixth Day of October, 2010

David J. Kappos
*Director of the United States Patent and Trademark Office*